(12) United States Patent
Krishnan et al.

(10) Patent No.: US 9,877,990 B2
(45) Date of Patent: Jan. 30, 2018

(54) COMPOSITIONS AND METHODS FOR THE TREATMENT OF WOUNDS, DISORDERS, AND DISEASES OF THE SKIN

(71) Applicant: Krystal Biotech, Inc., Pittsburgh, PA (US)

(72) Inventors: Suma Krishnan, San Francisco, CA (US); Pooja Agarwal, Germantown, MD (US)

(73) Assignee: Krystal Biotech, Inc., Pittsburgh, PA (US)

( * ) Notice: Subject to any disclaimer, the term of this patent is extended or adjusted under 35 U.S.C. 154(b) by 0 days.

(21) Appl. No.: 15/393,151

(22) Filed: Dec. 28, 2016

(65) Prior Publication Data
US 2017/0290866 A1     Oct. 12, 2017

Related U.S. Application Data

(60) Provisional application No. 62/320,316, filed on Apr. 8, 2016.

(51) Int. Cl.
| | |
|---|---|
| A61K 35/763 | (2015.01) |
| A61K 9/00 | (2006.01) |
| A61K 39/12 | (2006.01) |
| A61K 39/00 | (2006.01) |
| C12N 15/86 | (2006.01) |
| C12N 7/00 | (2006.01) |

(52) U.S. Cl.
CPC .......... *A61K 35/763* (2013.01); *A61K 9/0014* (2013.01)

(58) Field of Classification Search
CPC ............... A61K 39/12; A61K 2039/53; A61K 2039/5156; A61K 2039/5254; A61K 2039/5256; A61K 38/162; A61K 38/39; A61K 39/245; A61K 39/25; A61K 39/42; A61K 9/10; C07K 14/005; C07K 14/78; C12N 15/86; C12N 7/00; C12N 2710/16034; C12N 2710/24043; C12N 15/09; C12N 2710/16134; C12N 2710/16634; C12N 2710/16734

See application file for complete search history.

(56) References Cited

U.S. PATENT DOCUMENTS

| | | | |
|---|---|---|---|
| 5,658,724 A | 8/1997 | Deluca | |
| 5,998,174 A | 12/1999 | Glorioso et al. | |
| 6,106,826 A * | 8/2000 | Brandt ............... | A61K 38/1825 424/93.2 |
| 6,887,490 B1 * | 5/2005 | Jahoda ............... | A61K 48/00 435/320.1 |
| 9,314,505 B2 * | 4/2016 | Wise ............... | A61K 38/2066 |
| 2003/0082142 A1 * | 5/2003 | Coffin ............... | C12N 15/86 424/93.2 |
| 2013/0331547 A1 * | 12/2013 | Hall ............... | C07K 14/005 530/350 |
| 2014/0256798 A1 * | 9/2014 | Osborn ............... | A61K 31/7088 514/44 R |
| 2014/0288155 A1 * | 9/2014 | Hovnanian ............... | C12N 15/113 514/44 A |
| 2015/0352191 A1 | 12/2015 | South et al. | |

FOREIGN PATENT DOCUMENTS

| | | |
|---|---|---|
| CN | 102212559 B | 4/2014 |
| WO | 2000/040734 A1 | 7/2000 |
| WO | 2015/009952 A1 | 1/2015 |
| WO | 2015/117021 A1 | 8/2015 |

OTHER PUBLICATIONS

Christiano AM. Collagen, type VII, alpha 1 (epidermolysis bullosa, dystrophic, dominant and recessive) [*Homo sapiens*]. NCBI Reference Sequence: NP_000085.1. Dep. Mar. 19, 1999.*
Aldawsari M, Chougule MB, Babu RJ. Progress in Topical siRNA Delivery Approaches for Skin Disorders. Curr Pharm Des. 2015;21(31):4594-605.*
Andtbacka RH, et. al. Talimogene Laherparepvec Improves Durable Response Rate in Patients With Advanced Melanoma. J Clin Oncol. Sep. 1, 2015;33(25):2780-8.*
Siprashvili Z, Nguyen NT, Bezchinsky MY, Marinkovich MP, Lane AT, Khavari PA. Long-term type VII collagen restoration to human epidermolysis bullosa skin tissue. Hum Gene Ther. Oct. 2010;21(10):1299-310.*
Deluca et al., "Isolation and Characterization of Deletion Mutants of Herpes Simplex Virus Type 1 in the Gene Encoding Immediate-Early Regulatory Protein ICP4", Journal of Virology, vol. 56, No. 2, Nov. 1985, pp. 558-570.
Grant, Kyle, "Production and Purification of Highly Replication Defective Hsv-1 Based Gene Therapy Vectors", Doctoral Dissertation, University of Pittsburgh, 2008, 137 pages.
Kim et al., "Microneedles for Drug and Vaccine Delivery", Advanced Drug Delivery Reviews, vol. 64, 2012, pp. 1547-1568.
Samaniego et al., "Persistence and Expression of the Herpes Simplex Virus Genome in the Absence of Immediate-Early Proteins", Journal of Virology, vol. 72, No. 4, Apr. 1998, pp. 3307-3320.
Silva et al., "Herpes Virus Amplicon Vectors", Viruses, vol. 1, 2009, pp. 594-629.
Watanabe et al., "Properties of a Herpes Simplex Virus Multiple Immediate-early Gene-Deleted Recombinant as a Vaccine Vector", Virology, vol. 357, 2007, pp. 186-198.

(Continued)

*Primary Examiner* — Rachel B Gill
(74) *Attorney, Agent, or Firm* — Morrison & Foerster LLP

(57) ABSTRACT

The present disclosure relates, in part, to pharmaceutical compositions comprising one or more polynucleotides suitable for enhancing, increasing, augmenting, and/or supplementing the levels of Collagen alpha-1 (VII) chain polypeptide and/or Lysyl hydroxylase 3 polypeptide and/or Keratin type I cytoskeletal 17 polypeptide in a subject. The present disclosure also relates, in part, to pharmaceutical compositions and methods of use for providing prophylactic, palliative, or therapeutic relief of a wound, disorder, or disease of the skin in a subject, including a subject having, or at risk of developing, one or more symptoms of epidermolysis bullosa.

36 Claims, 17 Drawing Sheets
(7 of 17 Drawing Sheet(s) Filed in Color)

(56) References Cited

OTHER PUBLICATIONS

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.
Georgiadis et al., "Lentiviral Engineered Fibroblasts Expressing Codon-Optimized COL7A1 Restore Anchoring Fibrils in RDEB", Journal of Investigative Dermatology, vol. 136, 2016, pp. 284-292.
Goto et al., "Fibroblasts Show More Potential as Target Cells than Keratinocytes in COL7A1 Gene Therapy of Dystrophic Epidermolysis Bullosa", Journal of Investigative Dermatology, vol. 126, 2006, pp. 766-772.
International Search Report and Written Opinion received for PCT Patent Application No. PCT/US2016/068974, dated May 18, 2017, 20 pages.
Invitation to Pay Additional Fee received for PCT Patent Application No. PCT/US2016/068974, dated Mar. 27, 2017, 8 pages.
Lu, et al., "Topical Application of Viral Vectors for Epidermal Gene Transfer", The Journal of Investigative Dermatology, vol. 108, No. 5, May 1997, pp. 803-808.
Mayr et al., "Gene Therapy for the COL7A1 Gene", Chapter 23, Intech, 2013, pp. 561-589.
Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.
Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.
Salmon-Ehr et al., "Implication of Interleukin-4 in Wound Healing", Laboratory Investigation, vol. 80, No. 8, Aug. 2000, pp. 1337-1343.
Siprashvili et al., "Long-Term Type VII Collagen Restoration to Human Epidermolysis Bullosa Skin Tissue", Human Gene Therapy, vol. 21, Oct. 2010, pp. 1299-1310.
Uitto et al., "Progress toward Treatment and Cure of Epidermolysis Bullosa: Summary of the DEBRA International Research Symposium EB2015", Journal of Investigative Dermatology, vol. 136, 2016, pp. 352-358.
Watt et al., "Lysyl Hydroxylase 3 Localizes to Epidermal Basement Membrane and Is Reduced in Patients with Recessive Dystrophic Epidermolysis Bullosa", Plos One, vol. 10, No. 9, Sep. 18, 2015, pp. 1-15.
Weiss et al., "The Role of Interleukin 10 in the Pathogenesis and Potential Treatment of Skin Diseases", Journal of the American Academy of Dermatology, vol. 50, No. 5, May 2004, pp. 657-675.
Wolfe et al., "Engineering Herpes Simplex Viral Vectors for Therapeutic Gene Transfer", Chapter 6, Gene and Cell Therapy, 2004, pp. 103-129.
Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.

\* cited by examiner

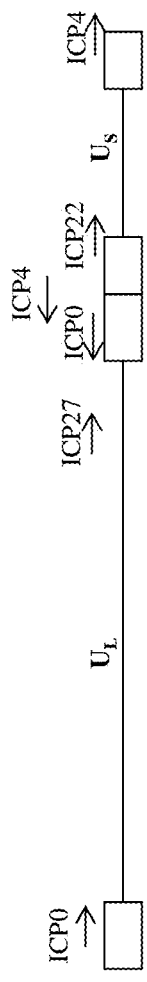
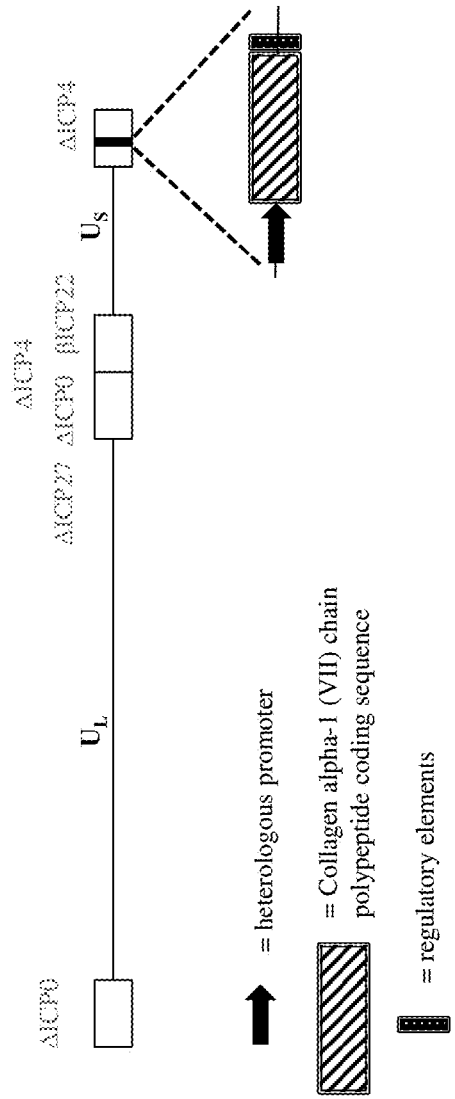
FIG. 1A
FIG. 1B

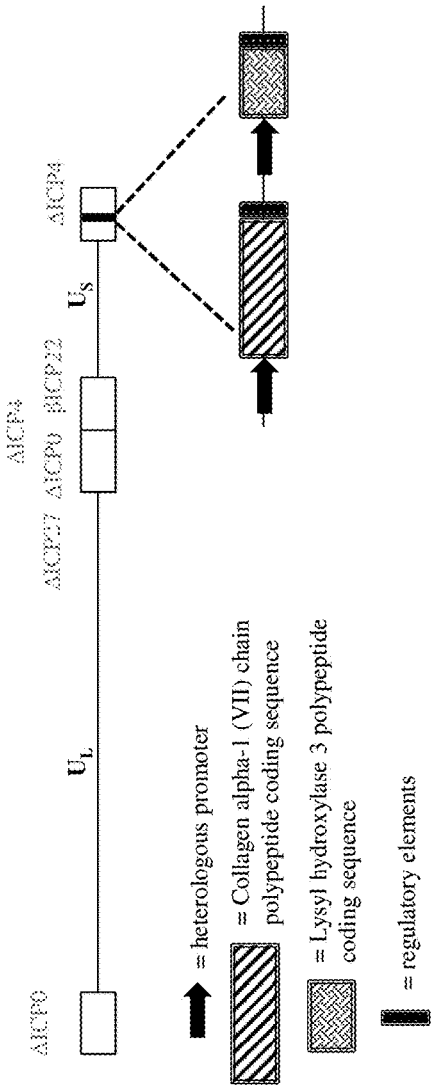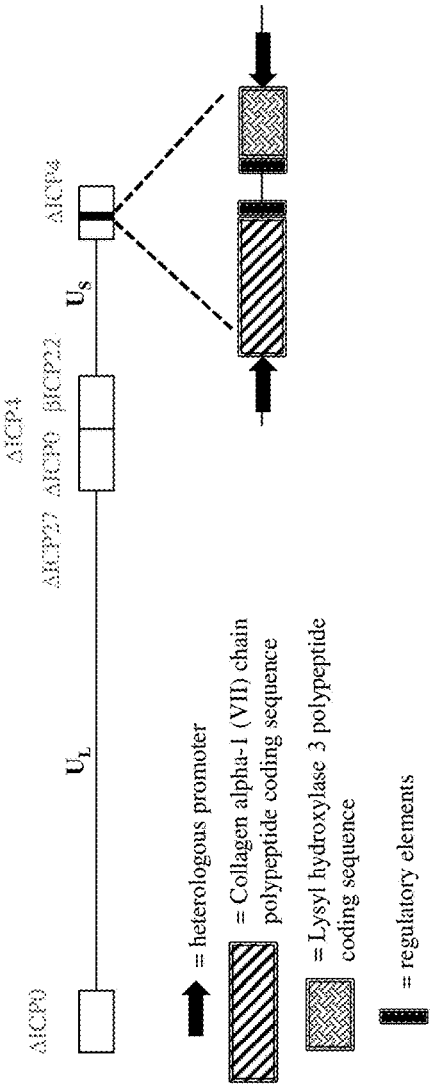
FIG. 1C
FIG. 1D

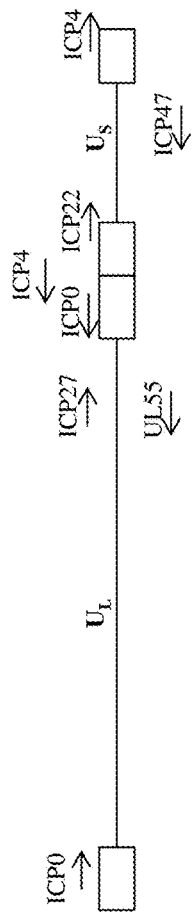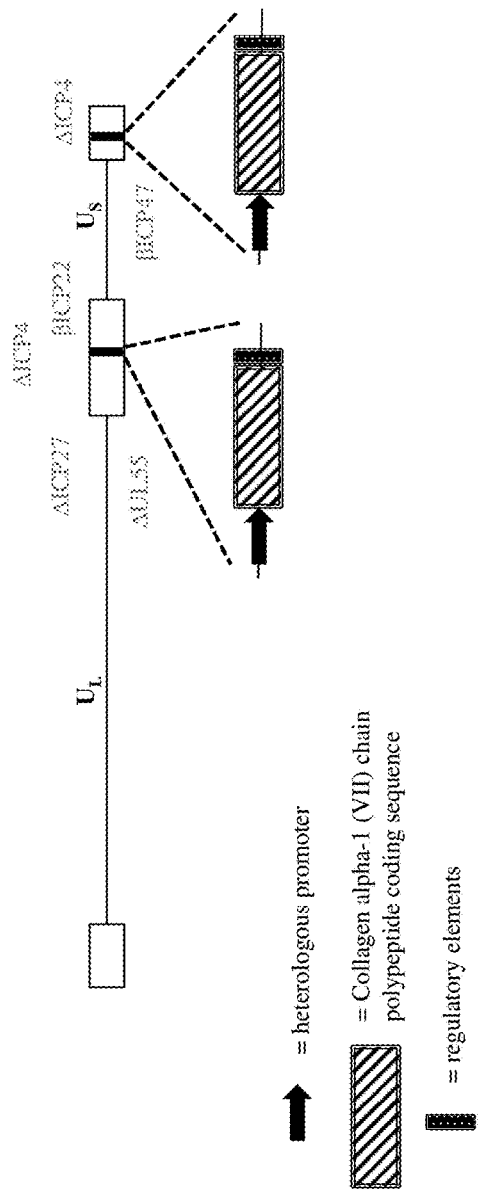
FIG. 2A
FIG. 2B

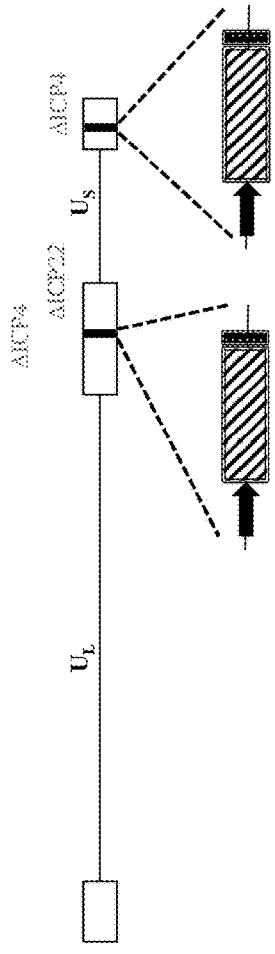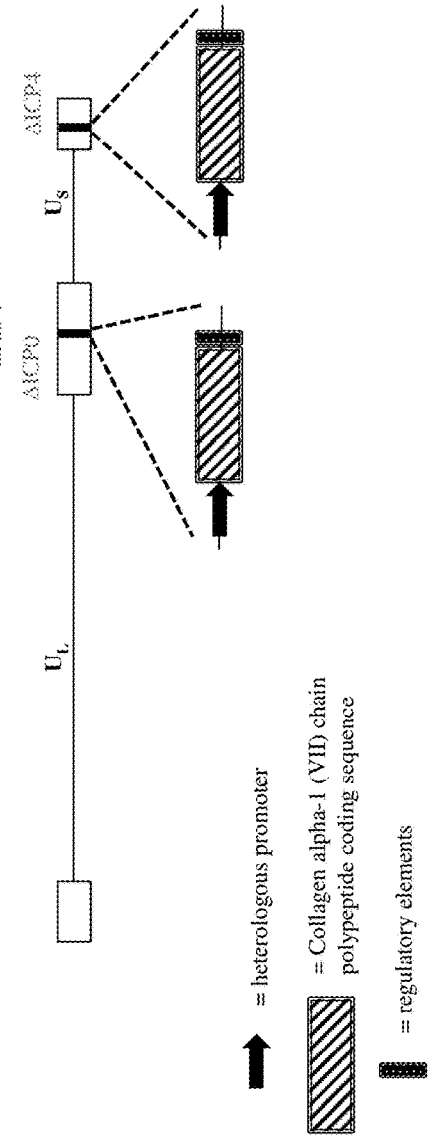
FIG. 2C
FIG. 2D

COMPOSITIONS AND METHODS FOR THE TREATMENT OF WOUNDS, DISORDERS, AND DISEASES OF THE SKIN

CROSS REFERENCE TO RELATED APPLICATIONS

This application claims the priority benefit of U.S. Provisional Application Ser. No. 62/320,316, filed Apr. 8, 2016, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761342000100SEQLIST.txt, date recorded: Dec. 28, 2016, size: 394 KB).

FIELD OF THE INVENTION

The present disclosure relates, in part, to pharmaceutical compositions and methods of use for providing prophylactic, palliative, or therapeutic relief of a wound, disorder, or disease of the skin in a subject, including a subject having, or at risk of developing, one or more symptoms of epidermolysis bullosa.

BACKGROUND

A number of serious disease-related skin conditions are associated with one or more genetic disorders in patients suffering from these diseases. One such disease, epidermolysis bullosa (EB), is a group of genetic disorders that cause the skin and mucous membranes of an affected individual to blister and erode in response to minor injury or friction, such as scraping, rubbing, or scratching. Dystrophic epidermolysis bullosa (DEB) is one of the major forms of EB. The signs and symptoms of this condition vary widely among affected individuals, ranging from mild (blistering may only affect the hands, feet, knees, and elbows) to severe (widespread blistering and scarring, possibly leading to vision loss, disfigurement, and other serious, and sometimes fatal, medical conditions).

Dystrophic epidermolysis bullosa is classified into three major types. Autosomal dominant dystrophic epidermolysis bullosa (referred to as dominant dystrophic epidermolysis bullosa or DDEB) is typically the mildest form, with blistering often restricted to the hands, feet knees and elbows. The other two types of dystrophic epidermolysis bullosa, Hallopeau-Siemens type recessive dystrophic epidermolysis bullosa, and non-Hallopeau-Siemens type recessive epidermolysis bullosa (collectively referred to as recessive dystrophic epidermolysis bullosa or RDEB) are more severe. RDEB is most often characterized by extensive blistering and scarring of the skin and mucosal membranes. Blisters are routinely present over the whole body, including on mucous membranes (such as the lining of the mouth and digestive tract), and healing of these blisters results in extensive scarring. Damage to the mouth and esophagus can make it difficult to chew and swallow food, leading to chronic malnutrition and slow growth. Complications from extensive scarring can include fusion of the fingers and toes, joint deformities, and eye inflammation leading to vision loss. Additionally, patients suffering from RDEB have a high risk of developing squamous cell carcinoma, which can be unusually aggressive in this patient population, often becoming life-threatening. Although the three types of dystrophic epidermolysis bullosa differ in severity, they have many shared features, and are caused by the same genetic mutations.

Dystrophic epidermolysis bullosa is caused by mutations to the Col7a1 gene, which encodes the Collagen alpha-1 (VII) chain protein (Collagen 7). More than 240 distinct mutations to this gene have been identified in DEB patients. Additionally, a significant decrease in expression of the PLOD3 gene, which encodes the collagen modifying Lysyl hydroxylase 3 enzyme (LH3), has also been observed in dystrophic epidermolysis patients. Collagen alpha-1 (VII) chain protein functions to strengthen and stabilize the skin, while Lysyl hydroxylase 3 plays a critical role in the synthesis and secretion of functional Collagen alpha-1 (VII) chain protein. Briefly, Col7a1 transcripts are translated, and the resulting peptides are post-translationally modified by hydroxylating their proline residues (by prolyl hydroxylases) and their lysine residues (by lysyl hydroxylases, such as LH3). Hydroxylysine residues can then be glycosylated, and subsequently, three glycosylated peptides form a triple helix known as pro-collagen, and are secreted from the cell. The secreted pro-collagen can then associate in to higher-order structures, forming anchoring fibrils. The anchoring fibrils are then available to help organize, stabilize, and aid in adherence of the epithelial basement membrane. The epithelial basement membrane is responsible for anchoring the epithelium to the underlying loose connective tissue, and is essential for dermal-epidermal stability (dermoepidermal junction integrity). Mutations in the Col7a1 gene, and diminished levels of PLOD3 expression, impair the ability of Collagen alpha-1 (VII) chain protein to properly connect the epidermis to the dermis in dystrophic epidermolysis bullosa patients, leading to fragile skin.

Treatment options for epidermolysis bullosa patients are limited, and current care focuses on managing the symptoms of the disease, including providing medication to control pain and itching, administering oral antibiotics to stave off infections resulting from open wounds on the skin and mucosa, and surgical strategies to address scarring and deformities. Investigational methods for treating the underlying causes of epidermolysis bullosa include administering purified Collagen 7, fibroblasts containing Collagen 7, or viral vectors encoding Collagen 7, by intradermal injection. Because many DEB patients have multiple wounds spanning large areas of trauma-prone sites (such as the sacrum, hips, feet, lower back, and hands), any treatment involving intradermal injection would be extremely invasive, as these large wound areas would all need to be injected, likely repeatedly, although injection time intervals are unclear.

Thus there exists a clear need for less invasive/minimally invasive/non-invasive treatment options for epidermolysis bullosa patients that can address the deficiencies in the Collagen alpha-1 (VII) chain protein, as well as deficiencies in the Lysyl hydroxylase 3 protein, observed in this patient population.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

BRIEF SUMMARY

In order to meet these needs, the present disclosure relates, in part, to pharmaceutical compositions and methods of use for providing prophylactic, palliative, or therapeutic relief of a wound, disorder, or disease of the skin in a subject, especially in a subject having, or at risk of developing, one or more symptoms of epidermolysis bullosa. In particular, the present disclosure relates, in part, to a method of treating an individual by administering (e.g., topically or transdermally administering) a pharmaceutical composition comprising one or more polynucleotides encoding a Collagen alpha-1 (VII) chain polypeptide, a Lysyl hydroxylase 3 polypeptide, a Keratin type I cytoskeletal 17 polypeptide and/or a chimeric polypeptide thereof.

Accordingly, certain aspects of the present disclosure relate to a pharmaceutical composition comprising a virus comprising a vector, wherein the vector comprises one or more transgenes encoding a Collagen alpha-1 (VII) chain polypeptide, a Lysyl hydroxylase 3 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the herpes simplex virus comprises a modified envelope. In some embodiments, the modified envelope alters the herpes simplex virus tissue tropism relative to a wild-type herpes simplex virus. In some embodiments, the modified envelope comprises a mutant herpes simplex virus glycoprotein. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the one or more transgenes comprises an miRNA binding site. In some embodiments, the one or more transgenes are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiment, the vector comprises a transgene encoding a Collagen alpha-1 (VII) chain polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the vector comprises at least a first transgene and a second transgene. In some embodiments, the first transgene encodes a Collagen alpha-1 (VII) chain polypeptide and the second transgene encodes a Lysyl hydroxylase 3 polypeptide. In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the first and second ORFs are separated by an internal ribosomal entry site (IRES). In some embodiments, the Collagen alpha-1 (VII) chain polypeptide and the Lysyl hydroxylase 3 polypeptide are at about an equimolar ratio when the polypeptides are expressed in one or more target cells of a subject. In some embodiments, the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject. In some embodiments, the chimeric polypeptide comprises a linker polypeptide between the Collagen alpha-1 (VII) chain polypeptide and the Lysyl hydroxylase 3 polypeptide. In some embodiments, the linker polypeptide is a T2A, P2A, E2A, or F2A linker polypeptide. In some embodiments, the linker polypeptide has at least 80% sequence identity to the sequence of SEQ ID NO: 6, SEQ ID NO: 8, SEQ ID NO: 10 or SEQ ID NO: 12. In some embodiments, the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, the chimeric polypeptide enhances, increases, augments, and/or supplements anchoring fibril formation, epithelial basement membrane organization, and/or epithelial basement adherence of a subject when the polypeptide is expressed in one or more target cells of the subject.

Other aspects of the present disclosure relate to a method of providing prophylactic, palliative, or therapeutic relief of a wound, disorder, or disease of the skin in a subject, the method comprising topically or transdermally administering a pharmaceutical composition capable of enhancing, increasing, augmenting, and/or supplementing the levels of a Collagen alpha-1 (VII) chain polypeptide and/or a Lysyl hydroxylase 3 polypeptide in one or more cells of the subject. In some embodiments, the pharmaceutical composition comprises a virus comprising a vector, wherein the vector comprises one or more transgenes encoding a Collagen alpha-1 (VII) chain polypeptide, a Lysyl hydroxylase 3 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the herpes simplex virus comprises a modified envelope. In some embodiments, the modified envelope alters the herpes simplex virus tissue tropism relative to a wild-type herpes simplex virus. In some embodiments, the modified envelope comprises a mutant herpes simplex virus glycoprotein. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the one or more transgenes comprises an miRNA binding site. In some embodiments, the one or more transgenes are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiments, the vector comprises a transgene encoding a Collagen alpha-1 (VII) chain polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the vector comprises at least a first transgene and a second transgene. In some embodiments, the first transgene encodes a Collagen alpha-1 (VII) chain polypeptide and the second transgene encodes a Lysyl hydroxylase 3 polypeptide. In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the first and second ORFs are separated by an internal ribosomal entry site (IRES). In some embodiments, the Collagen alpha-1 (VII) chain polypeptide and the Lysyl hydroxylase 3 polypeptide are at about an equimolar ratio when the polypeptides are expressed in one or more target cells of a subject. In some embodiments, the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject. In some embodiments, the chimeric polypeptide comprises a linker polypeptide between the Collagen alpha-1 (VII) chain polypeptide and the Lysyl hydroxylase 3 polypeptide. In some embodiments, the linker polypeptide is a T2A, P2A, E2A, or F2A linker polypeptide. In some embodiments, the linker polypeptide has at least 80% sequence identity to the sequence of SEQ ID NO: 6, SEQ ID NO: 8, SEQ ID NO: 10 or SEQ ID NO: 12. In some embodiments, the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, the chimeric polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the pharmaceutical composition is administered one, two three, four, five or more times per day. In some embodiments, the pharmaceutical composition is administered to one or more affected and/or unaffected areas of the subject. In some embodiments, the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3gene), autosomal recessive congenital ichthyosis, xeroderma pigmentosa, and pemphigoid.

Other aspects of the present disclosure relate to an isolated chimeric polypeptide, wherein the isolated chimeric polypeptide comprises a Collagen alpha-1 (VII) chain polypeptide, a Lysyl hydroxylase 3 polypeptide, and a linker polypeptide, wherein the Collagen alpha-1 (VII) chain polypeptide and the Lysyl hydroxylase 3 polypeptide are separated by the linker polypeptide, to polynucleotides encoding the same, to vectors comprising the polynucleotides, and to host cells comprising the vectors. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the polynucleotide within one or more viral gene loci. In some embodiments, the recombinant herpes simplex virus genome comprises the polynucleotide within one or more of the ICP4 viral gene loci. In some embodiments, the recombinant herpes simplex virus genome comprises the polynucleotide within the UL41 viral gene locus.

Other aspects of the present disclosure relate to a vector comprising one or more polynucleotides encoding a Collagen alpha-1 (VII) chain polypeptide, a Lysyl hydroxylase 3 polypeptide, a Keratin type I cytoskeletal 17 polypeptide, or any combinations thereof, wherein the vector is a recombinant herpes simplex virus genome, and to host cells comprising the vector. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more polynucleotides within one or more viral gene loci. In some embodiments, the recombinant herpes simplex virus genome comprises the one or more polynucleotides within one or more of the ICP4 viral gene loci. In some embodiments, the recombinant herpes simplex virus genome comprises the one or more polynucleotides within the UL41 viral gene locus. In some embodiments, the vector comprises one polynucleotide encoding a Collagen alpha-1 (VII) chain polypeptide. In some embodiments, the vector comprises two polynucleotides encoding a Collagen alpha-1 (VII) chain polypeptide.

Other aspects of the present disclosure relate to methods of collecting a herpes simplex virus, wherein a vector of interest is packaged within said herpes simplex virus. In some embodiments the method comprises the steps of contacting a host cell with a vector encoding a helper virus, contacting said host cell with a HSV-1 amplicon or HSV-1 hybrid amplicon comprising one or more polynucleotides described herein, and collecting the Herpes simplex virus generated by said host cell. In some embodiments, the method comprises the steps of contacting a complementing host cell with a recombinant herpes simplex virus genome vector comprising one or more polynucleotides described herein, and collecting the herpes simplex virus generated by said complementing host cell. In some embodiments, the collected herpes simplex virus is a herpes simplex type 1 virus, a herpes simplex type 2 virus, or any derivatives thereof.

Other aspects of the present disclosure relate to a kit comprising a pharmaceutical composition described herein and instructions for administering the pharmaceutical composition.

Other aspects of the present disclosure relate to relate to a pharmaceutical composition comprising a virus comprising a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the pharmaceutically acceptable carrier is suitable for subcutaneous or intradermal administration. In some embodiments, the one or more transgenes comprises an miRNA binding site. In some embodiment, the vector comprises a transgene encoding a Collagen alpha-1 (VII) chain polypeptide. In some embodiment, the vector comprises a transgene encoding a Lysyl hydroxylase 3 polypeptide. In some embodiment, the vector comprises a transgene encoding a Keratin type I cytoskeletal 17 polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the Keratin type I cytoskeletal 17 polypeptide has at least 80% sequence identity to the sequence of SEQ ID NO: 30. In some embodiments, the Keratin type I cytoskeletal 17 polypeptide is a fragment, wherein the fragment has at least 100 consecutive amino acids of SEQ ID NO: 30. In some embodiments, the Keratin type I cytoskeletal 17 polypeptide enhances, increases, augments, and/or supplements wound healing in a subject. In some embodiments, the vector comprises at least a first transgene and a second transgene. In some embodiments, the first transgene and the second transgene each encode a Collagen alpha-1 (VII) chain polypeptide. In some embodiments, the first transgene encodes a Collagen alpha-1 (VII) chain polypeptide and the second transgene encodes a Lysyl hydroxylase 3 polypeptide. In some embodiments, the first transgene encodes a Collagen alpha-1 (VII) chain polypeptide and the second transgene encodes a Keratin type I cytoskeletal 17 polypeptide. In some embodiments, the first transgene encodes a Lysyl hydroxylase 3 polypeptide and the second transgene encodes a Keratin type I cytoskeletal 17 polypeptide. In some embodiments, the vector comprises at least a first transgene, a second transgene, and a third transgene. In some embodiments, the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Other aspects of the present disclosure relate to a method of providing prophylactic, palliative, or therapeutic relief of a wound, disorder, or disease of the skin in a subject, the method comprising administering to the subject a pharmaceutical composition comprising a vector, wherein the vector is a recombinant herpes simplex virus genome, and wherein the pharmaceutical composition is capable of enhancing, increasing, augmenting, and/or supplementing the levels of a Collagen alpha-1 (VII) chain polypeptide and/or a Lysyl hydroxylase 3 polypeptide and/or a Keratin type I cytoskeletal 17 polypeptide in one or more cells of the subject. In some embodiments, the pharmaceutical composition comprises a virus comprising the vector, wherein the vector comprises one or more transgenes encoding a Collagen alpha-1 (VII) chain polypeptide, a Lysyl hydroxylase 3 polypeptide, a Keratin type I cytoskeletal 17 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the pharmaceutically acceptable carrier is suitable for subcutaneous or intradermal administration. In some embodiments, the one or more transgenes comprises an miRNA binding site. In some embodiments, the vector comprises a transgene encoding a Collagen alpha-1 (VII) chain polypeptide. In some embodiments, the vector comprises a transgene encoding a Lysyl hydroxylase 3 polypeptide. In some embodiments, the vector comprises a transgene encoding a Keratin type I cytoskeletal 17 polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the Keratin type I cytoskeletal 17 polypeptide has at least 80% sequence identity to the sequence of SEQ ID NO: 30. In some embodiments, the Keratin type I cytoskeletal 17 polypeptide is a fragment, wherein the fragment has at least 100 consecutive amino acids of SEQ ID NO: 30. In some embodiments, the Keratin type I cytoskeletal 17 polypeptide enhances, increases, augments, and/or supplements wound healing in a subject. In some embodiments, the vector comprises at least a first transgene and a second transgene. In some embodiments, the first transgene and the second transgene each encode a Collagen alpha-1 (VII) chain polypeptide. In some embodiments, the first transgene encodes a Collagen alpha-1 (VII) chain polypeptide and the second transgene encodes a Lysyl hydroxylase 3 polypeptide. In some embodiments, the first transgene encodes a Collagen alpha-1 (VII) chain polypeptide and the second transgene encodes a Keratin type I cytoskeletal 17 polypeptide. In some embodiments, the first transgene encodes a Lysyl hydroxylase 3 polypeptide and the second transgene encodes a Keratin type I cytoskeletal 17 polypeptide. In some embodiments, the vector comprises at least a first transgene, a second transgene, and a third transgene. In some embodiments, the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide. In some embodiments, the pharmaceutical composition is administered topically or transdermally to the subject. In some embodiments, the pharmaceutical composition is administered subcutaneously or intradermally to the subject. In some embodiments, the pharmaceutical composition is administered one, two three, four, five or more times per day. In some embodiments, the pharmaceutical composition is administered to one or more affected and/or unaffected areas of the subject. In some embodiments, the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-F show schematics of wild-type and modified herpes simplex virus genomes. FIG. 1A shows a wild-type herpes simplex virus genome. FIG. 1B shows a modified herpes simplex virus genome comprising a transgene encoding a Collagen alpha-1 (VII) chain polypeptide. FIG. 1C shows a modified herpes simplex virus genome comprising two transgenes, one encoding a Collagen alpha-1 (VII) chain polypeptide and the other encoding a Lysyl hydroxylase 3 polypeptide, with the transgenes encoded on the same strand of DNA. FIG. 1D shows a modified herpes simplex virus genome comprising two transgenes, one encoding a Collagen alpha-1 (VII) chain polypeptide and the other encoding a Lysyl hydroxylase 3 polypeptide, with the transgenes encoded on opposite strands of DNA in an antisense orientation. FIG. 1E shows a modified herpes simplex virus genome comprising a transgene that is polycistronic, encoding a Collagen alpha-1 (VII) chain polypeptide and a Lysyl hydroxylase 3 polypeptide separated by an internal ribosomal entry site (IRES). FIG. 1F shows a modified herpes simplex virus genome comprising a transgene encoding a chimeric polypeptide comprising a Collagen alpha-1 (VII) chain polypeptide, a linker polypeptide, and a Lysyl hydroxylase 3 polypeptide.

FIGS. 2A-G show additional schematics of wild-type and modified herpes simplex virus genomes. FIG. 2A shows a wild-type herpes simplex virus genome. FIG. 2B shows a modified herpes simplex virus genome comprising deletions of the coding sequences of ICP4 (both copies), ICP27, and UL55 and deletions of the promoter sequences of ICP22 and ICP47, with two transgenes encoding Collagen alpha-1 (VII) chain polypeptides integrated at the ICP4 loci. FIG. 2C shows a modified herpes simplex virus genome comprising deletions of the coding sequences of ICP4 (both copies) and ICP22, with two transgenes encoding Collagen alpha-1 (VII) chain polypeptides integrated at the ICP4 loci. FIG. 2D shows a modified herpes simplex virus genome comprising deletions of the coding sequences of ICP0 and ICP4 (both copies), with two transgenes encoding Collagen alpha-1 (VII) chain polypeptides integrated at the ICP4 loci. FIG. 2E shows a modified herpes simplex virus genome comprising deletions of the coding sequences of ICP0, ICP4 (both copies), and ICP22, with two transgenes encoding Collagen alpha-1 (VII) chain polypeptides integrated at the ICP4 loci. FIG. 2F shows a modified herpes simplex virus genome comprising deletions of the coding sequences of ICP0, ICP4 (both copies), ICP22, and ICP27, with two transgenes encoding Collagen alpha-1 (VII) chain polypeptides integrated at the ICP4 loci. FIG. 2G shows a modified herpes simplex virus genome comprising deletions of the coding sequences of ICP0, ICP4 (both copies), ICP22, ICP27, and UL55, with two transgenes encoding Collagen alpha-1 (VII) chain polypeptides integrated at the ICP4 loci.

FIGS. 5A-5B show human Col7 protein expression detected in KB103-infected cells. FIG. 5A shows human Col7 protein expression in uninfected normal and RDEB fibroblasts, as well as fibroblasts infected with KB103 at the indicated multiplicity of infection (MOI). FIG. 5B shows human Col7 protein expression in uninfected normal and RDEB keratinocytes, as well as keratinocytes infected with KB103 at the indicated multiplicity of infection (MOI). Human GAPDH protein expression is shown as a loading control.

DETAILED DESCRIPTION

Figure 1E:
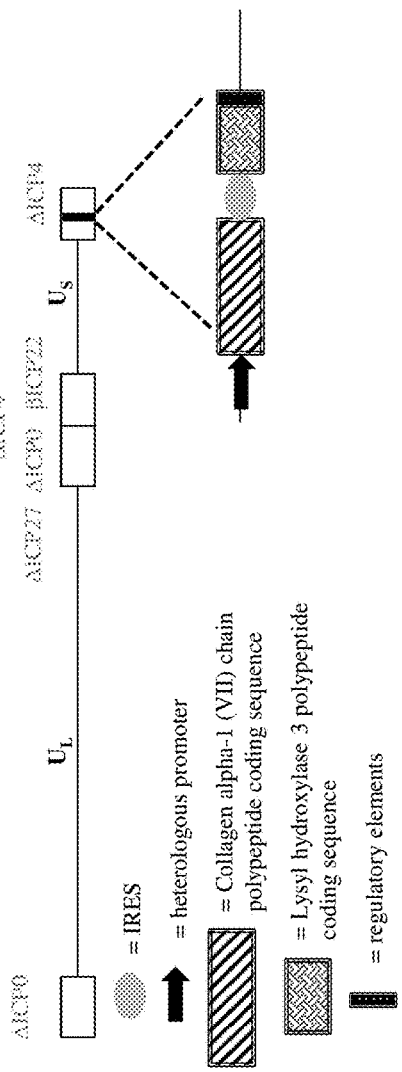

The present disclosure relates, in part, to pharmaceutical compositions comprising one or more polynucleotides encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the pharmaceutical composition comprises a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the vector comprises one or more transgenes suitable for enhancing, increasing, augmenting, and/or supplementing the levels of Collagen alpha-1 (VII) chain polypeptide and/or Lysyl hydroxylase 3 polypeptide and/or Keratin type I cytoskeletal 17 polypeptide in one or more cells of a subject. The present disclosure also relates, in part, to methods of providing prophylactic, palliative, or therapeutic relief of a wound, disorder, or disease of the skin (e.g. dystrophic epidermolysis bullosa) in a subject by administering (e.g., topically or transdermally administering) a pharmaceutical composition described herein.

The following description sets forth exemplary methods, parameters, and the like. It should be recognized, however, that such description is not intended as a limitation on the scope of the present disclosure but is instead provided as a description of exemplary embodiments.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "about" refers to the usual error range for the respective value readily known to the skilled person in this technical field. Reference to "about" a value or parameter herein includes (and describes) embodiments that are directed to that value or parameter per se.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "internal ribosome entry site" or "IRES" refers to a nucleotide sequence that allows for translation initiation in the middle, e.g. after the first start codon, of an mRNA sequence.

As used herein, an "untranslated region" or "UTR" refers to unstranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some aspects, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice and rats, etc. In some embodiments, the mammal is human.

As used herein, "topical administration" or "topically administering" refers to the delivery of a composition to a subject by contacting, directly or otherwise, a formulation comprising the composition to all or a portion of the skin of a subject. The term encompasses several routes of administration including, but not limited to, topical and transdermal. Topical administration is used as a means to deliver a composition to the epidermis or dermis of a subject, or to specific strata thereof.

As used herein, an "effective amount" is at least the minimum amount required to effect a measurable improvement or prevention of one or more symptoms of a particular disorder. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, delaying the progression of the disease, and/or prolonging survival. An effective amount can be administered in one or more administrations.

Pharmaceutical Compositions

Polynucleotides

In one aspect, provided herein is a pharmaceutical composition comprising one or more polynucleotides encoding a Collagen alpha-1 (VII) chain (Col7) polypeptide, a Lysyl hydroxylase 3 (LH3) polypeptide, a Keratin type I cytoskeletal 17 (KRT17) polypeptide, and/or a chimeric polypeptide thereof. In some embodiments, the pharmaceutical composition comprises one or more polynucleotides encoding a Collagen alpha-1 (VII) chain polypeptide. In some embodiments, the pharmaceutical composition comprises one or more polynucleotides encoding a Lysyl hydroxylase 3 polypeptide. In some embodiments, the pharmaceutical composition comprises one or more polynucleotides encoding a Keratin type I cytoskeletal 17 polypeptide. In some embodiments, the pharmaceutical composition comprises one or more polynucleotides encoding a chimeric polypeptide. In some embodiments, the pharmaceutical composition comprises one or more polynucleotides encoding a Collagen alpha-1 (VII) chain polypeptide and a Lysyl hydroxylase 3 polypeptide. In some embodiments, the pharmaceutical composition comprises one or more polynucleotides encoding a Collagen alpha-1 (VII) chain polypeptide and a Keratin type I cytoskeletal 17 polypeptide. In some embodiments, the pharmaceutical composition comprises one or more polynucleotides encoding a Lysyl hydroxylase 3 polypeptide and a Keratin type I cytoskeletal 17 polypeptide. In some embodiments, the pharmaceutical composition comprises one or more polynucleotides encoding a Collagen alpha-1 (VII) chain polypeptide, a Lysyl hydroxylase 3 polypeptide, and a Keratin type I cytoskeletal 17 polypeptide.

In some embodiments, the pharmaceutical composition comprises a vector, wherein the vector encodes one or more transgenes comprising a polynucleotide described herein. In some embodiments, the pharmaceutical composition comprises a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the vector comprises one or more transgenes encoding a Collagen alpha-1 (VII) chain polypeptide. In some embodiments, the vector comprises one or more transgenes encoding a Lysyl hydroxylase 3 polypeptide. In some embodiments, the vector comprises one or more transgenes encoding a Keratin type I cytoskeletal 17 polypeptide. In some embodiments, the vector comprises one or more transgenes encoding a chimeric polypeptide. In some embodiments, the vector comprises one or more transgenes encoding a Collagen alpha-1 (VII) chain polypeptide and one or more transgenes encoding a Lysyl hydroxylase 3 polypeptide. In some embodiments, the vector comprises one or more transgenes encoding a Collagen alpha-1 (VII) chain polypeptide and one or more transgenes encoding a Keratin type I cytoskeletal 17 polypeptide. In some embodiments, the vector comprises one or more transgenes encoding a Lysyl hydroxylase 3 polypeptide and one or more transgenes encoding a Keratin type I cytoskeletal 17 polypeptide. In some embodiments, the vector comprises one or more transgenes encoding a Collagen alpha-1 (VII) chain polypeptide, one or more transgenes encoding a Lysyl hydroxylase 3 polypeptide, and one or more transgenes encoding a Keratin type I cytoskeletal 17 polypeptide.

In some embodiments, the pharmaceutical composition comprises a synthetic RNA, wherein the synthetic RNA encodes one or more transgenes comprising a polynucleotide described herein. In some embodiments, the pharmaceutical composition comprises a synthetic RNA, wherein the synthetic RNA comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the synthetic RNA comprises one or more transgenes encoding a Collagen alpha-1 (VII) chain polypeptide. In some embodiments, the synthetic RNA comprises one or more transgenes encoding a Lysyl hydroxylase 3 polypeptide. In some embodiments, the synthetic RNA comprises one or more transgenes encoding a Keratin type I cytoskeletal 17 polypeptide. In some embodiments, the synthetic RNA comprises one or more transgenes encoding a chimeric polypeptide. In some embodiments, the synthetic RNA comprises one or more transgenes encoding a Collagen alpha-1 (VII) chain polypeptide and one or more transgenes encoding a Lysyl hydroxylase 3 polypeptide. In some embodiments, the synthetic RNA comprises one or more transgenes encoding a Collagen alpha-1 (VII) chain polypeptide and one or more transgenes encoding a Keratin type I cytoskeletal 17 polypeptide. In some embodiments, the synthetic RNA comprises one or more transgenes encoding a Lysyl hydroxylase 3 polypeptide and one or more transgenes encoding a Keratin type I cytoskeletal 17 polypeptide. In some embodiments, the synthetic RNA comprises one or more transgenes encoding a Collagen alpha-1 (VII) chain polypeptide, one or more transgenes encoding a Lysyl hydroxylase 3 polypeptide, and one or more transgenes encoding a Keratin type I cytoskeletal 17 polypeptide.

Collagen Alpha-1 (VII) Chain

In some aspects, a polynucleotide of the present disclosure encodes a Collagen alpha-1 (VII) chain polypeptide. An example of a polynucleotide that encodes a Collagen alpha-1 (VII) chain polypeptide is SEQ ID NO: 1. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 1.

In some embodiments, a polynucleotide encoding a Collagen alpha-1 (VII) chain polypeptide is a polynucleotide that encodes an N-terminal truncation, a C-terminal truncation, or a fragment of a Collagen alpha-1 (VII) chain polypeptide. Polynucleotides encoding an N-terminal truncation, a C-terminal truncation, or a fragment of a Collagen alpha-1 (VII) chain polypeptide include polynucleotides that have at least 25, at least 50, at least 75, at least 100, at least 125, at least 150, at least 175, at least 200, at least 250, at least 300, or at least 350, at least 500, at least 1000, at least 2500, at least 5000, at least 7500, but fewer than 8835, consecutive nucleotides of SEQ ID NO: 1.

In some embodiments, a polynucleotide encoding a Collagen alpha-1 (VII) chain polypeptide is a polynucleotide that encodes a polypeptide having an amino acid sequence of SEQ ID NO: 2. In some embodiments, a polynucleotide encoding a Collagen alpha-1 (VII) chain polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2. In some embodiments, the present disclosure relates to polynucleotides that encode polypeptides that are homologs of the H. sapiens Collagen alpha-1 (VII) chain polypeptide. Methods of identifying polypeptides that are homologs of a polypeptide of interest are well known to one of skill in the art.

In some embodiments, a polynucleotide encoding a Collagen alpha-1 (VII) chain polypeptide is a polynucleotide that encodes N-terminal truncations, C-terminal truncations, or fragments of the amino acid sequence of SEQ ID NO: 2. N-terminal truncations, C-terminal truncations, or fragments may comprise at least 10, at least 12, at least 14, at least 16, at least 18, at least 20, at least 30, at least 40, at least 50, at least 75, at least 100, at least 250, at least 500, at least 750, at least 1000, at least 1500, at least 2000, or at least 2500, but fewer than 2944, consecutive amino acids of SEQ ID NO: 2.

In some embodiments, the polynucleotide encoding a Collagen alpha-1 (VII) chain polypeptide expresses the Collagen alpha-1 (VII) chain polypeptide when the polynucleotide is delivered into one or more target cells of a subject. In some embodiments, expression of the Collagen alpha-1 (VII) chain polypeptide enhances, increases, augments, and/or supplements the levels of a Collagen alpha-1 chain polypeptide in one or more target cells. In some embodiments, expression of the Collagen alpha-1 (VII) chain polypeptide enhances, increases, augments, and/or supplements the function of a Collagen alpha-1 chain polypeptide in one or more target cells. In some embodiments, expression of the Collagen alpha-1 (VII) chain polypeptide enhances, increases, augments, and/or supplements the activity of a Collagen alpha-1 chain polypeptide in one or more target cells. In some embodiments, expression of the Collagen alpha-1 (VII) chain polypeptide enhances, increases, augments, and/or supplements anchoring fibril formation of the subject. In some embodiments, expression of the Collagen alpha-1 (VII) chain polypeptide enhances, increases, augments, and/or supplements epithelial basement membrane organization and/or epithelial basement adherence of the subject. In some embodiments, expression of the Collagen alpha-1 (VII) chain polypeptide enhances, increases, augments, and/or supplements dermoepidermal junction integrity of the subject.

Lysyl Hydroxylase 3

In some aspects, a polynucleotide of the present disclosure encodes a Lysyl hydroxylase 3 polypeptide. An example of a polynucleotide that encodes a Lysyl hydroxylase 3 polypeptide is SEQ ID NO: 3. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 3.

In some embodiments, a polynucleotide encoding a Lysyl hydroxylase 3 polypeptide is a polynucleotide that encodes an N-terminal truncation, a C-terminal truncation, or a fragment of a Lysyl hydroxylase 3 polypeptide. Polynucleotides encoding an N-terminal truncation, a C-terminal truncation, or a fragment of a Lysyl hydroxylase 3 polypeptide include polynucleotides that have at least 25, at least 50, at least 75, at least 100, at least 125, at least 150, at least 175, at least 200, at least 250, at least 300, at least 350, at least 500, at least 750, at least 1000, at least 1500, or at least 2000, but fewer than 2217, consecutive nucleotides of SEQ ID NO: 3.

In some embodiments, a polynucleotide encoding a Lysyl hydroxylase 3 polypeptide is a polynucleotide that encodes a polypeptide having an amino acid sequence of SEQ ID NO: 4. In some embodiments, a polynucleotide encoding a Lysyl hydroxylase 3 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4. In some embodiments, the present disclosure relates to polynucleotides encoding polypeptides that are homologs of the *H. sapiens* Lysyl hydroxylase 3 polypeptide. Methods of identifying polypeptides that are homologs of a polypeptide of interest are well known to one of skill in the art.

In some embodiments, a polynucleotide encoding a Lysyl hydroxylase 3 polypeptide is a polynucleotide that encodes N-terminal truncations, C-terminal truncations, or fragments of the amino acid sequence of SEQ ID NO: 4. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, or at least 700, but fewer than 738, consecutive amino acids of SEQ ID NO: 4.

In some embodiments, the polynucleotide encoding a Lysyl hydroxylase 3 polypeptide expresses the Lysyl hydroxylase 3 polypeptide when the polynucleotide is delivered into one or more target cells of a subject. In some embodiments, expression of the Lysyl hydroxylase 3 polypeptide enhances, increases, augments, and/or supplements the levels of a Lysyl hydroxylase 3 polypeptide in one or more target cells. In some embodiments, expression of the Lysyl hydroxylase 3 polypeptide enhances, increases, augments, and/or supplements the function of a Lysyl hydroxylase 3 polypeptide in one or more target cells. In some embodiments, expression of the Lysyl hydroxylase 3 polypeptide enhances, increases, augments, and/or supplements the activity of a Lysyl hydroxylase 3 polypeptide in one or more target cells. In some embodiments, expression of the Lysyl hydroxylase 3 polypeptide enhances, increases, augments, and/or supplements the formation of hydroxylysine residues on one or more collagen polypeptides of the subject. In some embodiments, expression of the Lysyl hydroxylase 3 polypeptide enhances, increases, augments, and/or supplements anchoring fibril formation of the subject. In some embodiments, expression of the Lysyl hydroxylase 3 polypeptide enhances, increases, augments, and/or supplements epithelial basement membrane organization and/or epithelial basement adherence of the subject. In some embodiments, expression of the Lysyl hydroxylase 3 polypeptide enhances, increases, augments, and/or supplements dermoepidermal junction integrity of the subject.

In some embodiments, the polynucleotide encoding a Collagen alpha-1 (VII) chain polypeptide and the polynucleotide encoding a Lysyl hydroxylase 3 polypeptide are delivered to the same cell of a subject. In some embodiments, the polynucleotide encoding a Collagen alpha-1 chain (VII) polypeptide and the polynucleotide encoding a Lysyl hydroxylase 3 polypeptide express the Collagen alpha-1 (VII) chain polypeptide and the Lysyl hydroxylase 3 polypeptide when the polynucleotides are delivered into the same cell of a subject. In some embodiments, the polynucleotide encoding a Collagen alpha-1 (VII) chain polypeptide and the polynucleotide encoding a Lysyl hydroxylase 3 polypeptide express the Collagen alpha-1 (VII) chain polypeptide and Lysyl hydroxylase 3 polypeptide at equimolar ratios.

Keratin Type I Cytoskeletal 17

In some aspects, a polynucleotide of the present disclosure encodes a Keratin type I cytoskeletal 17 polypeptide. An example of a polynucleotide that encodes a Keratin type I cytoskeletal 17 polypeptide is SEQ ID NO: 29. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 29.

In some embodiments, a polynucleotide encoding a Keratin type I cytoskeletal 17 polypeptide is a polynucleotide that encodes an N-terminal truncation, a C-terminal truncation, or a fragment of a Keratin type I cytoskeletal 17 polypeptide. Polynucleotides encoding an N-terminal truncation, a C-terminal truncation, or a fragment of a Collagen alpha-1 (VII) chain polypeptide include polynucleotides that have at least 25, at least 50, at least 75, at least 100, at least 125, at least 150, at least 175, at least 200, at least 250, at least 300, or at least 350, at least 500, at least 1000, at least 1250, but fewer than 1299, consecutive nucleotides of SEQ ID NO: 29.

In some embodiments, a polynucleotide encoding a Keratin type I cytoskeletal 17 polypeptide is a polynucleotide that encodes a polypeptide having an amino acid sequence of SEQ ID NO: 30. In some embodiments, a polynucleotide encoding a Keratin type I cytoskeletal 17 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 30. In some embodiments, the present disclosure relates to polynucleotides that encode polypeptides that are homologs of the *H. sapiens* Keratin type I cytoskeletal 17 polypeptide. Methods of identifying polypeptides that are homologs of a polypeptide of interest are well known to one of skill in the art.

In some embodiments, a polynucleotide encoding a Keratin type I cytoskeletal 17 polypeptide is a polynucleotide that encodes N-terminal truncations, C-terminal truncations, or fragments of the amino acid sequence of SEQ ID NO: 30. N-terminal truncations, C-terminal truncations, or fragments may comprise at least 10, at least 12, at least 14, at least 16, at least 18, at least 20, at least 30, at least 40, at least 50, at least 75, at least 100, at least 150, at least 200, at least 250, at least 300, at least 350, at least 400, at least 425, but fewer than 432, consecutive amino acids of SEQ ID NO: 30.

In some embodiments, the polynucleotide encoding a Keratin type I cytoskeletal 17 polypeptide expresses the Keratin type I cytoskeletal 17 polypeptide when the polynucleotide is delivered into one or more target cells of a subject. In some embodiments, expression of the Keratin type I cytoskeletal 17 polypeptide enhances, increases, augments, and/or supplements the levels of a Keratin type I cytoskeletal 17 polypeptide in one or more target cells. In some embodiments, expression of the Keratin type I cytoskeletal 17 polypeptide enhances, increases, augments, and/or supplements the function of a Keratin type I cytoskeletal 17 polypeptide in one or more target cells. In some embodiments, expression of the Keratin type I cytoskeletal 17 polypeptide enhances, increases, augments, and/or supplements the activity of a Keratin type I cytoskeletal 17 polypeptide in one or more target cells. In some embodiments, expression of the Keratin type I cytoskeletal 17 polypeptide enhances, increases, augments, and/or supplements wound healing in the subject.

Chimeric Polypeptide Comprising Linker

In some embodiments, a polynucleotide of the present disclosure encodes a chimeric polypeptide comprising a Collagen alpha-1 (VII) chain polypeptide and a Lysyl hydroxylase 3 polypeptide. In some embodiments, the polynucleotide encoding a chimeric polypeptide further comprises a polynucleotide encoding a linker polypeptide. In some embodiments, the polynucleotide encoding a linker polypeptide is a polynucleotide encoding a cleavable linker polypeptide. Examples of polynucleotides encoding cleavable linker polypeptides may include, but are not limited to, polynucleotides encoding a T2A, P2A, E2A, or F2A linker polypeptide. In some embodiments, the polynucleotide encoding a linker polypeptide is a polynucleotide encoding a T2A linker polypeptide. In some embodiments, the polynucleotide encoding a linker polypeptide is a polynucleotide encoding a P2A linker polypeptide. In some embodiments, the polynucleotide encoding a linker polypeptide is a polynucleotide encoding an E2A linker polypeptide. In some embodiments, the polynucleotide encoding a linker polypeptide is a polynucleotide encoding an F2A linker polypeptide.

In some aspects, a polynucleotide of the present disclosure encodes a linker polypeptide. Examples of polynucleotides that encode linker polypeptides are SEQ ID NO: 5, SEQ ID NO: 7, SEQ ID NO: 9, and SEQ ID NO: 11. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 5, SEQ ID NO: 7, SEQ ID NO: 9, or SEQ ID NO: 11.

In some embodiments, a polynucleotide encoding a linker polypeptide is a polynucleotide that encodes an N-terminal truncation, a C-terminal truncation, or a fragment of a linker polypeptide. Polynucleotides encoding an N-terminal truncation, a C-terminal truncation, or a fragment of a linker polypeptide include polynucleotides that have at least 5, at least 10, at least 15, at least 20, at least 25, at least 30, at least 35, at least 40, at least 45, at least 50, at least 55, or at least 60, but fewer than 66, consecutive nucleotides of SEQ ID NO: 5, SEQ ID NO: 7, SEQ ID NO: 9, or SEQ ID NO: 11.

In some embodiments, a polynucleotide encoding a linker polypeptide is a polynucleotide that encodes a polypeptide having an amino acid sequence of SEQ ID NO: 6, SEQ ID NO: 8, SEQ ID NO: 10 or SEQ ID NO: 12. In some embodiments, a polynucleotide encoding a linker polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 6, SEQ ID NO: 8, SEQ ID NO: 10, or SEQ ID NO: 12.

In some embodiments, a polynucleotide encoding a linker polypeptide is a polynucleotide that encodes N-terminal truncations, C-terminal truncations, or fragments of the amino acid sequence of SEQ ID NO: 6, SEQ ID NO: 8, SEQ ID NO: 10, or SEQ ID NO: 12. N-terminal truncations, C-terminal truncations, or fragments may comprise at least 4, at least 6, at least 8, at least 10, at least 12, at least 14, at least 16, at least 18, or at least 20, but fewer than 22, consecutive amino acids of SEQ ID NO: 6, SEQ ID NO: 8, SEQ ID NO: 10, or SEQ ID NO: 12.

In some embodiments, the polynucleotide encoding a linker polypeptide further comprises a polynucleotide encoding one or more furin cleavage sites. In some embodiments, the polynucleotide encoding one or more furin cleavage sites encode an amino acid sequence that is the same or substantially similar to the sequence of the canonical furin cleavage site (Arg-X-(Arg/Lys)-Arg). In some embodiments, the one or more furin cleavage sites are encoded upstream of the linker polypeptide. In some embodiments, the one or more furin cleavage sites are encoded downstream of the linker polypeptide. In some embodiments, the one or more furin cleavage sites are encoded upstream of a T2A linker polypeptide. In some embodiments, the one or more furin cleavage sites are encoded downstream of a T2A linker polypeptide. In some embodiments, the one or more furin cleavage sites are encoded upstream of a P2A linker polypeptide. In some embodiments, the one or more furin cleavage sites are encoded downstream of a P2A linker polypeptide. In some embodiments, the one or more furin cleavage sites are encoded upstream of an E2A linker polypeptide. In some embodiments, the one or more furin cleavage sites are encoded downstream of an E2A linker polypeptide. In some embodiments, the one or more furin cleavage sites are encoded upstream of an F2A linker polypeptide. In some embodiments, the one or more furin cleavage sites are encoded downstream of an F2A linker polypeptide.

In some embodiments, the polynucleotide encoding a chimeric polypeptide encodes a chimeric polypeptide comprising a Collagen alpha-1 (VII) chain polypeptide, a linker polypeptide, and a Lysyl hydroxylase 3 polypeptide. In some embodiments, the polynucleotide encoding a chimeric polypeptide comprises, from 5' to 3', a polynucleotide encoding a Collagen alpha-1 (VII) chain polypeptide, a polynucleotide encoding a linker polypeptide, and a polynucleotide encoding a Lysyl hydroxylase 3 polypeptide. In some embodiments, the polynucleotide encoding a chimeric polypeptide comprises, from 5' to 3', a polynucleotide encoding a Lysyl hydroxylase 3 polypeptide, a polynucleotide encoding a linker polypeptide, and a polynucleotide encoding a Collagen alpha-1 (VII) chain polypeptide.

Examples of polynucleotides encoding chimeric polypeptides comprising a Collagen alpha-1 (VII) chain polypeptide, a linker polypeptide, and a Lysyl hydroxylase 3 polypeptide are SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, a polynucleotide encoding a chimeric polypeptide is a polynucleotide that encodes an N-terminal truncation, a C-terminal truncation, or a fragment of a chimeric polypeptide. Polynucleotides encoding an N-terminal truncation, a C-terminal truncation, or a fragment of a chimeric polypeptide include polynucleotides that have at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 2000, at least 3000, at least 4000, at least 5000, at least 6000, at least 7000, at least 8000, at least 9000, or at least 10000, but fewer than 11121, consecutive nucleotides of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes a polypeptide having an amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes N-terminal truncations, C-terminal truncations, or fragments of the amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. N-terminal truncations, C-terminal truncations, or fragments may comprise at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1250, at least 1500, at least 1750, at least 2000, at least 2250, at least 2500, at least 2750, at least 3000, at least 3250, or at least 3500, but fewer than 3706, consecutive amino acids of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

In some embodiments, the polynucleotide encoding a chimeric polypeptide expresses the chimeric polypeptide when the polynucleotide is delivered into one or more target cells of a subject. In some embodiments, the chimeric polypeptide is cleaved after being expressed in one or more target cells. In some embodiments, the chimeric polypeptide is cleaved within the linker polypeptide when expressed in one or more target cells. In some embodiments, the chimeric polypeptide is cleaved into two polypeptides, one comprising the Collagen alpha-1 (VII) chain polypeptide and the other comprising the Lysyl hydroxylase 3 polypeptide. In some embodiments, expression of the chimeric polypeptide enhances, increases, augments, and/or supplements the levels of a Collagen alpha-1 chain polypeptide and/or a Lysyl hydroxylase 3 polypeptide in one or more target cells. In some embodiments, expression of the chimeric polypeptide enhances, increases, augments, and/or supplements the function of a Collagen alpha-1 chain polypeptide and/or a Lysyl hydroxylase 3 polypeptide in one or more target cells. In some embodiments, expression of the chimeric polypeptide enhances, increases, augments, and/or supplements the activity of a Collagen alpha-1 chain polypeptide and/or a Lysyl hydroxylase 3 polypeptide in one or more target cells. In some embodiments, expression of the chimeric polypeptide enhances, increases, augments, and/or supplements the formation of hydroxylysine residues on one or more collagen polypeptides of the subject. In some embodiments, expression of the chimeric polypeptide enhances, increases, augments, and/or supplements anchoring fibril formation of the subject. In some embodiments, expression of the chimeric polypeptide enhances, increases, augments, and/or supplements epithelial basement membrane organization and/or epithelial basement adherence of the subject. In some embodiments, expression of the chimeric polypeptide enhances, increases, augments, and/or supplements dermoepidermal junction integrity of the subject.

Polynucleotides of the present disclosure may be codon-optimized. In some embodiments, polynucleotides of the present disclosure are codon-optimized for human cells. In some embodiments, polynucleotides of the present disclosure are codon-optimized for mouse cells. In some embodiments, polynucleotides of the present disclosure are codon-optimized for rat cells. In some embodiments, polynucleotides of the present disclosure are codon-optimized for hamster cells. In some embodiments, polynucleotides of the present disclosure are codon-optimized for canine cells. In some embodiments, polynucleotides of the present disclosure are codon-optimized for yeast cells. In some embodiments, polynucleotides of the present disclosure are codon-optimized for bacterial cells. Polynucleotides of the present disclosure may be DNA polynucleotides, RNA polynucleotides, or a combination of one or more DNA polynucleotides and one or more RNA polynucleotides.

Vectors

In some aspects, the present disclosure relates to vectors, preferably expression vectors, containing one or more polynucleotides described herein. In some embodiments, the vectors are DNA vectors. Generally, vectors suitable to maintain, propagate, or express polynucleotides to produce one or more polypeptides in a subject may be used. Examples of suitable vectors include, but are not limited to, plasmids, cosmids, episomes, transposons, and viral vectors (e.g., adenoviral, vaccinia viral, Sindbis-viral, measles, herpes viral, lentiviral, retroviral, adeno-associated viral vectors, etc.). In some embodiments, the vector is capable of autonomous replication in a host cell. In some embodiments, the vector is incapable of autonomous replication in a host cell. In some embodiments, the vector is capable of integrating into a host DNA. Methods for making vectors containing one or more polynucleotides of interest are well known to one of skill in the art.

In some embodiments, the vector is a herpes simplex virus vector. In some embodiments, the herpes simplex virus vector is a herpes virus amplicon vector. Herpes virus amplicon vectors, including structural features and methods of making the vectors, are generally known in the art (de Silva S. and Bowers W. "Herpes Virus Amplicon Vectors". *Viruses* 2009, 1, 594-629). In some embodiments, the vector is an HSV-1 amplicon. In some embodiments, the vector is an HSV-1 hybrid amplicon. Examples of HSV-1 hybrid amplicons may include, but are not limited to, HSV/AAV hybrid amplicons, HSV/EBV hybrid amplicons, HSV/EBV/ RV hybrid amplicons, and HSV/Sleeping Beauty hybrid amplicons. In some embodiments, the vector is an HSV/ AAV hybrid amplicon. In some embodiments, the vector is an HSV/EBV hybrid amplicon. In some embodiments, the vector is an HSV/EBV/RV hybrid amplicon. In some embodiments, the vector is an HSV/Sleeping Beauty hybrid amplicons.

In some embodiments, the herpes simplex virus vector is a recombinant herpes simplex virus genome. In some embodiments, the recombinant herpes simplex virus genome has been engineered to decrease or eliminate expression of one or more toxic herpes simplex virus genes. Methods of engineering recombinant herpes simplex virus genomes are generally described in WO2015/009952. In some embodiments, the recombinant herpes simplex virus genome comprises an inactivating mutation. Examples of inactivating mutations may include, but are not limited to, deletions, insertions, point mutations, and rearrangements. In some embodiments, the recombinant herpes simplex virus genome comprises an inactivating mutation in at least one, at least two, at least three, at least four, at least five, at least six, at least seven, or all eight of the ICP0, ICP4, ICP22, ICP27, ICP47, tk, UL4 land UL55 herpes simplex virus genes. In some embodiments, the recombinant herpes simplex virus genome comprises an inactivating mutation in the ICP0 gene. In some embodiments, the recombinant herpes simplex virus genome comprises an inactivating mutation in the ICP4 (one or both copies) gene. In some embodiments, the recombinant herpes simplex virus genome comprises an inactivating mutation in the ICP22 gene. In some embodiments, the recombinant herpes simplex virus genome comprises an inactivating mutation in the ICP27 gene. In some embodiments, the recombinant herpes simplex virus genome comprises an inactivating mutation in the ICP47 gene. In some embodiments, the recombinant herpes simplex virus genome comprises an inactivating mutation in the UL41 gene. In some embodiments, the recombinant herpes simplex virus genome comprises an inactivating mutation in the UL55 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes and a deletion in the promoter region of the ICP22 and ICP47 genes. In some embodiments, the recombinant herpes simplex virus genome further comprises an inactivating mutation in the UL41 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies) and ICP22 genes. In some embodiments, the recombinant herpes simplex virus genome comprises an inactivating mutation in the ICP0 and ICP4 (one or both copies) genes. In some embodiments, the recombinant herpes simplex virus genome comprises an inactivating mutation in the ICP0, ICP4 (one or both copies), and ICP22 genes. In some embodiments, the recombinant herpes simplex virus genome comprises an inactivating mutation in the ICP0, ICP4 (one or both copies), ICP22, and ICP27 genes. In some embodiments, the recombinant herpes simplex virus genome comprises an inactivating mutation in the ICP0, ICP4 (one or both copies), ICP22, ICP27 and UL55 genes. In some embodiments, the inactivating mutation in the ICP0, ICP4 (one or both copies), ICP22, ICP27 and/or UL55 genes comprises a deletion of the coding sequence of the ICP0, ICP4 (one or both copies), ICP22, ICP27 and/or UL55 genes. In some embodiments, the recombinant herpes simplex virus genome comprises a deletion in the coding sequence of the ICP0, ICP4 (one or both copies), ICP22, ICP27, and UL55 genes. In some embodiments, the recombinant herpes simplex virus genome further comprises an inactivating mutation in the ICP47 gene. In some embodiments, the recombinant herpes simplex virus genome further comprises an inactivating mutation in the UL41 gene. In some embodiments, the recombinant herpes simplex virus genome further comprises an inactivating mutation in the ICP47 gene and the UL41 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP22, ICP27, ICP47, and UL55 genes. In some embodiments, the recombinant herpes simplex virus genome comprises an inactivating mutation in the ICP0, ICP4 (one or both copies), ICP22, and ICP27 genes. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0, ICP4, ICP22, ICP27, ICP47, tk, UL41 and UL55 herpes simplex viral gene loci. In some embodiments, a recombinant herpes simplex virus genome comprises one or more polynucleotide of the present disclosure within one or more of the viral ICP4 gene loci (e.g., a recombinant virus carrying a polynucleotide encoding Col7 in one or both of the ICP4 loci, a recombinant virus carrying a polynucleotide encoding LH3 in one or both of the ICP4 loci, a recombinant virus carrying a polynucleotide encoding KRT17 in one or both of the ICP4 loci, a recombinant virus carrying a polynucleotide encoding Col7 in one of the ICP4 loci and a polynucleotide encoding KRT17 in the other ICP4 loci, a recombinant virus carrying a polynucleotide encoding Col7 in one of the ICP4 loci and a polynucleotide encoding LH3 in the other ICP4 loci, a recombinant virus carrying a polynucleotide encoding LH3 in one of the ICP4 loci and a polynucleotide encoding KRT17 in the other ICP4 loci, etc.). In some embodiments, a recombinant herpes simplex virus genome comprises one or more polynucleotide of the present disclosure within the viral UL41 gene locus. In some embodiments, a recombinant herpes simplex virus genome comprises one or more polynucleotide of the present disclosure within the viral ICP47 gene locus. In some embodiments, a recombinant herpes simplex virus genome comprises one or more polynucleotides of the present disclosure within one or more of the viral ICP4 gene loci, and one or more polynucleotide of the present disclosure within the viral UL41 gene locus (e.g., a recombinant virus carrying a polynucleotide encoding Col7 in one or both of the ICP4 loci and a polynucleotide encoding LH3 in the UL41 locus, a recombinant virus carrying a polynucleotide encoding Col7 in one or both of the ICP4 loci and a polynucleotide encoding Col7 in the UL41 locus, a recombinant virus carrying a polynucleotide encoding Col7 in one or both of the ICP4 loci and a polynucleotide encoding KRT17 in the UL41 locus, a recombinant virus carrying a polynucleotide encoding LH3 in one or both of the ICP4 loci and a polynucleotide encoding LH3 in the UL41 locus, a recombinant virus carrying a polynucleotide encoding LH3 in one or both of the ICP4 loci and a polynucleotide encoding Col7 in the UL41 locus, a recombinant virus carrying a polynucleotide encoding LH3 in one or both of the ICP4 loci and a polynucleotide encoding KRT17 in the UL41 locus, a recombinant virus carrying a polynucleotide encoding KRT17 in one or both of the ICP4 loci and a polynucleotide encoding LH3 in the UL41 locus, a recombinant virus carrying a polynucleotide encoding KRT17 in one or both of the ICP4 loci and a polynucleotide encoding Col7 in the UL41 locus, a recombinant virus carrying a polynucleotide encoding KRT17 in one or both of the ICP4 loci and a polynucleotide encoding KRT17 in the UL41 locus, etc.).

A vector may include a polynucleotide of the present disclosure in a form suitable for expression of the polynucleotide in a host cell. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of promoters suitable for transcription in mammalian host cells may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), or from heterologous mammalian promoters (such as the actin promoter, an immunoglobulin promoter, from heat-shock promoters, and the like), provided such promoters are compatible with the host cells. In some embodiments, polynucleotides of the present disclosure are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiments, the one or more heterologous promoters are one or more of constitutive promoters, tissue-specific promoters, temporal promoters, spatial promoters, inducible promoters and repressible promoters. Regulatory sequences may include those which direct constitutive expression of a nucleotide sequence, as well as tissue-specific regulatory and/or inducible sequences. The design of the expression vector can depend on such factors as the host cell to be contacted with a polynucleotide of the present disclosure, the level of expression of protein desired, and the like. The expression vectors of the present disclosure can be introduced into host cells to thereby produce proteins or polypeptides (e.g., Collagen alpha-1 (VII) chain polypeptides, Lysyl hydroxylase 3 polypeptides, Keratin type I cytoskeletal 17 polypeptides, chimeric polypeptides, and the like) encoded by polynucleotides as described herein.

In some embodiments, a vector of the present disclosure comprises one or more transgenes comprising one or more polynucleotide described herein. The one or more transgenes may be inserted in any orientation in the vector. If the vector comprises two or more transgenes (e.g., two or more, three or more, etc.), the transgenes may be inserted in the same orientation or opposite orientations to one another. Without wishing to be bound be theory, incorporating two transgenes into a vector in an antisense orientation may help to avoid read-through and ensure proper expression of each transgene. In some embodiments, the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and/or chimeric polypeptides thereof. In some embodiments, the vector comprises a single transgene encoding a Collagen alpa-1 (VII) chain polypeptide. In some embodiments, the vector comprises two transgenes each encoding a Collagen alpa-1 (VII) chain polypeptide. In some embodiments, the vector comprises three transgenes each encoding a Collagen alpa-1 (VII) chain polypeptide. In some embodiments, the vector comprises a single transgene encoding a Lysyl hydroxylase 3 polypeptide. In some embodiments, the vector comprises two transgenes each encoding a Lysyl hydroxylase 3 polypeptide. In some embodiments, the vector comprises three transgenes each encoding a Lysyl hydroxylase 3 polypeptide. In some embodiments, the vector comprises a single transgene encoding a Keratin type I cytoskeletal 17 polypeptide. In some embodiments, the vector comprises two transgenes each encoding a Keratin type I cytoskeletal 17 polypeptide. In some embodiments, the vector comprises three transgenes each encoding a Keratin type I cytoskeletal 17 polypeptide. In some embodiments, the vector comprises a single transgene encoding a chimeric polypeptide comprising a Collagen alpha-1 (VII) chain polypeptide, a Lysyl hydroxylase 3 polypeptide, and/or a Keratin type I cytoskeletal 17 polypeptide.

In some embodiments, the vector comprises at least two transgenes (e.g. two, three, four, five, six, seven or more transgenes). In some embodiments, the at least first transgene encodes a Collagen alpha-1 (VII) chain polypeptide and the at least second transgene encodes a Lysyl hydroxylase 3 polypeptide. In some embodiments, the at least first transgene encodes a Lysyl hydroxylase 3 polypeptide and the at least second transgene encodes a Collagen alpha-1 (VII) chain polypeptide. In some embodiments, the at least first transgene encodes a Collagen alpha-1 (VII) chain polypeptide and the at least second transgene encodes a Keratin type I cytoskeletal 17 polypeptide. In some embodiments, the at least first transgene encodes a Keratin type I cytoskeletal 17 polypeptide and the at least second transgene encodes a Collagen alpha-1 (VII) chain polypeptide. In some embodiments, the at least first transgene encodes a Lysyl hydroxylase 3 polypeptide and the at least second transgene encodes a Keratin type I cytoskeletal 17 polypeptide. In some embodiments, the at least first transgene encodes a Keratin type I cytoskeletal 17 polypeptide and the at least second transgene encodes a Lysyl hydroxylase 3 polypeptide. In some embodiments, the at least first transgene encodes a Collagen alpha-1 (VII) chain polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide. In some embodiments, the at least first transgene encodes a Lysyl hydroxylase 3 polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide. In some embodiments, the at least first transgene encodes a Keratin type I cytoskeletal 17 polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide.

In some embodiments, the vector comprises at least three transgenes (e.g. three, four, five, six, seven or more transgenes). In some embodiments, the at least first transgene encodes a Collagen alpha-1 (VII) chain polypeptide, the at least second transgene encodes a Lysyl hydroxylase 3 polypeptide, and the at least third transgene encodes a Keratin type I cytoskeletal 17 polypeptide.

In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the polycistronic transgene encodes a Lysyl hydroxylase 3 polypeptide on a first open reading frame (ORF) and a Collagen alpha-1 (VII) chain polypeptide on a second open reading frame (ORF). In some embodiments, the polycistronic transgene encodes a Collagen alpha-1 (VII) chain polypeptide on a first open reading frame (ORF) and a keratin type I cytoskeletal 17 polypeptide on a second open reading frame (ORF). In some embodiments, the polycistronic transgene encodes a Keratin type I cytoskeletal polypeptide on a first open reading frame (ORF) and a Collagen alpha-1 (VII) chain polypeptide on a second open reading frame (ORF). In some embodiments, the polycistronic transgene encodes a Lysyl hydroxylase 3 polypeptide on a first open reading frame (ORF) and a keratin type I cytoskeletal 17 polypeptide on a second open reading frame (ORF). In some embodiments, the polycistronic transgene encodes a Keratin type I cytoskeletal polypeptide on a first open reading frame (ORF) and a Lysyl hydroxylase 3 polypeptide on a second open reading frame (ORF).

In some embodiments, the polycistronic transgene encodes a Collagen alpha-1 (VII) chain polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the polycistronic transgene encodes a Lysyl hydroxylase 3 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the polycistronic transgene encodes a Keratin type I cytoskeletal 17 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the first and second ORFs are separated by an internal ribosomal entry site (IRES).

In some embodiments, the polycistronic transgene encodes a Collagen alpha-1 (VII) chain polypeptide on a first open reading frame (ORF), a Keratin type I cytoskeletal 17 polypeptide on a second open reading frame (ORF), and a Lysyl hydroxylase 3 polypeptide on a third open reading frame (ORF). In some embodiments, the polycistronic transgene encodes a Collagen alpha-1 (VII) chain polypeptide on a first open reading frame (ORF), a Lysyl hydroxylase 3 polypeptide on a second open reading frame (ORF), and a Keratin type I cytoskeletal 17 polypeptide on a third open reading frame (ORF). In some embodiments, the polycistronic transgene encodes a Lysyl hydroxylase 3 polypeptide on a first open reading frame (ORF), a Collagen alpha-1 (VII) chain polypeptide on a second open reading frame (ORF), and a Keratin type I cytoskeletal 17 polypeptide on a third open reading frame (ORF). In some embodiments, the polycistronic transgene encodes a Lysyl hydroxylase 3 polypeptide on a first open reading frame (ORF), a Keratin type I cytoskeletal 17 polypeptide on a second open reading frame (ORF), and a Collagen alpha-1 (VII) chain polypeptide on a third open reading frame (ORF). In some embodiments, the polycistronic transgene encodes a Keratin type I cytoskeletal 17 polypeptide on a first open reading frame (ORF), a Lysyl hydroxylase 3 polypeptide on a second open reading frame (ORF), and a Collagen alpha-1 (VII) chain polypeptide on a third open reading frame (ORF). In some embodiments, the polycistronic transgene encodes a Keratin type I cytoskeletal 17 polypeptide on a first open reading frame (ORF), a Collagen alpha-1 (VII) chain polypeptide on a second open reading frame (ORF), and a Lysyl hydroxylase 3 polypeptide on a third open reading frame (ORF). In some embodiments, the first, second, and third ORFs are separated by an internal ribosomal entry site (IRES).

Examples of suitable IRES's may include, but are not limited to, a virally-derived IRES (e.g. an IRES derived from a poliovirus, rhinovirus, encephalomyocarditis virus, foot-and-mouth disease virus, hepatitis C virus, classic swine fever virus, rous sarcoma virus, human immunodeficiency virus, cricket paralysis virus, Kaposi's sarcoma-associated herpesvirus, etc.) and a cellular mRNA-derived IRES (e.g. an IRES derived from growth factor mRNAs, such as fibroblast growth factor 2, platelet-derived growth factor B, and vascular endothelial growth factor, an IRES derived from transcription factor mRNAs, such as antennapedia, ultrapithoraxm, and NF-κB repressing factor, an IRES derived from oncogene mRNAs, such as c-myc, pim-1, and protein kinase $p58^{PITSLRE}$, etc.).

Vectors of the present disclosure may further encode additional coding and non-coding sequences. Examples of additional coding and non-coding sequences may include, but are not limited to, sequences encoding additional polypeptide tags, introns, 5' and 3' UTRs, and the like. Examples of suitable polypeptide tags may include, but are not limited, to any combination of purification tags, such as his-tags, flag-tags, maltose binding protein and glutathione-S-transferase tags, detection tags, such as tags that may be detected photometrically (e.g., red fluorescent protein, etc.) and tags that have a detectable enzymatic activity (e.g., alkaline phosphatase, etc.), tags containing secretory sequences, leader sequences, and/or stabilizing sequences, protease cleavage sites (e.g., furin cleavage sites, TEV cleavage sites, Thrombin cleavage sites), and the like. In some embodiments, the 5' and/or 3'UTRs increase the stability, localization, and/or translational efficiency of the polynucleotides. In some embodiments, the 5' and/or 3'UTRs are modified to increase the stability, localization, and/or translational efficiency of the one or more polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target transgene expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance transgene expression in specific cell types.

Synthetic RNA Polynucleotides

In some aspects, the present disclosure relates to synthetic RNAs, in particular synthetic mRNAs, containing one or more polynucleotides described herein. In some embodiments, the synthetic mRNA polynucleotides comprise a 5'-cap structure. Examples of 5'-cap structures may include, but are not limited to, cap-0, cap-1, cap-2, and cap-3 structures, and derivatives thereof. In some embodiments, the synthetic mRNA polynucleotides comprise a 3'-poly(A) tail. In some embodiments, the synthetic mRNA polynucleotides comprise one or more 5' and/or 3' UTRs flanking the one or more coding sequences contained within the synthetic mRNA polynucleotides. In some embodiments, the 5' and/or 3' UTRs increase the stability, localization, and/or translational efficiency of the synthetic mRNA polynucleotides. In some embodiments, the 5' and/or 3' UTRs are modified to increase the stability, localization, and/or translational efficiency of the synthetic mRNA polynucleotides. In some embodiments, the 5' and/or 3' UTRs improve the level and/or duration of protein expression. In some embodiments, the 5' and/or 3' UTRs are modified to improve the level and/or duration of protein expression. In some embodiments, the 5' and/or 3'UTRs include elements (e.g., miRNA binding sites, etc.) that may limit off-target expression (e.g., inhibiting expression in specific cell types (e.g., neuronal cells), at specific times in the cell cycle, at specific developmental stages, etc.). In some embodiments, the 5' UTRs comprise a Kozak sequence. In some embodiments, the Kozak sequence is the same or substantially similar to the Kozak consensus sequence. Methods for making synthetic mRNA polynucleotides containing one or more polynucleotides of interest are well known to one of skill in the art.

In some aspects, the synthetic mRNA polynucleotides of the present disclosure comprise one or more modified ribonucleotides. Examples of modified ribonucleotides may include, but are not limited to, 2-thiouridine, 5-azauridine, pseudouridine, 4-thiouridine, 5-methyluridine, 5-aminouridine, 5-hydroxyuridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino- 5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In some embodiments, a polynucleotide encoding a Collagen alpha-1 (VII) chain polypeptide and a polynucleotide encoding a Lysyl hydroxylase 3 polypeptide are contained within two separate synthetic mRNA polynucleotides. In some embodiments, a polynucleotide encoding a Collagen alpha-1 (VII) chain polypeptide and a polynucleotide encoding a Keratin type I cytoskeletal 17 polypeptide are contained within two separate synthetic mRNA polynucleotides. In some embodiments, a polynucleotide encoding a Lysyl hydroxylase 3 polypeptide and a polynucleotide encoding a Keratin type I cytoskeletal 17 polypeptide are contained within two separate synthetic mRNA polynucleotides. In some embodiments, a polynucleotide encoding a Collagen alpha-1 (VII) chain polypeptide, a polynucleotide encoding a Lysyl hydroxylase 3 polypeptide, and a polynucleotide encoding a Keratin type I cytoskeletal 17 polypeptide are contained within three separate synthetic mRNA polynucleotides.

In some embodiments, a polynucleotide encoding a Collagen alpha-1 (VII) chain polypeptide, a polynucleotide encoding a Lysyl hydroxylase 3 polypeptide, and/or a polynucleotide encoding a Keratin type I cytoskeletal 17 polypeptide is a single contiguous polynucleotide contained within a single synthetic mRNA polynucleotide. In some embodiments, the single contiguous polynucleotide encodes a Collagen alpha-1 (VII) chain polypeptide on a first open reading frame (ORF) and a Lysyl hydroxylase 3 polypeptide on a second open reading frame (ORF) in a single synthetic mRNA. In some embodiments, the single contiguous polynucleotide encodes a Lysyl hydroxylase 3 polypeptide on a first open reading frame (ORF) and a Collagen alpha-1 (VII) chain polypeptide on a second open reading frame (ORF) in a single synthetic mRNA. In some embodiments, the single contiguous polynucleotide encodes a Collagen alpha-1 (VII) chain polypeptide on a first open reading frame (ORF) and a keratin type I cytoskeletal 17 polypeptide on a second open reading frame (ORF) in a single synthetic mRNA. In some embodiments, the single contiguous polynucleotide encodes a Keratin type I cytoskeletal polypeptide on a first open reading frame (ORF) and a Collagen alpha-1 (VII) chain polypeptide on a second open reading frame (ORF) in a single synthetic mRNA. In some embodiments, the single contiguous polynucleotide encodes a Lysyl hydroxylase 3 polypeptide on a first open reading frame (ORF) and a keratin type I cytoskeletal 17 polypeptide on a second open reading frame (ORF) in a single synthetic mRNA. In some embodiments, the single contiguous polynucleotide encodes a Keratin type I cytoskeletal polypeptide on a first open reading frame (ORF) and a Lysyl hydroxylase 3 polypeptide on a second open reading frame (ORF) in a single synthetic mRNA. In some embodiments, the single contiguous polynucleotide encodes a Collagen alpha-1 (VII) chain polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the single contiguous polynucleotide encodes a Lysyl hydroxylase 3 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the single contiguous polynucleotide encodes a Keratin type I cytoskeletal 17 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the two ORFs are separated by an IRES.

In some embodiments, the single contiguous polynucleotide encodes a Collagen alpha-1 (VII) chain polypeptide on a first open reading frame (ORF), a Keratin type I cytoskeletal 17 polypeptide on a second open reading frame (ORF), and a Lysyl hydroxylase 3 polypeptide on a third open reading frame (ORF) in a single synthetic mRNA. In some embodiments, the single contiguous polynucleotide encodes a Collagen alpha-1 (VII) chain polypeptide on a first open reading frame (ORF), a Lysyl hydroxylase 3 polypeptide on a second open reading frame (ORF), and a Keratin type I cytoskeletal 17 polypeptide on a third open reading frame (ORF) in a single synthetic mRNA. In some embodiments, the single contiguous polynucleotide encodes a Lysyl hydroxylase 3 polypeptide on a first open reading frame (ORF), a Collagen alpha-1 (VII) chain polypeptide on a second open reading frame (ORF), and a Keratin type I cytoskeletal 17 polypeptide on a third open reading frame (ORF) in a single synthetic mRNA. In some embodiments, the single contiguous polynucleotide encodes a Lysyl hydroxylase 3 polypeptide on a first open reading frame (ORF), a Keratin type I cytoskeletal 17 polypeptide on a second open reading frame (ORF), and a Collagen alpha-1 (VII) chain polypeptide on a third open reading frame (ORF) in a single synthetic mRNA. In some embodiments, the single contiguous polynucleotide encodes a Keratin type I cytoskeletal 17 polypeptide on a first open reading frame (ORF), a Lysyl hydroxylase 3 polypeptide on a second open reading frame (ORF), and a Collagen alpha-1 (VII) chain polypeptide on a third open reading frame (ORF) in a single synthetic mRNA. In some embodiments, the single contiguous polynucleotide encodes a Keratin type I cytoskeletal 17 polypeptide on a first open reading frame (ORF), a Collagen alpha-1 (VII) chain polypeptide on a second open reading frame (ORF), and a Lysyl hydroxylase 3 polypeptide on a third open reading frame (ORF) in a single synthetic mRNA. In some embodiments, the first, second, and third ORFs are separated by an internal ribosomal entry site (IRES).

Examples of suitable IRES's may include, but are not limited to, a virally-derived IRES (e.g. an IRES derived from a poliovirus, rhinovirus, encephalomyocarditis virus, foot-and-mouth disease virus, hepatitis C virus, classic swine fever virus, rous sarcoma virus, human immunodeficiency virus, cricket paralysis virus, Kaposi's sarcoma-associated herpesvirus, etc.) and a cellular mRNA-derived IRES (e.g. an IRES derived from growth factor mRNAs, such as fibroblast growth factor 2, platelet-derived growth factor B, and vascular endothelial growth factor, an IRES derived from transcription factor mRNAs, such as antennapedia, ultrapithoraxm, and NF-κB repressing factor, an IRES derived from oncogene mRNAs, such as c-myc, pim-1, and protein kinase $p58^{PITSLRE}$, etc.).

In some embodiments, a polynucleotide encoding any of the chimeric polypeptides comprising a Collagen alpha-1 (VII) chain polypeptide, a Lysyl hydroxylase 3 polypeptide, and/or a Keratin type I cytoskeletal 17 polypeptide described herein is encoded on a single ORF within a synthetic mRNA polynucleotide.

Synthetic mRNA polynucleotides of the present disclosure may further encode additional coding sequences. Examples of additional coding sequences may include, but are not limited to, sequences encoding additional polypeptide tags. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., red fluorescent protein, etc.) and tags that have a detectable enzymatic activity (e.g., alkaline phosphatase, etc.), tags containing secretory sequences, leader sequences, and/or stabilizing sequences, protease cleavage sites (such as furin cleavage sites), and the like.

Delivery Vehicle

Certain aspects of the present disclosure relate to a pharmaceutical composition comprising a delivery vehicle comprising one or more polynucleotides described herein. In some embodiments, the delivery vehicle is suitable for delivering one or more polynucleotides into one or more target cells.

In some embodiments, the delivery vehicle is a virus. Examples of viral delivery vehicles may include, but are not limited to, adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is replication-competent. In some embodiments, the virus has been modified to alter its tissue tropism relative to the tissue tropism of an unmodified, wild-type virus. Methods for producing a virus comprising one or more polynucleotides are well known to one of skill in the art.

In some embodiments, the viral delivery vehicle is a herpes simplex virus. Herpes simplex virus delivery vehicles may be produced by a process disclosed, for example, in WO2015/009952. In some embodiments, the herpes simplex virus comprises a modified envelope. In some embodiments, the modified envelope comprises one or more (e.g., one, two, three, four or more) mutant herpes simplex virus glycoproteins. Examples of herpes simplex virus glycoproteins may include, but are not limited to, the glycoproteins gB, gD, gH, and gL. In some embodiments, the modified envelope alters the herpes simplex virus tissue tropism relative to a wild-type herpes simplex virus. In some embodiments, the herpes simplex virus is a herpes simplex type 1 virus, a herpes simplex type 2 virus, of any derivatives thereof. In some embodiments, the virus is a herpes simplex type 1 virus. In some embodiments, the virus is a herpes simplex type 2 virus.

In some embodiments, the delivery vehicle is a non-viral delivery vehicle. In some embodiments, the non-viral delivery vehicle is a chemical-based delivery vehicle (a chemical-based delivery reagent). Examples of chemical-based delivery vehicles may include, but are not limited to, calcium phosphate, dendrimers, liposomes (cationic liposomes, non-cationic liposome, and mixtures), exosomes, charged lipids, and cationic polymers (such as DEAE-dextran, polyethylenimine, and the like). In some embodiments, the non-viral delivery vehicle is a non-chemical delivery vehicle. Examples of non-chemical delivery vehicles may include, but are not limited to, electroporation, nucleofection, sonoporation, optical transfection, and particle-based vehicles (such as a gene gun, magnet-assisted transfection, impalefection, particle bombardment, and the like). In some embodiments, the non-viral delivery vehicle is a dendrimer, liposome, exosome, charged lipid or cationic polymer. In some embodiments, the non-viral delivery vehicle is a dendrimer. In some embodiments, the non-viral delivery vehicle is a liposome. In some embodiments, the non-viral delivery vehicle is an exosome. In some embodiments, the non-viral delivery vehicle is a charged lipid. In some embodiments, the non-viral delivery vehicle is a cationic polymer. Methods for producing one or more polynucleotides of interest in a complex with a non-viral delivery vehicle are well known to one of skill in the art.

Pharmaceutically Acceptable Carrier

Certain aspects of the present disclosure relates to a pharmaceutical composition comprising a pharmaceutically acceptable carrier. In some embodiments, the pharmaceutically acceptable carrier is a carrier sufficient for topical and/or transdermal administration/application. In some embodiments, the pharmaceutically acceptable carrier is a carrier sufficient for subcutaneous and/or intradermal administration/application. In some embodiments, the pharmaceutically acceptable carrier is minimally invasive or non-invasive. Pharmaceutically acceptable carriers are generally nontoxic to recipients at the dosages and concentrations employed, and may include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; polyols such as glycerol (e.g., formulations including 10% glycerol); salt-forming counter-ions such as sodium; metal complexes (e.g. Zn-protein complexes); and/or non-ionic surfactants such as polyethylene glycol (PEG). A thorough discussion of pharmaceutically acceptable carriers is available in REMINGTON'S PHARMACEUTICAL SCIENCES (Mack Pub. Co., N.J. 1991).

In some embodiments, the pharmaceutically acceptable carrier is suitable for topical or transdermal applications/administrations. Examples of carriers suitable for use in a topical or transdermal application/administration may include, but are not limited to, ointments, pastes, creams, suspensions, emulsions, fatty ointments, gels, powders, lotions, solutions, sprays, patches, microneedle arrays, and inhalants. In some embodiments, the pharmaceutically acceptable carrier comprises one or more of an ointment, paste, cream, suspension, emulsion, fatty ointment, gel, powder, lotion, solution, spray, and an inhalant. In some embodiments, the pharmaceutically acceptable carrier comprises an ointment. In some embodiments, the pharmaceutically acceptable carrier comprises a paste. In some embodiments, the pharmaceutically acceptable carrier comprises a cream. In some embodiments, the pharmaceutically acceptable carrier comprises a suspension. In some embodiments, the pharmaceutically acceptable carrier comprises an emulsion. In some embodiments, the pharmaceutically acceptable carrier comprises a gel. In some embodiments, the pharmaceutically acceptable carrier comprises a powder. In some embodiments, the pharmaceutically acceptable carrier comprises a lotion. In some embodiments, the pharmaceutically acceptable carrier comprises a solution. In some embodiments, the pharmaceutically acceptable carrier comprises a spray. In some embodiments, the pharmaceutically acceptable carrier comprises an inhalant. In some embodiments, the pharmaceutical carrier comprises a patch (e.g. a patch that adheres to the skin). In some embodiments, the pharmaceutically acceptable carrier comprises a microneedle array. Methods for making and using microneedle arrays suitable for pharmaceutical composition delivery are generally known in the art (Kim Y. et al. "Microneedles for drug and vaccine delivery". *Advanced Drug Delivery Reviews* 2012, 64 (14): 1547-68).

In some embodiments, the pharmaceutically acceptable carrier comprises a combination of two, three, four, five or more different pharmaceutically acceptable carriers suitable for topical or transdermal applications/administrations.

In some embodiments, the pharmaceutically acceptable carrier further comprises one or more additional components. Examples of additional components may include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like.

Pharmaceutical compositions and formulations as described herein may be prepared by mixing the delivery vehicle comprising one or more polynucleotides described herein with one or more pharmaceutically acceptable carriers. The formulations to be used for in vivo administration are generally sterile. Sterility may be readily accomplished, e.g., by filtration through sterile filtration membranes.

Methods of Treatment

The present disclosure relates, in part, to pharmaceutical compositions and methods of use for providing prophylactic, palliative, or therapeutic relief of a wound, disorder, or disease of the skin in a subject. Examples of diseases or disorders of the skin may include, but are not limited to, epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid. In some embodiments, the disease or disorder of the skin is epidermolysis bullosa. In some embodiments, a subject has, or at risk of developing, one or more symptoms of epidermolysis bullosa.

The polynucleotides and pharmaceutical compositions described herein are useful for providing prophylactic, palliative, or therapeutic relief of a wound, disorder, or disease of the skin in a subject, including the treatment of one or more symptoms of epidermolysis bullosa (e.g., recessive dystrophic epidermolysis bullosa, dominant dystrophic epidermolysis bullosa, etc.). Pharmaceutical compositions of the present disclosure may be administered by any suitable method known in the art, including, without limitation, by oral administration, sublinguall administration, buccal administration, topical administration, rectal administration, via inhalation, transdermal administration, subcutaneous injection, intradermal injection, intravenous (IV) injection, intra-arterial injection, intramuscular injection, intracardiac injection, intraosseous injection, intraperitoneal injection, transmucosal administration, vaginal administration, intravitreal administration, intra-articular administration, periarticular administration, local administration, epicutaneous administration, or any combinations thereof. The pharmaceutical compositions may be delivered to an individual via a variety of routes, including, but not limited to, subcutaneous, intradermal, topical, transdermal, and transmucosal administrations. The present disclosure thus also encompasses methods of delivering any of the polynucleotides or pharmaceutical compositions described herein to an individual (such as an individual having, or at risk of developing, epidermolysis bullosa).

In some embodiments, there is provided prophylactic, palliative, or therapeutic relief of a wound, disorder, or disease of the skin in a subject comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the subject. In some embodiments, the pharmaceutical composition is administered intradermally and/or subcutaneously. In some embodiments, the pharmaceutical composition is administered topically and/or trandermally. In some embodiments, there is provided prophylactic, palliative, or therapeutic relief of a wound, disorder, or disease of the skin in a subject comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or a Keratin type I cytoskeletal 17 polypeptide in one or more cells of the subject. The pharmaceutical composition may be any pharmaceutical composition described herein. In some embodiments, the individual is suffering from epidermolysis bullosa. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, a pharmaceutical composition described herein may be used to treat or alleviate one or more symptoms of epidermolysis bullosa. Symptoms of epidermolysis bullosa (e.g., recessive dystrophic epidermolysis bullosa, dominant dystrophic epidermolysis bullosa, etc.) may include, but are not limited to blisters on the skin (especially blisters on the hands, feet, knees, and elbows), blisters on the mucosa, scarring of the skin, scarring of the mucosa, skin erosion, deformity of fingernails and/or toenails, loss of fingernails and/or toenails, internal blistering (including on the vocal chords, esophagus, and upper airway), thickening of the skin (especially thickening of the skin on the palms and the soles of the feet), blistering of the scalp, scarring of the scalp, hair loss (scarring alopecia), thin-appearing skin, atrophic scarring, milia, dental conditions (such as tooth decay and poorly formed enamel), joint deformities, fusion of the fingers and toes, and dysphagia.

In some embodiments, there is provided a method of therapeutically treating an individual suffering from epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or a Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of therapeutically treating an individual suffering from epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, there is provided a method of prophylactically treating an individual suffering from epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of prophylactically treating an individual suffering from epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, there is provided a method of prophylactically treating an individual at risk of developing epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of prophylactically treating an individual at risk of developing epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is at risk of developing dystrophic epidermolysis bullosa. In some embodiments, the individual is at risk of developing dominant dystrophic epidermolysis bullosa. In some embodiments, the individual is at risk of developing recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, administering to an individual an effective amount of any of the pharmaceutical compositions described herein enhances, increases, augments, and/or supplements the levels of a Collagen alpha-1 chain polypeptide and/or a Lysyl hydroxylase 3 polypeptide and/or Keratin type I cytoskeletal 17 polypeptide in one or more cells of the individual. In some embodiments, administering to an individual an effective amount of any of the pharmaceutical compositions described herein enhances, increases, augments, and/or supplements the function of a Collagen alpha-1 chain polypeptide and/or a Lysyl hydroxylase 3 polypeptide and/or a Keratin type I cytoskeletal 17 polypeptide in one or more cells of the individual. In some embodiments, administering to an individual an effective amount of any of the pharmaceutical compositions described herein enhances, increases, augments, and/or supplements the activity of a Collagen alpha-1 chain polypeptide and/or a Lysyl hydroxylase 3 polypeptide and/or Keratin type I cytoskeletal 17 polypeptide in one or more cells of the individual.

In some embodiments, administering to an individual an effective amount of any of the pharmaceutical compositions described herein enhances, increases, augments, and/or supplements anchoring fibril formation of the individual. In some embodiments, administering to an individual an effective amount of any of the pharmaceutical compositions described herein enhances, increases, augments, and/or supplements epithelial basement membrane organization of the individual. In some embodiments, administering to an individual an effective amount of any of the pharmaceutical compositions described herein enhances, increases, augments, and/or supplements epithelial basement adherence of the individual. In some embodiments, administering to an individual an effective amount of any of the pharmaceutical compositions described herein enhances, increases, augments, and/or supplements dermoepidermal junction integrity of the individual. In some embodiments, administering to an individual an effective amount of any of the pharmaceutical compositions described herein enhances, increases, augments, and/or supplements wound healing in the individual. Without wishing to be bound by theory, it is believed that increasing, augmenting, and/or supplementing the levels of a Collagen alpha-1 (VII) chain polypeptide in one or more cells of an individual, by administering one or more of the pharmaceutical compositions described herein, will allow for increased production and secretion of functional Collagen alpha-1 (VII) chain protein in the individual. Without wishing to be bound by theory, it is believed that increasing, augmenting, and/or supplementing the levels of a Lysyl hydroxylase 3 polypeptide in one or more cells of an individual, by administering one or more of the pharmaceutical compositions described herein, will increase the post-translation modification of Collagen alpha-1 (VII) chain polypeptides, enhancing production and/or secretion of functional Collagen alpha-1 (VII) chain protein in the individual. Without wishing to be bound by theory, it is further believed that increasing, augmenting, and/or supplementing the levels of a Collagen alpha-1 (VII) chain polypeptide and a Lysyl hydroxylase 3 polypeptide in the same cell of an individual, by administering one or more of the pharmaceutical compositions described herein (be it by contacting a cell with two separate polynucleotides expressing the polypeptides, by contacting a cell with a single contiguous polynucleotide separately expressing the two polypeptides, or by contacting a cell with a single contiguous polynucleotide expressing a chimeric polypeptide), will have an additive effect on enhancing the production and secretion of functional Collagen alpha-1 (VII) chain protein. Without wishing to be bound by theory, it is believed that increased production and secretion of functional Collagen alpha-1 (VII) chain protein will allow for improved anchoring fibril formation, helping organize, stabilize, and aid in the adherence of the epithelial basement membrane in the individual. Without wishing to be bound by theory, it is believed that ultimately, this will lead to increased dermal-epidermal stability for those suffering from epidermolysis bullosa, treating existing wounds, and preventing or delaying reformation of wounds in the treated areas.

Isolated Polynucleotides and Polypeptides

Certain aspects of the present disclosure relate to isolated polynucleotides comprising a polynucleotide encoding a Collagen alpha-1 (VII) chain polypeptide. Other aspects of the present disclosure relate to isolated polynucleotides comprising a polynucleotide encoding a Lysyl hydroxylase 3 polypeptide. Other aspects of the present disclosure relate to isolated polynucleotides comprising a polynucleotide encoding a Keratin type I cytoskeletal 17 polypeptide.

Other aspects of the present disclosure relate to isolated polynucleotides comprising a polynucleotide encoding a Collagen alpha-1 (VII) chain polypeptide and a polynucleotide encoding a Lysyl hydroxylase 3 polypeptide separated by a polynucleotide encoding a linker polypeptide. In some embodiments, the isolated polynucleotide encodes a chimeric polypeptide comprising a Collagen alpha-1 (VII) chain polypeptide, a linker polypeptide, and a Lysyl hydroxylase 3 polypeptide.

In some embodiments, the polynucleotide encoding a linker polypeptide further comprises a polynucleotide encoding one or more furin cleavage sites. In some embodiments, the one or more furin cleavage sites are encoded upstream of the linker polypeptide. In some embodiments, the one or more furin cleavage sites are encoded downstream of the linker polypeptide. In some embodiments, the one or more furin cleavage sites are encoded upstream of a T2A linker polypeptide. In some embodiments, the one or more furin cleavage sites are encoded downstream of a T2A linker polypeptide. In some embodiments, the one or more furin cleavage sites are encoded upstream of a P2A linker polypeptide. In some embodiments, the one or more furin cleavage sites are encoded downstream of a P2A linker polypeptide. In some embodiments, the one or more furin cleavage sites are encoded upstream of an E2A linker polypeptide. In some embodiments, the one or more furin cleavage sites are encoded downstream of an E2A linker polypeptide. In some embodiments, the one or more furin cleavage sites are encoded upstream of an F2A linker polypeptide. In some embodiments, the one or more furin cleavage sites are encoded downstream of an F2A linker polypeptide.

An example of a polynucleotide encoding a Collagen alpha-1 (VII) chain polypeptide is SEQ ID NO: 1. Polynucleotides encoding a Collagen alpha-1 (VII) chain polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 1.

An example of a polynucleotide encoding a Lysyl hydroxylase 3 polypeptide is SEQ ID NO: 3. Polynucleotides encoding a Lysyl hydroxylase 3 polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ NO: 3.

An example of a polynucleotide encoding a Keratin type I cytoskeletal 17 polypeptide is SEQ ID NO: 29. Polynucleotides encoding a Keratin type I cytoskeletal 17 polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 29.

Examples of polynucleotides encoding linker polypeptides are SEQ ID NO: 5, SEQ ID NO: 7, SEQ ID NO: 9, and SEQ ID NO: 11. Polynucleotides encoding linker polypeptides also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 5, SEQ ID NO: 7, SEQ ID NO: 9, or SEQ ID NO: 11.

Examples of polynucleotides that encode chimeric polypeptides comprising a Collagen alpha-1 (VII) chain polypeptide, a linker polypeptide, and a Lysyl hydroxylase 3 polypeptide are SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Polynucleotides that encode chimeric polypeptides also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

Further aspects of the present disclosure relate to one or more (e.g., one or more, two or more, three or more, etc.) isolated polynucleotides described herein contained within a vector. In some embodiments, the vector is an adenoviral vector, an adeno-associated viral vector, a retroviral vector, a lentiviral vector, a herpes simplex viral vector, a vaccinia viral vector, or any hybrid viral vector thereof. In some embodiments, the vector is a herpes simplex viral vector. In some embodiments, the vector comprises one or more (e.g., one or more, two or more, three or more, four or more, five or more, etc.) transgenes.

In some embodiments, the herpes simplex virus vector is a herpes virus amplicon vector. In some embodiments, the vector is an HSV-1 amplicon. In some embodiments, the vector is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and HSV/Sleeping Beauty hybrid amplicons. In some embodiments, the vector is an HSV/AAV hybrid amplicon. In some embodiments, the vector is an HSV/EBV hybrid amplicon. In some embodiments, the vector is an HSV/EBV/RV hybrid amplicon. In some embodiments, the vector is an HSV/Sleeping Beauty hybrid amplicons. Further aspects of the present disclosure relate to a method of producing a viral delivery vehicle containing one or more polynucleotides described herein. In some embodiments, the method comprises contacting a host cell with one or more viral vectors containing one or more isolated polynucleotides described herein, and collecting the viral delivery vehicle generated by the host cell. Methods of culturing cells and contacting cells with one or more viral vectors of interest (e.g. by transduction or transfection) are well known to one of skill in the art.

In some embodiments, the herpes simplex virus vector is a recombinant herpes simplex virus genome. In some embodiments, the recombinant herpes simplex virus genome has been engineered to decrease or eliminate expression of one or more toxic herpes simplex virus genes. In some embodiments, the recombinant herpes simplex virus genome comprises an inactivating mutation. Examples of inactivating mutations may include, but are not limited to, deletions (e.g., deletion of the coding sequence of a gene or deletion of one or more of the gene's transcriptional regulatory elements), insertions, point mutations, and rearrangements. In some embodiments, the recombinant herpes simplex virus genome comprises an inactivating mutation in one or more immediate early genes. In some embodiments, the recombinant herpes simplex virus genome comprises an inactivating mutation in at least one, at least two, at least three, at least four, at least five, at least six, at least seven, or all eight of the ICP0, ICP4, ICP22, ICP27, ICP47, tk, UL4 land UL55 herpes simplex virus genes. In some embodiments, the recombinant herpes simplex virus genome comprises an inactivating mutation is in the ICP0 gene. In some embodiments, the recombinant herpes simplex virus genome comprises an inactivating mutation is in the ICP4 gene. In some embodiments, the recombinant herpes simplex virus genome comprises an inactivating mutation is in the ICP22 gene. In some embodiments, the recombinant herpes simplex virus genome comprises an inactivating mutation is in the ICP27 gene. In some embodiments, the recombinant herpes simplex virus genome comprises an inactivating mutation is in the ICP4, ICP22, and ICP27 genes. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the recombinant herpes simplex virus genome comprises an inactivating mutation is in the ICP0, ICP4, ICP22, and ICP27 genes. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, an isolated recombinant herpes simplex virus genome comprises one or more (e.g., one or more, two or more, three or more, four or more, five or more, etc.) polynucleotides (e.g., transgenes) of the present disclosure within one, two, three, four, five, six, seven or more viral gene loci. Examples of suitable viral loci may include, without limitation, the ICP0, ICP4, ICP22, ICP27, ICP47, tk, UL41 and UL55 herpes simplex viral gene loci. In some embodiments, an isolated recombinant herpes simplex virus genome comprises one or more polynucleotide of the present disclosure within one or more of the viral ICP4 gene loci (e.g., a recombinant virus carrying a polynucleotide encoding Col7 in one or both of the ICP4 loci, a recombinant virus carrying a polynucleotide encoding LH3 in one or both of the ICP4 loci, a recombinant virus carrying a polynucleotide encoding KRT17 in one or both of the ICP4 loci, a recombinant virus carrying a polynucleotide encoding Col7 in one of the ICP4 loci and a polynucleotide encoding KRT17 in the other ICP4 loci, a recombinant virus carrying a polynucleotide encoding Col7 in one of the ICP4 loci and a polynucleotide encoding LH3 in the other ICP4 loci, a recombinant virus carrying a polynucleotide encoding LH3 in one of the ICP4 loci and a polynucleotide encoding KRT17 in the other ICP4 loci, etc.). In some embodiments, an isolated recombinant herpes simplex virus genome comprises one or more polynucleotide of the present disclosure within the viral UL41 gene locus. In some embodiments, an isolated recombinant herpes simplex virus genome comprises one or more polynucleotide of the present disclosure within the viral ICP47 gene locus. In some embodiments, an isolated recombinant herpes simplex virus genome comprises one or more polynucleotides of the present disclosure within one or more of the viral ICP4 gene loci, and one or more polynucleotide of the present disclosure within the viral UL41 gene locus (e.g., a recombinant virus carrying a polynucleotide encoding Col7 in one or both of the ICP4 loci and a polynucleotide encoding LH3 in the UL41 locus, a recombinant virus carrying a polynucleotide encoding Col7 in one or both of the ICP4 loci and a polynucleotide encoding Col7 in the UL41 locus, a recombinant virus carrying a polynucleotide encoding Col7 in one or both of the ICP4 loci and a polynucleotide encoding KRT17 in the UL41 locus, a recombinant virus carrying a polynucleotide encoding LH3 in one or both of the ICP4 loci and a polynucleotide encoding LH3 in the UL41 locus, a recombinant virus carrying a polynucleotide encoding LH3 in one or both of the ICP4 loci and a polynucleotide encoding Col7 in the UL41 locus, a recombinant virus carrying a polynucleotide encoding LH3 in one or both of the ICP4 loci and a polynucleotide encoding KRT17 in the UL41 locus, a recombinant virus carrying a polynucleotide encoding KRT17 in one or both of the ICP4 loci and a polynucleotide encoding LH3 in the UL41 locus, a recombinant virus carrying a polynucleotide encoding KRT17 in one or both of the ICP4 loci and a polynucleotide encoding Col7 in the UL41 locus, a recombinant virus carrying a polynucleotide encoding KRT17 in one or both of the ICP4 loci and a polynucleotide encoding KRT17 in the UL41 locus, etc.).

In some aspects, the isolated polynucleotides described herein are contained within a synthetic mRNA. In some embodiments, the synthetic mRNA comprises one or more modified ribonucleotides.

Certain aspects of the present disclosure relate to isolated polypeptides comprising a Collagen alpha-1 (VII) chain polypeptide. Other aspects of the present disclosure relate to isolated polypeptides comprising a Lysyl hydroxylase 3 polypeptide. Other aspects of the present disclosure relate to isolated polypeptides comprising a Keratin type I cytoskeletal 17 polypeptide.

Other aspects of the present disclosure relate to isolated chimeric polypeptides comprising a Collagen alpha-1 (VII) chain polypeptide and a Lysyl hydroxylase 3 polypeptide separated by a linker polypeptide.

In some embodiments, the linker polypeptide further comprises one or more furin cleavage sites. In some embodiments, the amino acid sequence of the furin cleavage site is the same or substantially similar to the sequence of the canonical furin cleavage site (Arg-X-(Arg/Lys)-Arg). In some embodiments, the one or more furin cleavage sites are at the N-terminus of the linker polypeptide. In some embodiments, the one or more furin cleavage sites are at the C-terminus of the linker polypeptide. In some embodiments, the linker polypeptide comprises, from N-terminus to C-terminus, one or more furin cleavage sites and a T2A linker polypeptide. In some embodiments, the linker polypeptide comprises, from N-terminus to C-terminus, a T2A linker polypeptide and one or more furin cleavage sites. In some embodiments, the linker polypeptide comprises, from N-terminus to C-terminus, one or more furin cleavage sites and a P2A linker polypeptide. In some embodiments, the linker polypeptide comprises, from N-terminus to C-terminus, a P2A linker polypeptide and one or more furin cleavage sites. In some embodiments, the linker polypeptide comprises, from N-terminus to C-terminus, one or more furin cleavage sites and an E2A linker polypeptide. In some embodiments, the linker polypeptide comprises, from N-terminus to C-terminus, an E2A linker polypeptide and one or more furin cleavage sites. In some embodiments, the linker polypeptide comprises, from N-terminus to C-terminus, one or more furin cleavage sites and an F2A linker polypeptide. In some embodiments, the linker polypeptide comprises, from N-terminus to C-terminus, an F2A linker polypeptide and one or more furin cleavage sites.

In some aspects, the isolated polypeptide comprising a Collagen alpha-1 (VII) chain polypeptide comprises the amino acid sequence of SEQ ID NO: 2. Isolated polypeptides may also comprise a Collagen alpha-1 (VII) chain polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2.

In some aspects, the isolated polypeptide comprising a Lysyl hydroxylase 3 polypeptide comprises the amino acid sequence of SEQ ID NO: 4. Isolated polypeptides may also comprise a Lysyl hydroxylase 3 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4.

In some aspects, the isolated polypeptide comprising a Keratin type I cytoskeletal 17 polypeptide comprises the amino acid sequence of SEQ ID NO: 30. Isolated polypeptides may also comprise a Keratin type I cytoskeletal 17 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 30.

In some aspects, the chimeric polypeptide comprises a Collagen alpha-1 (VII) chain polypeptide containing the amino acid sequence of SEQ ID NO: 2. Chimeric polypeptides may also comprise a Collagen alpha-1 (VII) chain polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ NO: 2.

In some aspects, the chimeric polypeptide comprises a Lysyl hydroxylase 3 polypeptide containing the amino acid sequence of SEQ ID NO: 4. Chimeric polypeptides may also comprise a Lysyl hydroxylase 3 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4.

In some aspects, the chimeric polypeptide comprises a linker polypeptide containing the amino acid sequence of SEQ ID NO: 6, SEQ ID NO: 8, SEQ ID NO: 10 or SEQ ID NO: 12. Chimeric polypeptides may also comprise a linker polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 6, SEQ ID NO: 8, SEQ ID NO: 10 or SEQ ID NO: 12.

In some aspects, the chimeric polypeptide is the amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. Chimeric polypeptides may also be an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Host Cells

Certain aspects of the present disclosure relate to one or more host cells comprising a vector comprising a polynucleotide described herein. In some embodiments, the vector is any of the isolated recombinant herpes simplex virus vectors described herein. In some embodiments, the host cells are bacterial cells (e.g., *E. coli* cells, etc.). In some embodiments, the host cells are fungal cells (e.g., *S. cerevisiae* cells, etc.). In some embodiments, the host cells are insect cells (e.g., S2 cells, etc.). In some embodiments, the host cells are mammalian cells. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like. In some embodiments, the vector is an adenoviral vector, an adeno-associated viral vector, a retroviral vector, a lentiviral vector, a herpes simplex viral vector, a vaccinia viral vector, or any hybrid viral vectors thereof. In some embodiments, the vector is a herpes simplex viral vector. In some embodiments, the vector is an HSV-1 amplicon or HSV-1 hybrid amplicon. In some embodiments, the host cells comprise a helper virus. In some embodiments, the host cells comprising a helper virus are contacted with a vector described herein. In some embodiments, contacting a host cell comprising a helper virus with an HSV-1 amplicon or HSV-1 hybrid amplicon described herein results in the production of a virus comprising one or more vectors described herein. In some embodiments, the virus is collected from the supernatant of the contacted host cell. Methods of generating virus by contacting host cells comprising a helper virus with an HSV-1 amplicon or HSV-1/hybrid amplicon are known in the art. In some embodiments, the host cell is a complementing host cell. In some embodiments, the complementing host cell expresses one or more genes that are inactivated in any of the viral vectors described herein. In some embodiments, the complementing host cell is contacted with a recombinant herpes simplex virus genome described herein. In some embodiments, contacting a complementing host cell with a recombinant herpes simplex virus genome described herein results in the production of a virus comprising one or more vectors described herein. In some embodiments, the virus is collected from the supernatant of the contacted host cell. Methods of generating virus by contacting complementing host cells with a recombinant herpes simplex virus are generally described in WO2015/009952.

Articles of Manufacture or Kits

Certain aspects of the present disclosure relate to an article of manufacture or a kit comprising a pharmaceutical composition described herein. In some embodiments, the article of manufacture or kit comprises a package insert comprising instructions for administering the pharmaceutical composition to provide prophylactic, palliative, or therapeutic relief of a wound, disorder, or disease of the skin in a subject.

In some embodiments, the delivery vehicle comprising one or more polynucleotides described herein and pharmaceutically acceptable carrier are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, and the like.

Enumerated Embodiments

Embodiment 1: A pharmaceutical composition comprising:

a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, and a chimeric polypeptide thereof; and b) a pharmaceutically acceptable carrier.

Embodiment 2: The pharmaceutical composition of embodiment 1, wherein the virus is an adenovirus, adeno-associated virus, retrovirus, lentivirus, sendai virus, herpes simplex virus, vaccinia virus, or any hybrid virus thereof.

Embodiment 3: The pharmaceutical composition of embodiment 1, wherein the virus is a herpes simplex virus (HSV).

Embodiment 4: The pharmaceutical composition of any of embodiments 1 to 3, wherein the virus is replication-defective.

Embodiment 5: The pharmaceutical composition of embodiment 3, wherein the herpes simplex virus is a herpes simplex type 1 virus, a herpes simplex type 2 virus, or any derivatives thereof.

Embodiment 6: The pharmaceutical composition of embodiment 3, wherein the herpes simplex virus comprises a modified envelope.

Embodiment 7: The pharmaceutical composition of embodiment 6, wherein the modified envelope alters the herpes simplex virus tissue tropism relative to a wild-type herpes simplex virus.

Embodiment 8: The pharmaceutical composition of embodiment 6, wherein the modified envelope comprises a mutant herpes simplex virus glycoprotein.

Embodiment 9: The pharmaceutical composition of embodiment 1, wherein the vector is an HSV-1 amplicon or an HSV-1 hybrid amplicon.

Embodiment 10: The pharmaceutical composition of embodiment 9, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 11: The pharmaceutical composition of embodiment 1, wherein the vector is a recombinant herpes simplex virus genome.

Embodiment 12: The pharmaceutical composition of embodiment 11, wherein the recombinant herpes simplex virus genome is a recombinant HSV-1 genome, a recombinant HSV-2 genome, or any derivatives thereof.

Embodiment 13: The pharmaceutical composition of embodiment 11 or 12, wherein the recombinant herpes simplex virus genome comprises an inactivating mutation in an immediate early herpes simplex virus gene.

Embodiment 14: The pharmaceutical composition of embodiment 13, wherein the herpes simplex virus gene is selected from the group consisting of ICP0, ICP4, ICP22, ICP27, ICP47, tk, UL41, and UL55.

Embodiment 15: The pharmaceutical composition of any of embodiments 11 to 14, wherein the recombinant herpes simplex virus genome comprises an inactivating mutation in the ICP4 and ICP22 genes.

Embodiment 16: The pharmaceutical composition of any of embodiments 11 to 14, wherein the recombinant herpes simplex virus genome comprises an inactivating mutation in the ICP0 and ICP4 genes.

Embodiment 17: The pharmaceutical composition of embodiment 15 or embodiment 16, wherein the recombinant herpes simplex virus genome comprises an inactivating mutation in the ICP0, ICP4, and ICP22 genes.

Embodiment 18: The pharmaceutical composition of any of embodiments 15 to 17, wherein the recombinant herpes simplex virus genome comprises an inactivating mutation in the ICP0, ICP4, ICP22, and ICP27 genes.

Embodiment 19: The pharmaceutical composition of any of embodiments 15 to 18, wherein the recombinant herpes simplex virus genome comprises an inactivating mutation in the ICP0, ICP4, ICP22, ICP27, and UL55 genes.

Embodiment 20: The pharmaceutical composition of any of embodiments 15 to 18, wherein the inactivating mutation is a deletion of the coding sequence of the genes.

Embodiment 21: The pharmaceutical composition of any of embodiments 15 to 20, further comprising an inactivating mutation in the ICP47 gene.

Embodiment 22: The pharmaceutical composition of any of embodiments 11 to 21, further comprising an inactivating mutation in the UL41 gene.

Embodiment 23: The pharmaceutical composition of any of embodiments 11 to 22, wherein the recombinant herpes simplex virus genome comprises the one or more transgenes within one or more viral gene loci.

Embodiment 24: The pharmaceutical composition of any of embodiments 11 to 23, wherein the recombinant herpes simplex virus genome comprises the one or more transgenes within one or more of the ICP4 viral gene loci.

Embodiment 25: The pharmaceutical composition of any of embodiments 11 to 24, wherein the recombinant herpes simplex virus genome comprises the one or more transgenes within the UL41 viral gene locus.

Embodiment 26: The pharmaceutical composition of embodiment 1, wherein the vector is capable of replicating within a target cell when delivered into said target cell.

Embodiment 27: The pharmaceutical composition of embodiment 1, wherein the pharmaceutically acceptable carrier is suitable for topical or transdermal administration.

Embodiment 28: The pharmaceutical composition of embodiment 1, wherein the one or more transgenes comprises an miRNA binding site.

Embodiment 29: The pharmaceutical composition of embodiment 1, wherein the one or more transgenes are operably linked to one or more heterologous promoters.

Embodiment 30: The pharmaceutical composition of embodiment 29, wherein the one or more heterologous promoters are selected from the group consisting of the human cytomegalovirus (HCMV) immediate early promoter, the elongation factor-1 (EF1) promoter, and any combinations thereof.

Embodiment 31: The pharmaceutical composition of embodiment 1, wherein the vector comprises a transgene encoding a Collagen alpha-1 (VII) chain polypeptide.

Embodiment 32: The pharmaceutical composition of embodiment 1, wherein the vector comprises two transgenes, wherein each transgene encodes a Collagen alpha-1 (VII) chain polypeptide.

Embodiment 33: The pharmaceutical composition of embodiment 1, wherein the Collagen alpha-1 (VII) chain polypeptide has at least 80% sequence identity to the sequence of SEQ NO: 2.

Embodiment 34: The pharmaceutical composition of embodiment 1, wherein the collagen alpha-1 (VII) chain polypeptide is a fragment, wherein the fragment has at least 100 consecutive amino acids of SEQ ID NO: 2.

Embodiment 35: The pharmaceutical composition of embodiment 1, wherein the Collagen alpha-1 (VII) chain polypeptide enhances, increases, augments, and/or supplements anchoring fibril formation of a subject when the polypeptide is expressed in one or more target cells of the subject.

Embodiment 36: The pharmaceutical composition of embodiment 1, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 37: The pharmaceutical composition of embodiment 1, wherein the Lysyl hydroxylase 3 polypeptide has at least 80% sequence identity to the sequence of SEQ ID NO: 4.

Embodiment 38: The pharmaceutical composition of embodiment 1, wherein the Lysyl hydroxylase 3 polypeptide is a fragment, wherein the fragment has at least 100 consecutive amino acids of SEQ ID NO: 4.

Embodiment 39: The pharmaceutical composition of embodiment 1, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 40: The pharmaceutical composition of embodiment 1, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 41: The pharmaceutical composition of embodiment 1, wherein the vector comprises at least a first transgene and a second transgene.

Embodiment 42: The pharmaceutical composition of embodiment 41, wherein the first transgene encodes a Collagen alpha-1 (VII) chain polypeptide and the second transgene encodes a Lysyl hydroxylase 3 polypeptide.

Embodiment 43: The pharmaceutical composition of embodiment 1, wherein the vector comprises a transgene that is polycistronic.

Embodiment 44: The pharmaceutical composition of embodiment 43, wherein the polycistronic transgene encodes a Collagen alpha-1 (VII) chain polypeptide on a first open reading frame (ORF) and a Lysyl hydroxylase 3 polypeptide on a second open reading frame (ORF).

Embodiment 45: The pharmaceutical composition of embodiment 44, wherein the first and second ORFs are separated by an internal ribosomal entry site (IRES).

Embodiment 46: The pharmaceutical composition of any of embodiments 42 to 45, wherein the Collagen alpha-1 (VII) chain polypeptide and the Lysyl hydroxylase 3 polypeptide are at about an equimolar ratio when the polypeptides are expressed in one or more target cells of a subject.

Embodiment 47: The pharmaceutical composition of any of embodiments 42 to 45, wherein the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject.

Embodiment 48: The pharmaceutical composition of embodiment 1, wherein the chimeric polypeptide comprises a linker polypeptide between the Collagen alpha-1 (VII) chain polypeptide and the Lysyl hydroxylase 3 polypeptide.

Embodiment 49: The pharmaceutical composition of embodiment 48, wherein the linker polypeptide is a T2A, P2A, E2A, or F2A linker polypeptide.

Embodiment 50: The pharmaceutical composition of embodiment 48 or 49, wherein the linker polypeptide has at least 80% sequence identity to the sequence of SEQ ID NO: 6, SEQ ID NO: 8, SEQ ID NO: 10 or SEQ ID NO: 12.

Embodiment 51: The pharmaceutical composition of any of embodiments 48 to 50, wherein the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 52: The pharmaceutical composition of any of embodiments 48 to 51, wherein the chimeric polypeptide enhances, increases, augments, and/or supplements anchoring fibril formation, epithelial basement membrane organization, and/or epithelial basement adherence of a subject when the polypeptide is expressed in one or more target cells of the subject.

Embodiment 53: A method of providing prophylactic, palliative, or therapeutic relief of a wound, disorder, or disease of the skin in a subject, the method comprising topically or transdermally administering a pharmaceutical composition capable of enhancing, increasing, augmenting, and/or supplementing the levels of a Collagen alpha-1 (VII) chain polypeptide and/or a Lysyl hydroxylase 3 polypeptide in one or more cells of the subject.

Embodiment 54: The method of embodiment 53, wherein the pharmaceutical composition comprises:
a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, and a chimeric polypeptide thereof; and b) a pharmaceutically acceptable carrier.

Embodiment 55: The method of embodiment 54, wherein the virus is an adenovirus, adeno-associated virus, retrovirus, lentivirus, sendai virus, herpes simplex virus, vaccinia virus, or any hybrid virus thereof.

Embodiment 56: The method of embodiment 54, wherein the virus is a herpes simplex virus (HSV).

Embodiment 57: The method of any of embodiments 54 to 56, wherein the virus is replication-defective.

Embodiment 58: The method of embodiment 56, wherein the herpes simplex virus is a herpes simplex type 1 virus, a herpes simplex type 2 virus, or any derivatives thereof.

Embodiment 59: The method of embodiment 56, wherein the herpes simplex virus comprises a modified envelope.

Embodiment 60: The method of embodiment 59, wherein the modified envelope alters the herpes simplex virus tissue tropism relative to a wild-type herpes simplex virus.

Embodiment 61: The method of embodiment 59, wherein the modified envelope comprises a mutant herpes simplex virus glycoprotein.

Embodiment 62: The method of embodiment 54, wherein the vector is an HSV-1 amplicon or an HSV-1 hybrid amplicon.

Embodiment 63: The method of embodiment 62, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 64: The method of embodiment 54, wherein the vector is a recombinant herpes simplex virus genome.

Embodiment 65: The method of embodiment 64, wherein the recombinant herpes simplex virus genome is a recombinant HSV-1 genome, a recombinant HSV-2 genome, or any derivatives thereof.

Embodiment 66: The method of embodiment 64 or 65, wherein the recombinant herpes simplex virus genome comprises an inactivating mutation in an immediate early herpes simplex virus gene.

Embodiment 67: The method of embodiment 66, wherein the herpes simplex virus gene is selected from the group consisting of ICP0, ICP4, ICP22, ICP27, ICP47, tk, UL41, and UL55.

Embodiment 68: The method of any of embodiments 64 to 67, wherein the recombinant herpes simplex virus genome comprises an inactivating mutation in the ICP4 and ICP22 genes.

Embodiment 69: The method of any of embodiments 64 to 67, wherein the recombinant herpes simplex virus genome comprises an inactivating mutation in the ICP0 and ICP4 genes.

Embodiment 70: The method of embodiment 68 or 69, wherein the recombinant herpes simplex virus genome comprises an inactivating mutation in the ICP0, ICP4, and ICP22 genes.

Embodiment 71: The method of any of embodiments 68 to 70, wherein the recombinant herpes simplex virus genome comprises an inactivating mutation in the ICP0, ICP4, ICP22, and ICP27 genes.

Embodiment 72: The method of any of embodiments 68 to 71, wherein the recombinant herpes simplex virus genome comprises an inactivating mutation in the ICP0, ICP4, ICP22, ICP27, and UL55 genes.

Embodiment 73: The method of any of embodiments 68 to 72, wherein the inactivating mutation is a deletion of the coding sequence of the genes.

Embodiment 74: The method of any of embodiments 68 to 73, further comprising an inactivating mutation in the ICP47 gene.

Embodiment 75: The method of any of embodiments 64 to 74, further comprising an inactivating mutation in the UL41 gene.

Embodiment 76: The method of any of embodiments 64 to 75, wherein the recombinant herpes simplex virus genome comprises the one or more transgenes within one or more viral gene loci.

Embodiment 77: The method of any of embodiments 64 to 76, wherein the recombinant herpes simplex virus genome comprises the one or more transgenes within one or more of the ICP4 viral gene loci.

Embodiment 78: The method of any of embodiments 64 to 77, wherein the recombinant herpes simplex virus genome comprises the one or more transgenes within the UL41 viral gene locus.

Embodiment 79: The method of embodiment 54, wherein the vector is capable of replicating within a target cell when delivered into said target cell.

Embodiment 80: The method of embodiment 54, wherein the pharmaceutically acceptable carrier is suitable for topical or transdermal administration.

Embodiment 81: The method of embodiment 54, wherein the one or more transgenes comprises an miRNA binding site.

Embodiment 82: The method of embodiment 54, wherein the one or more transgenes are operably linked to one or more heterologous promoters.

Embodiment 83: The method of embodiment 82, wherein the one or more heterologous promoters are selected from the group consisting of the human cytomegalovirus (HCMV) immediate early promoter, the elongation factor-1 (EF1) promoter, and any combinations thereof.

Embodiment 84: The method of embodiment 54, wherein the vector comprises a transgene encoding a Collagen alpha-1 (VII) chain polypeptide.

Embodiment 85: The method of embodiment 54, wherein the vector comprises two transgenes, wherein each transgene encodes a Collagen alpha-1 (VII) chain polypeptide.

Embodiment 86: The method of embodiment 54, wherein the Collagen alpha-1 (VII) chain polypeptide has at least 80% sequence identity to the sequence of SEQ ID NO: 2.

Embodiment 87: The method of embodiment 54, wherein the Collagen alpha-1 (VII) chain polypeptide is a fragment, wherein the fragment has at least 100 consecutive amino acids of SEQ ID NO: 2.

Embodiment 88: The method of embodiment 54, wherein the Collagen alpha-1 (VII) chain polypeptide enhances, increases, augments, and/or supplements anchoring fibril formation of a subject when the polypeptide is expressed in one or more target cells of the subject.

Embodiment 89: The method of embodiment 54, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 90: The method of embodiment 54, wherein the Lysyl hydroxylase 3 polypeptide has at least 80% sequence identity to the sequence of SEQ ID NO: 4.

Embodiment 91: The method of embodiment 54, wherein the Lysyl hydroxylase 3 polypeptide is a fragment, wherein the fragment has at least 100 consecutive amino acids of SEQ ID NO: 4.

Embodiment 92: The method of embodiment 54, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 93: The method of embodiment 54, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 94: The method of embodiment 54, wherein the vector comprises at least a first transgene and a second transgene.

Embodiment 95: The method of embodiment 94, wherein the first transgene encodes a Collagen alpha-1 (VII) chain polypeptide and the second transgene encodes a Lysyl hydroxylase 3 polypeptide.

Embodiment 96: The method of embodiment 54, wherein the vector comprises a transgene that is polycistronic.

Embodiment 97: The method of embodiment 96, wherein the polycistronic transgene encodes a Collagen alpha-1 (VII) chain polypeptide on a first open reading frame (ORF) and a Lysyl hydroxylase 3 polypeptide on a second open reading frame (ORF).

Embodiment 98: The method of embodiment 97, wherein the first and second ORFs are separated by an internal ribosomal entry site (IRES).

Embodiment 99: The method of any of embodiments 95 to 98, wherein the Collagen alpha-1 (VII) chain polypeptide and the Lysyl hydroxylase 3 polypeptide are at about an equimolar ratio when the polypeptides are expressed in one or more target cells of a subject.

Embodiment 100: The method of any of embodiments 95 to 98, wherein the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject.

Embodiment 101: The method of embodiment 54, wherein the chimeric polypeptide comprises a linker polypeptide between the Collagen alpha-1 (VII) chain polypeptide and the Lysyl hydroxylase 3 polypeptide.

Embodiment 102: The method of embodiment 101, wherein the linker polypeptide is a T2A, P2A, E2A, or F2A linker polypeptide.

Embodiment 103: The method of embodiment 101 or 102, wherein the linker polypeptide has at least 80% sequence identity to the sequence of SEQ ID NO: 6, SEQ ID NO: 8, SEQ NO: 10 or SEQ NO: 12.

Embodiment 104: The method of any of embodiments 101 to 103, wherein the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 105: The method of any of embodiments 101 to 104, wherein the chimeric polypeptide enhances, increases, augments, and/or supplements anchoring fibril formation, epithelial basement membrane organization, and/or epithelial basement adherence of a subject when the polypeptide is expressed in one or more target cells of the subject.

Embodiment 106: The method of embodiment 53, wherein the pharmaceutical composition is administered one, two three, four, five or more times per day.

Embodiment 107: The method of embodiment 53, wherein the pharmaceutical composition is administered to one or more affected and/or unaffected areas of the subject.

Embodiment 108: The method of embodiment 53, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

Embodiment 109: An isolated chimeric polypeptide, wherein the isolated chimeric polypeptide comprises;
a) a Collagen alpha-1 (VII) chain polypeptide;
b) a Lysyl hydroxylase 3 polypeptide; and
c) a linker polypeptide;
wherein the Collagen alpha-1 (VII) chain polypeptide and the Lysyl hydroxylase 3 polypeptide are separated by the linker polypeptide.

Embodiment 110: The isolated chimeric polypeptide of embodiment 109, wherein the Collagen alpha-1 (VII) chain polypeptide has at least 80% sequence identity to the sequence of SEQ NO: 2.

Embodiment 111: The isolated chimeric polypeptide of embodiment 109, wherein the Lysyl hydroxylase 3 polypeptide has at least 80% sequence identity to the sequence of SEQ ID NO: 4.

Embodiment 112: The isolated chimeric polypeptide of embodiment 109, wherein the linker polypeptide has at least 80% sequence identity to the sequence of SEQ ID NO: 6, SEQ ID NO: 8, SEQ ID NO: 10 or SEQ ID NO: 12.

Embodiment 113: The isolated chimeric polypeptide of any of embodiments 109 to 112, wherein the isolated chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 114: A polynucleotide encoding the chimeric polypeptide of any of embodiments 109 to 113.

Embodiment 115: A vector comprising the polynucleotide of embodiment 114.

Embodiment 116: The vector of embodiment 115, wherein the vector is an HSV-1 amplicon or an HSV-1 hybrid amplicon.

Embodiment 117: The vector of embodiment 116 wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 118: The vector of embodiment 115, wherein the vector is a recombinant herpes simplex virus genome.

Embodiment 119: The vector of embodiment 118, wherein the recombinant herpes simplex virus genome is a recombinant HSV-1 genome, a recombinant HSV-2 genome, or any derivatives thereof.

Embodiment 120: The vector of embodiment 118 or 119, wherein the recombinant herpes simplex virus genome comprises an inactivating mutation in an immediate early herpes simplex virus gene.

Embodiment 121: The vector of embodiment 120, wherein the herpes simplex virus gene is selected from the group consisting of ICP0, ICP4, ICP22, ICP27, ICP47, tk, UL41, and UL55.

Embodiment 122: The vector of any of embodiments 118 to 121, wherein the recombinant herpes simplex virus genome comprises an inactivating mutation in the ICP4 and ICP22 genes.

Embodiment 123: The vector of any of embodiments 118 to 121, wherein the recombinant herpes simplex virus genome comprises an inactivating mutation in the ICP0 and ICP4 genes.

Embodiment 124: The vector of embodiment 122 or 123, wherein the recombinant herpes simplex virus genome comprises an inactivating mutation in the ICP0, ICP4, and ICP22 genes.

Embodiment 125: The vector of any of embodiments 122 to 124, wherein the recombinant herpes simplex virus genome comprises an inactivating mutation in the ICP0, ICP4, ICP22, and ICP27 genes.

Embodiment 126: The vector of any of embodiments 122 to 125, wherein the recombinant herpes simplex virus genome comprises an inactivating mutation in the ICP0, ICP4, ICP22, ICP27, and UL55 genes.

Embodiment 127: The vector of any of embodiments 122 to 126, wherein the inactivating mutation is a deletion of the coding sequence of the genes.

Embodiment 128: The vector of any of embodiments 122 to 127, further comprising an inactivating mutation in the ICP47 gene.

Embodiment 129: The vector of any of embodiments 118 to 128, further comprising an inactivating mutation in the UL41 gene.

Embodiment 130: The vector of any of embodiments 118 to 129, wherein the recombinant herpes simplex virus genome comprises the polynucleotide within one or more viral gene loci.

Embodiment 131: The vector of any of embodiments 118 to130, wherein the recombinant herpes simplex virus genome comprises the polynucleotide within one or more of the ICP4 viral gene loci.

Embodiment 132: The vector of any of embodiments 118 to131, wherein the recombinant herpes simplex virus genome comprises the polynucleotide within the UL41 viral gene locus.

Embodiment 133: A vector comprising one or more polynucleotides encoding a Collagen alpha-1 (VII) chain polypeptide, a Lysyl hydroxylase 3 polypeptide, a Keratin type I cytoskeletal 17 polypeptide, or any combinations thereof, wherein the vector is a recombinant herpes simplex virus genome.

Embodiment 134: The vector of embodiment 133, wherein the recombinant herpes simplex virus genome is a recombinant HSV-1 genome, a recombinant HSV-2 genome, or any derivatives thereof.

Embodiment 135: The vector of embodiment 133 or 134, wherein the recombinant herpes simplex virus genome comprises an inactivating mutation in an immediate early herpes simplex virus gene.

Embodiment 136: The vector of embodiment 135, wherein the herpes simplex virus gene is selected from the group consisting of ICP0, ICP4, ICP22, ICP27, ICP47, tk, UL41, and UL55.

Embodiment 137: The vector of any of embodiments 133 to 136, wherein the recombinant herpes simplex virus genome comprises an inactivating mutation in the ICP4 and ICP22 genes.

Embodiment 138: The vector of any of embodiments 133 to 136, wherein the recombinant herpes simplex virus genome comprises an inactivating mutation in the ICP0 and ICP4 genes.

Embodiment 139: The vector of embodiment 137 or 138, wherein the recombinant herpes simplex virus genome comprises an inactivating mutation in the ICP0, ICP4, and ICP22 genes.

Embodiment 140: The vector of any of embodiments 137 to 139, wherein the recombinant herpes simplex virus genome comprises an inactivating mutation in the ICP0, ICP4, ICP22, and ICP27 genes.

Embodiment 141: The vector of any of embodiments 137 to 140, wherein the recombinant herpes simplex virus genome comprises an inactivating mutation in the ICP0, ICP4, ICP22, ICP27, and UL55 genes.

Embodiment 142: The vector of any of embodiments 137 to 141, wherein the inactivating mutation is a deletion of the coding sequence of the genes.

Embodiment 143: The vector of any of embodiments 137 to 142, further comprising an inactivating mutation in the ICP47 gene.

Embodiment 144: The vector of any of embodiments 133 to 143, further comprising an inactivating mutation in the UL41 gene.

Embodiment 145: The vector of any of embodiments 133 to 144, wherein the recombinant herpes simplex virus genome comprises the one or more polynucleotides within one or more viral gene loci.

Embodiment 146: The vector of any of embodiments 133 to145, wherein the recombinant herpes simplex virus genome comprises the one or more polynucleotides within one or more of the ICP4 viral gene loci.

Embodiment 147: The vector of any of embodiments 133 to146, wherein the recombinant herpes simplex virus genome comprises the one or more polynucleotides within the UL41 viral gene locus.

Embodiment 148: The vector of any of embodiments 133 to147, wherein the vector comprises one polynucleotide encoding a Collagen alpha-1 (VII) chain polypeptide.

Embodiment 149: The vector of any of embodiments 133 to147, wherein the vector comprises two polynucleotides encoding a Collagen alpha-1 (VII) chain polypeptide.

Embodiment 150: A host cell comprising the vector of any of embodiments 115 to 149.

Embodiment 151: A method of collecting a herpes simplex virus, wherein a vector of interest is packaged within said herpes simplex virus, the method comprising;
a) contacting a host cell with a vector encoding a helper virus;
b) contacting said host cell with a vector of any of embodiments 115 to 117; and
c) collecting the Herpes simplex virus generated by said host cell.

Embodiment 152: A method of collecting a herpes simplex virus, wherein a vector of interest is packaged within said herpes simplex virus, the method comprising;
a) contacting a complementing host cell with a vector of any of embodiments 118 to 149; and
b) collecting the herpes simplex virus generated by said complementing host cell.

Embodiment 153: The method of embodiment 151 or 152, wherein the herpes simplex virus is a herpes simplex type 1 virus, a herpes simplex type 2 virus, or any derivatives thereof.

Embodiment 154: A kit comprising:
a) the pharmaceutical composition of any of embodiments 1 to 52; and
b) instructions for administering the pharmaceutical composition.

Embodiment 155: A pharmaceutical composition comprising:
a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof; and
b) a pharmaceutically acceptable carrier.

Embodiment 156: The pharmaceutical composition of embodiment 155, wherein the virus is an adenovirus, adeno-associated virus, retrovirus, lentivirus, sendai virus, herpes simplex virus, vaccinia virus, or any hybrid virus thereof.

Embodiment 157: The pharmaceutical composition of embodiment 155, wherein the virus is a herpes simplex virus (HSV).

Embodiment 158: The pharmaceutical composition of any of embodiments 155 to 157, wherein the virus is replication-defective.

Embodiment 159: The pharmaceutical composition of any of embodiments 155 to 158, wherein the herpes simplex virus is a herpes simplex type 1 virus, a herpes simplex type 2 virus, or any derivatives thereof.

Embodiment 160: The pharmaceutical composition of any of embodiments 155 to 159, wherein the vector is an HSV-1 amplicon or an HSV-1 hybrid amplicon.

Embodiment 161: The pharmaceutical composition of embodiment 160, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 162: The pharmaceutical composition of any of embodiments 155 to 159, wherein the vector is a recombinant herpes simplex virus genome.

Embodiment 163: The pharmaceutical composition of embodiment 162, wherein the recombinant herpes simplex virus genome is a recombinant HSV-1 genome, a recombinant HSV-2 genome, or any derivatives thereof.

Embodiment 164: The pharmaceutical composition of embodiment 162 or 163, wherein the recombinant herpes simplex virus genome comprises an inactivating mutation in an immediate early herpes simplex virus gene.

Embodiment 165: The pharmaceutical composition of embodiment 164, wherein the herpes simplex virus gene is selected from the group consisting of ICP0, ICP4, ICP22, ICP27, ICP47, tk, UL41, and UL55.

Embodiment 166: The pharmaceutical composition of any of embodiments 162 to 165, wherein the recombinant herpes simplex virus genome comprises an inactivating mutation in the ICP4 and ICP22 genes.

Embodiment 167: The pharmaceutical composition of any of embodiments 162 to 165, wherein the recombinant herpes simplex virus genome comprises an inactivating mutation in the ICP0 and ICP4 genes.

Embodiment 168: The pharmaceutical composition of embodiment 166 or 167, wherein the recombinant herpes simplex virus genome comprises an inactivating mutation in the ICP0, ICP4, and ICP22 genes.

Embodiment 169: The pharmaceutical composition of any of embodiments 166 to 168, wherein the recombinant herpes simplex virus genome comprises an inactivating mutation in the ICP0, ICP4, ICP22, and ICP27 genes.

Embodiment 170: The pharmaceutical composition of any of embodiments 166 to 169, wherein the recombinant herpes simplex virus genome comprises an inactivating mutation in the ICP0, ICP4, ICP22, ICP27, and UL55 genes.

Embodiment 171: The pharmaceutical composition of any of embodiments 166 to 170, wherein the inactivating mutation is a deletion of the coding sequence of the genes.

Embodiment 172: The pharmaceutical composition of any of embodiments 166 to 171, further comprising an inactivating mutation in the ICP47 gene.

Embodiment 173: The pharmaceutical composition of any of embodiments 162 to 172, further comprising an inactivating mutation in the UL41 gene.

Embodiment 174: The pharmaceutical composition of any of embodiments 162 to 173, wherein the recombinant herpes simplex virus genome comprises the one or more transgenes within one or more viral gene loci.

Embodiment 175: The pharmaceutical composition of any of embodiments 162 to 174, wherein the recombinant herpes simplex virus genome comprises the one or more transgenes within one or more of the ICP4 viral gene loci.

Embodiment 176: The pharmaceutical composition of any of embodiments 162 to 175, wherein the recombinant herpes simplex virus genome comprises the one or more transgenes within the UL41 viral gene locus.

Embodiment 177: The pharmaceutical composition of embodiment 155, wherein the vector is capable of replicating within a target cell when delivered into said target cell.

Embodiment 178: The pharmaceutical composition of embodiment 155, wherein the pharmaceutically acceptable carrier is suitable for topical or transdermal administration.

Embodiment 179: The pharmaceutical composition of embodiment 155, wherein the pharmaceutically acceptable carrier is suitable for subcutaneous or intradermal administration.

Embodiment 180: The pharmaceutical composition of embodiment 155, wherein the one or more transgenes comprises an miRNA binding site.

Embodiment 181: The pharmaceutical composition of any of embodiments 155 to 180, wherein the vector comprises a transgene encoding a Collagen alpha-1 (VII) chain polypeptide.

Embodiment 182: The pharmaceutical composition of any of embodiments 155 to 180, wherein the vector comprises a transgene encoding a Lysyl hydroxylase 3 polypeptide.

Embodiment 183: The pharmaceutical composition of any of embodiments 155 to 180, wherein the vector comprises a transgene encoding a Keratin type I cytoskeletal 17 polypeptide.

Embodiment 184: The pharmaceutical composition of any of embodiments 155 to 180, wherein the Collagen alpha-1 (VII) chain polypeptide has at least 80% sequence identity to the sequence of SEQ ID NO: 2.

Embodiment 185: The pharmaceutical composition of any of embodiments 155 to 180, wherein the Collagen alpha-1 (VII) chain polypeptide is a fragment, wherein the fragment has at least 100 consecutive amino acids of SEQ ID NO: 2.

Embodiment 186: The pharmaceutical composition of any of embodiments 155 to 180, wherein the Collagen alpha-1 (VII) chain polypeptide enhances, increases, augments, and/or supplements anchoring fibril formation of a subject when the polypeptide is expressed in one or more target cells of the subject.

Embodiment 187: The pharmaceutical composition of any of embodiments 155 to 180, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 188: The pharmaceutical composition of any of embodiments 155 to 180, wherein the Lysyl hydroxylase 3 polypeptide has at least 80% sequence identity to the sequence of SEQ ID NO: 4.

Embodiment 189: The pharmaceutical composition of any of embodiments 155 to 180, wherein the Lysyl hydroxylase 3 polypeptide is a fragment, wherein the fragment has at least 100 consecutive amino acids of SEQ ID NO: 4.

Embodiment 190: The pharmaceutical composition of any of embodiments 155 to 180, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 191: The pharmaceutical composition of any of embodiments 155 to 180, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 192: The pharmaceutical composition of any of embodiments 155 to 180, wherein the Keratin type I cytoskeletal 17 polypeptide has at least 80% sequence identity to the sequence of SEQ ID NO: 30.

Embodiment 193: The pharmaceutical composition of any of embodiments 155 to 180, wherein the Keratin type I cytoskeletal 17 polypeptide is a fragment, wherein the fragment has at least 100 consecutive amino acids of SEQ ID NO: 30.

Embodiment 194: The pharmaceutical composition of any of embodiments 155 to 180, wherein the Keratin type I cytoskeletal 17 polypeptide enhances, increases, augments, and/or supplements wound healing in a subject.

Embodiment 195: The pharmaceutical composition of any of embodiments 155 to 194, wherein the vector comprises at least a first transgene and a second transgene.

Embodiment 196: The pharmaceutical composition of embodiment 195, wherein the first transgene and the second transgene each encode a Collagen alpha-1 (VII) chain polypeptide.

Embodiment 197: The pharmaceutical composition of embodiment 195, wherein the first transgene encodes a Collagen alpha-1 (VII) chain polypeptide and the second transgene encodes a Lysyl hydroxylase 3 polypeptide.

Embodiment 198: The pharmaceutical composition of embodiment 195, wherein the first transgene encodes a Collagen alpha-1 (VII) chain polypeptide and the second transgene encodes a Keratin type I cytoskeletal 17 polypeptide.

Embodiment 199: The pharmaceutical composition of embodiment 195, wherein the first transgene encodes a Lysyl hydroxylase 3 polypeptide and the second transgene encodes a Keratin type I cytoskeletal 17 polypeptide.

Embodiment 200: The pharmaceutical composition of embodiment 155, wherein the vector comprises at least a first transgene, a second transgene, and a third transgene.

Embodiment 201: The pharmaceutical composition of embodiment 200, wherein the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Embodiment 202: A method of providing prophylactic, palliative, or therapeutic relief of a wound, disorder, or disease of the skin in a subject, the method comprising administering to the subject a pharmaceutical composition comprising a vector, wherein the vector is a recombinant herpes simplex virus genome, and wherein the pharmaceutical composition is capable of enhancing, increasing, augmenting, and/or supplementing the levels of a Collagen alpha-1 (VII) chain polypeptide and/or a Lysyl hydroxylase 3 polypeptide and/or a Keratin type I cytoskeletal 17 polypeptide in one or more cells of the subject.

Embodiment 203: The method of embodiment 202, wherein the pharmaceutical composition comprises:
 a) a virus comprising the vector, wherein the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof; and
 b) a pharmaceutically acceptable carrier.

Embodiment 204: The method of embodiment 203, wherein the virus is an adenovirus, adeno-associated virus, retrovirus, lentivirus, sendai virus, herpes simplex virus, vaccinia virus, or any hybrid virus thereof.

Embodiment 205: The method of embodiment 203, wherein the virus is a herpes simplex virus (HSV).

Embodiment 206: The method of any of embodiments 203 to 205, wherein the virus is replication-defective.

Embodiment 207: The method of any of embodiment 203 to 206, wherein the herpes simplex virus is a herpes simplex type 1 virus, a herpes simplex type 2 virus, or any derivatives thereof.

Embodiment 208: The method of any of embodiments 202 to 207, wherein the recombinant herpes simplex virus genome is a recombinant HSV-1 genome, a recombinant HSV-2 genome, or any derivatives thereof.

Embodiment 209: The method of embodiment 202 to 208, wherein the recombinant herpes simplex virus genome comprises an inactivating mutation in an immediate early herpes simplex virus gene.

Embodiment 210: The method of embodiment 209, wherein the herpes simplex virus gene is selected from the group consisting of ICP0, ICP4, ICP22, ICP27, ICP47, tk, UL41, and UL55.

Embodiment 211: The method of any of embodiments 202 to 210, wherein the recombinant herpes simplex virus genome comprises an inactivating mutation in the ICP4 and ICP22 genes.

Embodiment 212: The method of any of embodiments 202 to 210, wherein the recombinant herpes simplex virus genome comprises an inactivating mutation in the ICP0 and ICP4 genes.

Embodiment 213: The method of embodiment 211 or 212, wherein the recombinant herpes simplex virus genome comprises an inactivating mutation in the ICP0, ICP4, and ICP22 genes.

Embodiment 214: The method of any of embodiments 211 to 213, wherein the recombinant herpes simplex virus genome comprises an inactivating mutation in the ICP0, ICP4, ICP22, and ICP27 genes.

Embodiment 215: The method of any of embodiments 211 to 214, wherein the recombinant herpes simplex virus genome comprises an inactivating mutation in the ICP0, ICP4, ICP22, ICP27, and UL55 genes.

Embodiment 216: The method of any of embodiments 211 to 215, wherein the inactivating mutation is a deletion of the coding sequence of the genes.

Embodiment 217: The method of any of embodiments 211 to 216, further comprising an inactivating mutation in the ICP47 gene.

Embodiment 218: The method of any of embodiments 202 to 217, further comprising an inactivating mutation in the UL41 gene.

Embodiment 219: The method of any of embodiments 202 to 218, wherein the recombinant herpes simplex virus genome comprises the one or more transgenes within one or more viral gene loci.

Embodiment 220: The method of any of embodiments 202 to 219, wherein the recombinant herpes simplex virus genome comprises the one or more transgenes within one or more of the ICP4 viral gene loci.

Embodiment 221: The method of any of embodiments 202 to 220, wherein the recombinant herpes simplex virus genome comprises the one or more transgenes within the UL41 viral gene locus.

Embodiment 222: The method of embodiment 202, wherein the vector is capable of replicating within a target cell when delivered into said target cell.

Embodiment 223: The method of embodiment 203, wherein the pharmaceutically acceptable carrier is suitable for topical or transdermal administration.

Embodiment 224: The method of embodiment 203, wherein the pharmaceutically acceptable carrier is suitable for subcutaneous or intradermal administration.

Embodiment 225: The method of embodiment 203, wherein the one or more transgenes comprises an miRNA binding site.

Embodiment 226: The method of any of embodiments 202 to 225, wherein the vector comprises a transgene encoding a Collagen alpha-1 (VII) chain polypeptide.

Embodiment 227: The method of any of embodiments 202 to 225, wherein the vector comprises a transgene encoding a Lysyl hydroxylase 3 polypeptide.

Embodiment 228: The method of any of embodiments 202 to 225, wherein the vector comprises a transgene encoding a Keratin type I cytoskeletal 17 polypeptide.

Embodiment 229: The method of any of embodiments 202 to 225, wherein the Collagen alpha-1 (VII) chain polypeptide has at least 80% sequence identity to the sequence of SEQ NO: 2.

Embodiment 230: The method of any of embodiments 202 to 225, wherein the Collagen alpha-1 (VII) chain polypeptide is a fragment, wherein the fragment has at least 100 consecutive amino acids of SEQ ID NO: 2.

Embodiment 231: The method of any of embodiments 202 to 225, wherein the Collagen alpha-1 (VII) chain polypeptide enhances, increases, augments, and/or supplements anchoring fibril formation of a subject when the polypeptide is expressed in one or more target cells of the subject.

Embodiment 232: The method of any of embodiments 202 to 225, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 233: The method of any of embodiments 202 to 225, wherein the Lysyl hydroxylase 3 polypeptide has at least 80% sequence identity to the sequence of SEQ ID NO: 4.

Embodiment 234: The method of any of embodiments 202 to 225, wherein the Lysyl hydroxylase 3 polypeptide is a fragment, wherein the fragment has at least 100 consecutive amino acids of SEQ ID NO: 4.

Embodiment 235: The method of any of embodiments 202 to 225, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 236: The method of any of embodiments 202 to 225, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 237: The method of any of embodiments 202 to 225, wherein the Keratin type I cytoskeletal 17 polypeptide has at least 80% sequence identity to the sequence of SEQ ID NO: 30.

Embodiment 238: The method of any of embodiments 202 to 225, wherein the Keratin type I cytoskeletal 17 polypeptide is a fragment, wherein the fragment has at least 100 consecutive amino acids of SEQ ID NO: 30.

Embodiment 239: The method of any of embodiments 202 to 225, wherein the Keratin type I cytoskeletal 17 polypeptide enhances, increases, augments, and/or supplements wound healing in a subject.

Embodiment 240: The method of any of embodiments 202 to 239, wherein the vector comprises at least a first transgene and a second transgene.

Embodiment 241: The method of embodiment 240, wherein the first transgene and the second transgene each encode a Collagen alpha-1 (VII) chain polypeptide.

Embodiment 242: The method of embodiment 240, wherein the first transgene encodes a Collagen alpha-1 (VII) chain polypeptide and the second transgene encodes a Lysyl hydroxylase 3 polypeptide.

Embodiment 243: The method of embodiment 240, wherein the first transgene encodes a Collagen alpha-1 (VII) chain polypeptide and the second transgene encodes a Keratin type I cytoskeletal 17 polypeptide.

Embodiment 244: The method of embodiment 240, wherein the first transgene encodes a Lysyl hydroxylase 3 polypeptide and the second transgene encodes a Keratin type I cytoskeletal 17 polypeptide.

Embodiment 245: The method of any of embodiments 202 to 239, wherein the vector comprises at least a first transgene, a second transgene, and a third transgene.

Embodiment 246: The method of embodiment 245, wherein the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Embodiment 247: The method of any of embodiments 202 to 246, wherein the pharmaceutical composition is administered topically or transdermally to the subject.

Embodiment 248: The method of any of embodiments 202 to 246, wherein the pharmaceutical composition is administered subcutaneously or intradermally to the subject.

Embodiment 249: The method of any of embodiments 202 to 248, wherein the pharmaceutical composition is administered one, two three, four, five or more times per day.

Embodiment 250: The method of any of embodiments 202 to 249, wherein the pharmaceutical composition is administered to one or more affected and/or unaffected areas of the subject.

Embodiment 251: The method of any of embodiments 202 to 250, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

The specification is considered to be sufficient to enable one skilled in the art to practice the invention. Various modifications of the invention in addition to those shown and described herein will become apparent to those skilled in the art from the foregoing description and fall within the scope of the appended claims.

EXAMPLES

The present disclosure will be more fully understood by reference to the following example. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1

Generating Modified Herpes Simplex Virus Vectors, and Producing/Isolating Virus Containing the Vectors To make modified herpes simplex virus genome vectors capable of expressing one or more transgenes in a target mammalian cell, a herpes simplex virus genome (FIG. 1A) is modified to inactivate the immediate early genes ICP0, ICP4, and ICP27, while the immediate early gene ICP22 is modified to include a heterologous, inducible promoter. This decreases the toxicity of the genome in mammalian cells. Next, a cassette is inserted into the modified herpes virus genome by restriction cloning. The cassette contains a heterologous promoter capable of expressing a transgene in a target mammalian cell. The promoter is operably linked to the nucleic acid sequence encoding a Collagen alpha-1 (VII) chain polypeptide, as well as downstream regulatory elements (FIG. 1B) ensuring proper production of the mRNA. Alternatively, the cassette includes two transgenes, each of which has its own heterologous promoter operably linked to the nucleic acid encoding either a Collagen alpha-1 (VII) chain polypeptide or a Lysyl hydroxylase 3 polypeptide. The transgenes are encoded either on the same strand of DNA (FIG. 1C), or on opposite strands of DNA in an antisense orientation (FIG. 1D). Linking each transgene with its own promoter and regulatory elements allows for independent expression of each coding sequence on separate mRNA transcripts. Expressing the transgenes from distinct promoters allows for the ability to operably link the coding sequences to different promoter types, which can drive expression of the transgenes at different levels, at different times in the cell cycle, in different cell types, or under the control of different inducers or repressors.

Figure 1F:
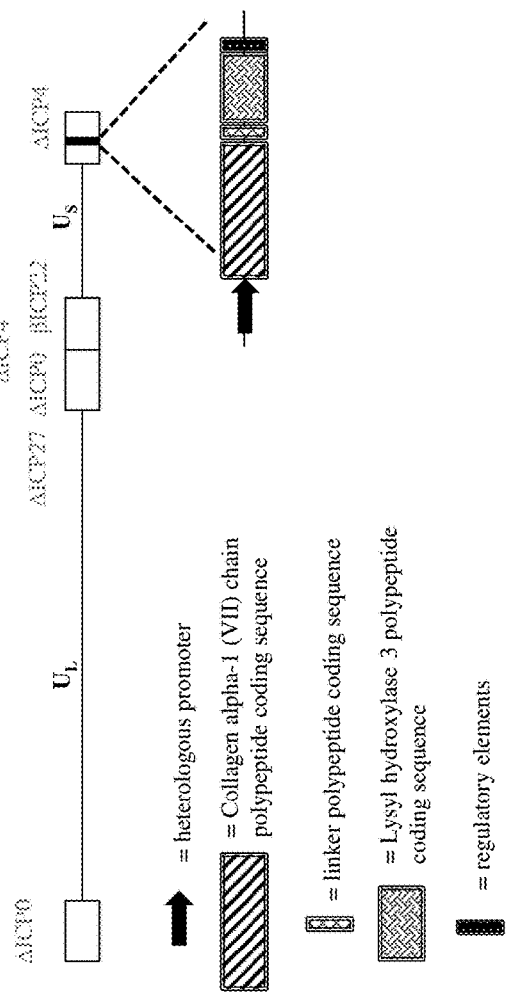

A modified herpes virus genome is also constructed that includes a cassette expressing a single mRNA encoding a Collagen alpha-1 (VII) chain polypeptide and a Lysyl hydroxylase 3 polypeptide separated by an internal ribosomal entry site (FIG. 1E). This allows for approximately equimolar production of each polypeptide when expressed in a target cell. Finally, a modified herpes virus genome is constructed that includes a cassette expressing a chimeric polypeptide. This chimeric polypeptide includes, from N-terminus to C-terminus, a Collagen alpha-1 (VII) chain polypeptide, a cleavable peptide linker, and a Lysyl hydroxylase 3 polypeptide (FIG. 1F).

Figure 2E:
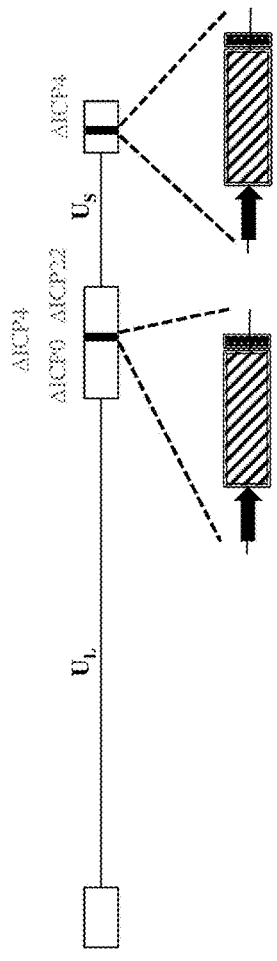
Figure 2F:
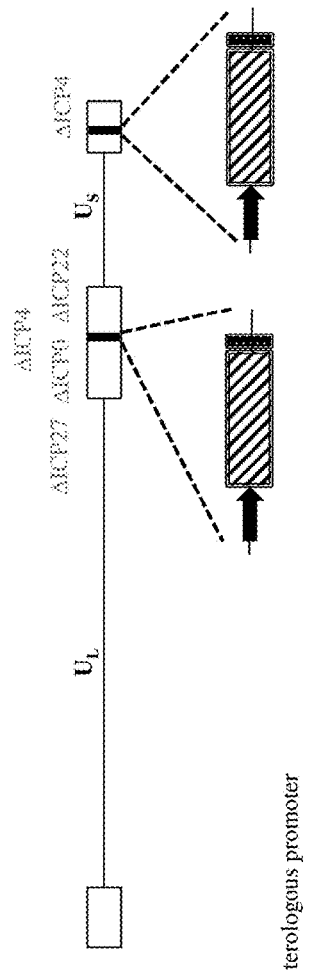

Additional modified herpes virus genomes are constructed that include two cassettes, each expressing Collagen alpha-1 (VII) chain polypeptides, where each cassette is inserted into a copy of the ICP4 gene locus (FIGS. 2B-2G) of the wild-type herpes simplex virus genome (FIG. 2A). These additional recombinant herpes virus genomes are constructed with various combinations of herpes virus gene deletions/modifications.

A recombinant herpes virus genome is constructed which contains deletions of the coding sequences of both copies of the ICP4 gene, as well as deletions of the coding sequences of the ICP27 and UL55 genes. These recombinant viruses are further modified to contain inactivating mutations in the promoter regions of the ICP22 and ICP47 genes such that the ICP22 and ICP47 genes are not expressed with normal kinetics (FIG. 2B).

Figure 2G:
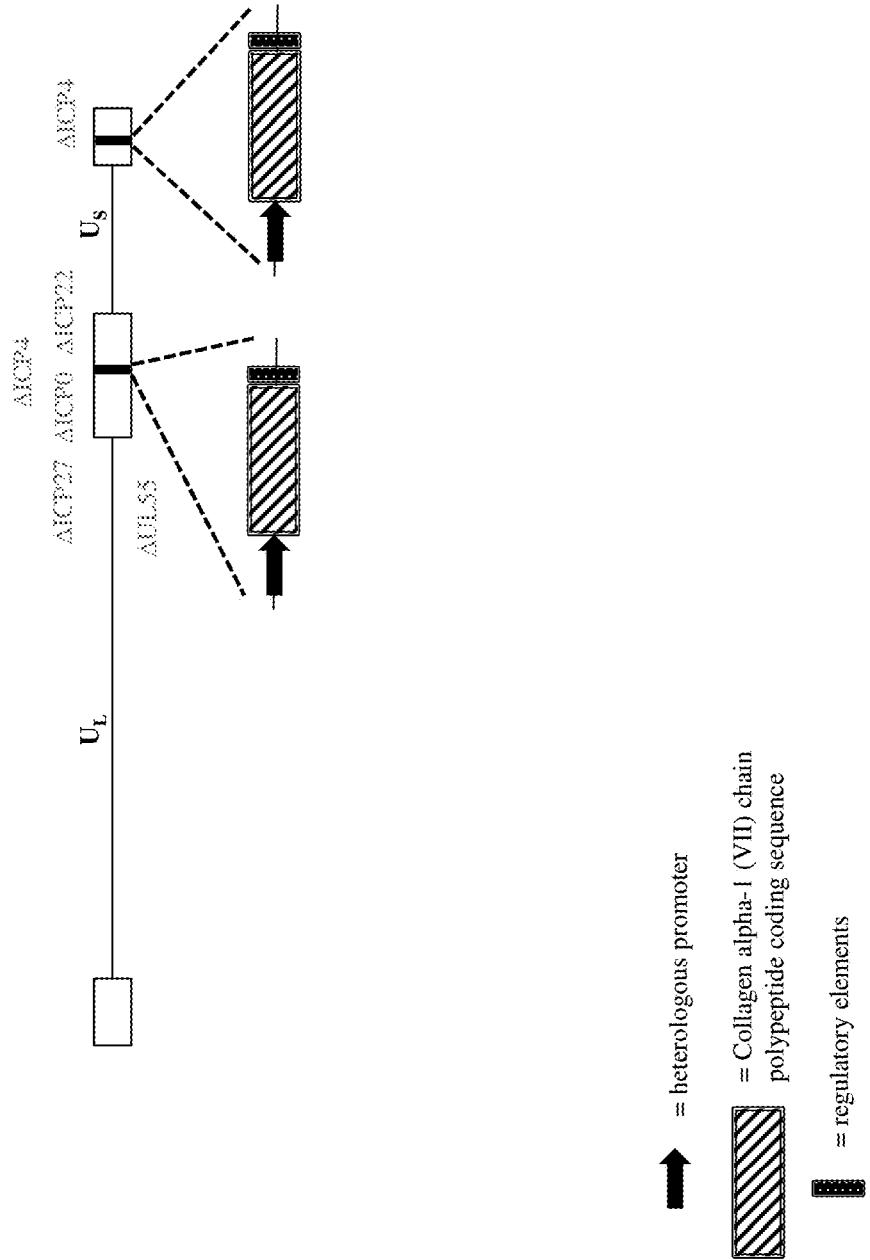

Further recombinant herpes simplex viruses are constructed which incorporate expression cassettes for Collagen alpha-1 (VII) chain polypeptides into both loci of the herpes ICP4 genes. These recombinant viruses include: viruses containing deletions of the coding sequences of the ICP22 gene and both copies of the ICP4 gene (FIG. 2C); deletions of the coding sequences of the ICP0 gene and both copies of the ICP4 gene (FIG. 2D); deletions of the coding sequences of the ICP0 and ICP22 genes, and both copies of the ICP4 gene (FIG. 2E); deletions of the coding sequences of the ICP0, ICP22, and ICP27 genes, and both copies of the ICP4 gene (FIG. 2F); and deletions of the coding sequences of the ICP0, ICP22, ICP27, and UL55 genes, and both copies of the ICP4 gene (FIG. 2G). Additional vectors are constructed based upon the vectors shown in FIGS. 2C-2G which further comprise one or more transgenes encoding one or more additional effectors (e.g., LH3, KRT17) in the ICP0 and/or UL41 loci.

These modified herpes simplex virus genome vectors are transfected into engineered Vero cells that are modified to express herpes virus genes. These engineered Vero cells secrete replication-defective herpes simplex virus with the modified genomes packaged within into the supernatant. The supernatant is then collected, concentrated, and sterile filtered through a 5 μm filter.

Example 2

Rescuing Col7 Expression with Replication Defective HSV-1

The following example describes the construction of a replication defective herpes simplex type-1 virus modified to express the human COL7A1 gene, and use of such a viral vector to rescue several defects observed in cells isolated from RDEB patients.

Methods

Cells and Cell Culture

Normal and RDEB human dermal fibroblasts and keratinocytes were isolated as described previously (NG, Y. Z. et al. (2012) *Cancer Res.* 72: 3522-3534; Rheinwald, J. G. and Green, H. (1975) *Cell* 6: 331-42). Cells were cultured according to standard techniques.

Construction of KB103

The KB103 vector was generated from D3GFP, a replication-defective HSV-1 vector backbone harboring GFP in place of the viral ICP4. The sequence of the GFP in D3GFP was replaced with the coding sequence of human COL7A1 using a transfer plasmid by cloning COL7A1 into the EcoRI site of the ICP4 recombination plasmid pSASB3. A mixed transfection/infection of the COL7A1 containing transfer plasmid and D3GFP vector was performed on VeroD cells. Resulting plaques which did not express GFP were isolated and tested by western blot for Col7 protein expression.

Virus Purification

KB103 virus was purified according to standard techniques (See Diefenbach, R. and Fraefel, C. *Herpes Simplex Virus*. New York: Humana Press, 2014).

Viral Infections

Cells were seeded in duplicates or triplicates in six-well plates at approximately 50% confluency one day prior to viral infection. An additional well was seeded in parallel for cell counting and MOI determination. 24 hours after cell seeding, cells from one well were trypsinized and counted to calculate the MOI, and viral stocks were thawed and diluted in cell culture medium to achieve the desired MOI. Culture medium was aspirated from each well to be infected, and 500 μL of KB103-containing medium (or control medium) was added to each well. Plates were incubated at 37° C. with 5-7.5% $CO_2$ for 1.5-2 hours with intermittent rocking every 15-20 minutes, then 1.5-2 mL of complete cell culture medium was added to each well, and the plates were incubated for 24-72 hours at 37° C. After incubation, the cells and supernatants were harvested and processed for analysis.

mRNA Quantification

Col7 transcripts were amplified from RNA isolated from primary RDEB keratinocytes after infection using a SYBR PCR assay (Sybr Select Master Mix, Life Technologies) according to the manufacturer's protocol. Col7 transcript levels were normalized to β-actin transcript levels.

Western Blot Analysis

Cell lysates were generated from cells 48 hours post-infection, and western blots were carried out according to standard techniques using the following antibodies: rabbit anti-human Col7 polyclonal antibody (Sigma, Cat. # HPA042420), mouse anti-human GAPDH antibody (Santa Cruz Biotechnology, Cat. # sc-365062), rabbit anti-LH3 antibody (Protein Tech, Cat. # 11027-1-AP), and mouse anti-TSP1 antibody (Santa Cruz Biotechnology, Cat. # sc-59887).

Immunofluorescence

Cells were plated on cover slips prior to infection, fixed 48 hours post-infection, and stained with a primary rabbit anti-human Col7 polyclonal antibody (Sigma, Cat. # HPA042420), washed, and further stained with a fluorescently labelled anti-rabbit secondary antibody (Invitrogen, Cat. 3 A11012). Cell nuclei were stained with DAPI using standard techniques.

Cellular Adhesion 96-well plates were coated with 10, 20, or 50 μg/mL rat tail Collagen 1 (Marathon Laboratory Supply) or human fibronectin (Sigma-Aldrich) in 100 μL reaction volume at 4° C. overnight, then washed with PBS, and blocked with PBS+0.1% BSA for 1 hour at 37° C. Mock (control) infected or KB103 infected RDEB keratinocytes ($2.4*10^4$ cells in 100 μL of DMEM/HamF12+0.1% BSA) were added to the plates and incubated at 37° C. for 40-90 minutes. Wells were washed three times with PBS to remove any unbound cells, and adherent cells were fixed with PFE for 20 minutes. The fixed cells were then treated with 70% ethanol, stained with crystal violet, resolved in 100% ethanol, and were quantified by measuring absorbance at 630 nm.

Skin Equivalent (SE) Organotypic Cultures

A skin equivalent organotypic culture composed of RDEB fibroblasts and keratinocytes was used to evaluate the expression of Col7 at the basement membrane zone (BMZ). Briefly, RDEB fibroblasts ($2*10^5$ cells per well) were embedded in fibrin gel matrix in six-well plates and incubated in DMEM+10% serum containing ascorbic acid and aprotinin for 24 hours at 37° C. and 5% $CO_2$. RDEB keratinocytes ($1*10^6$ cells per well) were then seeded on the matrix, grown to confluence in DMEM/F-12 keratinocyte medium containing 50 mg/mL of ascorbic acid, and raised at the air-liquid interface. Two days post raising, KB103 virus was added to the cultures (at an MOI of 3) and incubated for 1.5 hours. Following incubation, cultures were washed and incubated for 5-14 days to favor stratification and differentiation into an epithelium. Skin equivalents (SEs) were manually detached from the plates and embedded in optimal cutting temperature compound, frozen in liquid nitrogen, and cut into 6 mm sections for immunofluorescence staining with a monoclonal anti-Col7 antibody.

Results

KB103 Pharmacology in Normal and RDEB Cells

A number of ex vivo approaches have been undertaken to deliver the human COL7A1 gene to primary cells isolated from RDEB patients in an attempt to correct Col7 deficiencies (Ortiz-Urda, S. et al. (2003) *J. Clin. Invest.* 111(2) 251-5; Woodley, D. T. et al. (2003) *J. Invest. Dematol.* 121(5) 1021-8). Although successful in achieving durable correction of key disease features, an ex vivo gene delivery strategy for treating epidermolysis bullosa has a number of key disadvantages, including high cost, poor graft takes, surgical debridement, complex bandaging and wound care, and the high potential for post-surgical infection. An attractive alternate route for gene therapy is the use of viral or non-viral vectors to deliver gene products. However, non-viral vectors using plasmid DNA suffer from very low gene transfer efficiency when injected or topically administered, while the most widely used viral vectors in human gene therapy trials (retroviral vectors) do not infect non-dividing cells. This is problematic for gene delivery to the skin, as manipulation of the tissue (such as wounding) to create an adequate population of dividing cells would be required for retroviral gene therapy. Large-capacity adenoviral vectors can deliver genome-sized transcription units and survive in transduced cells for long periods of time, but the toxicity and immunogenicity of adenoviral particles, as well as the requirements for helper virus during vector production, remain as significant hurdles for their use in human gene therapy strategies. While replication-defective HSV vectors have been employed as delivery vehicles in a number of pre-clinical studies, no pre-clinical evidence supporting the use of HSV-based viral vectors for epidermolysis bullosa or other dermatological applications has been reported.

Figure 3:
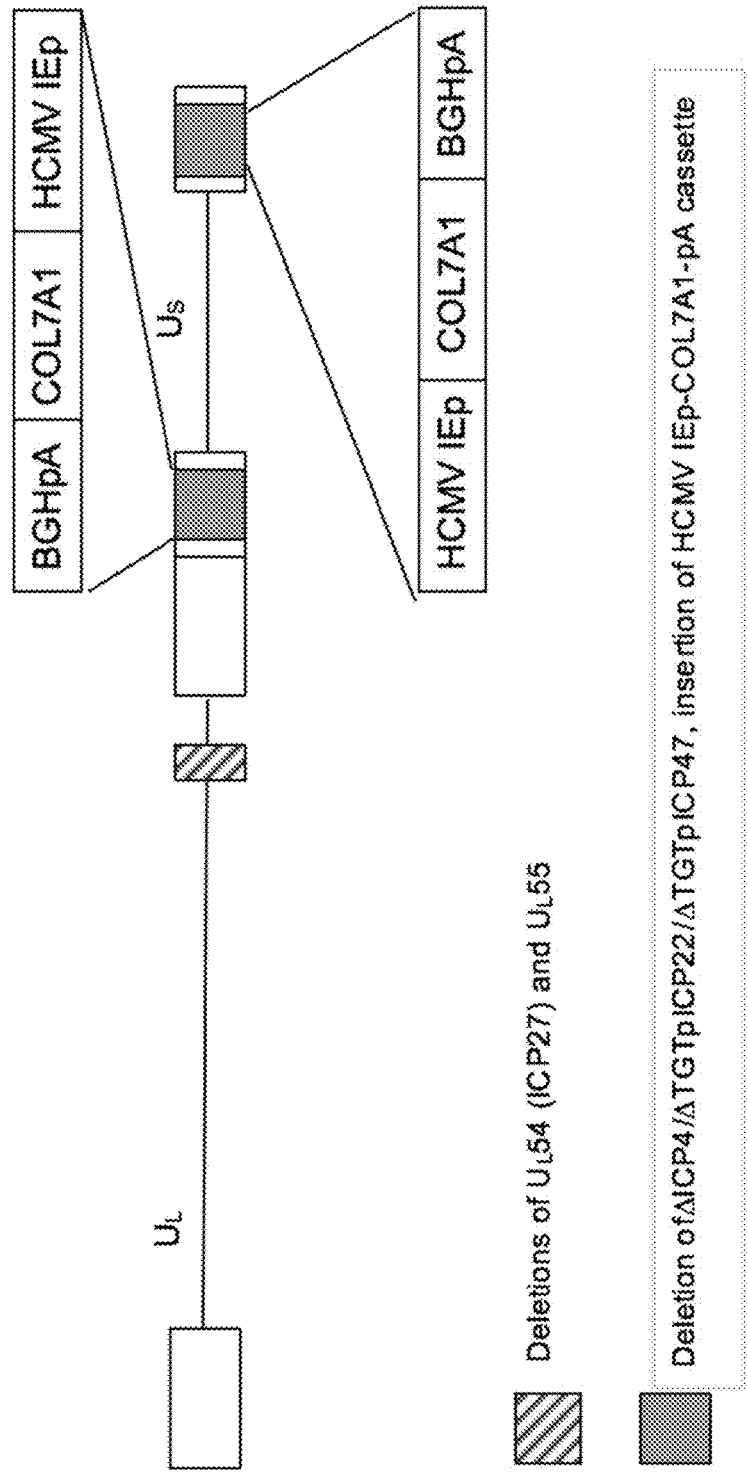
FIG. 3 shows a schematic of "KB103", a replication-defective herpes simplex type-1 virus (HSV-1) carrying a human collagen 7 (COL7A1) expression cassette.

To this end, a replication defective herpes simplex type-1 virus (HSV-1) encoding the human COL7A1 gene was developed as a novel vector useful for gene therapy treatment of DEB patients. An HSV-1 virus was modified to harbor complete deletions of the viral ICP4, ICP27, and UL55 genes, with the ICP4 deletion resulting in the removal of the upstream promoter sequences driving the transcription of the immediate early viral genes ICP22 and ICP47. The virus was further modified to include a human cytomegalovirus (HCMV) immediate early promoter-driven human COL7A1 expression cassette encoded within both copies of the deleted ICP4 loci, resulting in a replication-defective HSV-1 vector, termed KB103, suitable for delivering human COL7A1 to target cells (FIG. 3).

To test the ability of KB103 to deliver and express Col7 in human cells, and to rescue Col7 deficiencies in RDEB patients, patient-derived human dermal fibroblasts and keratinocytes were isolated from healthy individuals, as well as individuals suffering from RDEB, and these primary cells were infected with KB103 at various MOIs. 24-72 hours post infection, COL7A1 gene expression was measured by real-time PCR in transduced cells, while Col7 protein expression was analyzed in parallel by both western blot and immunofluorescence analysis.

Figure 4A:
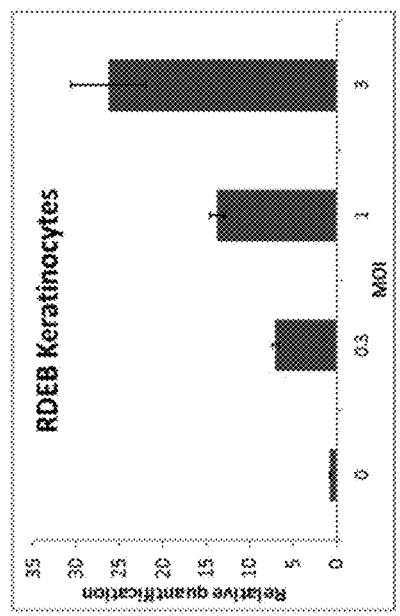
FIGS. 4A-4B show dose-dependent increases in COLT transcript levels from KB103-infeted RDEB human dermal keratinocytes (FIG. 4A) and RDEB human dermal fibroblasts (FIG. 4B). Transcripts were quantified relative to β-actin levels and normalized to expression in uninfected cells.
Figure 4B:
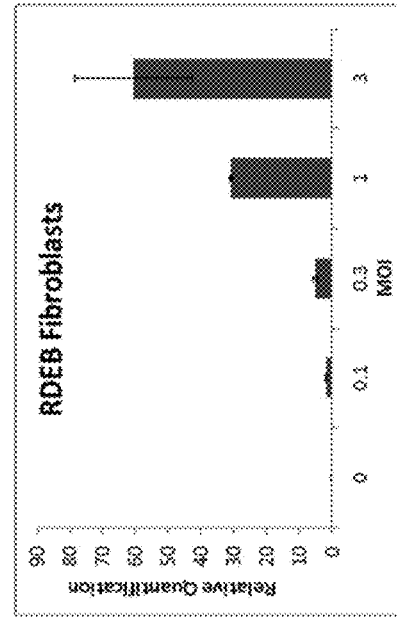

Dose-dependent increases in COL7A1 gene expression were observed in RDEB keratinocytes (FIG. 4A) and fibroblasts (FIG. 4B) infected with KB103. KB103 infection increased COL7A1 gene expression by approximately 7.5 fold, 12.5 fold, and 25 fold in RDEB keratinocytes infected at an MOI of 0.3, 1, and 3, respectively (FIG. 4A). Surprisingly, even more drastic changes in COL7A1 gene expression was observed in infected RDEB fibroblasts. While infections at an MOI of 0.1 and 0.3 showed moderate increases in COL7A1 gene expression, an approximate 30 fold increase in COL7A1 gene expression was measured for RDEB fibroblasts infected at an MOI of 1, while a 60 fold increase was observed in this cell type infected at an MOI of 3. This data showed that COL7A1 gene expression was massively upregulated in RDEB primary cells after infection with KB103.

Figures 5A, 5B:
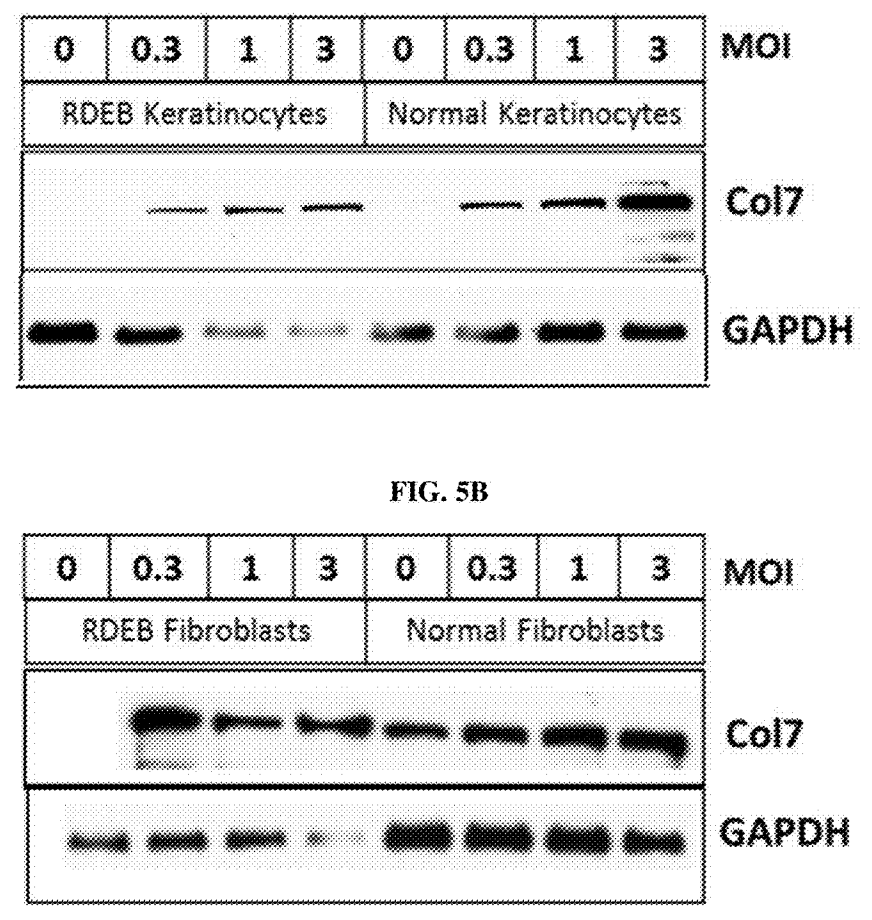

Consequently, robust Col7 protein expression was also observed in cells infected with KB103. Col7 protein expression was detected in both normal and RDEB keratinocytes (FIG. 5A) and fibroblasts (FIG. 5B) 48 hours after infection with KB103 at an MOI of 0.3, 1, and 3, with an apparent dose-dependent increase in Col7 protein expression observed at higher viral titers. Expression of Col7 was observed in both the supernatants and cell lysates from infected cells. Surprisingly, RDEB fibroblasts infected at an MOI of 0.3 showed higher levels of Col7 than was observed in uninfected normal fibroblasts (FIG. 5B), suggesting complete rescue of Col7 expression in RDEB fibroblasts using KB103, even at low viral titers. No obvious effects on cell morphology using high viral doses (MOI of 3) were observed. Additionally, no negative impacts on fibroblast or keratinocyte cell proliferation using high doses of KB103 were indicated in these experiments, as determined by GAPDH expression.

Figure 6:
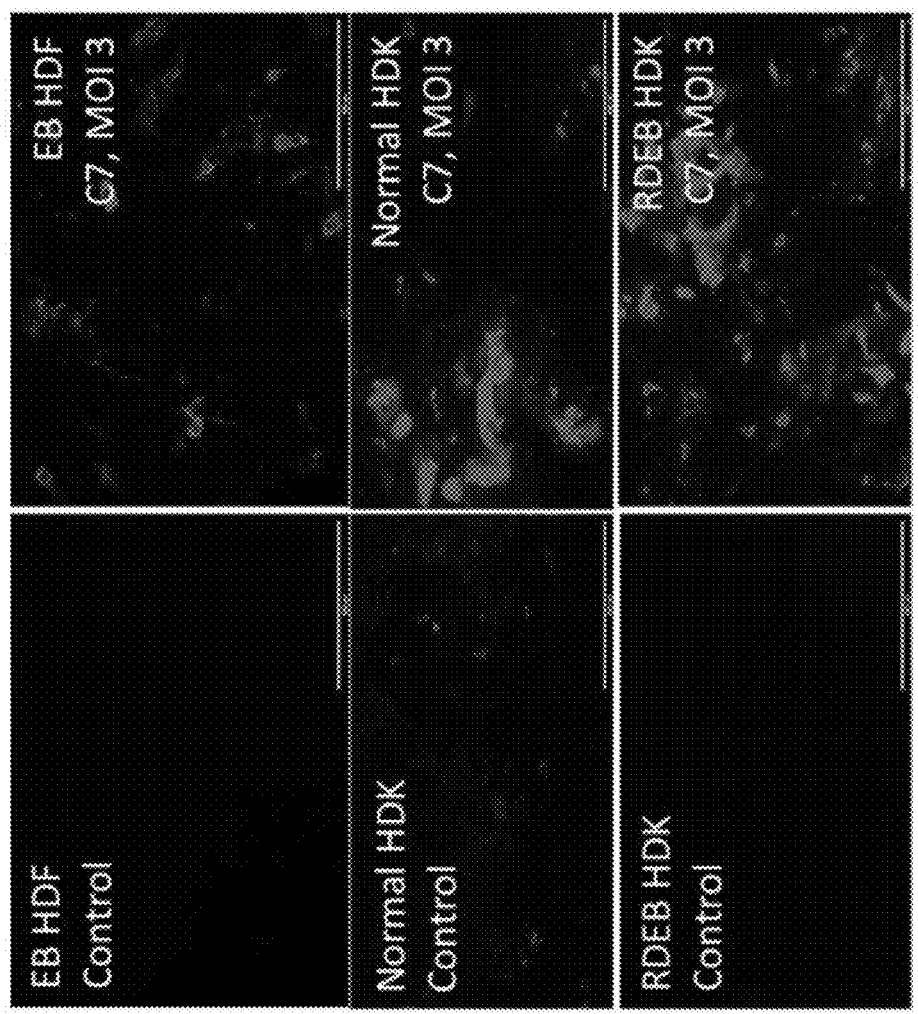
FIG. 6 shows human COL7A1 protein expression in uninfected (control) or KB103 infected (C7, MOI 3) RDEB human dermal fibroblasts (EB HDF), normal human dermal keratinocytes (Normal HDK), and RDEB human dermal keratinocytes (RDEB HDK), as assessed by immunofluorescence.

In agreement with the above experiments, a robust and dose-dependent increase in Col7 protein expression was confirmed in normal and RDEB cells infected with KB103, as demonstrated by immunofluorescent detection of Col7 protein expression (FIG. 6). As expected, no Col7 protein was detected in uninfected RDEB human dermal fibroblasts or keratinocytes; limited Col7 protein was detected in uninfected normal keratinocytes and fibroblasts. However, infection with KB103 was capable of rescuing Col7 protein expression in RDEB fibroblasts and keratinocytes at or above the levels observed in uninfected normal cells. Furthermore, infection efficiency of KB103 (at an MOI of 3) was calculated to be ≥95% based on an assessment of three or more independent panels for each infected replicate, showing that KB103 efficiently delivered and expressed the COL7A1 expression cassette. Taken together, this data suggested that KB103 was capable of delivering and expressing COL7A1 in normal and RDEB primary cells, and that KB103 was well tolerated by both human dermal fibroblasts and keratinocytes.

Functional Assessment of KB103 in RDEB Cells

Figure 7:
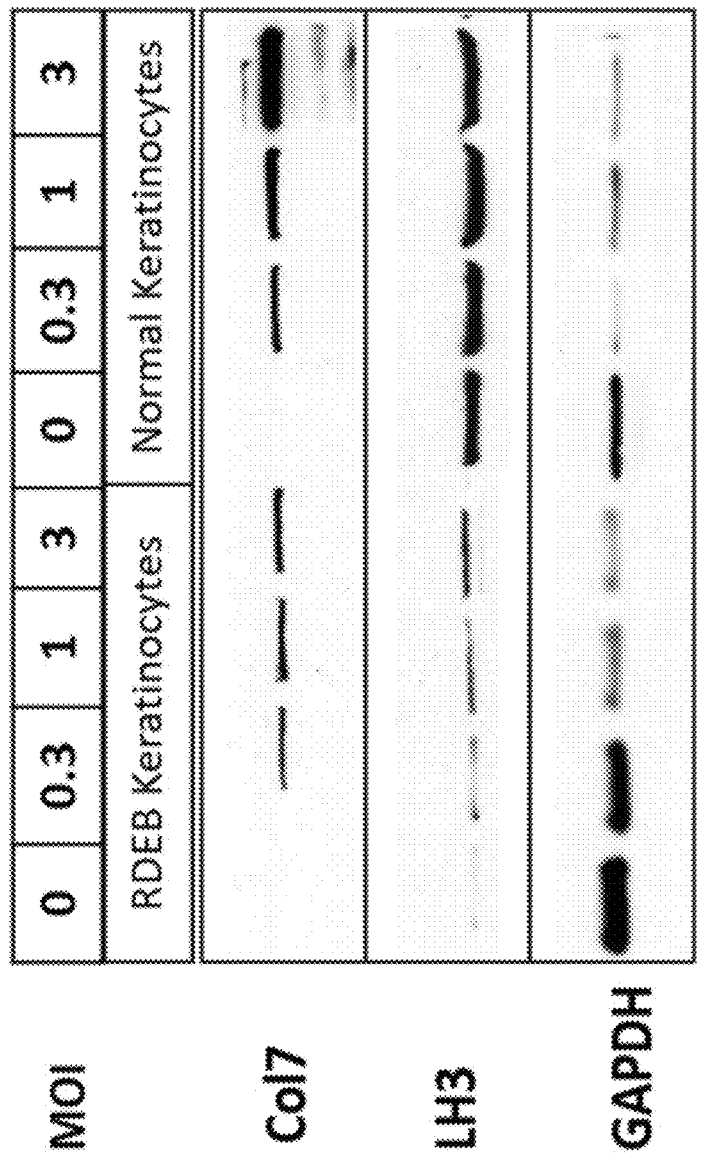
FIG. 7 shows human Col7 and LH3 protein expression in uninfected normal and RDEB human dermal keratinocytes, as well as keratinocytes infected with KB103 at the indicated MOI. Human GAPDH protein expression is shown as a loading control.

The functionality of the human Col7 protein expressed from KB103 was next investigated in human dermal fibroblasts and keratinocytes. First, the effect of Col7 expression on the levels of lysyl hydroxylase 3 was tested in KB103-infected cells. LH3 is required for the deposition and organization of extracellular matrix, and it has been reported that LH3 levels are reduced in RDEB skin (Watt, S. A. et al. (2015) *PLoS One* 10(9): p. e0137639). Little to no LH3 was observed in uninfected RDEB keratinocytes relative to normal keratinocytes (FIG. 7, lanes 1 vs. 5), in agreement with previous studies. However, unexpectedly, a dose-dependent increase in LH3 levels, concomitant with increased Col7 protein expression, was observed in RDEB keratinocytes infected with KB103 (FIG. 7), suggesting that KB103 was capable of rescuing not only Col7 protein expression, but also LH3 expression in RDEB cells.

Figure 8:
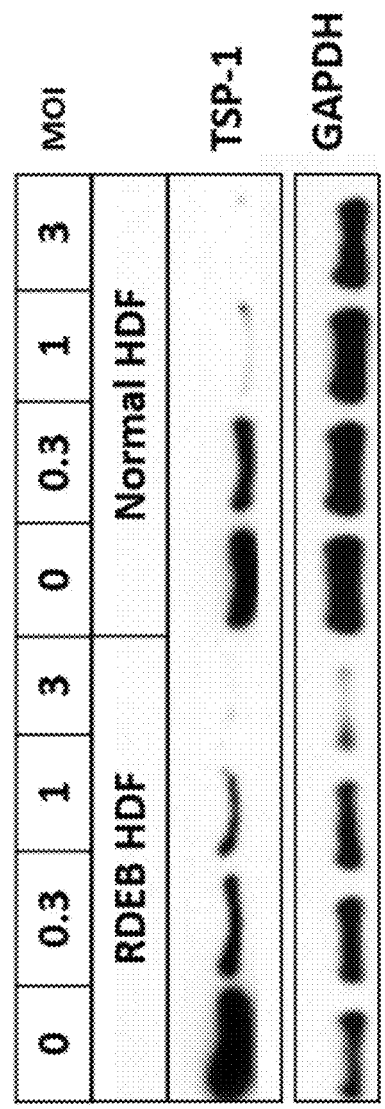
FIG. 8 shows human TSP-1 protein expression in uninfected normal and RDEB human dermal fibroblasts, as well as fibroblasts infected with KB103 at the indicated MOI. Human GAPDH protein expression is shown as a loading control.

Next, the effect of Col7 expression on TSP-1 levels was tested. TSP-1 is a negative regulator of angiogenesis, and has been reported to be increased in RDEB fibroblasts (Ng, Y. Z. et al. (2012) *Cancer Res.* 72(14): p. 3522-34). In agreement with previous studies, higher levels of TSP-1 were observed in uninfected RDEB vs. normal human dermal fibroblasts (FIG. 8, lanes 1 and 4). Surprisingly, TSP-1 protein expression was robustly inhibited upon infection of either normal or RDEB fibroblasts infected with KB103 (FIG. 8). This data suggested that KB103 may not only increase Col7 and LH3 levels in infected cells, but may also promote angiogenesis by inhibiting the negative regulator TSP-1.

Figure 9B:
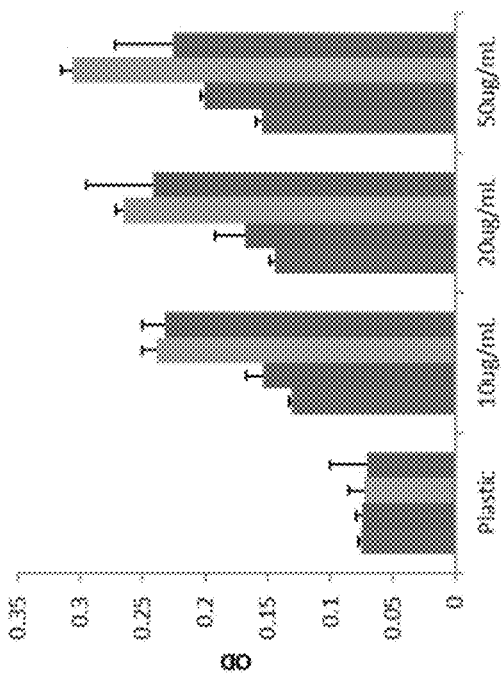
FIGS. 9A-9B show cellular adhesion of uninfected (control) RDEB human dermal keratinocytes, and keratinocytes infected with KB103 at the indicated MOIs, to wells treated with increasing concentration of rat tail Collagen 1 (FIG. 9A) and human Fibronectin (FIG. 9B)
Figure 9A:
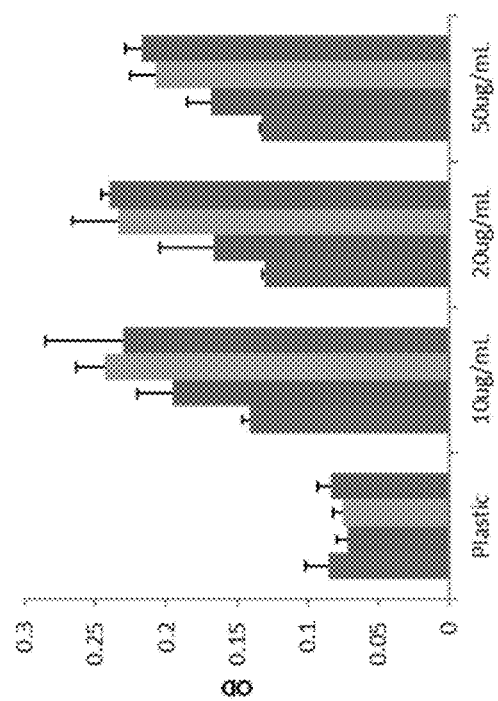

Finally, the ability of KB103 to increase cellular adherence of RDEB keratinocytes to either Collagen 1 or Fibronectin was tested. A dose-dependent increase in cellular adherence to both Collagen 1 and Fibronectin was observed in RDEB keratinocytes infected with KB103 at various MOIs (FIGS. 9A and 9B). Infection of RDEB keratinocytes at all MOIs tested showed higher adhesion to wells treated with all concentrations of both substrates relative to uninfected (control) cells. Taken together, this data indicated that the human Col7 protein expressed from KB103 was functional in the transduced cells. Functionality of this protein was indicated by its ability to increase LH3 protein levels, decrease TSP-1 protein levels, and improve cellular adherence to both Collagen 1 and Fibronectin relative to mock-infected samples.

KB103 Pharmacology and Toxicity in RDEB Organotypic Cultures

Figure 10:
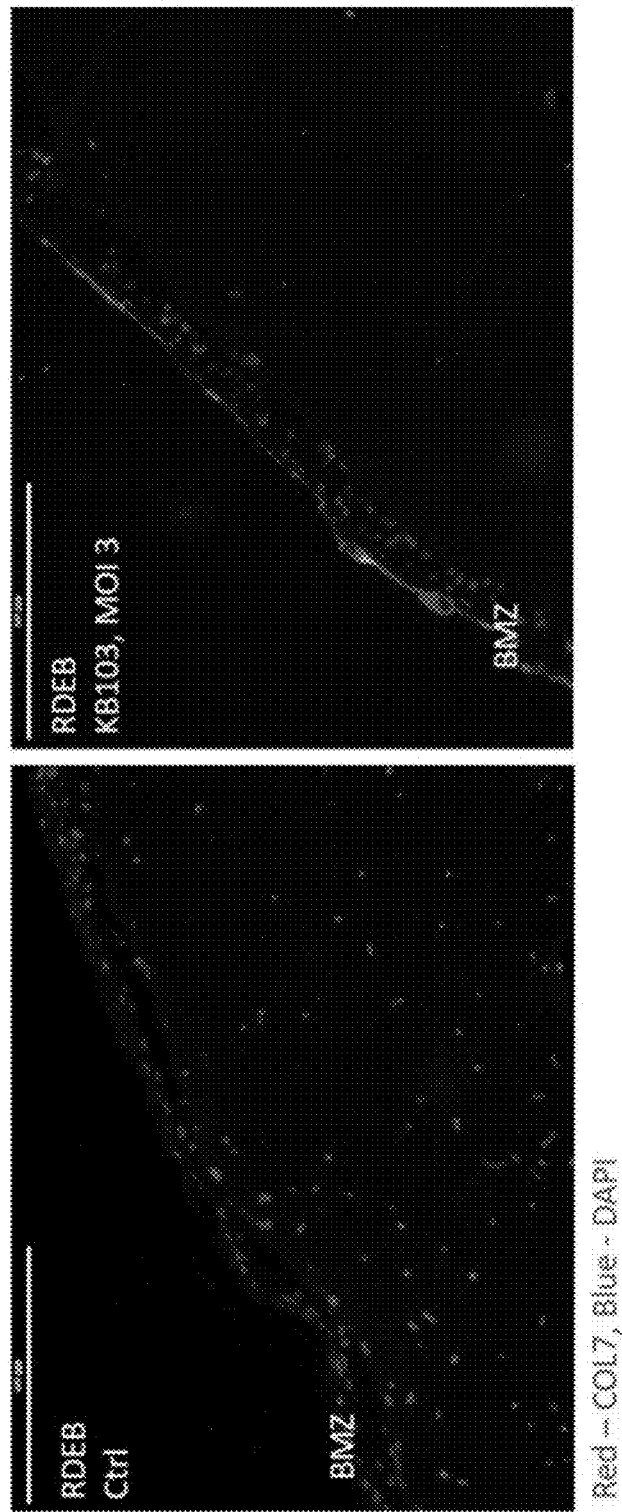
FIG. 10 shows Col7 deposition at the basement membrane zone (BMZ) in KB103 infected skin-equivalent organotypic cultures by immunofluorescence.

A skin equivalent (SE) organotypic culture composed of RDEB fibroblasts and keratinocytes was used to evaluate the expression of Col7 protein expressed from KB103 at the Basement Membrane Zone (BMZ). RDEB fibroblasts and keratinocytes were mock infected or infected with KB103 at an MOI of 3, and incubated for 5 days to favor stratification and differentiation into epithelium. The resulting skin equivalents (SEs) were isolated, sectioned, and stained for immunofluorescence to detect Col7 protein expression. Col7 expression was detected in these organotypic cultures from cells infected with KB103, and the initiation of Col7 protein deposition at the BMZ was observed relative to mock-infected controls (FIG. 10). This data suggested that not only could KB103 deliver COL7A1 and express Col7 protein efficiently, but the Col7 protein began to organize in organotypic cultures similar to the pattern of organization expected for Col7 protein in vivo.

Taken as whole, these experiments revealed, for the first time, that a replication-defective HSV-1 vector may be employed as a vehicle for delivering a COL7A1 expression cassette into primary cells isolated from epidermolysis bullosa patients. Moreover, these data revealed that Col7 protein could be expressed at high levels from this expression cassette in two different human cell types from healthy individuals, as well as individuals suffering from a dermatological disorder. Finally, the Col7 protein was shown to be functional, as it was capable of increasing expression of LH3, decreasing expression of TSP-1, increasing cellular adherence to Collagen 1 and Fibronectin, and could organize in organotypic cultures in a pattern similar to the organization of Col7 in vivo. Without wishing to be bound by theory, the data presented herein suggests that KB103 and other HSV-1 vectors may be useful as novel in vivo treatment strategies for epidermolysis bullosa and/or other dermatological applications.

Example 3

In Vivo Col7 Expression Using Replication Defective HSV-1

The following example describes the use of a replication defective herpes simplex type-1 virus (modified to contain a human COL7A1 transgene) as a delivery vehicle for expression of human Col7 protein in vivo.

Methods

Construction and Purification of KB103

The KB103 virus was constructed and purified as described in Example 2 above.

Viral Infections

KB103 virus was delivered to wild-type Balb/c or skhl-elite mice by intradermal injection as follows: each animal was injected once at 2-4 sites within the flank region of the animal with $1 \times 10^8$ plaque forming units (PFU) of virus/site in a volume of 50 µL. Animals were sacrificed 48 hours post KB103 administration, and the inject sites were harvested and processed for either real time qPCR or immunofluorescence analysis.

For qPCR analysis, skin tissue was dissected down to the fascia using a 6 mm punch biopsy tool. The biopsy was bisected into two pieces, and each piece was snap frozen using liquid nitrogen. Total RNA and DNA were isolated from one half of the biopsy using the Qiagen AllPrep DNA/RNA kit.

For immunofluorescence analysis, a circular area approximately one cm in diameter was excised from skin at the injection site, cut in half, and mounted in OCT so that the central portion of the circular area was facing upward. The prepared samples were freeze plunged into liquid nitrogen cooled isopentane, and stored at −80° C.

mRNA Quantification

Col7 transcripts were amplified from RNA isolated from mouse dermal tissue after KB103 injection using a 2-step protocol: 1) cDNA synthesis was carried out using the superscript III First Strand Synthesis kit (Thermofisher, Cat. # 18-080-051), and 2) qPCR amplification was performed using the Quantitect Probe PCR kit (Qiagen, Cat. # 204345) according to the manufacturer's protocol. 100 ng of cDNA was used in each reaction. Col7 transcript levels were normalized to GAPDH transcript levels.

Genome Copy Quantification

The copy number of KB103 viral genomes in the KB103 injected mice was quantified by qPCR amplification using the Quantitect Probe PCR kit (Qiagen Cat. # 204345). 100 ng of mouse genomic DNA was used in each reaction, and mouse genomic GAPDH was used as a control.

Immunofluorescence

Tissue sections from mice injected with KB103 were fixed, and subsequently stained with a primary rabbit anti-human Col7 polyclonal antibody (Sigma, Cat. # HPA042420), washed, and further stained with a fluorescently labelled anti-rabbit secondary antibody (Invitrogen, Cat. 3 A11012). Cell nuclei were stained with DAPI using standard techniques.

Results

Figure 11:
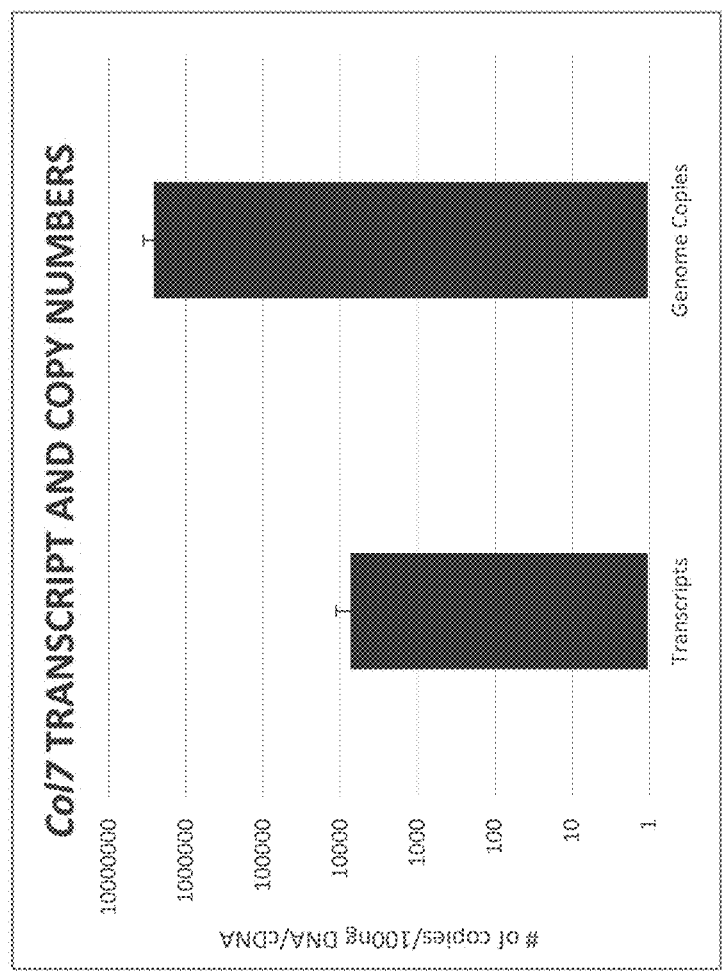
FIG. 11 shows the quantification of viral genome copy number and human Col7 transcript levels in tissue isolated from KB103-infected mice.
Figure 12:
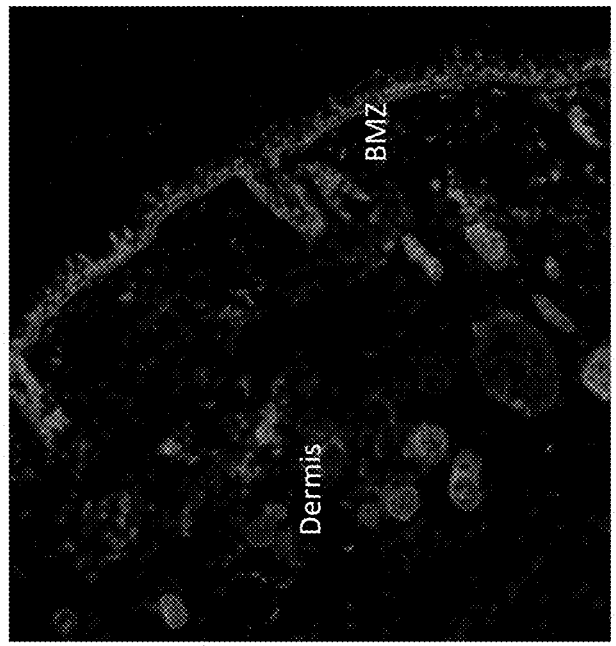
FIG. 12 shows human Col7 protein expression in dermal tissue from KB103-infected mice by immunofluorescence, including the initiation of human Col7 deposition at the basement membrane zone (BMZ).

To test the ability of KB103 to successfully deliver and express human Col7 protein in vivo, mice were intradermally administered the KB103 virus. Viral genome copy number in infected mouse tissue was assessed, and delivery of high levels (>1,000,000 viral genome copies/100 ng mouse DNA) of the KB103 viral genome was observed in the mice (FIG. 11). Next, the ability of the ability of the virus to express human Col7 in vivo was examined. Quantification of human Col7 transcripts in KB103-infected mice were measured and assessed compared to expression of a control mouse housekeeping gene. High levels of human Col7 transcript were observed in the infected mouse tissue (FIG. 11), suggesting that the delivered viral genomes were capable of successfully expressing their human gene cargo. Finally, the ability of KB103 to express Col7 protein was tested in the infected mice. Mouse dermal tissue was excised from mice after infection, and Col7 protein expression was assessed by immunohistochemical staining of the mouse tissue. High levels of human Col7 protein were detected after tissue staining (FIG. 12). Surprisingly, not only was human Col7 protein expressed from the KB103 virus in mouse dermis, but the initiation of deposition of human Col7 at the Basement Membrane Zone in KB103-infected mice was observed (FIG. 12). Without wishing to be bound by theory, this data suggests that: 1) the KB103 virus can successfully infect relevant tissue in vivo, delivering high genome copy numbers to these tissues tissue, 2) delivery of the KB103 virus to relevant tissue results in significant expression of the encoded human genes on this virus, and 3) KB103 not only successfully expresses human Col7 protein in vivo, but this protein is capable of beginning to organize (e.g. at the Basement Membrane Zone) in a way suggesting its ability to rescue endogenous Col7 defects in affected individuals.

The invention claimed is:

1. A pharmaceutical composition useful for topical, transdermal, subcutaneous, and/or intradermal treatment of skin wounds in a subject comprising:
   a) a herpes simplex virus (HSV) comprising a recombinant herpes simplex virus genome, wherein the recombinant herpes simplex virus genome comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof; and
   b) a pharmaceutically acceptable carrier;
wherein the HSV has reduced cytotoxicity as compared to a wild-type herpes simplex virus.

2. The pharmaceutical composition of claim 1, wherein the HSV comprising the recombinant herpes simplex virus genome is replication-defective.

3. The pharmaceutical composition of claim 1, wherein the recombinant herpes simplex virus genome comprises an inactivating mutation in a herpes simplex virus gene.

4. The pharmaceutical composition of claim 3, wherein the herpes simplex virus gene is selected from the group consisting of infected cell protein (ICP)0, ICP4, ICP22, ICP27, ICP47, thymidine kinase (tk), long unique region (UL)41, and UL55.

5. The pharmaceutical composition of claim 1, wherein the recombinant herpes simplex virus genome comprises the one or more transgenes within one or more viral gene loci.

6. The pharmaceutical composition of claim 5, wherein the recombinant herpes simplex virus genome comprises the one or more transgenes within one or more of the ICP4 viral gene loci.

7. The pharmaceutical composition of claim 1, wherein the pharmaceutically acceptable carrier is suitable for a route of administration selected from the group consisting of topical administration, transdermal administration, subcutaneous administration, intradermal administration, and any combinations thereof.

8. The pharmaceutical composition of claim 1, wherein the recombinant herpes simplex virus genome comprises a transgene encoding a Collagen alpha-1 (VII) chain polypeptide.

9. The pharmaceutical composition of claim 8, wherein the Collagen alpha-1 (VII) chain polypeptide has at least 80% sequence identity to the sequence of SEQ ID NO: 2.

10. The pharmaceutical composition of claim 8, wherein the Collagen alpha-1 (VII) chain polypeptide enhances, increases, augments, and/or supplements anchoring fibril formation of a subject when the polypeptide is expressed in one or more target cells of the subject.

11. The pharmaceutical composition of claim 8, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

12. A method of providing prophylactic, palliative, or therapeutic relief of a wound, disorder, or disease of the skin in a subject, the method comprising administering to the subject a pharmaceutical composition comprising:
   a) a herpes simplex virus (HSV) comprising a recombinant herpes simplex virus genome, wherein the recombinant herpes simplex virus genome comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof; and
   b) a pharmaceutically acceptable carrier;
wherein the HSV has reduced cytotoxicity as compared to a wild-type herpes simplex virus.

13. The method of claim 12, wherein the HSV comprising the recombinant herpes simplex virus genome is replication-defective.

14. The method of claim 12, wherein the recombinant herpes simplex virus genome comprises an inactivating mutation in a herpes simplex virus gene.

15. The method of claim 14, wherein the herpes simplex virus gene is selected from the group consisting of ICP0, ICP4, ICP22, ICP27, ICP47, tk, UL41, and UL55.

16. The method of claim 12, wherein the recombinant herpes simplex virus genome comprises the one or more transgenes within one or more viral gene loci.

17. The method of claim 16, wherein the recombinant herpes simplex virus genome comprises the one or more transgenes within one or more of the ICP4 viral gene loci.

18. The method of claim 12, wherein the pharmaceutically acceptable carrier is suitable for a route of administration selected from the group consisting of topical administration, transdermal administration, subcutaneous administration, intradermal administration, and any combinations thereof.

19. The method of claim 12, wherein the recombinant herpes simplex virus genome comprises a transgene encoding a Collagen alpha-1 (VII) chain polypeptide.

20. The method of claim 19, wherein the Collagen alpha-1 (VII) chain polypeptide has at least 80% sequence identity to the sequence of SEQ ID NO: 2.

21. The method of claim 19, wherein the Collagen alpha-1 (VII) chain polypeptide enhances, increases, augments, and/or supplements anchoring fibril formation of a subject when the polypeptide is expressed in one or more target cells of the subject.

22. The method of claim 19, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

23. The method of claim 12, wherein the pharmaceutical composition is administered topically or transdermally to the subject.

24. The method of claim 12, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

25. The composition of claim 1, wherein the pharmaceutically acceptable carrier is a hydroxypropyl methylcellulose gel.

26. The composition of claim 1, wherein the subject suffers from epidermolysis bullosa (EB).

27. The composition of claim 1, wherein the subject is a human.

28. The composition of claim 1, wherein the pharmaceutically acceptable carrier is phosphate buffer.

29. The composition of claim 1, wherein the pharmaceutically acceptable carrier is suitable for topical administration.

30. The composition of claim 1, wherein the HSV comprising the recombinant herpes simplex virus genome is replication-competent.

31. The method of claim 12, wherein the pharmaceutically acceptable carrier is a hydroxypropyl methylcellulose gel.

32. The method of claim 12, wherein the pharmaceutically acceptable carrier is phosphate buffer.

33. The method of claim 12, wherein the pharmaceutically acceptable carrier is suitable for topical administration.

34. The method of claim 12, wherein the disease or disorder of the skin is epidermolysis bullosa (EB).

35. The method of claim 12, wherein the subject is a human.

36. The method of claim 12, wherein the HSV comprising the recombinant herpes simplex virus genome is replication-competent.

* * * * *

SEQUENCE LISTING

<160> NUMBER OF SEQ ID NOS: 30

<210> SEQ ID NO 1
<211> LENGTH: 8835
<212> TYPE: DNA
<213> ORGANISM: Homo sapiens

<400> SEQUENCE: 1

```
atgacgctgc ggcttctggt ggccgcgctc tgcgccggga tcctggcaga ggcgccccga      60
gtgcgagccc agcacaggga gagagtgacc tgcacgcgcc tttacgccgc tgacattgtg     120
ttcttactgg atggctcctc atccattggc cgcagcaatt ccgcgaggt ccgcagcttt      180 ctcgaagggc tggtgctgcc tttctctgga gcagccagtg cacagggtgt gcgctttgcc    240
acagtgcagt acagcgatga cccacggaca gagttcggcc tggatgcact tggctctggg    300
ggtgatgtga tccgcgccat ccgtgagctt agctacaagg ggggcaacac tcgcacaggg    360
gctgcaattc tccatgtggc tgaccatgtc ttcctgcccc agctggcccg acctggtgtc    420
cccaaggtct gcatcctgat cacagacggg aagtcccagg acctggtgga cacagctgcc    480
caaaggctga aggggcaggg ggtcaagcta tttgctgtgg ggatcaagaa tgctgaccct    540
gaggagctga agcgagttgc ctcacagccc accagtgact tcttcttctt cgtcaatgac    600
ttcagcatct tgaggacact actgccctc gtttcccgga gagtgtgcac gactgctggt    660
ggcgtgcctg tgacccgacc tccggatgac tcgacctctg ctccacgaga cctggtgctg    720
tctgagccaa gcagccaatc cttgagagta cagtggacag cggccagtgg ccctgtgact    780
ggctacaagg tccagtacac tcctctgacg gggctgggac agccactgcc gagtgagcgg    840
caggaggtga acgtcccagc tggtgagacc agtgtgcggc tgcgggtct ccggccactg    900 accgagtacc aagtgactgt gattgccctc tacgccaaca gcatcgggga ggctgtgagc    960
gggacagctc ggaccactgc cctagaaggg ccggaactga ccatccagaa taccacagcc   1020
cacagcctcc tggtggcctg gcggagtgtg ccaggtgcca ctggctaccg tgtgacatgg   1080
cgggtcctca gtgtgggcc cacacagcag caggagctgg gccctgggca gggttcagtg   1140
ttgctgcgtg acttggagcc tggcacggac tatgaggtga ccgtgagcac cctatttggc   1200
cgcagtgtgg ggcccgccac ttccctgatg gctcgcactg acgcttctgt tgagcagacc   1260
ctgcgcccgg tcatcctggg ccccacatcc atcctccttt cctggaactt ggtgcctgag   1320
```

```
gcccgtggct accggttgga atggcggcgt gagactggct tggagccacc gcagaaggtg      1380
gtactgccct ctgatgtgac ccgctaccag ttggatgggc tgcagccggg cactgagtac      1440
cgcctcacac tctacactct gctggagggc cacgaggtgg ccacccctgc aaccgtggtt      1500
cccactggac cagagctgcc tgtgagccct gtaacagacc tgcaagccac cgagctgccc      1560
gggcagcggg tgcgagtgtc ctggagccca gtccctggtg ccacccagta ccgcatcatt      1620
gtgcgcagca cccaggggt tgagcggacc ctggtgcttc ctgggagtca cacagcattc      1680
gacttggatg acgttcaggc tgggcttagc tacactgtgc gggtgtctgc tcgagtgggt      1740
ccccgtgagg gcagtgccag tgtcctcact gtccgccggg agccggaaac tccacttgct      1800
gttccagggc tgcgggttgt ggtgtcagat gcaacgcgag tgagggtggc ctggggaccc      1860
gtccctggag ccagtggatt tcggattagc tggagcacag gcagtggtcc ggagtccagc      1920
cagacactgc ccccagactc tactgccaca gacatcacag gctgcagcc tggaaccacc      1980 taccaggtgg ctgtgtcggt actgcgaggc agagaggagg gccctgctgc agtcatcgtg      2040
gctcgaacgg acccactggg cccagtgagg acggtccatg tgactcaggc cagcagctca      2100
tctgtcacca ttacctggac cagggttcct ggcgccacag gatacagggt ttcctggcac      2160
tcagcccacg gccagagaa atcccagttg gtttctgggg aggccacggt ggctgagctg      2220
gatggactgg agccagatac tgagtatacg gtgcatgtga gggcccatgt ggctggcgtg      2280
gatgggcccc ctgcctctgt ggttgtgagg actgccctg agcctgtggg tcgtgtgtcg      2340
aggctgcaga tcctcaatgc ttccagcgac gttctacgga tcacctgggt aggggtcact      2400
ggagccacag cttacagact ggcctggggc cggagtgaag gcggcccat gaggcaccag      2460 atactcccag gaaacacaga ctctgcagag atccggggtc tcgaaggtgg agtcagctac      2520
tcagtgcgag tgactgcact tgtcggggac cgcgagggca cctgtctc cattgttgtc      2580 actacgccgc ctgaggctcc gccagccctg ggacgcttc acgtggtgca gcgcggggag      2640
cactcgctga ggctgcgctg ggagccggtg cccagagcgc agggcttcct tctgcactgg      2700
caacctgagg gtggccagga acagtcccgg gtcctggggc ccgagctcag cagctatcac      2760
ctggacgggc tggagccagc gacacagtac cgcgtgaggc tgagtgtcct agggccagct      2820
ggagaagggc cctctgcaga ggtgactgcg cgcactgagt cacctcgtgt tccaagcatt      2880
gaactacgtg tggtggacac ctcgatcgac tcggtgactt tggcctggac tccagtgtcc      2940
agggcatcca gctacatcct atcctggcgg ccactcagag gccctggcca ggaagtgcct      3000
gggtccccgc agacacttcc agggatctca agctcccagc gggtgacagg gctagagcct      3060
ggcgtctctt acatcttctc cctgacgcct gtcctggatg tgtgcgggg tcctgaggca      3120 tctgtcacac agacgccagt gtgccccgt ggcctggcgg atgtggtgtt cctaccacat      3180
gccactcaag acaatgctca ccgtgcggag gctacgagga gggtcctgga gcgtctggtg      3240
ttggcacttg ggcctcttgg gccacaggca gttcaggttg cctgctgtc ttacagtcat      3300 cggccctccc cactgttccc actgaatggc tcccatgacc ttggcattat cttgcaaagg      3360
atccgtgaca tgccctacat ggacccaagt gggaacaacc tgggcacagc cgtggtcaca      3420
gctcacagat acatgttggc accagatgct cctgggcgcc gccagcacgt accagggtg      3480 atggttctgc tagtggatga acccttgaga ggtgacatat tcagccccat ccgtgaggcc      3540
caggcttctg gcttaatgt ggtgatgttg ggaatggctg gagcggaccc agagcagctg      3600
cgtcgcttgg cgccgggtat ggactctgtc cagaccttct tcgccgtgga tgatgggcca      3660
agcctggacc aggcagtcag tggtctggcc acagccctgt gtcaggcatc cttcactact      3720
```

```
cagccccggc cagagccctg cccagtgtat tgtccaaagg gccagaaggg ggaacctgga      3780
gagatgggcc tgagaggaca agttgggcct cctggcgacc ctggcctccc gggcaggacc      3840
ggtgctcccg gccccagggg ccccctgga agtgccactg ccaagggcga gaggggcttc       3900
cctggagcag atgggcgtcc aggcagccct ggccgcgccg ggaatcctgg accccgtgga      3960 gccctggcc taaagggctc tccagggttg cctggccctc gtggggaccc gggagagcga       4020
ggacctcgag gcccaaaggg ggagccgggg gctcccggac aagtcatcgg aggtgaagga      4080
cctgggcttc ctgggcggaa aggggaccct ggaccatcgg gccccctgg acctcgtgga       4140 ccactggggg acccaggacc ccgtggcccc cagggcttc ctggaacagc catgaagggt       4200
gacaaaggcg atcgtgggga gcgggtccc cctggaccag gtgaaggtgg cattgctcct       4260
ggggagcctg ggctgccggg tcttcccgga agccctggac ccaaggccc cgttggcccc      4320 cctggaaaga aaggagaaaa aggtgactct gaggatggag ctccaggcct cccaggacaa     4380
cctgggtctc cgggtgagca gggcccacgg ggacctcctg gagctattgg ccccaaaggt     4440
gaccggggct ttccagggcc cctgggtgag gctggagaga agggcgaacg tggaccccca     4500
ggcccagcgg gatcccgggg gctgccaggg gttgctggac gtcctggagc caagggtcct    4560
gaagggccac caggacccac tggccgccaa ggagagaagg gggagcctgg tcgccctggg    4620
gaccctgcag tggtgggacc tgctgttgct ggacccaaag gagaaaaggg agatgtgggg   4680
cccgctgggc ccagaggagc taccggagtc caaggggaac ggggcccacc cggcttggtt  4740
cttcctggag accctggccc caagggagac cctggagacc gggtcccat tggccttact    4800 ggcagagcag gaccccccagg tgactcaggg cctcctggag agaagggaga ccctgggcgg   4860
cctggccccc caggacctgt tggccccga ggacgagatg tgaagttgg agagaaaggt    4920 gacgagggtc ctccgggtga cccgggtttg cctggaaaag caggcgagcg tggccttcgg    4980
ggggcacctg gagttcgggg gcctgtgggt gaaaagggag accagggaga tcctggagag   5040
gatggacgaa atggcagccc tggatcatct ggacccaagg gtgaccgtgg ggagccgggt   5100 ccccaggac ccccgggacg gctggtagac acaggacctg gagccagaga aagggagag    5160 cctggggacc gcggacaaga gggtcctcga gggcccaagg gtgatcctgg cctccctgga   5220 gccctgggg aaaggggcat tgaagggttt cggggacccc caggcccaca ggggaccca    5280 ggtgtccgag gccagcagg agaaaaggg accggggtc cccctgggct ggatggccgg     5340
agcggactgg atgggaaacc aggagccgct gggccctctg gccgaatgg tgctgcaggc    5400 aaagctgggg acccagggag agacgggctt ccaggcctcc gtggagaaca gggcctccct  5460 ggccccctctg gtcccctgg attaccggga aagccaggcg aggatggcaa acctggcctg   5520
aatgaaaaaa acgagaacc tggggaccct ggagaagacg ggaggaaggg agagaaagga   5580
gattcaggcg cctctgggag agaaggtcgt gatggcccca agggtgagcg tggagctcct  5640
ggtatccttg gaccccaggg gcctccaggc ctcccaggc cagtgggccc tcctggccag   5700
ggttttcctg gtgtcccagg aggcacgggc cccaagggtg accgtgggga gactggatcc  5760
aaaggggagc agggcctccc tggagagcgt ggcctgcgag gagagcctgg aagtgtgccg   5820
aatgtggatc ggttgctgga aactgctggc atcaaggcat ctgccctgcg ggagatcgtg    5880
gagacctggg atgagagctc tggtagcttc ctgcctgtgc ccgaacggcg tcgaggcccc    5940
aaggggaact caggcgaaca gggccccca ggcaaggagg gccccatcgg ctttcctgga   6000
gaacgcgggc tgaagggcga ccgtggagac cctggccctc agggggccacc tggtctggcc   6060
```

```
cttggggaga ggggccccccc cgggccttcc ggccttgccg gggagcctgg aaagcctggt   6120
attcccgggc tcccaggcag ggctgggggt gtgggagagg caggaaggcc aggagagagg   6180
ggagaacggg gagagaaagg agaacgtgga gaacagggca gagatggccc tcctggactc   6240
cctggaaccc ctgggccccc cggaccccct ggcccaagg tgtctgtgga tgagccaggt   6300
cctggactct ctggagaaca gggaccccct ggactcaagg gtgctaaggg ggagccgggc   6360
agcaatggtg accaaggtcc caaaggagac aggggtgtgc caggcatcaa aggagaccgg   6420
ggagagcctg gaccgagggg tcaggacggc aacccgggtc taccaggaga gcgtggtatg   6480
gctgggcctg aagggaagcc gggtctgcag ggtccaagag gccccctgg cccagtgggt   6540 ggtcatggag accctggacc acctggtgcc ccgggtcttg ctggccctgc aggaccccaa   6600
ggaccttctg gcctgaaggg ggagcctgga gagacaggac ctccaggacg gggcctgact   6660
ggacctactg gagctgtggg acttcctgga ccccccggcc cttcaggcct tgtgggtcca   6720
caggggtctc caggtttgcc tggacaagtg ggggagacag ggaagccggg agccccaggt   6780
cgagatggtg ccagtggaaa agatggagac agagggagcc ctggtgtgcc agggtcacca   6840
ggtctgcctg gcctgtcgg acctaaagga gaacctggcc ccacggggc ccctggacag   6900 gctgtggtcg ggctccctgg agcaaaggga gagaaggag cccctggagg ccttgctgga   6960
gacctggtgg gtgagccggg agccaaaggt gaccgaggac tgccagggcc gcgaggcgag   7020
aagggtgaag ctgccgtgc aggggagccc ggagaccctg ggaagatgg tcagaaaggg   7080 gctccaggac ccaaaggttt caagggtgac ccaggagtcg gggtcccggg ctcccctggg   7140
cctcctggcc ctcaggtgt gaaggagat ctgggcctcc ctggcctgcc cggtgctcct   7200
ggtgttgttg ggttcccggg tcagacaggc cctcgaggag agatgggtca gccaggccct   7260
agtggagagc ggggtctggc aggcccccca gggagagaag gaatcccagg acccctgggg   7320
ccacctggac caccggggtc agtgggacca cctgggggcct ctggactcaa aggagacaag   7380
ggagaccctg gagtagggct gcctggggcc cgaggcgagc gtgggagcc aggcatccgg   7440 ggtgaagatg gccgccccgg ccaggaggga ccccgaggac tcacggggcc ccctggcagc   7500
aggggagagc gtgggagaa gggtgatgtt gggagtgcag gactaaaggg tgacaaggga   7560
gactcagctg tgatcctggg gcctccaggc ccacggggtg ccaaggggga catgggtgaa   7620
cgagggcctc ggggcttgga tggtgacaaa ggacctcggg gagacaatgg ggaccctggt   7680
gacaagggca gcaagggaga gcctggtgac aagggctcag ccgggttgcc aggactgcgt   7740
ggactcctgg gaccccaggg tcaacctggt gcagcaggga tccctggtga cccgggatcc   7800
ccaggaaagg atgagtgcc tggtatccga ggagaaaag gagatgttgg cttcatgggt   7860 ccccgggggcc tcaagggtga acggggagtg aagggagcct gtggccttga tggagagaag   7920
ggagacaagg gagaagctgg tcccccaggc cgccccgggc tggcaggaca caaaggagag   7980 atggggagc ctggtgtgcc gggccagtcg ggggcccctg gcaaggaggg cctgatcggt   8040
cccaagggtg accgaggctt tgacgggcag ccaggcccca gggtgaccca gggcgagaaa   8100
ggggagcggg gaaccccagg aattggggc ttccaggcc ccagtggaaa tgatggctct   8160
gctggtcccc cagggccacc tggcagtgtt ggtccagag gccccgaagg acttcagggc   8220
cagaagggtg agcgaggtcc ccccggagag agagtggtgg gggctcctgg ggtccctgga   8280
gctcctggcg agagaggga gcaggggcgg ccagggcctg ccggtcctcg aggcgagaag   8340
ggagaagctg cactgacgga ggatgacatc cggggcttg tgcgccaaga gatgagtcag   8400
cactgtgcct gccagggcca gttcatcgca tctggatcac gaccctcc tagttatgct   8460
```

```
gcagacactg ccggctccca gctccatgct gtgcctgtgc tccgcgtctc tcatgcagag   8520
gaggaagagc gggtaccccc tgaggatgat gagtactctg aatactccga gtattctgtg   8580
gaggagtacc aggaccctga agctccttgg gatagtgatg acccctgttc cctgccactg   8640
gatgagggct cctgcactgc ctacaccctg cgctggtacc atcgggctgt gacaggcagc   8700
acagaggcct gtcacccttt tgtctatggt ggctgtggag ggaatgccaa ccgttttggg   8760
acccgtgagg cctgcgagcg ccgctgccca cccgggtgg tccagagcca ggggacaggt   8820
actgcccagg actga                                                    8835
```

<210> SEQ ID NO 2
<211> LENGTH: 2944
<212> TYPE: PRT
<213> ORGANISM: Homo sapiens

<400> SEQUENCE: 2

```
Met Thr Leu Arg Leu Leu Val Ala Ala Leu Cys Ala Gly Ile Leu Ala
 1               5                  10                  15

Glu Ala Pro Arg Val Arg Ala Gln His Arg Glu Arg Val Thr Cys Thr
                20                  25                  30

Arg Leu Tyr Ala Ala Asp Ile Val Phe Leu Leu Asp Gly Ser Ser Ser
            35                  40                  45

Ile Gly Arg Ser Asn Phe Arg Glu Val Arg Ser Phe Leu Glu Gly Leu
        50                  55                  60

Val Leu Pro Phe Ser Gly Ala Ala Ser Ala Gln Gly Val Arg Phe Ala
 65                  70                  75                  80

Thr Val Gln Tyr Ser Asp Asp Pro Arg Thr Glu Phe Gly Leu Asp Ala
                 85                  90                  95

Leu Gly Ser Gly Gly Asp Val Ile Arg Ala Ile Arg Glu Leu Ser Tyr
            100                 105                 110

Lys Gly Gly Asn Thr Arg Thr Gly Ala Ala Ile Leu His Val Ala Asp
        115                 120                 125

His Val Phe Leu Pro Gln Leu Ala Arg Pro Gly Val Pro Lys Val Cys
    130                 135                 140

Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
    290                 295                 300
```

```
Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
            325                 330                 335

Asn Thr Thr Ala His Ser Leu Leu Val Ala Trp Arg Ser Val Pro Gly
                340                 345                 350

Ala Thr Gly Tyr Arg Val Thr Trp Arg Val Leu Ser Gly Gly Pro Thr
            355                 360                 365

Gln Gln Gln Glu Leu Gly Pro Gly Gln Gly Ser Val Leu Leu Arg Asp
            370              375              380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
            435                 440                 445

Arg Arg Glu Thr Gly Leu Glu Pro Pro Gln Lys Val Val Leu Pro Ser
450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
            515                 520                 525

Ser Pro Val Pro Gly Ala Thr Gln Tyr Arg Ile Ile Val Arg Ser Thr
530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
            595                 600                 605

Ser Asp Ala Thr Arg Val Arg Val Ala Trp Gly Pro Val Pro Gly Ala
610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
            675                 680                 685

Val Arg Thr Val His Val Thr Gln Ala Ser Ser Ser Val Thr Ile
            690                 695                 700

Thr Trp Thr Arg Val Pro Gly Ala Thr Gly Tyr Arg Val Ser Trp His
705                 710                 715                 720
```

```
Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750

Val Arg Ala His Val Ala Gly Val Asp Gly Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
            980                 985                 990

Arg Gly Pro Gly Gln Glu Val Pro Gly Ser Pro Gln Thr Leu Pro Gly
        995                 1000                1005

Ile Ser Ser Ser Gln Arg Val Thr Gly Leu Glu Pro Gly Val Ser Tyr
    1010                1015                1020

Ile Phe Ser Leu Thr Pro Val Leu Asp Gly Val Arg Gly Pro Glu Ala
1025                1030                1035                1040

Ser Val Thr Gln Thr Pro Val Cys Pro Arg Gly Leu Ala Asp Val Val
            1045                1050                1055

Phe Leu Pro His Ala Thr Gln Asp Asn Ala His Arg Ala Glu Ala Thr
        1060                1065                1070

Arg Arg Val Leu Glu Arg Leu Val Leu Ala Leu Gly Pro Leu Gly Pro
    1075                1080                1085

Gln Ala Val Gln Val Gly Leu Leu Ser Tyr Ser His Arg Pro Ser Pro
    1090                1095                1100

Leu Phe Pro Leu Asn Gly Ser His Asp Leu Gly Ile Ile Leu Gln Arg
1105                1110                1115                1120

Ile Arg Asp Met Pro Tyr Met Asp Pro Ser Gly Asn Asn Leu Gly Thr
            1125                1130                1135

Ala Val Val Thr Ala His Arg Tyr Met Leu Ala Pro Asp Ala Pro Gly
```

-continued

```
                1140                1145                1150
Arg Arg Gln His Val Pro Gly Val Met Val Leu Leu Val Asp Glu Pro
            1155                1160                1165
Leu Arg Gly Asp Ile Phe Ser Pro Ile Arg Glu Ala Gln Ala Ser Gly
1170                1175                1180
Leu Asn Val Val Met Leu Gly Met Ala Gly Ala Asp Pro Glu Gln Leu
1185                1190                1195                1200
Arg Arg Leu Ala Pro Gly Met Asp Ser Val Gln Thr Phe Phe Ala Val
            1205                1210                1215
Asp Asp Gly Pro Ser Leu Asp Gln Ala Val Ser Gly Leu Ala Thr Ala
            1220                1225                1230
Leu Cys Gln Ala Ser Phe Thr Thr Gln Pro Arg Pro Glu Pro Cys Pro
            1235                1240                1245
Val Tyr Cys Pro Lys Gly Gln Lys Gly Glu Pro Gly Glu Met Gly Leu
            1250                1255                1260
Arg Gly Gln Val Gly Pro Pro Gly Asp Pro Gly Leu Pro Gly Arg Thr
1265                1270                1275                1280
Gly Ala Pro Gly Pro Gln Gly Pro Pro Gly Ser Ala Thr Ala Lys Gly
            1285                1290                1295
Glu Arg Gly Phe Pro Gly Ala Asp Gly Arg Pro Gly Ser Pro Gly Arg
            1300                1305                1310
Ala Gly Asn Pro Gly Thr Pro Gly Ala Pro Gly Leu Lys Gly Ser Pro
            1315                1320                1325
Gly Leu Pro Gly Pro Arg Gly Asp Pro Gly Glu Arg Gly Pro Arg Gly
            1330                1335                1340
Pro Lys Gly Glu Pro Gly Ala Pro Gly Gln Val Ile Gly Gly Glu Gly
1345                1350                1355                1360
Pro Gly Leu Pro Gly Arg Lys Gly Asp Pro Gly Pro Ser Gly Pro Pro
            1365                1370                1375
Gly Pro Arg Gly Pro Leu Gly Asp Pro Gly Pro Arg Gly Pro Pro Gly
            1380                1385                1390
Leu Pro Gly Thr Ala Met Lys Gly Asp Lys Gly Asp Arg Gly Glu Arg
            1395                1400                1405
Gly Pro Pro Gly Pro Gly Glu Gly Gly Ile Ala Pro Gly Glu Pro Gly
    1410                1415                1420
Leu Pro Gly Leu Pro Gly Ser Pro Gly Pro Gln Gly Pro Val Gly Pro
1425                1430                1435                1440
Pro Gly Lys Lys Gly Glu Lys Gly Asp Ser Glu Asp Gly Ala Pro Gly
            1445                1450                1455
Leu Pro Gly Gln Pro Gly Ser Pro Gly Glu Gln Gly Pro Arg Gly Pro
            1460                1465                1470
Pro Gly Ala Ile Gly Pro Lys Gly Asp Arg Gly Phe Pro Gly Pro Leu
            1475                1480                1485
Gly Glu Ala Gly Glu Lys Gly Glu Arg Gly Pro Pro Gly Pro Ala Gly
            1490                1495                1500
Ser Arg Gly Leu Pro Gly Val Ala Gly Arg Pro Gly Ala Lys Gly Pro
1505                1510                1515                1520
Glu Gly Pro Pro Gly Pro Thr Gly Arg Gln Gly Glu Lys Gly Glu Pro
            1525                1530                1535
Gly Arg Pro Gly Asp Pro Ala Val Val Gly Pro Ala Val Ala Gly Pro
            1540                1545                1550
Lys Gly Glu Lys Gly Asp Val Gly Pro Ala Gly Pro Arg Gly Ala Thr
            1555                1560                1565
```

Gly Val Gln Gly Glu Arg Gly Pro Pro Gly Leu Val Leu Pro Gly Asp
        1570                1575                1580

Pro Gly Pro Lys Gly Asp Pro Gly Asp Arg Gly Pro Ile Gly Leu Thr
1585                1590                1595                1600

Gly Arg Ala Gly Pro Pro Gly Asp Ser Gly Pro Pro Gly Glu Lys Gly
        1605                1610                1615

Asp Pro Gly Arg Pro Gly Pro Pro Gly Pro Val Gly Pro Arg Gly Arg
        1620                1625                1630

Asp Gly Glu Val Gly Glu Lys Gly Asp Glu Gly Pro Pro Gly Asp Pro
        1635                1640                1645

Gly Leu Pro Gly Lys Ala Gly Glu Arg Gly Leu Arg Gly Ala Pro Gly
        1650                1655                1660

Val Arg Gly Pro Val Gly Glu Lys Gly Asp Gln Gly Asp Pro Gly Glu
1665                1670                1675                1680

Asp Gly Arg Asn Gly Ser Pro Gly Ser Ser Gly Pro Lys Gly Asp Arg
        1685                1690                1695

Gly Glu Pro Gly Pro Pro Gly Pro Pro Gly Arg Leu Val Asp Thr Gly
        1700                1705                1710

Pro Gly Ala Arg Glu Lys Gly Glu Pro Gly Asp Arg Gly Gln Glu Gly
        1715                1720                1725

Pro Arg Gly Pro Lys Gly Asp Pro Gly Leu Pro Gly Ala Pro Gly Glu
        1730                1735                1740

Arg Gly Ile Glu Gly Phe Arg Gly Pro Pro Gly Pro Gln Gly Asp Pro
1745                1750                1755                1760

Gly Val Arg Gly Pro Ala Gly Glu Lys Gly Asp Arg Gly Pro Pro Gly
        1765                1770                1775

Leu Asp Gly Arg Ser Gly Leu Asp Gly Lys Pro Gly Ala Ala Gly Pro
        1780                1785                1790

Ser Gly Pro Asn Gly Ala Ala Gly Lys Ala Gly Asp Pro Gly Arg Asp
        1795                1800                1805

Gly Leu Pro Gly Leu Arg Gly Glu Gln Gly Leu Pro Gly Pro Ser Gly
        1810                1815                1820

Pro Pro Gly Leu Pro Gly Lys Pro Gly Glu Asp Gly Lys Pro Gly Leu
1825                1830                1835                1840

Asn Gly Lys Asn Gly Glu Pro Gly Asp Pro Gly Glu Asp Gly Arg Lys
        1845                1850                1855

Gly Glu Lys Gly Asp Ser Gly Ala Ser Gly Arg Glu Gly Arg Asp Gly
        1860                1865                1870

Pro Lys Gly Glu Arg Gly Ala Pro Gly Ile Leu Gly Pro Gln Gly Pro
        1875                1880                1885

Pro Gly Leu Pro Gly Pro Val Gly Pro Pro Gly Gln Gly Phe Pro Gly
        1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
        1925                1930                1935

Gly Ser Val Pro Asn Val Asp Arg Leu Leu Glu Thr Ala Gly Ile Lys
        1940                1945                1950

Ala Ser Ala Leu Arg Glu Ile Val Glu Thr Trp Asp Glu Ser Ser Gly
        1955                1960                1965

Ser Phe Leu Pro Val Pro Glu Arg Arg Gly Pro Lys Gly Asp Ser
        1970                1975                1980

-continued

Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
            2005                2010                2015

Pro Gly Leu Ala Leu Gly Glu Arg Gly Pro Pro Gly Pro Ser Gly Leu
        2020                2025                2030

Ala Gly Glu Pro Gly Lys Pro Gly Ile Pro Gly Leu Pro Gly Arg Ala
    2035                2040                2045

Gly Gly Val Gly Glu Ala Gly Arg Pro Gly Glu Arg Gly Glu Arg Gly
2050                2055                2060

Glu Lys Gly Glu Arg Gly Glu Gln Gly Arg Asp Gly Pro Pro Gly Leu
2065                2070                2075                2080

Pro Gly Thr Pro Gly Pro Pro Gly Pro Pro Gly Pro Lys Val Ser Val
            2085                2090                2095

Asp Glu Pro Gly Pro Gly Leu Ser Gly Glu Gln Gly Pro Pro Gly Leu
            2100                2105                2110

Lys Gly Ala Lys Gly Glu Pro Gly Ser Asn Gly Asp Gln Gly Pro Lys
        2115                2120                2125

Gly Asp Arg Gly Val Pro Gly Ile Lys Gly Asp Arg Gly Glu Pro Gly
    2130                2135                2140

Pro Arg Gly Gln Asp Gly Asn Pro Gly Leu Pro Gly Glu Arg Gly Met
2145                2150                2155                2160

Ala Gly Pro Glu Gly Lys Pro Gly Leu Gln Gly Pro Arg Gly Pro Pro
            2165                2170                2175

Gly Pro Val Gly Gly His Gly Asp Pro Gly Pro Pro Gly Ala Pro Gly
            2180                2185                2190

Leu Ala Gly Pro Ala Gly Pro Gln Gly Pro Ser Gly Leu Lys Gly Glu
        2195                2200                2205

Pro Gly Glu Thr Gly Pro Pro Gly Arg Gly Leu Thr Gly Pro Thr Gly
    2210                2215                2220

Ala Val Gly Leu Pro Gly Pro Pro Gly Pro Ser Gly Leu Val Gly Pro
2225                2230                2235                2240

Gln Gly Ser Pro Gly Leu Pro Gly Gln Val Gly Glu Thr Gly Lys Pro
            2245                2250                2255

Gly Ala Pro Gly Arg Asp Gly Ala Ser Gly Lys Asp Gly Asp Arg Gly
            2260                2265                2270

Ser Pro Gly Val Pro Gly Ser Pro Gly Leu Pro Gly Pro Val Gly Pro
        2275                2280                2285

Lys Gly Glu Pro Gly Pro Thr Gly Ala Pro Gly Gln Ala Val Val Gly
    2290                2295                2300

Leu Pro Gly Ala Lys Gly Glu Lys Gly Ala Pro Gly Gly Leu Ala Gly
2305                2310                2315                2320

Asp Leu Val Gly Glu Pro Gly Ala Lys Gly Asp Arg Gly Leu Pro Gly
            2325                2330                2335

Pro Arg Gly Glu Lys Gly Glu Ala Gly Arg Ala Gly Glu Pro Gly Asp
            2340                2345                2350

Pro Gly Glu Asp Gly Gln Lys Gly Ala Pro Gly Pro Lys Gly Phe Lys
        2355                2360                2365

Gly Asp Pro Gly Val Gly Val Pro Gly Ser Pro Gly Pro Pro Gly Pro
    2370                2375                2380

Pro Gly Val Lys Gly Asp Leu Gly Leu Pro Gly Leu Pro Gly Ala Pro
2385                2390                2395                2400

Gly Val Val Gly Phe Pro Gly Gln Thr Gly Pro Arg Gly Glu Met Gly 2405                2410                2415

Gln Pro Gly Pro Ser Gly Glu Arg Gly Leu Ala Gly Pro Pro Gly Arg
            2420                2425                2430

Glu Gly Ile Pro Gly Pro Leu Gly Pro Pro Gly Pro Pro Gly Ser Val
        2435                2440                2445

Gly Pro Pro Gly Ala Ser Gly Leu Lys Gly Asp Lys Gly Asp Pro Gly
    2450                2455                2460

Val Gly Leu Pro Gly Pro Arg Gly Glu Arg Gly Glu Pro Gly Ile Arg
2465                2470                2475                2480

Gly Glu Asp Gly Arg Pro Gly Gln Glu Gly Pro Arg Gly Leu Thr Gly
                2485                2490                2495

Pro Pro Gly Ser Arg Gly Glu Arg Gly Glu Lys Gly Asp Val Gly Ser
            2500                2505                2510

Ala Gly Leu Lys Gly Asp Lys Gly Asp Ser Ala Val Ile Leu Gly Pro
        2515                2520                2525

Pro Gly Pro Arg Gly Ala Lys Gly Asp Met Gly Glu Arg Gly Pro Arg
    2530                2535                2540

Gly Leu Asp Gly Asp Lys Gly Pro Arg Gly Asp Asn Gly Asp Pro Gly
2545                2550                2555                2560

Asp Lys Gly Ser Lys Gly Glu Pro Gly Asp Lys Gly Ser Ala Gly Leu
                2565                2570                2575

Pro Gly Leu Arg Gly Leu Leu Gly Pro Gln Gly Gln Pro Gly Ala Ala
            2580                2585                2590

Gly Ile Pro Gly Asp Pro Gly Ser Pro Gly Lys Asp Gly Val Pro Gly
        2595                2600                2605

Ile Arg Gly Glu Lys Gly Asp Val Gly Phe Met Gly Pro Arg Gly Leu
    2610                2615                2620

Lys Gly Glu Arg Gly Val Lys Gly Ala Cys Gly Leu Asp Gly Glu Lys
2625                2630                2635                2640

Gly Asp Lys Gly Glu Ala Gly Pro Pro Gly Arg Pro Gly Leu Ala Gly
                2645                2650                2655

His Lys Gly Glu Met Gly Glu Pro Gly Val Pro Gly Gln Ser Gly Ala
            2660                2665                2670

Pro Gly Lys Glu Gly Leu Ile Gly Pro Lys Gly Asp Arg Gly Phe Asp
        2675                2680                2685

Gly Gln Pro Gly Pro Lys Gly Asp Gln Gly Glu Lys Gly Glu Arg Gly
    2690                2695                2700

Thr Pro Gly Ile Gly Gly Phe Pro Gly Pro Ser Gly Asn Asp Gly Ser
2705                2710                2715                2720

Ala Gly Pro Pro Gly Pro Pro Gly Ser Val Gly Pro Arg Gly Pro Glu
                2725                2730                2735

Gly Leu Gln Gly Gln Lys Gly Glu Arg Gly Pro Pro Gly Glu Arg Val
            2740                2745                2750

Val Gly Ala Pro Gly Val Pro Gly Ala Pro Gly Glu Arg Gly Glu Gln
        2755                2760                2765

Gly Arg Pro Gly Pro Ala Gly Pro Arg Gly Glu Lys Gly Glu Ala Ala
    2770                2775                2780

Leu Thr Glu Asp Asp Ile Arg Gly Phe Val Arg Gln Glu Met Ser Gln
2785                2790                2795                2800

His Cys Ala Cys Gln Gly Gln Phe Ile Ala Ser Gly Ser Arg Pro Leu
                2805                2810                2815

Pro Ser Tyr Ala Ala Asp Thr Ala Gly Ser Gln Leu His Ala Val Pro
            2820                2825                2830

Val Leu Arg Val Ser His Ala Glu Glu Glu Arg Val Pro Pro Glu
         2835                2840                2845

Asp Asp Glu Tyr Ser Glu Tyr Ser Glu Tyr Ser Val Glu Glu Tyr Gln
         2850                2855                2860

Asp Pro Glu Ala Pro Trp Asp Ser Asp Asp Pro Cys Ser Leu Pro Leu
2865                2870                2875                2880

Asp Glu Gly Ser Cys Thr Ala Tyr Thr Leu Arg Trp Tyr His Arg Ala
             2885                2890                2895

Val Thr Gly Ser Thr Glu Ala Cys His Pro Phe Val Tyr Gly Gly Cys
             2900                2905                2910

Gly Gly Asn Ala Asn Arg Phe Gly Thr Arg Glu Ala Cys Glu Arg Arg
             2915                2920                2925

Cys Pro Pro Arg Val Val Gln Ser Gln Gly Thr Gly Thr Ala Gln Asp
             2930                2935                2940

<210> SEQ ID NO 3
<211> LENGTH: 2217
<212> TYPE: DNA
<213> ORGANISM: Homo sapiens

<400> SEQUENCE: 3

| | |
|---|---|
| atgacctcct cggggcctgg accccggttc ctgctgctgc tgccgctgct gctgccccct | 60 |
| gcggcctcag cctccgaccg gccccggggc cgagacccgg tcaacccaga gaagctgctg | 120 |
| gtgatcactg tggccacagc tgaaaccgag gggtacctgc gtttcctgcg ctctgcggag | 180 |
| ttcttcaact acactgtgcg gaccctgggc ctggagaggg agtggcgagg gggtgatgtg | 240 |
| gctcgaacag ttggtggagg acagaaggtc cggtggttaa agaaggaaat ggagaaatac | 300 |
| gctgaccggg aggatatgat catcatgttt gtggatagct acgacgtgat tctggccggc | 360 |
| agccccacag agctgctgaa gaagttcgtc cagagtggca gccgcctgct cttctctgca | 420 |
| gagagcttct gctggcccga gtgggggctg gcggagcagt accctgaggt gggcacgggg | 480 |
| aagcgcttcc tcaattctgg tggattcatc ggttttgcca ccaccatcca ccaaatcgtg | 540 |
| cgccagtgga agtacaagga tgatgacgac gaccagctgt tctacacacg gctctacctg | 600 |
| gacccaggac tgagggagaa actcagccctt aatctggatc ataagtctcg gatctttcag | 660 |
| aacctcaacg ggctttttaga tgaagtggtt ttaaagtttg atcggaaccg tgtgcgtatc | 720 |
| cggaacgtgg cctacgacac gctccccatt gtggtccatg gaaacggtcc cactaagctg | 780 |
| cagctcaact acctgggaaa ctacgtcccc aatggctgga ctcctgaggg aggctgtggc | 840 |
| ttctgcaacc aggaccggag gacactcccg gggggcagc ctcccccccg ggtgtttctg | 900 |
| gccgtgtttg tggaacagcc tactccgttt ctgccccgct tcctgcagcg gctgctactc | 960 |
| ctggactatc ccccgacag ggtcacccctt ttcctgcaca caacgaggt cttccatgaa | 1020 |
| ccccacatcg ctgactcctg gccgcagctc caggaccact tctcagctgt gaagctcgtg | 1080 |
| gggccggagg aggctctgag cccaggcgag gccaggggaca tggccatgga cctgtgtcgg | 1140 |
| caggaccccg agtgtgagtt ctacttcagc ctggacgccg acgctgtcct caccaacctg | 1200 |
| cagaccctgc gtatcctcat tgaggagaac aggaaggtga tcgcccccat gctgtcccgc | 1260 |
| cacggcaagc tgtggtccaa cttctgggcc gccctgagcc ccgatgagta ctacgcccgc | 1320 |
| tccgaggact acgtggagct ggtgcagcgc aagcgagtgg tgtgtgtgaa tgtaccatac | 1380 |
| atctcccagg cctatgtgat ccggggtgat accctgcgga tggagctgcc ccagagggat | 1440 |
| gtgttctcgg gcagtgacac agacccggac atggccttct gtaagagctt cgagacaag | 1500 |

```
ggcatcttcc tccatctgag caatcagcat gaatttggcc ggctcctggc cacttccaga   1560
tacgacacgg agcacctgca ccccgacctc tggcagatct tcgacaaccc cgtcgactgg   1620
aaggagcagt acatccacga gaactacagc cgggccctgg aaggggaagg aatcgtggag   1680
cagccatgcc cggacgtgta ctggttccca ctgctgtcag aacaaatgtg tgatgagctg   1740
gtggcagaga tggagcacta cggccagtgg tcaggcggcc ggcatgagga ttcaaggctg   1800
gctggaggct acgagaatgt gcccaccgtg gacatccaca tgaagcaggt ggggtacgag   1860
gaccagtggc tgcagctgct gcggacgtat gtgggcccca tgaccgagag cctgttccc   1920 ggttaccaca ccaaggcgcg gcggtgatg aactttgtgg ttcgctaccg gccagacgag   1980
cagccgtctc tgcggccaca ccacgactca tccaccttca ccctcaacgt tgccctcaac   2040
cacaagggcc tggactatga gggaggtggc tgccgcttcc tgcgctacga ctgtgtgatc   2100
tcctccccga ggaagggctg ggcactcctg caccccggcc gcctcaccca ctaccacgag   2160
gggctgccaa cgacctgggg cacacgctac atcatggtgt cctttgtcga cccctga     2217
```

<210> SEQ ID NO 4
<211> LENGTH: 738
<212> TYPE: PRT
<213> ORGANISM: Homo sapiens

<400> SEQUENCE: 4

```
Met Thr Ser Ser Gly Pro Gly Pro Arg Phe Leu Leu Leu Leu Pro Leu
 1               5                  10                  15

Leu Leu Pro Pro Ala Ala Ser Ala Ser Asp Arg Pro Arg Gly Arg Asp
            20                  25                  30

Pro Val Asn Pro Glu Lys Leu Leu Val Ile Thr Val Ala Thr Ala Glu
        35                  40                  45

Thr Glu Gly Tyr Leu Arg Phe Leu Arg Ser Ala Glu Phe Phe Asn Tyr
    50                  55                  60

Thr Val Arg Thr Leu Gly Leu Gly Glu Glu Trp Arg Gly Gly Asp Val
65                  70                  75                  80

Ala Arg Thr Val Gly Gly Gly Gln Lys Val Arg Trp Leu Lys Lys Glu
                85                  90                  95

Met Glu Lys Tyr Ala Asp Arg Glu Asp Met Ile Ile Met Phe Val Asp
            100                 105                 110

Ser Tyr Asp Val Ile Leu Ala Gly Ser Pro Thr Glu Leu Leu Lys Lys
        115                 120                 125

Phe Val Gln Ser Gly Ser Arg Leu Leu Phe Ser Ala Glu Ser Phe Cys
    130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
            180                 185                 190

Leu Phe Tyr Thr Arg Leu Tyr Leu Asp Pro Gly Leu Arg Glu Lys Leu
        195                 200                 205

Ser Leu Asn Leu Asp His Lys Ser Arg Ile Phe Gln Asn Leu Asn Gly
    210                 215                 220

Ala Leu Asp Glu Val Val Leu Lys Phe Asp Arg Asn Arg Val Arg Ile
225                 230                 235                 240

Arg Asn Val Ala Tyr Asp Thr Leu Pro Ile Val Val His Gly Asn Gly
```

-continued

```
                        245                 250                 255
Pro Thr Lys Leu Gln Leu Asn Tyr Leu Gly Asn Tyr Val Pro Asn Gly
                260                 265                 270

Trp Thr Pro Glu Gly Gly Cys Gly Phe Cys Asn Gln Asp Arg Arg Thr
            275                 280                 285

Leu Pro Gly Gly Gln Pro Pro Arg Val Phe Leu Ala Val Phe Val
        290                 295                 300

Glu Gln Pro Thr Pro Phe Leu Pro Arg Phe Leu Gln Arg Leu Leu Leu
305                 310                 315                 320

Leu Asp Tyr Pro Pro Asp Arg Val Thr Leu Phe Leu His Asn Asn Glu
                325                 330                 335

Val Phe His Glu Pro His Ile Ala Asp Ser Trp Pro Gln Leu Gln Asp
            340                 345                 350

His Phe Ser Ala Val Lys Leu Val Gly Pro Glu Glu Ala Leu Ser Pro
                355                 360                 365

Gly Glu Ala Arg Asp Met Ala Met Asp Leu Cys Arg Gln Asp Pro Glu
        370                 375                 380

Cys Glu Phe Tyr Phe Ser Leu Asp Ala Asp Ala Val Leu Thr Asn Leu
385                 390                 395                 400

Gln Thr Leu Arg Ile Leu Ile Glu Glu Asn Arg Lys Val Ile Ala Pro
                405                 410                 415

Met Leu Ser Arg His Gly Lys Leu Trp Ser Asn Phe Trp Gly Ala Leu
            420                 425                 430

Ser Pro Asp Glu Tyr Tyr Ala Arg Ser Glu Asp Tyr Val Glu Leu Val
        435                 440                 445

Gln Arg Lys Arg Val Gly Val Trp Asn Val Pro Tyr Ile Ser Gln Ala
    450                 455                 460

Tyr Val Ile Arg Gly Asp Thr Leu Arg Met Glu Leu Pro Gln Arg Asp
465                 470                 475                 480

Val Phe Ser Gly Ser Asp Thr Asp Pro Asp Met Ala Phe Cys Lys Ser
                485                 490                 495

Phe Arg Asp Lys Gly Ile Phe Leu His Leu Ser Asn Gln His Glu Phe
            500                 505                 510

Gly Arg Leu Leu Ala Thr Ser Arg Tyr Asp Thr Glu His Leu His Pro
        515                 520                 525

Asp Leu Trp Gln Ile Phe Asp Asn Pro Val Asp Trp Lys Glu Gln Tyr
    530                 535                 540

Ile His Glu Asn Tyr Ser Arg Ala Leu Glu Gly Glu Gly Ile Val Glu
545                 550                 555                 560

Gln Pro Cys Pro Asp Val Tyr Trp Phe Pro Leu Leu Ser Glu Gln Met
                565                 570                 575

Cys Asp Glu Leu Val Ala Glu Met Glu His Tyr Gly Gln Trp Ser Gly
            580                 585                 590

Gly Arg His Glu Asp Ser Arg Leu Ala Gly Gly Tyr Glu Asn Val Pro
        595                 600                 605

Thr Val Asp Ile His Met Lys Gln Val Gly Tyr Glu Asp Gln Trp Leu
    610                 615                 620

Gln Leu Leu Arg Thr Tyr Val Gly Pro Met Thr Glu Ser Leu Phe Pro
625                 630                 635                 640

Gly Tyr His Thr Lys Ala Arg Ala Val Met Asn Phe Val Val Arg Tyr
                645                 650                 655

Arg Pro Asp Glu Gln Pro Ser Leu Arg Pro His His Asp Ser Ser Thr
            660                 665                 670
```

```
Phe Thr Leu Asn Val Ala Leu Asn His Lys Gly Leu Asp Tyr Glu Gly
            675                 680                 685

Gly Gly Cys Arg Phe Leu Arg Tyr Asp Cys Val Ile Ser Ser Pro Arg
    690                 695                 700

Lys Gly Trp Ala Leu Leu His Pro Gly Arg Leu Thr His Tyr His Glu
705                 710                 715                 720

Gly Leu Pro Thr Thr Trp Gly Thr Arg Tyr Ile Met Val Ser Phe Val
                725                 730                 735

Asp Pro

<210> SEQ ID NO 5
<211> LENGTH: 75
<212> TYPE: DNA
<213> ORGANISM: Artificial Sequence
<220> FEATURE:
<223> OTHER INFORMATION: Synthetic Construct

<400> SEQUENCE: 5
agggccaaga ggggcagcgg cgagggcagg ggcagcctgc tgacctgcgg cgacgtggag     60
gagaaccccg gcccc                                                     75

<210> SEQ ID NO 6
<211> LENGTH: 25
<212> TYPE: PRT
<213> ORGANISM: Artificial Sequence
<220> FEATURE:
<223> OTHER INFORMATION: Synthetic Construct

<400> SEQUENCE: 6

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25

<210> SEQ ID NO 7
<211> LENGTH: 66
<212> TYPE: DNA
<213> ORGANISM: Artificial Sequence
<220> FEATURE:
<223> OTHER INFORMATION: Synthetic Construct

<400> SEQUENCE: 7
ggaagcggag ctactaactt cagcctgctg aagcaggctg agacgtggag ggagaaccct     60
ggacct                                                               66

<210> SEQ ID NO 8
<211> LENGTH: 22
<212> TYPE: PRT
<213> ORGANISM: Artificial Sequence
<220> FEATURE:
<223> OTHER INFORMATION: Synthetic Construct

<400> SEQUENCE: 8

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 9
<211> LENGTH: 69
<212> TYPE: DNA
```

```
<213> ORGANISM: Artificial Sequence
<220> FEATURE:
<223> OTHER INFORMATION: Synthetic Construct

<400> SEQUENCE: 9
ggaagcggac agtgtactaa ttatgctctc ttgaaattgg ctggagatgt tgagagcaac      60
cctggacct                                                              69

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Gly Ser Gly Gln Cys Thr Asn Tyr Ala Leu Leu Lys Leu Ala Gly Asp
 1               5                  10                  15

Val Glu Ser Asn Pro Gly Pro
            20

<210> SEQ ID NO 11
<211> LENGTH: 75
<212> TYPE: DNA
<213> ORGANISM: Artificial Sequence
<220> FEATURE:
<223> OTHER INFORMATION: Synthetic Construct

<400> SEQUENCE: 11
ggaagcggag tgaaacagac tttgaatttt gaccttctca gttggcggg agacgtggag       60 tccaaccctg gacct                                                       75

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Gly Ser Gly Val Lys Gln Thr Leu Asn Phe Asp Leu Leu Lys Leu Ala
 1               5                  10                  15

Gly Asp Val Glu Ser Asn Pro Gly Pro
            20                  25

<210> SEQ ID NO 13
<211> LENGTH: 11121
<212> TYPE: DNA
<213> ORGANISM: Artificial Sequence
<220> FEATURE:
<223> OTHER INFORMATION: Synthetic Construct

<400> SEQUENCE: 13
atgacgctgc ggcttctggt ggccgcgctc tgcgccggga tcctggcaga ggcgccccga      60
gtgcgagccc agcacaggga gagagtgacc tgcacgcgcc tttacgccgc tgacattgtg     120
ttcttactgg atggctcctc atccattggc cgcagcaatt tcgcgaggt ccgcagcttt      180 ctcgaaggc tggtgctgcc tttctctgga gcagccagtg cacagggtgt gcgctttgcc     240
acagtgcagt acagcgatga cccacggaca gagttcggcc tggatgcact ggctctggg     300 ggtgatgtga tccgcgccat ccgtgagctt agctacaagg ggcaacac tcgcacaggg      360 gctgcaattc tccatgtggc tgaccatgtc ttcctgcccc agctggccg acctggtgtc     420
```

```
cccaaggtct gcatcctgat cacagacggg aagtcccagg acctggtgga cacagctgcc    480
caaaggctga aggggcaggg ggtcaagcta tttgctgtgg ggatcaagaa tgctgaccct    540
gaggagctga agcgagttgc ctcacagccc accagtgact tcttcttctt cgtcaatgac    600
ttcagcatct tgaggacact actgccctc gtttcccgga gagtgtgcac gactgctggt     660
ggcgtgcctg tgacccgacc tccggatgac tcgacctctg ctccacgaga cctggtgctg    720
tctgagccaa gcagccaatc cttgagagta cagtggacag cggccagtgg ccctgtgact    780
ggctacaagg tccagtacac tcctctgacg ggctgggac agccactgcc gagtgagcgg     840
caggaggtga acgtcccagc tggtgagacc agtgtgcggc tgcggggtct ccggccactg    900
accgagtacc aagtgactgt gattgccctc tacgccaaca gcatcgggga ggctgtgagc    960
gggacagctc ggaccactgc cctagaaggg ccggaactga ccatccagaa taccacagcc   1020
cacagcctcc tggtggcctg gcggagtgtg ccaggtgcca ctggctaccg tgtgacatgg   1080
cgggtcctca gtggtgggcc cacacagcag caggagctgg ccctgggca gggttcagtg    1140 ttgctgcgtg acttggagcc tggcacggac tatgaggtga ccgtgagcac cctatttggc   1200
cgcagtgtgg ggcccgccac ttccctgatg gctcgcactg acgcttctgt tgagcagacc   1260
ctgcgcccgg tcatcctggg ccccacatcc atcctccttt cctggaactt ggtgcctgag   1320
gcccgtggct accggttgga atggcggcgt gagactggct tggagccacc gcagaaggtg   1380
gtactgccct ctgatgtgac ccgctaccag ttggatgggc tgcagccggg cactgagtac   1440
cgcctcacac tctacactct gctggagggc cacgaggtgg ccacccctgc aaccgtggtt   1500
cccactggac cagagctgcc tgtgagccct gtaacagacc tgcaagccac cgagctgccc   1560
gggcagcggg tgcgagtgtc ctggagccca gtccctggtg ccacccagta ccgcatcatt   1620
gtgcgcagca cccaggggg tgagcggacc ctggtgcttc ctgggagtca gacagcattc    1680
gacttggatg acgttcaggc tgggcttagc tacactgtgc gggtgtctgc tcgagtgggt   1740
ccccgtgagg gcagtgccag tgtcctcact gtccgccggg agccggaaac tccacttgct   1800
gttccagggc tgcgggttgt ggtgtcagat gcaacgcgag tgagggtggc ctggggaccc   1860
gtccctggag ccagtggatt tcggattagc tggagcacag cagtggtcc ggagtccagc    1920 cagacactgc ccccagactc tactgccaca gacatcacag gctgcagcc tggaaccacc    1980 taccaggtgg ctgtgtcggt actgcgaggc agagaggagg gccctgctgc agtcatcgtg   2040
gctcgaacgg acccactggg cccagtgagg acggtccatg tgactcaggc cagcagctca   2100
tctgtcacca ttacctggac cagggttcct ggcgccacag gatacagggt ttcctggcac   2160
tcagcccacg gccagagaa atcccagttg gtttctgggg aggccacggt ggctgagctg    2220
gatggactga agcagatac tgagtatacg gtgcatgtga gggcccatgt ggctggcgtg   2280
gatgggcccc ctgcctctgt ggttgtgagg actgccctg agcctgtggg tcgtgtgtcg    2340
aggctgcaga tcctcaatgc ttccagcgac gttctacgga tcacctgggt aggggtcact   2400
ggagccacag cttacagact ggcctggggc cggagtgaag gcggccccat gaggcaccag   2460
atactcccag aaacacaga ctctgcagag atcggggtc tcgaaggtgg agtcagctac     2520
tcagtgcgag tgactgcact tgtcggggac cgcgagggca cacctgtctc cattgttgtc   2580
actacgccgc ctgaggctcc gccagccctg ggacgcttc acgtggtgca gcgcggggag   2640
cactcgctga ggctgcgctg ggagccggtg cccagagcgc agggcttcct tctgcactgg   2700
caacctgagg gtggccagga acagtcccgg gtcctggggc ccgagctcag cagctatcac   2760
```

```
ctggacgggc tggagccagc gacacagtac cgcgtgaggc tgagtgtcct agggccagct    2820
ggagaagggc cctctgcaga ggtgactgcg cgcactgagt cacctcgtgt tccaagcatt    2880
gaactacgtg tggtggacac ctcgatcgac tcggtgactt tggcctggac tccagtgtcc    2940
agggcatcca gctacatcct atcctggcgg ccactcagag gccctggcca ggaagtgcct    3000
gggtccccgc agacacttcc agggatctca agctcccagc gggtgacagg gctagagcct    3060
ggcgtctctt acatcttctc cctgacgcct gtcctggatg tgtgcgggg tcctgaggca     3120
tctgtcacac agacgccagt gtgccccgt ggcctggcgg atgtggtgtt cctaccacat     3180
gccactcaag acaatgctca ccgtgcgag gctacgagga gggtcctgga gcgtctggtg     3240
ttggcacttg ggcctcttgg gccacaggca gttcaggttg gcctgctgtc ttacagtcat    3300
cggccctccc cactgttccc actgaatggc tcccatgacc ttggcattat cttgcaaagg    3360
atccgtgaca tgccctacat ggacccaagt gggaacaacc tgggcacagc cgtggtcaca    3420
gctcacagat acatgttggc accagatgct cctgggcgcc gccagcacgt accaggggtg    3480
atggttctgc tagtggatga acccttgaga ggtgacatat tcagccccat ccgtgaggcc    3540
caggcttctg ggcttaatgt ggtgatgttg ggaatggctg gagcggaccc agagcagctg    3600
cgtcgcttgg cgccgggtat ggactctgtc cagaccttct tcgccgtgga tgatgggcca    3660
agcctggacc aggcagtcag tggtctggcc acagccctgt gtcaggcatc cttcactact    3720
cagccccggc cagagccctg cccagtgtat tgtccaaagg ccagaagggg gaacctggaa    3780
gagatgggcc tgagaggaca agttgggcct cctggcgacc ctggcctccc gggcaggacc    3840
ggtgctcccg gccccaggg gccccctgga agtgccactg ccaagggcga gaggggcttc     3900
cctggagcag atgggcgtcc aggcagccct ggccgcgccg ggaatcctgg gaccctgga    3960
gccctggcc taaagggctc tccagggttg cctggcctc gtggggaccc gggagagcga     4020
ggacctcgag gcccaaaggg ggagccgggg gctcccggac aagtcatcgg aggtgaagga    4080
cctgggcttc ctgggcggaa aggggaccct ggaccatcgg gcccccctgg acctcgtgga    4140
ccactggggg acccaggacc ccgtggcccc caggcttc ctggaacagc catgaagggt       4200
gacaaaggcg atcgtgggga gcgggtccc cctggaccag gtgaaggtgg cattgctcct      4260
ggggagcctg ggctgccggg tcttcccgga agccctggac cccaaggccc cgttggcccc    4320
cctggaaaga aaggagaaaa aggtgactct gaggatggag ctccaggcct cccaggacaa    4380
cctgggtctc cgggtgagca gggcccacgg ggacctcctg gagctattgg ccccaaaggt    4440
gaccggggct ttccagggcc cctgggtgag gctggagaga agggcgaacg tggacccca     4500
ggcccagcgg gatcccgggg gctgccaggg gttgctggac gtcctggagc caagggtcct    4560
gaagggccac caggacccac tggccgccaa ggagagaagg gggagcctgg tcgccctggg    4620
gaccctgcag tggtgggacc tgctgttgct ggacccaaag gagaaaaggg agatgtgggg    4680
cccgctgggc ccagaggagc taccggagtc aaggggaac ggggcccacc cggcttggtt     4740
cttcctggag accctggccc caaggagac cctgagacc ggggtcccat tggccttact       4800
ggcagagcag gacccccagg tgactcaggg cctcctggag agaagggaga ccctgggcgg    4860
cctgccccc aggacctgt tggccccga ggacgagatg tgaagttgg agagaaaggt          4920
gacgagggtc ctccgggtga cccgggtttg cctggaaaag caggcgagcg tggccttcgg    4980
ggggcacctg gagttcgggg gcctgtgggt gaaaagggag accaggagag tcctggagag    5040
gatgacgaa atggcagccc tggatcatct ggacccaagg gtgaccgtgg ggagccgggt      5100
ccccaggac cccgggacg gctggtagac acaggacctg gagccagaga gaaaggagag        5160
```

-continued

| | |
|---|---|
| cctgggacc gcggacaaga gggtcctcga gggcccaagg gtgatcctgg cctccctgga | 5220 |
| gccctgggg aaagggcat tgaagggttt cggggacccc caggcccaca ggggaccca | 5280 |
| ggtgtccgag gcccagcagg agaaagggt gaccggggtc ccctgggct ggatggccgg | 5340 |
| agcggactgg atgggaaacc aggagccgct gggccctctg gccgaatgg tgctgcaggc | 5400 |
| aaagctgggg acccagggag agacgggctt ccaggcctcc gtggagaaca gggcctccct | 5460 |
| ggcccctctg gtcccctgg attaccggga aagccaggcg aggatggcaa acctggcctg | 5520 |
| aatggaaaaa acgagaacc tggggaccct ggagaagacg ggaggaaggg agagaaagga | 5580 |
| gattcaggcg cctctgggag agaaggtcgt gatggcccca agggtgagcg tggagctcct | 5640 |
| ggtatccttg acccccaggg gcctccaggc ctcccagggc cagtgggccc tcctggccag | 5700 |
| ggttttcctg gtgtcccagg aggcacgggc cccaagggtg accgtgggga gactggatcc | 5760 |
| aaaggggagc agggcctccc tggagagcgt ggcctgcgag gagagcctgg aagtgtgccg | 5820 |
| aatgtggatc ggttgctgga aactgctggc atcaaggcat ctgccctgcg ggagatcgtg | 5880 |
| gagacctggg atgagagctc tggtagcttc ctgcctgtgc ccgaacggcg tcgaggcccc | 5940 |
| aaggggact caggcgaaca gggccccca ggcaaggagg gccccatcgg ctttcctgga | 6000 |
| gaacgcgggc tgaagggcga ccgtggagac cctggccctc aggggccacc tggtctggcc | 6060 |
| cttggggaga gggccccccc cgggccttcc ggccttgccg gggagcctgg aaagcctggt | 6120 |
| attcccgggc tccaggcag ggctgggggt gtgggagagg caggaaggcc aggagagagg | 6180 |
| ggagaacggg gagagaaagg agaacgtgga gaacagggca gagatggccc tcctggactc | 6240 |
| cctggaaccc ctgggcccc cggaccccct ggccccaagg tgtctgtgga tgagccaggt | 6300 |
| cctggactct ctggagaaca gggacccct ggactcaagg gtgctaaggg ggagccgggc | 6360 |
| agcaatggtg accaaggtcc caaggagac aggggtgtgc caggcatcaa aggagaccgg | 6420 |
| ggagagcctg gaccgagggg tcaggacggc aacccgggtc taccaggaga gcgtggtatg | 6480 |
| gctgggcctg aagggaagcc gggtctgcag ggtccaagag gccccctgg cccagtgggt | 6540 |
| ggtcatggag accctggacc acctggtgcc ccgggtcttg ctggccctgc aggaccccaa | 6600 |
| ggaccttctg gcctgaaggg ggagcctgga gagacaggac ctccaggacg gggcctgact | 6660 |
| ggacctactg gagctgtggg acttcctgga cccccggcc cttcaggcct tgtgggtcca | 6720 |
| cagggtctc caggtttgcc tggacaagtg ggggagacag ggaagccggg agccccaggt | 6780 |
| cgagatggtg ccagtggaaa agatggagac agagggagcc ctggtgtgcc agggtcacca | 6840 |
| ggtctgcctg gcctgtcgg acctaaagga gaacctggcc ccacggggc ccctggacag | 6900 |
| gctgtggtcg ggctccctgg agcaaaggga gagaagggag ccctggagg ccttgctgga | 6960 |
| gacctggtgg gtgagccggg agccaaaggt gaccgaggac tgccagggcc gcgaggcgag | 7020 |
| aagggtgaag ctggccgtgc aggggagccc ggagaccctg ggaagatgg tcagaaaggg | 7080 |
| gctccaggac ccaaaggttt caaggtgac ccaggagtcg gggtcccggg ctcccctggg | 7140 |
| cctcctggcc ctccaggtgt gaagggagat ctgggcctcc ctggcctgcc cggtgctcct | 7200 |
| ggtgttgttg ggttcccggg tcagacaggc cctcgaggag agatgggtca gccaggcct | 7260 |
| agtggagagc ggggtctggc aggccccca gggagagaag gaatcccagg accctgggg | 7320 |
| ccacctggac caccggggtc agtgggacca cctgggcct ctggactcaa aggagacaag | 7380 |
| ggagaccctg gagtagggct gcctgggccc gaggcgagcc gtgggagcc aggcatccgg | 7440 |
| ggtgaagatg gccgccccgg ccaggaggga cccgaggac tcacggggcc ccctggcagc | 7500 |

```
agggggagagc gtggggagaa gggtgatgtt gggagtgcag gactaaaggg tgacaaggga    7560
gactcagctg tgatcctggg gcctccaggc ccacggggtg ccaaggggga catgggtgaa    7620
cgagggcctc ggggcttgga tggtgacaaa ggacctcggg gagacaatgg ggaccctggt    7680
gacaagggca gcaagggaga gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aagggagcct gtggccttga tggagagaag    7920
ggagacaagg gagaagctgg tcccccaggc cgcccccggc tggcaggaca caaaggagag    7980 atggggagc ctggtgtgcc gggccagtcg ggggcccctg gcaaggaggg cctgatcggt    8040
cccaagggtg accgaggctt tgacgggcag ccaggcccca gggtgaccca gggcgagaaa    8100
ggggagcggg gaaccccagg aattggggc ttcccaggcc ccagtggaaa tgatggctct    8160
gctggtcccc cagggccacc tggcagtgtt ggtcccagag gccccgaagg acttcagggc    8220
cagaagggtg agcgaggtcc ccccggagag agagtggtgg gggctcctgg ggtccctgga    8280
gctcctggcg agagagggga gcaggggcgg ccagggcctg ccggtcctcg aggcgagaag    8340
ggagaagctg cactgacgga ggatgacatc cggggctttg tgcgccaaga gatgagtcag    8400
cactgtgcct gccagggcca gttcatcgca tctggatcac gacccctccc tagttatgct    8460
gcagacactg ccggctccca gctccatgct gtgcctgtgc tccgcgtctc tcatgcagag    8520
gaggaagagc gggtaccccc tgaggatgat gagtactctg aatactccga gtattctgtg    8580
gaggagtacc aggaccctga agctccttgg gatagtgatg acccctgttc cctgccactg    8640
gatgagggct cctgcactgc ctacaccctg cgctggtacc atcgggctgt gacaggcagc    8700
acagaggcct gtcacccttt tgtctatggt ggctgtggag ggaatgccaa ccgttttggg    8760
acccgtgagg cctgcgagcg ccgctgccca ccccgggtgg tccagagcca ggggacaggt    8820
actgcccagg acagggccaa gaggggcagc ggcgagggca ggggcagcct gctgacctgc    8880
ggcgacgtgg aggagaaccc cggccccacc tcctcggggc ctggaccccg gttcctgctg    8940
ctgctgccgc tgctgctgcc ccctgcggcc tcagcctccg accggccccg ggccgagac    9000 ccggtcaacc cagagaagct gctggtgatc actgtggcca cagctgaaac cgaggggtac    9060
ctgcgtttcc tgcgctctgc ggagttcttc aactacactg tgcggaccct gggcctggga    9120
gaggagtggc gaggggtga tgtggctcga acagttggtg gaggacagaa ggtccggtgg    9180
ttaaagaagg aaatggagaa atacgctgac cgggaggata tgatcatcat gtttgtggat    9240
agctacgacg tgattctggc cggcagcccc acagagctgc tgaagaagtt cgtccagagt    9300
ggcagccgcc tgctcttctc tgcagagagc ttctgctggc ccgagtgggg gctggcggag    9360
cagtaccctg aggtgggcac ggggaagcgc ttcctcaatt ctggtggatt catcggtttt    9420
gccaccacca tccaccaaat cgtgcgccag tggaagtaca aggatgatga cgacgaccag    9480
ctgttctaca cacggctcta cctggaccca ggactgagg agaaactcag ccttaatctg    9540
gatcataagt ctcggatctt tcagaacctc aacggggctt tagatgaagt ggttttaaag    9600
tttgatcgga accgtgtgcg tatccggaac gtggcctacg acacgctccc cattgtggtc    9660
catggaaacg gtcccactaa gctgcagctc aactacctgg gaaactacgt ccccaatggc    9720
tggactcctg agggaggctg tggcttctgc aaccaggacc ggaggacact cccgggggggg    9780 cagcctcccc ccggggtgtt tctggccgtg tttgtggaac agcctactcc gtttctgccc    9840
cgcttcctgc agcggctgct actcctggac tatcccccg acagggtcac ccttttcctg    9900
```

-continued

```
cacaacaacg aggtcttcca tgaacccac atcgctgact cctggccgca gctccaggac    9960
cacttctcag ctgtgaagct cgtggggccg gaggaggctc tgagcccagg cgaggccagg  10020
gacatggcca tggacctgtg tcggcaggac ccgagtgtg agttctactt cagcctggac   10080
gccgacgctg tcctcaccaa cctgcagacc ctgcgtatcc tcattgagga aacaggaag   10140
gtgatcgccc ccatgctgtc ccgccacggc aagctgtggt ccaacttctg gggcgccctg  10200
agccccgatg agtactacgc ccgctccgag gactacgtgg agctggtgca gcggaagcga  10260
gtgggtgtgt ggaatgtacc atacatctcc caggcctatg tgatccgggg tgataccctg  10320
cggatggagc tgccccagag ggatgtgttc tcgggcagtg acacagaccc ggacatggcc  10380
ttctgtaaga gctttcgaga caagggcatc ttcctccatc tgagcaatca gcatgaattt  10440
ggccggctcc tggccacttc cagatacgac acggagcacc tgcacccga cctctggcag   10500
atcttcgaca accccgtcga ctggaaggag cagtacatcc acgagaacta cagccgggcc  10560
ctggaagggg aaggaatcgt ggagcagcca tgcccggacg tgtactggtt cccactgctg  10620
tcagaacaaa tgtgtgatga gctggtggca gagatggagc actacggcca gtggtcaggc  10680
ggccggcatg aggattcaag gctggctgga ggctacgaga atgtgcccac cgtggacatc  10740
cacatgaagc aggtggggta cgaggaccag tggctgcagc tgctgcggac gtatgtgggc  10800
cccatgaccg agagcctgtt tcccggttac acaccaagg cgcggggcggt gatgaacttt   10860
gtggttcgct accggccaga cgagcagccg tctctgcggc acaccacga ctcatccacc   10920
ttcaccctca acgttgccct caaccacaag ggcctggact atgagggagg tggctgccgc   10980
ttcctgcgct acgactgtgt gatctcctcc ccgaggaagg gctgggcact cctgcacccc   11040
ggccgcctca cccactacca cgaggggctg ccaacgacct ggggcacacg ctacatcatg   11100
gtgtcctttg tcgaccctg a                                              11121
```

<210> SEQ ID NO 14
<211> LENGTH: 3706
<212> TYPE: PRT
<213> ORGANISM: Artificial Sequence
<220> FEATURE:
<223> OTHER INFORMATION: Synthetic Construct

<400> SEQUENCE: 14

```
Met Thr Leu Arg Leu Leu Val Ala Ala Leu Cys Ala Gly Ile Leu Ala
 1               5                  10                  15
Glu Ala Pro Arg Val Arg Ala Gln His Arg Glu Arg Val Thr Cys Thr
            20                  25                  30
Arg Leu Tyr Ala Ala Asp Ile Val Phe Leu Leu Asp Gly Ser Ser Ser
        35                  40                  45
Ile Gly Arg Ser Asn Phe Arg Glu Val Arg Ser Phe Leu Glu Gly Leu
    50                  55                  60
Val Leu Pro Phe Ser Gly Ala Ala Ser Ala Gln Gly Val Arg Phe Ala
65                  70                  75                  80
Thr Val Gln Tyr Ser Asp Asp Pro Arg Thr Glu Phe Gly Leu Asp Ala
                85                  90                  95
Leu Gly Ser Gly Gly Asp Val Ile Arg Ala Ile Arg Glu Leu Ser Tyr
            100                 105                 110
Lys Gly Gly Asn Thr Arg Thr Gly Ala Ala Ile Leu His Val Ala Asp
        115                 120                 125
His Val Phe Leu Pro Gln Leu Ala Arg Pro Gly Val Pro Lys Val Cys
    130                 135                 140
```

```
Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
            165                 170                 175

Asn Ala Asp Pro Glu Glu Leu Lys Arg Val Ala Ser Gln Pro Thr Ser
            180                 185                 190

Asp Phe Phe Phe Val Asn Asp Phe Ser Ile Leu Arg Thr Leu Leu
            195                 200                 205

Pro Leu Val Ser Arg Arg Val Cys Thr Thr Ala Gly Gly Val Pro Val
        210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
            245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
            325                 330                 335

Asn Thr Thr Ala His Ser Leu Leu Val Ala Trp Arg Ser Val Pro Gly
            340                 345                 350

Ala Thr Gly Tyr Arg Val Thr Trp Arg Val Leu Ser Gly Gly Pro Thr
        355                 360                 365

Gln Gln Gln Glu Leu Gly Pro Gly Gln Gly Ser Val Leu Leu Arg Asp
370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
            405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
        435                 440                 445

Arg Arg Glu Thr Gly Leu Glu Pro Pro Gln Lys Val Val Leu Pro Ser
        450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
            485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
            515                 520                 525

Ser Pro Val Pro Gly Ala Thr Gln Tyr Arg Ile Ile Val Arg Ser Thr
        530                 535                 540

Gln Gly Val Glu Arg Thr Leu Val Leu Pro Gly Ser Gln Thr Ala Phe
545                 550                 555                 560
```

-continued

Asp Leu Asp Asp Val Gln Ala Gly Leu Ser Tyr Thr Val Arg Val Ser
            565                 570                 575
Ala Arg Val Gly Pro Arg Glu Gly Ser Ala Ser Val Leu Thr Val Arg
        580                 585                 590
Arg Glu Pro Glu Thr Pro Leu Ala Val Pro Gly Leu Arg Val Val
    595                 600                 605
Ser Asp Ala Thr Arg Val Arg Val Ala Trp Gly Pro Val Pro Gly Ala
610                 615                 620
Ser Gly Phe Arg Ile Ser Trp Ser Thr Gly Ser Gly Pro Glu Ser Ser
625                 630                 635                 640
Gln Thr Leu Pro Pro Asp Ser Thr Ala Thr Asp Ile Thr Gly Leu Gln
                645                 650                 655
Pro Gly Thr Thr Tyr Gln Val Ala Val Ser Val Leu Arg Gly Arg Glu
            660                 665                 670
Glu Gly Pro Ala Ala Val Ile Val Ala Arg Thr Asp Pro Leu Gly Pro
        675                 680                 685
Val Arg Thr Val His Val Thr Gln Ala Ser Ser Ser Val Thr Ile
    690                 695                 700
Thr Trp Thr Arg Val Pro Gly Ala Thr Gly Tyr Arg Val Ser Trp His
705                 710                 715                 720
Ser Ala His Gly Pro Glu Lys Ser Gln Leu Val Ser Gly Glu Ala Thr
                725                 730                 735
Val Ala Glu Leu Asp Gly Leu Glu Pro Asp Thr Glu Tyr Thr Val His
            740                 745                 750
Val Arg Ala His Val Ala Gly Val Asp Gly Pro Pro Ala Ser Val Val
        755                 760                 765
Val Arg Thr Ala Pro Glu Pro Val Gly Arg Val Ser Arg Leu Gln Ile
    770                 775                 780
Leu Asn Ala Ser Ser Asp Val Leu Arg Ile Thr Trp Val Gly Val Thr
785                 790                 795                 800
Gly Ala Thr Ala Tyr Arg Leu Ala Trp Gly Arg Ser Glu Gly Gly Pro
                805                 810                 815
Met Arg His Gln Ile Leu Pro Gly Asn Thr Asp Ser Ala Glu Ile Arg
            820                 825                 830
Gly Leu Glu Gly Gly Val Ser Tyr Ser Val Arg Val Thr Ala Leu Val
        835                 840                 845
Gly Asp Arg Glu Gly Thr Pro Val Ser Ile Val Val Thr Thr Pro Pro
    850                 855                 860
Glu Ala Pro Pro Ala Leu Gly Thr Leu His Val Val Gln Arg Gly Glu
865                 870                 875                 880
His Ser Leu Arg Leu Arg Trp Glu Pro Val Pro Arg Ala Gln Gly Phe
                885                 890                 895
Leu Leu His Trp Gln Pro Glu Gly Gly Gln Glu Gln Ser Arg Val Leu
            900                 905                 910
Gly Pro Glu Leu Ser Ser Tyr His Leu Asp Gly Leu Gln Pro Ala Thr
        915                 920                 925
Gln Tyr Arg Val Arg Leu Ser Val Leu Gly Pro Ala Gly Glu Gly Pro
    930                 935                 940
Ser Ala Glu Val Thr Ala Arg Thr Glu Ser Pro Arg Val Pro Ser Ile
945                 950                 955                 960
Glu Leu Arg Val Val Asp Thr Ser Ile Asp Ser Val Thr Leu Ala Trp
                965                 970                 975
Thr Pro Val Ser Arg Ala Ser Ser Tyr Ile Leu Ser Trp Arg Pro Leu

```
                980             985             990
Arg Gly Pro Gly Gln Glu Val Pro Gly Ser Pro Gln Thr Leu Pro Gly
            995                 1000            1005

Ile Ser Ser Ser Gln Arg Val Thr Gly Leu Glu Pro Gly Val Ser Tyr
        1010                1015            1020

Ile Phe Ser Leu Thr Pro Val Leu Asp Gly Val Arg Gly Pro Glu Ala
1025            1030            1035            1040

Ser Val Thr Gln Thr Pro Val Cys Pro Arg Gly Leu Ala Asp Val Val
            1045            1050            1055

Phe Leu Pro His Ala Thr Gln Asp Asn Ala His Arg Ala Glu Ala Thr
            1060            1065            1070

Arg Arg Val Leu Glu Arg Leu Val Leu Ala Leu Gly Pro Leu Gly Pro
            1075            1080            1085

Gln Ala Val Gln Val Gly Leu Leu Ser Tyr Ser His Arg Pro Ser Pro
            1090            1095            1100

Leu Phe Pro Leu Asn Gly Ser His Asp Leu Gly Ile Ile Leu Gln Arg
1105            1110            1115            1120

Ile Arg Asp Met Pro Tyr Met Asp Pro Ser Gly Asn Asn Leu Gly Thr
            1125            1130            1135

Ala Val Val Thr Ala His Arg Tyr Met Leu Ala Pro Asp Ala Pro Gly
            1140            1145            1150

Arg Arg Gln His Val Pro Gly Val Met Val Leu Leu Val Asp Glu Pro
            1155            1160            1165

Leu Arg Gly Asp Ile Phe Ser Pro Ile Arg Glu Ala Gln Ala Ser Gly
            1170            1175            1180

Leu Asn Val Val Met Leu Gly Met Ala Gly Ala Asp Pro Glu Gln Leu
1185            1190            1195            1200

Arg Arg Leu Ala Pro Gly Met Asp Ser Val Gln Thr Phe Phe Ala Val
            1205            1210            1215

Asp Asp Gly Pro Ser Leu Asp Gln Ala Val Ser Gly Leu Ala Thr Ala
            1220            1225            1230

Leu Cys Gln Ala Ser Phe Thr Thr Gln Pro Arg Pro Glu Pro Cys Pro
            1235            1240            1245

Val Tyr Cys Pro Lys Gly Gln Lys Gly Glu Pro Gly Glu Met Gly Leu
            1250            1255            1260

Arg Gly Gln Val Gly Pro Pro Gly Asp Pro Gly Leu Pro Gly Arg Thr
1265            1270            1275            1280

Gly Ala Pro Gly Pro Gln Gly Pro Pro Gly Ser Ala Thr Ala Lys Gly
            1285            1290            1295

Glu Arg Gly Phe Pro Gly Ala Asp Gly Arg Pro Gly Ser Pro Gly Arg
            1300            1305            1310

Ala Gly Asn Pro Gly Thr Pro Gly Ala Pro Gly Leu Lys Gly Ser Pro
            1315            1320            1325

Gly Leu Pro Gly Pro Arg Gly Asp Pro Gly Glu Arg Gly Pro Arg Gly
            1330            1335            1340

Pro Lys Gly Glu Pro Gly Ala Pro Gly Gln Val Ile Gly Gly Glu Gly
1345            1350            1355            1360

Pro Gly Leu Pro Gly Arg Lys Gly Asp Pro Gly Pro Ser Gly Pro Pro
            1365            1370            1375

Gly Pro Arg Gly Pro Leu Gly Asp Pro Gly Arg Gly Pro Pro Gly
            1380            1385            1390

Leu Pro Gly Thr Ala Met Lys Gly Asp Lys Gly Asp Arg Gly Glu Arg
            1395            1400            1405
```

```
Gly Pro Pro Gly Pro Gly Glu Gly Gly Ile Ala Pro Gly Glu Pro Gly
    1410                1415                1420

Leu Pro Gly Leu Pro Gly Ser Pro Gly Pro Gln Gly Pro Val Gly Pro
1425                1430                1435                1440

Pro Gly Lys Lys Gly Glu Lys Gly Asp Ser Glu Asp Gly Ala Pro Gly
                1445                1450                1455

Leu Pro Gly Gln Pro Gly Ser Pro Gly Glu Gln Gly Pro Arg Gly Pro
            1460                1465                1470

Pro Gly Ala Ile Gly Pro Lys Gly Asp Arg Gly Phe Pro Gly Pro Leu
        1475                1480                1485

Gly Glu Ala Gly Glu Lys Gly Glu Arg Gly Pro Pro Gly Pro Ala Gly
    1490                1495                1500

Ser Arg Gly Leu Pro Gly Val Ala Gly Arg Pro Gly Ala Lys Gly Pro
1505                1510                1515                1520

Glu Gly Pro Pro Gly Pro Thr Gly Arg Gln Gly Glu Lys Gly Glu Pro
                1525                1530                1535

Gly Arg Pro Gly Asp Pro Ala Val Val Gly Pro Ala Val Ala Gly Pro
            1540                1545                1550

Lys Gly Glu Lys Gly Asp Val Gly Pro Ala Gly Pro Arg Gly Ala Thr
        1555                1560                1565

Gly Val Gln Gly Glu Arg Gly Pro Pro Gly Leu Val Leu Pro Gly Asp
    1570                1575                1580

Pro Gly Pro Lys Gly Asp Pro Gly Asp Arg Gly Pro Ile Gly Leu Thr
1585                1590                1595                1600

Gly Arg Ala Gly Pro Pro Gly Asp Ser Gly Pro Pro Gly Glu Lys Gly
                1605                1610                1615

Asp Pro Gly Arg Pro Gly Pro Pro Gly Pro Val Gly Pro Arg Gly Arg
            1620                1625                1630

Asp Gly Glu Val Gly Glu Lys Gly Asp Glu Gly Pro Pro Gly Asp Pro
        1635                1640                1645

Gly Leu Pro Gly Lys Ala Gly Glu Arg Gly Leu Arg Gly Ala Pro Gly
    1650                1655                1660

Val Arg Gly Pro Val Gly Glu Lys Gly Asp Gln Gly Asp Pro Gly Glu
1665                1670                1675                1680

Asp Gly Arg Asn Gly Ser Pro Gly Ser Ser Gly Pro Lys Gly Asp Arg
                1685                1690                1695

Gly Glu Pro Gly Pro Pro Gly Pro Pro Gly Arg Leu Val Asp Thr Gly
            1700                1705                1710

Pro Gly Ala Arg Glu Lys Gly Glu Pro Gly Asp Arg Gly Gln Glu Gly
        1715                1720                1725

Pro Arg Gly Pro Lys Gly Asp Pro Gly Leu Pro Gly Ala Pro Gly Glu
    1730                1735                1740

Arg Gly Ile Glu Gly Phe Arg Gly Pro Gly Pro Gln Gly Asp Pro
1745                1750                1755                1760

Gly Val Arg Gly Pro Ala Gly Glu Lys Gly Asp Arg Gly Pro Pro Gly
                1765                1770                1775

Leu Asp Gly Arg Ser Gly Leu Asp Gly Lys Pro Gly Ala Ala Gly Pro
            1780                1785                1790

Ser Gly Pro Asn Gly Ala Ala Gly Lys Ala Gly Asp Pro Gly Arg Asp
        1795                1800                1805

Gly Leu Pro Gly Leu Arg Gly Glu Gln Gly Leu Pro Gly Pro Ser Gly
    1810                1815                1820
```

```
Pro Pro Gly Leu Pro Gly Lys Pro Gly Glu Asp Gly Lys Pro Gly Leu
1825                1830                1835                1840

Asn Gly Lys Asn Gly Glu Pro Gly Asp Pro Gly Glu Asp Gly Arg Lys
            1845                1850                1855

Gly Glu Lys Gly Asp Ser Gly Ala Ser Gly Arg Glu Gly Arg Asp Gly
            1860                1865                1870

Pro Lys Gly Glu Arg Gly Ala Pro Gly Ile Leu Gly Pro Gln Gly Pro
        1875                1880                1885

Pro Gly Leu Pro Gly Pro Val Gly Pro Gly Gln Gly Phe Pro Gly
    1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
            1925                1930                1935

Gly Ser Val Pro Asn Val Asp Arg Leu Leu Glu Thr Ala Gly Ile Lys
            1940                1945                1950

Ala Ser Ala Leu Arg Glu Ile Val Glu Thr Trp Asp Glu Ser Ser Gly
            1955                1960                1965

Ser Phe Leu Pro Val Pro Glu Arg Arg Arg Gly Pro Lys Gly Asp Ser
    1970                1975                1980

Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
            2005                2010                2015

Pro Gly Leu Ala Leu Gly Glu Arg Gly Pro Pro Gly Pro Ser Gly Leu
            2020                2025                2030

Ala Gly Glu Pro Gly Lys Pro Gly Ile Pro Gly Leu Pro Gly Arg Ala
            2035                2040                2045

Gly Gly Val Gly Glu Ala Gly Arg Pro Gly Glu Arg Gly Glu Arg Gly
            2050                2055                2060

Glu Lys Gly Glu Arg Gly Glu Gln Gly Arg Asp Gly Pro Pro Gly Leu
2065                2070                2075                2080

Pro Gly Thr Pro Gly Pro Pro Gly Pro Pro Gly Pro Lys Val Ser Val
            2085                2090                2095

Asp Glu Pro Gly Pro Gly Leu Ser Gly Glu Gln Gly Pro Pro Gly Leu
            2100                2105                2110

Lys Gly Ala Lys Gly Glu Pro Gly Ser Asn Gly Asp Gln Gly Pro Lys
            2115                2120                2125

Gly Asp Arg Gly Val Pro Gly Ile Lys Gly Asp Arg Gly Glu Pro Gly
            2130                2135                2140

Pro Arg Gly Gln Asp Gly Asn Pro Gly Leu Pro Gly Glu Arg Gly Met
2145                2150                2155                2160

Ala Gly Pro Glu Gly Lys Pro Gly Leu Gln Gly Pro Arg Gly Pro Pro
            2165                2170                2175

Gly Pro Val Gly Gly His Gly Asp Pro Gly Pro Gly Ala Pro Gly
            2180                2185                2190

Leu Ala Gly Pro Ala Gly Pro Gln Gly Pro Ser Gly Leu Lys Gly Glu
        2195                2200                2205

Pro Gly Glu Thr Gly Pro Pro Gly Arg Gly Leu Thr Gly Pro Thr Gly
            2210                2215                2220

Ala Val Gly Leu Pro Gly Pro Pro Gly Pro Ser Gly Leu Val Gly Pro
2225                2230                2235                2240

Gln Gly Ser Pro Gly Leu Pro Gly Gln Val Gly Glu Thr Gly Lys Pro
```

```
                    2245                2250                2255

Gly Ala Pro Gly Arg Asp Gly Ala Ser Gly Lys Asp Gly Asp Arg Gly
                2260                2265                2270

Ser Pro Gly Val Pro Gly Ser Pro Gly Leu Pro Gly Pro Val Gly Pro
                2275                2280                2285

Lys Gly Glu Pro Gly Pro Thr Gly Ala Pro Gly Gln Ala Val Val Gly
                2290                2295                2300

Leu Pro Gly Ala Lys Gly Glu Lys Gly Ala Pro Gly Gly Leu Ala Gly
2305                2310                2315                2320

Asp Leu Val Gly Glu Pro Gly Ala Lys Gly Asp Arg Gly Leu Pro Gly
                2325                2330                2335

Pro Arg Gly Glu Lys Gly Glu Ala Gly Arg Ala Gly Glu Pro Gly Asp
                2340                2345                2350

Pro Gly Glu Asp Gly Gln Lys Gly Ala Pro Gly Pro Lys Gly Phe Lys
                2355                2360                2365

Gly Asp Pro Gly Val Gly Val Pro Gly Ser Pro Gly Pro Pro Gly Pro
                2370                2375                2380

Pro Gly Val Lys Gly Asp Leu Gly Leu Pro Gly Leu Pro Gly Ala Pro
2385                2390                2395                2400

Gly Val Val Gly Phe Pro Gly Gln Thr Gly Pro Arg Gly Glu Met Gly
                2405                2410                2415

Gln Pro Gly Pro Ser Gly Glu Arg Gly Leu Ala Gly Pro Pro Gly Arg
                2420                2425                2430

Glu Gly Ile Pro Gly Pro Leu Gly Pro Pro Gly Pro Pro Gly Ser Val
                2435                2440                2445

Gly Pro Pro Gly Ala Ser Gly Leu Lys Gly Asp Lys Gly Asp Pro Gly
                2450                2455                2460

Val Gly Leu Pro Gly Pro Arg Gly Glu Arg Gly Glu Pro Gly Ile Arg
2465                2470                2475                2480

Gly Glu Asp Gly Arg Pro Gly Gln Glu Gly Pro Arg Gly Leu Thr Gly
                2485                2490                2495

Pro Pro Gly Ser Arg Gly Glu Arg Gly Glu Lys Gly Asp Val Gly Ser
                2500                2505                2510

Ala Gly Leu Lys Gly Asp Lys Gly Asp Ser Ala Val Ile Leu Gly Pro
                2515                2520                2525

Pro Gly Pro Arg Gly Ala Lys Gly Asp Met Gly Glu Arg Gly Pro Arg
                2530                2535                2540

Gly Leu Asp Gly Asp Lys Gly Pro Arg Gly Asp Asn Gly Asp Pro Gly
2545                2550                2555                2560

Asp Lys Gly Ser Lys Gly Glu Pro Gly Asp Lys Gly Ser Ala Gly Leu
                2565                2570                2575

Pro Gly Leu Arg Gly Leu Leu Gly Pro Gln Gly Pro Gly Ala Ala
                2580                2585                2590

Gly Ile Pro Gly Asp Pro Gly Ser Pro Gly Lys Asp Gly Val Pro Gly
                2595                2600                2605

Ile Arg Gly Glu Lys Gly Asp Val Gly Phe Met Gly Pro Arg Gly Leu
                2610                2615                2620

Lys Gly Glu Arg Gly Val Lys Gly Ala Cys Gly Leu Asp Gly Glu Lys
2625                2630                2635                2640

Gly Asp Lys Gly Glu Ala Gly Pro Pro Gly Arg Pro Gly Leu Ala Gly
                2645                2650                2655

His Lys Gly Glu Met Gly Glu Pro Gly Val Pro Gly Gln Ser Gly Ala
                2660                2665                2670
```

```
Pro Gly Lys Glu Gly Leu Ile Gly Pro Lys Gly Asp Arg Gly Phe Asp
        2675                2680                2685
Gly Gln Pro Gly Pro Lys Gly Asp Gln Gly Glu Lys Gly Glu Arg Gly
            2690                2695                2700
Thr Pro Gly Ile Gly Gly Phe Pro Gly Pro Ser Gly Asn Asp Gly Ser
2705                2710                2715                2720
Ala Gly Pro Pro Gly Pro Pro Gly Ser Val Gly Pro Arg Gly Pro Glu
            2725                2730                2735
Gly Leu Gln Gly Gln Lys Gly Glu Arg Gly Pro Pro Gly Glu Arg Val
            2740                2745                2750
Val Gly Ala Pro Gly Val Pro Gly Ala Pro Gly Glu Arg Gly Glu Gln
            2755                2760                2765
Gly Arg Pro Gly Pro Ala Gly Pro Arg Gly Glu Lys Gly Glu Ala Ala
            2770                2775                2780
Leu Thr Glu Asp Asp Ile Arg Gly Phe Val Arg Gln Glu Met Ser Gln
2785                2790                2795                2800
His Cys Ala Cys Gln Gly Gln Phe Ile Ala Ser Gly Ser Arg Pro Leu
            2805                2810                2815
Pro Ser Tyr Ala Ala Asp Thr Ala Gly Ser Gln Leu His Ala Val Pro
            2820                2825                2830
Val Leu Arg Val Ser His Ala Glu Glu Glu Arg Val Pro Pro Glu
            2835                2840                2845
Asp Asp Glu Tyr Ser Glu Tyr Ser Glu Tyr Ser Val Glu Glu Tyr Gln
            2850                2855                2860
Asp Pro Glu Ala Pro Trp Asp Ser Asp Pro Cys Ser Leu Pro Leu
2865                2870                2875                2880
Asp Glu Gly Ser Cys Thr Ala Tyr Thr Leu Arg Trp Tyr His Arg Ala
            2885                2890                2895
Val Thr Gly Ser Thr Glu Ala Cys His Pro Phe Val Tyr Gly Gly Cys
            2900                2905                2910
Gly Gly Asn Ala Asn Arg Phe Gly Thr Arg Glu Ala Cys Glu Arg Arg
            2915                2920                2925
Cys Pro Pro Arg Val Val Gln Ser Gln Gly Thr Gly Thr Ala Gln Asp
            2930                2935                2940
Arg Ala Lys Arg Gly Ser Gly Glu Gly Arg Gly Ser Leu Leu Thr Cys
2945                2950                2955                2960
Gly Asp Val Glu Glu Asn Pro Gly Pro Thr Ser Ser Gly Pro Gly Pro
            2965                2970                2975
Arg Phe Leu Leu Leu Leu Pro Leu Leu Leu Pro Pro Ala Ala Ser Ala
            2980                2985                2990
Ser Asp Arg Pro Arg Gly Arg Asp Pro Val Asn Pro Glu Lys Leu Leu
            2995                3000                3005
Val Ile Thr Val Ala Thr Ala Glu Thr Glu Gly Tyr Leu Arg Phe Leu
            3010                3015                3020
Arg Ser Ala Glu Phe Phe Asn Tyr Thr Val Arg Thr Leu Gly Leu Gly
3025                3030                3035                3040
Glu Glu Trp Arg Gly Gly Asp Val Ala Arg Thr Val Gly Gly Gly Gln
            3045                3050                3055
Lys Val Arg Trp Leu Lys Lys Glu Met Glu Lys Tyr Ala Asp Arg Glu
            3060                3065                3070
Asp Met Ile Ile Met Phe Val Asp Ser Tyr Asp Val Ile Leu Ala Gly
            3075                3080                3085
```

```
Ser Pro Thr Glu Leu Leu Lys Lys Phe Val Gln Ser Gly Ser Arg Leu
    3090                3095                3100

Leu Phe Ser Ala Glu Ser Phe Cys Trp Pro Glu Trp Gly Leu Ala Glu
3105                3110                3115                3120

Gln Tyr Pro Glu Val Gly Thr Gly Lys Arg Phe Leu Asn Ser Gly Gly
            3125                3130                3135

Phe Ile Gly Phe Ala Thr Thr Ile His Gln Ile Val Arg Gln Trp Lys
        3140                3145                3150

Tyr Lys Asp Asp Asp Asp Gln Leu Phe Tyr Thr Arg Leu Tyr Leu
    3155                3160                3165

Asp Pro Gly Leu Arg Glu Lys Leu Ser Leu Asn Leu Asp His Lys Ser
    3170                3175                3180

Arg Ile Phe Gln Asn Leu Asn Gly Ala Leu Asp Glu Val Val Leu Lys
3185                3190                3195                3200

Phe Asp Arg Asn Arg Val Arg Ile Arg Asn Val Ala Tyr Asp Thr Leu
            3205                3210                3215

Pro Ile Val Val His Gly Asn Gly Pro Thr Lys Leu Gln Leu Asn Tyr
        3220                3225                3230

Leu Gly Asn Tyr Val Pro Asn Gly Trp Thr Pro Glu Gly Cys Gly
        3235                3240                3245

Phe Cys Asn Gln Asp Arg Arg Thr Leu Pro Gly Gly Gln Pro Pro
    3250                3255                3260

Arg Val Phe Leu Ala Val Phe Val Glu Gln Pro Thr Pro Phe Leu Pro
3265                3270                3275                3280

Arg Phe Leu Gln Arg Leu Leu Leu Asp Tyr Pro Pro Asp Arg Val
            3285                3290                3295

Thr Leu Phe Leu His Asn Asn Glu Val Phe His Glu Pro His Ile Ala
        3300                3305                3310

Asp Ser Trp Pro Gln Leu Gln Asp His Phe Ser Ala Val Lys Leu Val
    3315                3320                3325

Gly Pro Glu Glu Ala Leu Ser Pro Gly Glu Ala Arg Asp Met Ala Met
    3330                3335                3340

Asp Leu Cys Arg Gln Asp Pro Glu Cys Glu Phe Tyr Phe Ser Leu Asp
3345                3350                3355                3360

Ala Asp Ala Val Leu Thr Asn Leu Gln Thr Leu Arg Ile Leu Ile Glu
            3365                3370                3375

Glu Asn Arg Lys Val Ile Ala Pro Met Leu Ser Arg His Gly Lys Leu
        3380                3385                3390

Trp Ser Asn Phe Trp Gly Ala Leu Ser Pro Asp Glu Tyr Tyr Ala Arg
        3395                3400                3405

Ser Glu Asp Tyr Val Glu Leu Val Gln Arg Lys Arg Val Gly Val Trp
    3410                3415                3420

Asn Val Pro Tyr Ile Ser Gln Ala Tyr Val Ile Arg Gly Asp Thr Leu
3425                3430                3435                3440

Arg Met Glu Leu Pro Gln Arg Asp Val Phe Ser Gly Ser Asp Thr Asp
            3445                3450                3455

Pro Asp Met Ala Phe Cys Lys Ser Phe Arg Asp Lys Gly Ile Phe Leu
        3460                3465                3470

His Leu Ser Asn Gln His Glu Phe Gly Arg Leu Leu Ala Thr Ser Arg
        3475                3480                3485

Tyr Asp Thr Glu His Leu His Pro Asp Leu Trp Gln Ile Phe Asp Asn
    3490                3495                3500

Pro Val Asp Trp Lys Glu Gln Tyr Ile His Glu Asn Tyr Ser Arg Ala
```

```
                     3505                 3510                 3515                 3520
Leu Glu Gly Glu Gly Ile Val Glu Gln Pro Cys Pro Asp Val Tyr Trp
                3525                 3530                 3535

Phe Pro Leu Leu Ser Glu Gln Met Cys Asp Glu Leu Val Ala Glu Met
                3540                 3545                 3550

Glu His Tyr Gly Gln Trp Ser Gly Gly Arg His Glu Asp Ser Arg Leu
                3555                 3560                 3565

Ala Gly Gly Tyr Glu Asn Val Pro Thr Val Asp Ile His Met Lys Gln
                3570                 3575                 3580

Val Gly Tyr Glu Asp Gln Trp Leu Gln Leu Leu Arg Thr Val Gly
3585                 3590                 3595                 3600

Pro Met Thr Glu Ser Leu Phe Pro Gly Tyr His Thr Lys Ala Arg Ala
                3605                 3610                 3615

Val Met Asn Phe Val Val Arg Tyr Arg Pro Asp Glu Gln Pro Ser Leu
                3620                 3625                 3630

Arg Pro His His Asp Ser Ser Thr Phe Thr Leu Asn Val Ala Leu Asn
                3635                 3640                 3645

His Lys Gly Leu Asp Tyr Glu Gly Gly Gly Cys Arg Phe Leu Arg Tyr
                3650                 3655                 3660

Asp Cys Val Ile Ser Ser Pro Arg Lys Gly Trp Ala Leu Leu His Pro
3665                 3670                 3675                 3680

Gly Arg Leu Thr His Tyr His Glu Gly Leu Pro Thr Thr Trp Gly Thr
                3685                 3690                 3695

Arg Tyr Ile Met Val Ser Phe Val Asp Pro
                3700                 3705

<210> SEQ ID NO 15
<211> LENGTH: 11121
<212> TYPE: DNA
<213> ORGANISM: Artificial Sequence
<220> FEATURE:
<223> OTHER INFORMATION: Synthetic Construct

<400> SEQUENCE: 15
atgacctcct cggggcctgg accccggttc ctgctgctgc tgccgctgct gctgcccct      60 gcggcctcag cctccgaccg gccccgggc cgagacccgg tcaacccaga gaagctgctg     120
gtgatcactg tggccacagc tgaaaccgag gggtacctgc gtttcctgcg ctctgcggag     180
ttcttcaact acactgtgcg gaccctgggc ctgggagagg agtggcgagg gggtgatgtg     240
gctcgaacag ttggtggagg acagaaggtc cggtggttaa agaaggaaat ggagaaatac     300
gctgaccggg aggatatgat catcatgttt gtggatagct acgacgtgat tctggccggc     360
agccccacag agctgctgaa gaagttcgtc cagagtggca gccgcctgct cttctctgca     420
gagagcttct gctggcccga gtgggggctg gcggagcagt accctgaggt gggcacgggg     480
aagcgcttcc tcaattctgg tggattcatc ggttttgcca ccaccatcca ccaaatcgtg     540
cgccagtgga agtacaagga tgatgacgac accagctgt tctacacacg gctctacctg     600
gacccaggac tgagggagaa actcagcctt aatctggatc ataagtctcg gatctttcag     660
aacctcaacg gggctttaga tgaagtggtt ttaaagtttg atcggaaccg tgtgcgtatc     720
cggaacgtgg cctacgacac gctccccatt gtggtccatg aaacggtcc cactaagctg     780 cagctcaact acctgggaaa ctacgtcccc aatggctgga ctcctgaggg aggctgtggc     840
ttctgcaacc aggaccggag gacactcccg gggggcagc ctccccccg gtgtttctg     900 gccgtgtttg tggaacagcc tactccgttt ctgccccgct tcctgcagcg gctgctactc     960
```

```
ctggactatc cccccgacag ggtcacccct tcctgcaca acaacgaggt cttccatgaa    1020
ccccacatcg ctgactcctg gccgcagctc caggaccact tctcagctgt gaagctcgtg    1080
gggccggagg aggctctgag cccaggcgag gccagggaca tggccatgga cctgtgtcgg    1140
caggaccccg agtgtgagtt ctacttcagc ctggacgccg acgctgtcct caccaacctg    1200
cagaccctgc gtatcctcat tgaggagaac aggaaggtga tcgcccccat gctgtcccgc    1260
cacggcaagc tgtggtccaa cttctggggc ccctgagcc ccgatgagta ctacgcccgc    1320
tccgaggact acgtggagct ggtgcagcgg aagcgagtgg gtgtgtggaa tgtaccatac    1380
atctcccagg cctatgtgat ccggggtgat accctgcgga tggagctgcc ccagagggat    1440
gtgttctcgg gcagtgacac agacccggac atggccttct gtaagagctt cgagacaag     1500 ggcatcttcc tccatctgag caatcagcat gaatttggcc ggctcctggc cacttccaga    1560
tacgacacgg agcacctgca ccccgacctc tggcagatct tcgacaaccc cgtcgactgg    1620
aaggagcagt acatccacga gaactacagc cgggccctgg aaggggaagg aatcgtggag    1680
cagccatgcc cggacgtgta ctggttccca ctgctgtcag aacaaatgtg tgatgagctg    1740
gtggcagaga tggagcacta cggccagtgg tcaggcggcc ggcatgagga ttcaaggctg    1800
gctggaggct acgagaatgt gcccaccgtg gacatccaca tgaagcaggt ggggtacgag    1860
gaccagtggc tgcagctgct gcggacgtat gtgggcccca tgaccgagag cctgtttccc    1920
ggttaccaca ccaaggcgcg ggcggtgatg aactttgtgg ttcgctaccg gccagacgag    1980
cagccgtctc tgcggccaca ccacgactca tccaccttca ccctcaacgt tgccctcaac    2040
cacaagggcc tggactatga gggaggtggc tgccgcttcc tgcgctacga ctgtgtgatc    2100
tcctccccga ggaagggctg ggcactcctg caccccggcc gcctcaccca ctaccacgag    2160
gggctgccaa cgacctgggg cacacgctac atcatggtgt cctttgtcga ccccagggcc    2220
aagaggggca gcggcgaggg caggggcagc ctgctgacct gcggcgacgt ggaggagaac    2280
cccggcccca cgctgcggct tctggtggcc gcgctctgcg ccgggatcct ggcagaggcg    2340
ccccgagtgc gagcccagca cagggagaga gtgacctgca cgcgccttta cgccgctgac    2400
attgtgttct tactggatgg ctcctcatcc attggccgca gcaatttccg cgaggtccgc    2460
agctttctcg aagggctggt gctgcctttc tctggagcag ccagtgcaca gggtgtgcgc    2520
tttgccacag tgcagtacag cgatgaccca cggacagagt tcggcctgga tgcacttggc    2580
tctgggggtg atgtgatccg cgccatccgt gagcttagct acaaggggg caacactcgc    2640 acaggggctg caattctcca tgtggctgac catgtcttcc tgccccagct ggcccgacct    2700
ggtgtcccca aggtctgcat cctgatcaca gacgggaagt cccaggacct ggtggacaca    2760 gctgccaaa ggctgaaggg gcaggggtc aagctatttg ctgtggggat caagaatgct    2820
gaccctgagg agctgaagcg agttgcctca cagcccacca gtgacttctt cttcttcgtc    2880
aatgacttca gcatcttgag gacactactg ccctcgtttt cccggagagt gtgcacgact    2940
gctggtggcg tgcctgtgac ccgacctccg gatgactcga cctctgctcc acgagacctg    3000
gtgctgtctg agccaagcag ccaatccttg agagtacagt ggacagcggc cagtggccct    3060
gtgactggct acaaggtcca gtacactcct ctgacggggc tggacagcc actgccgagt    3120 gagcggcagg aggtgaacgt cccagctggt gagaccagtg tgcggctgcg gggtctccgg    3180
ccactgaccg agtaccaagt gactgtgatt gccctctacg ccaacagcat cggggaggct    3240
gtgagcggga cagctcggac cactgcccta gaagggccgg aactgaccat ccagaatacc    3300
```

```
acagcccaca gcctcctggt ggcctggcgg agtgtgccag gtgccactgg ctaccgtgtg      3360
acatggcggg tcctcagtgg tgggcccaca cagcagcagg agctgggccc tgggcagggt      3420
tcagtgttgc tgcgtgactt ggagcctggc acggactatg aggtgaccgt gagcacccta      3480
tttggccgca gtgtgggscc cgccacttcc ctgatggctc gcactgacgc ttctgttgag      3540
cagaccctgc gcccggtcat cctgggcccc acatccatcc tcctttcctg gaacttggtg      3600
cctgaggccc gtggctaccg gttggaatgg cggcgtgaga ctggcttgga gccaccgcag      3660
aaggtggtac tgccctctga tgtgacccgc taccagttgg atgggctgca gccgggcact      3720
gagtaccgcc tcacactcta cactctgctg gagggccacg aggtggccac ccctgcaacc      3780
gtggttccca ctggaccaga gctgcctgtg agccctgtaa cagacctgca agccaccgag      3840
ctgcccgggc agcgggtgcg agtgtcctgg agcccagtcc ctggtgccac ccagtaccgc      3900
atcattgtgc gcagcaccca gggggttgag cggaccctgg tgcttcctgg gagtcagaca      3960
gcattcgact tggatgacgt tcaggctggg cttagctaca ctgtgcgggt gtctgctcga      4020
gtgggtcccc gtgagggcag tgccagtgtc ctcactgtcc gccgggagcc ggaaactcca      4080
cttgctgttc cagggctgcg ggttgtggtg tcagatgcaa cgcgagtgag ggtggcctgg      4140
ggacccgtcc ctggagccag tggatttcgg attagctgga gcacaggcag tggtccggag      4200
tccagccaga cactgccccc agactctact gccacagaca tcacagggct gcagcctgga      4260
accacctacc aggtggctgt gtcggtactg cgaggcagag aggagggccc tgctgcagtc      4320
atcgtggctc gaacggaccc actgggccca gtgaggacgg tccatgtgac tcaggccagc      4380
agctcatctg tcaccattac ctggaccagg gttcctggcg ccacaggata cagggtttcc      4440
tggcactcag cccacggccc agagaaatcc cagttggttt ctggggaggc cacggtggct      4500
gagctggatg gactggagcc agatactgag tatacggtgc atgtgagggc ccatgtggct      4560
ggcgtggatg ggccccctgc ctctgtggtt gtgaggactg cccctgagcc tgtgggtcgt      4620
gtgtcgaggc tgcagatcct caatgcttcc agcgacgttc tacggatcac ctgggtaggg      4680
gtcactggag ccacagctta cagactggcc tggggccgga gtgaaggcgg ccccatgagg      4740
caccagatac tcccaggaaa cacagactct gcagagatcc ggggtctcga aggtggagtc      4800
agctactcag tgcgagtgac tgcacttgtc ggggaccgcg agggcacacc tgtctccatt      4860
gttgtcacta cgccgcctga ggctccgcca gccctgggga cgcttcacgt ggtgcagcgc      4920
ggggagcact cgctgaggct gcgctgggag ccggtgccca gagcgcaggg cttccttctg      4980
cactggcaac ctgagggtgg ccaggaacag tcccgggtcc tggggcccga gctcagcagc      5040
tatcacctgg acgggctgga gccagcgaca cagtaccgcg tgaggctgag tgtcctaggg      5100
ccagctggag aagggccctc tgcagaggtg actgcgcgca ctgagtcacc tcgtgttcca      5160
agcattgaac tacgtgtggt ggacacctcg atcgactcgg tgactttggc ctggactcca      5220
gtgtccaggg catccagcta catcctatcc tggcggccac tcagaggccc tggccaggaa      5280
gtgcctgggt ccccgcagac acttccaggg atctcaagct cccagcgggt gacagggcta      5340
gagcctggcg tctcttacat cttctcccctg acgccctgtcc tggatggtgt gcggggtcct      5400
gaggcatctg tcacacagac gccagtgtgc cccgtgtggcc tggcggatgt ggtgttccta      5460
ccacatgcca ctcaagacaa tgctcaccgt gcggaggcta cgaggagggt cctggagcgt      5520
ctggtgttgg cacttgggcc tcttgggcca caggcagttc aggttggcct gctgtcttac      5580
agtcatcggc cctcccccact gttcccactg aatggctccc atgaccttgg cattatcttg      5640
caaaggatcc gtgacatgcc ctacatggac ccaagtggga acaacctggg cacagccgtg      5700
```

```
gtcacagctc acagatacat gttggcacca gatgctcctg ggcgccgcca gcacgtacca   5760
ggggtgatgg ttctgctagt ggatgaaccc ttgagaggtg acatattcag ccccatccgt   5820
gaggcccagg cttctgggct taatgtggtg atgttgggaa tggctggagc ggacccagag   5880
cagctgcgtc gcttggcgcc gggtatggac tctgtccaga ccttcttcgc cgtggatgat   5940
gggccaagcc tggaccaggc agtcagtggt ctggccacag ccctgtgtca ggcatccttc   6000
actactcagc cccggccaga gccctgccca gtgtattgtc caaagggcca gaaggggaa    6060 cctggagaga tgggcctgag aggacaagtt gggcctcctg gcgaccctgg cctcccgggc   6120
aggaccggtg ctcccggccc caggggccc cctggaagtg ccactgccaa gggcgagagg    6180
ggcttccctg gagcagatgg gcgtccaggc agccctggcc gcgcgggaa tcctgggacc     6240 cctggagccc ctggcctaaa gggctctcca ggttgcctg ccctcgtgg gacccggga     6300 gagcgaggac ctcgaggccc aaaggggag ccggggctc ccggacaagt catcggaggt    6360
gaaggacctg gcttcctgg gcggaaaggg gaccctggac catcgggccc cctggacct     6420 cgtggaccac tgggggaccc aggaccccgt ggccccccag ggcttcctgg aacagccatg   6480
aagggtgaca aggcgatcg tggggagcgg ggtcccctg gaccaggtga aggtggcatt    6540
gctcctgggg agcctgggct gccgggtctt cccggaagcc ctggacccca aggcccgtt    6600 ggccccctg gaaagaaagg agaaaaaggt gactctgagg atggagctcc aggcctcca    6660 ggacaacctg ggtctccggg tgagcagggc ccacggggac ctcctggagc tattggcccc  6720
aaaggtgacc ggggctttcc agggccctg ggtgaggctg gagagaaggg cgaacgtgga   6780
cccccaggcc cagcgggatc ccgggggctg ccaggggttg ctggacgtcc tggagccaag  6840
ggtcctgaag ggccaccagg acccactggc cgccaaggag agaaggggga gcctggtcgc   6900
cctggggacc ctgcagtggt gggacctgct gttgctggac ccaaaggaga aagggagat    6960 gtggggcccg ctgggcccag aggagctacc ggagtccaag gggaacgggg cccacccggc   7020
ttggttcttc ctggagaccc tggccccaag ggagaccctg gagaccgggg tcccattggc   7080
cttactggca gagcaggacc cccaggtgac tcagggcctc ctggagagaa gggagaccct   7140
gggcggcctg gccccccagg acctgttggc ccccgaggac gagatggtga agttggagag   7200
aaaggtgacg agggtcctcc gggtgacccg ggtttgcctg gaaaagcagg cgagcgtggc   7260
cttcgggggg cacctggagt tcgggggcct gtgggtgaaa agggagacca gggagatcct   7320
ggagaggatg gacgaaatgg cagccctgga tcatctggac ccaagggtga ccgtggggag   7380
ccgggtcccc caggaccccc gggacggctg gtagacacag acctggagc cagagagaag   7440 ggagagcctg ggaccgcgg acaagagggt cctcgagggc caagggtga tcctggcctc    7500 cctggagccc ctggggaaag gggcattgaa gggtttcggg accccccagg cccacagggg   7560
gacccaggtg tccgaggccc agcaggagaa aagggtgacc gggtccccc tgggctggat    7620 ggccggagcg gactggatgg gaaaccagga gccgctgggc cctctgggcc gaatggtgct   7680
gcaggcaaag ctgggacccc agggagagac gggcttccag gcctccgtgg agaacagggc   7740
ctccctggcc cctctggtcc ccctggatta ccgggaaagc caggcgagga tgcaaacct    7800 ggcctgaatg gaaaaaacgg agaacctggg gaccctggaa agacgggag gaaggagag    7860 aaaggagatt caggcgcctc tgggagagaa ggtcgtgatg ccccaagggt gagcgtgga    7920 gctcctggta tccttggacc ccaggggcct ccaggcctcc cagggccagt gggccctcct   7980
ggccagggtt ttcctggtgt cccaggaggc acgggcccca agggtgaccg tggggagact   8040
```

```
ggatccaaag gggagcaggg cctccctgga gagcgtggcc tgcgaggaga gcctggaagt    8100
gtgccgaatg tggatcggtt gctggaaact gctggcatca aggcatctgc cctgcgggag    8160
atcgtggaga cctgggatga gagctctggt agcttcctgc ctgtgcccga acggcgtcga    8220
ggccccaagg gggactcagg cgaacagggc cccccaggca aggagggccc catcggcttt    8280
cctggagaac gcgggctgaa gggcgaccgt ggagaccctg gccctcaggg gccacctggt    8340
ctggcccttg gggagagggg cccccccggg ccttccggcc ttgccgggga gcctggaaag    8400
cctggtattc ccgggctccc aggcagggct ggggtgtgg gagaggcagg aaggccagga    8460
gagaggggag aacggggaga gaaaggagaa cgtggagaac agggcagaga tggccctcct    8520
ggactccctg gaaccctgg gcccccgga cccctggcc ccaaggtgtc tgtggatgag    8580
ccaggtcctg gactctctgg agaacaggga ccccctggac tcaagggtgc taaggggag    8640 ccgggcagca atggtgacca aggtcccaaa ggagacaggg gtgtgccagg catcaaagga    8700
gaccggggag agcctggacc gagggtcag gacggcaacc cggtctacc aggagagcgt    8760 ggtatggctg ggcctgaagg gaagccgggt ctgcagggtc caagaggccc ccctggccca    8820
gtgggtggtc atggagaccc tggaccacct ggtgccccgg gtcttgctgg ccctgcagga    8880
ccccaaggac cttctggcct gaaggggag cctggagaga caggacctcc aggacggggc    8940
ctgactggac ctactggagc tgtgggactt cctggacccc ccggcccttc aggccttgtg    9000
ggtccacagg ggtctccagg tttgcctgga caagtggggg agacagggaa gccgggagcc    9060
ccaggtcgag atggtgccag tggaaaagat ggagacagag ggagccctgg tgtgccaggg    9120
tcaccaggtc tgcctggccc tgtcggacct aaaggagaac ctggcccac gggggcccct    9180 ggacaggctg tggtcgggct ccctggagca agggagagga agggagcccc tggaggcctt    9240
gctggagacc tggtgggtga gccgggagcc aaagtgacc gaggactgcc agggccgcga    9300
ggcgagaagg gtgaagctgg ccgtgcaggg gagcccggag accctgggga agatggtcag    9360 aaagggctc caggacccaa aggttttcaag ggtgacccag gagtcgggt cccgggctcc    9420 cctgggcctc ctggccctcc aggtgtgaag ggagatctgg gcctccctgg cctgcccgt    9480 gctcctggtg ttgttgggtt ccggggtcag acaggcctc gaggagagat gggtcagcca    9540
ggccctagtg gagagcgggg tctggcaggc ccccaggga gagaaggaat cccaggaccc    9600
ctggggccac ctggaccacc gggtcagtg gaccacctg ggcctctgg actcaaagga    9660 gacaagggag accctggagt agggctgcct gggccccgag gcgagcgtgg ggagccaggc    9720
atccggggtg aagatggccg cccccggcag gagggacccc gaggactcac ggggccccct    9780
ggcagcaggg gagagcgtgg ggagaagggt gatgttggga gtgcaggact aaagggtgac    9840
aagggagact cagctgtgat cctggggcct ccaggcccac ggggtgccaa ggggacatg    9900 ggtgaacgag ggcctcgggg cttggatggt gacaaaggac ctcggggaga caatgggac    9960 cctggtgaca agggcagcaa gggagagcct ggtgacaagg gctcagccgg gttgccagga   10020
ctgcgtggac tcctgggacc ccagggtcaa cctggtgcag cagggatccc tggtgacccg   10080
ggatccccag gaaaggatgg agtgcctggt atccgaggag aaaaaggaga tgttggcttc   10140
atgggtcccc gggcctcaa gggtgaacgg ggagtgaagg gagcctgtgg ccttgatgga   10200
gagaagggag acaaggaga agctggtccc ccaggccgcc ccgggctggc aggacacaaa   10260
ggagagatgg gggagcctgg tgtgccggc cagtcggggg cccctggcaa ggagggcctg   10320
atcggtccca agggtgaccg aggctttgac gggcagccag gccccaaggg tgaccaggc   10380 gagaaagggg agcggggaac cccaggaatt gggggcttcc caggccccag tggaaatgat   10440
```

```
ggctctgctg gtcccccagg gccacctggc agtgttggtc ccagaggccc cgaaggactt    10500
cagggccaga agggtgagcg aggtccccccc ggagagagag tggtgggggc tcctggggtc    10560
```

```
ggctctgctg gtcccccagg gccacctggc agtgttggtc ccagaggccc cgaaggactt    10500
cagggccaga agggtgagcg aggtccccccc ggagagagag tggtgggggc tcctggggtc    10560
cctggagctc ctggcgagag aggggagcag gggcggccag ggcctgccgg tcctcgaggc    10620
gagaagggag aagctgcact gacggaggat gacatccggg gctttgtgcg ccaagagatg    10680
agtcagcact gtgcctgcca gggccagttc atcgcatctg gatcacgacc cctccctagt    10740
tatgctgcag acactgccgg ctcccagctc catgctgtgc ctgtgctccg cgtctctcat    10800
gcagaggagg aagagcgggt accccctgag gatgatgagt actctgaata ctccgagtat    10860
tctgtggagg agtaccagga ccctgaagct ccttgggata gtgatgaccc ctgttccctg    10920
ccactggatg agggctcctg cactgcctac accctgcgct ggtaccatcg ggctgtgaca    10980
ggcagcacag aggcctgtca cccttttgtc tatggtggct gtggagggaa tgccaaccgt    11040
tttgggaccc gtgaggcctg cgagcgccgc tgcccacccc gggtggtcca gagccagggg    11100
acaggtactg cccaggactg a                                              11121
```

<210> SEQ ID NO 16
<211> LENGTH: 3706
<212> TYPE: PRT
<213> ORGANISM: Artificial Sequence
<220> FEATURE:
<223> OTHER INFORMATION: Synthetic Construct

<400> SEQUENCE: 16

```
Met Thr Ser Ser Gly Pro Gly Pro Arg Phe Leu Leu Leu Pro Leu
 1               5                  10                  15

Leu Leu Pro Pro Ala Ala Ser Ala Ser Asp Arg Pro Arg Gly Arg Asp
            20                  25                  30

Pro Val Asn Pro Glu Lys Leu Val Ile Thr Val Ala Thr Ala Glu
            35                  40                  45

Thr Glu Gly Tyr Leu Arg Phe Leu Arg Ser Ala Glu Phe Phe Asn Tyr
        50                  55                  60

Thr Val Arg Thr Leu Gly Leu Gly Glu Glu Trp Arg Gly Gly Asp Val
65                  70                  75                  80

Ala Arg Thr Val Gly Gly Gly Gln Lys Val Arg Trp Leu Lys Lys Glu
                85                  90                  95

Met Glu Lys Tyr Ala Asp Arg Glu Asp Met Ile Ile Met Phe Val Asp
            100                 105                 110

Ser Tyr Asp Val Ile Leu Ala Gly Ser Pro Thr Glu Leu Leu Lys Lys
        115                 120                 125

Phe Val Gln Ser Gly Ser Arg Leu Leu Phe Ser Ala Glu Ser Phe Cys
    130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
            180                 185                 190

Leu Phe Tyr Thr Arg Leu Tyr Leu Asp Pro Gly Leu Arg Glu Lys Leu
        195                 200                 205

Ser Leu Asn Leu Asp His Lys Ser Arg Ile Phe Gln Asn Leu Asn Gly
    210                 215                 220

Ala Leu Asp Glu Val Val Leu Lys Phe Asp Arg Asn Arg Val Arg Ile
225                 230                 235                 240
```

-continued

```
Arg Asn Val Ala Tyr Asp Thr Leu Pro Ile Val His Gly Asn Gly
                245                 250                 255
Pro Thr Lys Leu Gln Leu Asn Tyr Leu Gly Asn Tyr Val Pro Asn Gly
            260                 265                 270
Trp Thr Pro Glu Gly Gly Cys Gly Phe Cys Asn Gln Asp Arg Arg Thr
        275                 280                 285
Leu Pro Gly Gly Gln Pro Pro Arg Val Phe Leu Ala Val Phe Val
290                 295                 300
Glu Gln Pro Thr Pro Phe Leu Pro Arg Phe Leu Gln Arg Leu Leu Leu
305                 310                 315                 320
Leu Asp Tyr Pro Pro Asp Arg Val Thr Leu Phe Leu His Asn Asn Glu
                325                 330                 335
Val Phe His Glu Pro His Ile Ala Asp Ser Trp Pro Gln Leu Gln Asp
            340                 345                 350
His Phe Ser Ala Val Lys Leu Val Gly Pro Glu Glu Ala Leu Ser Pro
        355                 360                 365
Gly Glu Ala Arg Asp Met Ala Met Asp Leu Cys Arg Gln Asp Pro Glu
370                 375                 380
Cys Glu Phe Tyr Phe Ser Leu Asp Ala Asp Ala Val Leu Thr Asn Leu
385                 390                 395                 400
Gln Thr Leu Arg Ile Leu Ile Glu Glu Asn Arg Lys Val Ile Ala Pro
                405                 410                 415
Met Leu Ser Arg His Gly Lys Leu Trp Ser Asn Phe Trp Gly Ala Leu
            420                 425                 430
Ser Pro Asp Glu Tyr Tyr Ala Arg Ser Glu Asp Tyr Val Glu Leu Val
        435                 440                 445
Gln Arg Lys Arg Val Gly Val Trp Asn Val Pro Tyr Ile Ser Gln Ala
450                 455                 460
Tyr Val Ile Arg Gly Asp Thr Leu Arg Met Glu Leu Pro Gln Arg Asp
465                 470                 475                 480
Val Phe Ser Gly Ser Asp Thr Asp Pro Asp Met Ala Phe Cys Lys Ser
                485                 490                 495
Phe Arg Asp Lys Gly Ile Phe Leu His Leu Ser Asn Gln His Glu Phe
            500                 505                 510
Gly Arg Leu Leu Ala Thr Ser Arg Tyr Asp Thr Glu His Leu His Pro
        515                 520                 525
Asp Leu Trp Gln Ile Phe Asp Asn Pro Val Asp Trp Lys Glu Gln Tyr
530                 535                 540
Ile His Glu Asn Tyr Ser Arg Ala Leu Glu Gly Glu Gly Ile Val Glu
545                 550                 555                 560
Gln Pro Cys Pro Asp Val Tyr Trp Phe Pro Leu Leu Ser Glu Gln Met
                565                 570                 575
Cys Asp Glu Leu Val Ala Glu Met Glu His Tyr Gly Gln Trp Ser Gly
            580                 585                 590
Gly Arg His Glu Asp Ser Arg Leu Ala Gly Gly Tyr Glu Asn Val Pro
        595                 600                 605
Thr Val Asp Ile His Met Lys Gln Val Gly Tyr Glu Asp Gln Trp Leu
610                 615                 620
Gln Leu Leu Arg Thr Tyr Val Gly Pro Met Thr Glu Ser Leu Phe Pro
625                 630                 635                 640
Gly Tyr His Thr Lys Ala Arg Ala Val Met Asn Phe Val Val Arg Tyr
                645                 650                 655
```

```
Arg Pro Asp Glu Gln Pro Ser Leu Arg Pro His His Asp Ser Ser Thr
            660                 665                 670

Phe Thr Leu Asn Val Ala Leu Asn His Lys Gly Leu Asp Tyr Glu Gly
    675                 680                 685

Gly Gly Cys Arg Phe Leu Arg Tyr Asp Cys Val Ile Ser Ser Pro Arg
690                 695                 700

Lys Gly Trp Ala Leu Leu His Pro Gly Arg Leu Thr His Tyr His Glu
705                 710                 715                 720

Gly Leu Pro Thr Thr Trp Gly Thr Arg Tyr Ile Met Val Ser Phe Val
            725                 730                 735

Asp Pro Arg Ala Lys Arg Gly Ser Gly Glu Gly Arg Gly Ser Leu Leu
        740                 745                 750

Thr Cys Gly Asp Val Glu Glu Asn Pro Gly Pro Thr Leu Arg Leu Leu
    755                 760                 765

Val Ala Ala Leu Cys Ala Gly Ile Leu Ala Glu Ala Pro Arg Val Arg
770                 775                 780

Ala Gln His Arg Glu Arg Val Thr Cys Thr Arg Leu Tyr Ala Ala Asp
785                 790                 795                 800

Ile Val Phe Leu Leu Asp Gly Ser Ser Ser Ile Gly Arg Ser Asn Phe
            805                 810                 815

Arg Glu Val Arg Ser Phe Leu Glu Gly Leu Val Leu Pro Phe Ser Gly
        820                 825                 830

Ala Ala Ser Ala Gln Gly Val Arg Phe Ala Thr Val Gln Tyr Ser Asp
    835                 840                 845

Asp Pro Arg Thr Glu Phe Gly Leu Asp Ala Leu Gly Ser Gly Gly Asp
850                 855                 860

Val Ile Arg Ala Ile Arg Glu Leu Ser Tyr Lys Gly Gly Asn Thr Arg
865                 870                 875                 880

Thr Gly Ala Ala Ile Leu His Val Ala Asp His Val Phe Leu Pro Gln
            885                 890                 895

Leu Ala Arg Pro Gly Val Pro Lys Val Cys Ile Leu Ile Thr Asp Gly
        900                 905                 910

Lys Ser Gln Asp Leu Val Asp Thr Ala Ala Gln Arg Leu Lys Gly Gln
    915                 920                 925

Gly Val Lys Leu Phe Ala Val Gly Ile Lys Asn Ala Asp Pro Glu Glu
930                 935                 940

Leu Lys Arg Val Ala Ser Gln Pro Thr Ser Asp Phe Phe Phe Phe Val
945                 950                 955                 960

Asn Asp Phe Ser Ile Leu Arg Thr Leu Leu Pro Leu Val Ser Arg Arg
            965                 970                 975

Val Cys Thr Thr Ala Gly Gly Val Pro Val Thr Arg Pro Pro Asp Asp
        980                 985                 990

Ser Thr Ser Ala Pro Arg Asp Leu Val Leu Ser Glu Pro Ser Ser Gln
    995                1000                1005

Ser Leu Arg Val Gln Trp Thr Ala Ala Ser Gly Pro Val Thr Gly Tyr
   1010                1015                1020

Lys Val Gln Tyr Thr Pro Leu Thr Gly Leu Gly Gln Pro Leu Pro Ser
1025                1030                1035                1040

Glu Arg Gln Glu Val Asn Val Pro Ala Gly Glu Thr Ser Val Arg Leu
           1045                1050                1055

Arg Gly Leu Arg Pro Leu Thr Glu Tyr Gln Val Thr Val Ile Ala Leu
       1060                1065                1070

Tyr Ala Asn Ser Ile Gly Glu Ala Val Ser Gly Thr Ala Arg Thr Thr
```

```
              1075                1080                1085
Ala Leu Glu Gly Pro Glu Leu Thr Ile Gln Asn Thr Thr Ala His Ser
            1090                1095                1100

Leu Leu Val Ala Trp Arg Ser Val Pro Gly Ala Thr Gly Tyr Arg Val
1105                1110                1115                1120

Thr Trp Arg Val Leu Ser Gly Gly Pro Thr Gln Gln Gln Glu Leu Gly
                1125                1130                1135

Pro Gly Gln Gly Ser Val Leu Leu Arg Asp Leu Glu Pro Gly Thr Asp
            1140                1145                1150

Tyr Glu Val Thr Val Ser Thr Leu Phe Gly Arg Ser Val Gly Pro Ala
            1155                1160                1165

Thr Ser Leu Met Ala Arg Thr Asp Ala Ser Val Glu Gln Thr Leu Arg
        1170                1175                1180

Pro Val Ile Leu Gly Pro Thr Ser Ile Leu Leu Ser Trp Asn Leu Val
1185                1190                1195                1200

Pro Glu Ala Arg Gly Tyr Arg Leu Glu Trp Arg Arg Glu Thr Gly Leu
                1205                1210                1215

Glu Pro Pro Gln Lys Val Val Leu Pro Ser Asp Val Thr Arg Tyr Gln
            1220                1225                1230

Leu Asp Gly Leu Gln Pro Gly Thr Glu Tyr Arg Leu Thr Leu Tyr Thr
            1235                1240                1245

Leu Leu Glu Gly His Glu Val Ala Thr Pro Ala Thr Val Val Pro Thr
        1250                1255                1260

Gly Pro Glu Leu Pro Val Ser Pro Val Thr Asp Leu Gln Ala Thr Glu
1265                1270                1275                1280

Leu Pro Gly Gln Arg Val Arg Val Ser Trp Ser Pro Val Pro Gly Ala
                1285                1290                1295

Thr Gln Tyr Arg Ile Ile Val Arg Ser Thr Gln Gly Val Glu Arg Thr
            1300                1305                1310

Leu Val Leu Pro Gly Ser Gln Thr Ala Phe Asp Leu Asp Asp Val Gln
            1315                1320                1325

Ala Gly Leu Ser Tyr Thr Val Arg Val Ser Ala Arg Val Gly Pro Arg
        1330                1335                1340

Glu Gly Ser Ala Ser Val Leu Thr Val Arg Arg Glu Pro Glu Thr Pro
1345                1350                1355                1360

Leu Ala Val Pro Gly Leu Arg Val Val Ser Asp Ala Thr Arg Val
                1365                1370                1375

Arg Val Ala Trp Gly Pro Val Pro Gly Ala Ser Gly Phe Arg Ile Ser
            1380                1385                1390

Trp Ser Thr Gly Ser Gly Pro Glu Ser Ser Gln Thr Leu Pro Pro Asp
        1395                1400                1405

Ser Thr Ala Thr Asp Ile Thr Gly Leu Gln Pro Gly Thr Thr Tyr Gln
        1410                1415                1420

Val Ala Val Ser Val Leu Arg Gly Arg Glu Glu Gly Pro Ala Ala Val
1425                1430                1435                1440

Ile Val Ala Arg Thr Asp Pro Leu Gly Pro Val Arg Thr Val His Val
                1445                1450                1455

Thr Gln Ala Ser Ser Ser Ser Val Thr Ile Thr Trp Thr Arg Val Pro
            1460                1465                1470

Gly Ala Thr Gly Tyr Arg Val Ser Trp His Ser Ala His Gly Pro Glu
        1475                1480                1485

Lys Ser Gln Leu Val Ser Gly Glu Ala Thr Val Ala Glu Leu Asp Gly
            1490                1495                1500
```

```
Leu Glu Pro Asp Thr Glu Tyr Thr Val His Val Arg Ala His Val Ala
1505                1510                1515                1520

Gly Val Asp Gly Pro Pro Ala Ser Val Val Arg Thr Ala Pro Glu
            1525                1530                1535

Pro Val Gly Arg Val Ser Arg Leu Gln Ile Leu Asn Ala Ser Ser Asp
            1540                1545                1550

Val Leu Arg Ile Thr Trp Val Gly Val Thr Gly Ala Thr Ala Tyr Arg
            1555                1560                1565

Leu Ala Trp Gly Arg Ser Glu Gly Gly Pro Met Arg His Gln Ile Leu
    1570                1575                1580

Pro Gly Asn Thr Asp Ser Ala Glu Ile Arg Gly Leu Glu Gly Gly Val
1585                1590                1595                1600

Ser Tyr Ser Val Arg Val Thr Ala Leu Val Gly Asp Arg Glu Gly Thr
            1605                1610                1615

Pro Val Ser Ile Val Val Thr Thr Pro Pro Glu Ala Pro Pro Ala Leu
            1620                1625                1630

Gly Thr Leu His Val Val Gln Arg Gly Glu His Ser Leu Arg Leu Arg
            1635                1640                1645

Trp Glu Pro Val Pro Arg Ala Gln Gly Phe Leu Leu His Trp Gln Pro
    1650                1655                1660

Glu Gly Gly Gln Glu Gln Ser Arg Val Leu Gly Pro Glu Leu Ser Ser
1665                1670                1675                1680

Tyr His Leu Asp Gly Leu Glu Pro Ala Thr Gln Tyr Arg Val Arg Leu
            1685                1690                1695

Ser Val Leu Gly Pro Ala Gly Glu Gly Pro Ser Ala Glu Val Thr Ala
            1700                1705                1710

Arg Thr Glu Ser Pro Arg Val Pro Ser Ile Glu Leu Arg Val Val Asp
            1715                1720                1725

Thr Ser Ile Asp Ser Val Thr Leu Ala Trp Thr Pro Val Ser Arg Ala
            1730                1735                1740

Ser Ser Tyr Ile Leu Ser Trp Arg Pro Leu Arg Gly Pro Gly Gln Glu
1745                1750                1755                1760

Val Pro Gly Ser Pro Gln Thr Leu Pro Gly Ile Ser Ser Ser Gln Arg
            1765                1770                1775

Val Thr Gly Leu Glu Pro Gly Val Ser Tyr Ile Phe Ser Leu Thr Pro
            1780                1785                1790

Val Leu Asp Gly Val Arg Gly Pro Glu Ala Ser Val Thr Gln Thr Pro
            1795                1800                1805

Val Cys Pro Arg Gly Leu Ala Asp Val Val Phe Leu Pro His Ala Thr
            1810                1815                1820

Gln Asp Asn Ala His Arg Ala Glu Ala Thr Arg Arg Val Leu Glu Arg
1825                1830                1835                1840

Leu Val Leu Ala Leu Gly Pro Leu Gly Pro Gln Ala Val Gln Val Gly
            1845                1850                1855

Leu Leu Ser Tyr Ser His Arg Pro Ser Pro Leu Phe Pro Leu Asn Gly
            1860                1865                1870

Ser His Asp Leu Gly Ile Ile Leu Gln Arg Ile Arg Asp Met Pro Tyr
            1875                1880                1885

Met Asp Pro Ser Gly Asn Asn Leu Gly Thr Ala Val Val Thr Ala His
    1890                1895                1900

Arg Tyr Met Leu Ala Pro Asp Ala Pro Gly Arg Arg Gln His Val Pro
1905                1910                1915                1920
```

-continued

Gly Val Met Val Leu Leu Val Asp Glu Pro Leu Arg Gly Asp Ile Phe
                1925                1930                1935

Ser Pro Ile Arg Glu Ala Gln Ala Ser Gly Leu Asn Val Val Met Leu
                1940                1945                1950

Gly Met Ala Gly Ala Asp Pro Glu Gln Leu Arg Arg Leu Ala Pro Gly
                1955                1960                1965

Met Asp Ser Val Gln Thr Phe Phe Ala Val Asp Gly Pro Ser Leu
                1970                1975                1980

Asp Gln Ala Val Ser Gly Leu Ala Thr Ala Leu Cys Gln Ala Ser Phe
1985                1990                1995                2000

Thr Thr Gln Pro Arg Pro Glu Pro Cys Pro Val Tyr Cys Pro Lys Gly
                2005                2010                2015

Gln Lys Gly Glu Pro Gly Glu Met Gly Leu Arg Gly Gln Val Gly Pro
                2020                2025                2030

Pro Gly Asp Pro Gly Leu Pro Gly Arg Thr Gly Ala Pro Gly Pro Gln
                2035                2040                2045

Gly Pro Pro Gly Ser Ala Thr Ala Lys Gly Glu Arg Gly Phe Pro Gly
                2050                2055                2060

Ala Asp Gly Arg Pro Gly Ser Pro Gly Arg Ala Gly Asn Pro Gly Thr
2065                2070                2075                2080

Pro Gly Ala Pro Gly Leu Lys Gly Ser Pro Gly Leu Pro Gly Pro Arg
                2085                2090                2095

Gly Asp Pro Gly Glu Arg Gly Pro Arg Gly Pro Lys Gly Glu Pro Gly
                2100                2105                2110

Ala Pro Gly Gln Val Ile Gly Gly Glu Gly Pro Gly Leu Pro Gly Arg
                2115                2120                2125

Lys Gly Asp Pro Gly Pro Ser Gly Pro Pro Gly Pro Arg Gly Pro Leu
                2130                2135                2140

Gly Asp Pro Gly Pro Arg Gly Pro Pro Gly Leu Pro Gly Thr Ala Met
2145                2150                2155                2160

Lys Gly Asp Lys Gly Asp Arg Gly Glu Arg Gly Pro Pro Gly Pro Gly
                2165                2170                2175

Glu Gly Gly Ile Ala Pro Gly Glu Pro Gly Leu Pro Gly Leu Pro Gly
                2180                2185                2190

Ser Pro Gly Pro Gln Gly Pro Val Gly Pro Pro Gly Lys Lys Gly Glu
                2195                2200                2205

Lys Gly Asp Ser Glu Asp Gly Ala Pro Gly Leu Pro Gly Gln Pro Gly
                2210                2215                2220

Ser Pro Gly Glu Gln Gly Pro Arg Gly Pro Pro Gly Ala Ile Gly Pro
2225                2230                2235                2240

Lys Gly Asp Arg Gly Phe Pro Gly Pro Leu Gly Glu Ala Gly Glu Lys
                2245                2250                2255

Gly Glu Arg Gly Pro Pro Gly Pro Ala Gly Ser Arg Gly Leu Pro Gly
                2260                2265                2270

Val Ala Gly Arg Pro Gly Ala Lys Gly Pro Glu Gly Pro Pro Gly Pro
                2275                2280                2285

Thr Gly Arg Gln Gly Glu Lys Gly Glu Pro Gly Arg Pro Gly Asp Pro
                2290                2295                2300

Ala Val Val Gly Pro Ala Val Ala Gly Pro Lys Gly Glu Lys Gly Asp
2305                2310                2315                2320

Val Gly Pro Ala Gly Pro Arg Gly Ala Thr Gly Val Gln Gly Glu Arg
                2325                2330                2335

Gly Pro Pro Gly Leu Val Leu Pro Gly Asp Pro Gly Pro Lys Gly Asp

-continued

```
                2340                2345                2350
Pro Gly Asp Arg Gly Pro Ile Gly Leu Thr Gly Arg Ala Gly Pro Pro
            2355                2360                2365
Gly Asp Ser Gly Pro Pro Gly Glu Lys Gly Asp Pro Gly Arg Pro Gly
        2370                2375                2380
Pro Pro Gly Pro Val Gly Pro Arg Gly Arg Asp Gly Glu Val Gly Glu
2385                2390                2395                2400
Lys Gly Asp Glu Gly Pro Pro Gly Asp Pro Gly Leu Pro Gly Lys Ala
            2405                2410                2415
Gly Glu Arg Gly Leu Arg Gly Ala Pro Gly Val Arg Gly Pro Val Gly
            2420                2425                2430
Glu Lys Gly Asp Gln Gly Asp Pro Gly Glu Asp Gly Arg Asn Gly Ser
            2435                2440                2445
Pro Gly Ser Ser Gly Pro Lys Gly Asp Arg Gly Glu Pro Gly Pro Pro
            2450                2455                2460
Gly Pro Pro Gly Arg Leu Val Asp Thr Gly Pro Gly Ala Arg Glu Lys
2465                2470                2475                2480
Gly Glu Pro Gly Asp Arg Gly Gln Glu Gly Pro Arg Gly Pro Lys Gly
            2485                2490                2495
Asp Pro Gly Leu Pro Gly Ala Pro Gly Glu Arg Gly Ile Glu Gly Phe
            2500                2505                2510
Arg Gly Pro Pro Gly Pro Gln Gly Asp Pro Gly Val Arg Gly Pro Ala
            2515                2520                2525
Gly Glu Lys Gly Asp Arg Gly Pro Pro Gly Leu Asp Gly Arg Ser Gly
            2530                2535                2540
Leu Asp Gly Lys Pro Gly Ala Ala Gly Pro Ser Gly Pro Asn Gly Ala
2545                2550                2555                2560
Ala Gly Lys Ala Gly Asp Pro Gly Arg Asp Gly Leu Pro Gly Leu Arg
            2565                2570                2575
Gly Glu Gln Gly Leu Pro Gly Pro Ser Gly Pro Pro Gly Leu Pro Gly
            2580                2585                2590
Lys Pro Gly Glu Asp Gly Lys Pro Gly Leu Asn Gly Lys Asn Gly Glu
            2595                2600                2605
Pro Gly Asp Pro Gly Glu Asp Gly Arg Lys Gly Glu Lys Gly Asp Ser
            2610                2615                2620
Gly Ala Ser Gly Arg Glu Gly Arg Asp Gly Pro Lys Gly Glu Arg Gly
2625                2630                2635                2640
Ala Pro Gly Ile Leu Gly Pro Gln Gly Pro Pro Gly Leu Pro Gly Pro
            2645                2650                2655
Val Gly Pro Pro Gly Gln Gly Phe Pro Gly Val Pro Gly Gly Thr Gly
            2660                2665                2670
Pro Lys Gly Asp Arg Gly Glu Thr Gly Ser Lys Gly Glu Gln Gly Leu
            2675                2680                2685
Pro Gly Glu Arg Gly Leu Arg Gly Glu Pro Gly Ser Val Pro Asn Val
            2690                2695                2700
Asp Arg Leu Leu Glu Thr Ala Gly Ile Lys Ala Ser Ala Leu Arg Glu
2705                2710                2715                2720
Ile Val Glu Thr Trp Asp Glu Ser Ser Gly Ser Phe Leu Pro Val Pro
            2725                2730                2735
Glu Arg Arg Arg Gly Pro Lys Gly Asp Ser Gly Glu Gln Gly Pro Pro
            2740                2745                2750
Gly Lys Glu Gly Pro Ile Gly Phe Pro Gly Glu Arg Gly Leu Lys Gly
            2755                2760                2765
```

```
Asp Arg Gly Asp Pro Gly Pro Gln Gly Pro Pro Gly Leu Ala Leu Gly
        2770                2775                2780

Glu Arg Gly Pro Pro Gly Pro Ser Gly Leu Ala Gly Glu Pro Gly Lys
2785                2790                2795                2800

Pro Gly Ile Pro Gly Leu Pro Gly Arg Ala Gly Gly Val Gly Glu Ala
            2805                2810                2815

Gly Arg Pro Gly Glu Arg Gly Glu Arg Gly Glu Lys Gly Glu Arg Gly
        2820                2825                2830

Glu Gln Gly Arg Asp Gly Pro Pro Gly Leu Pro Gly Thr Pro Gly Pro
            2835                2840                2845

Pro Gly Pro Pro Gly Pro Lys Val Ser Val Asp Glu Pro Gly Pro Gly
        2850                2855                2860

Leu Ser Gly Glu Gln Gly Pro Pro Gly Leu Lys Gly Ala Lys Gly Glu
2865                2870                2875                2880

Pro Gly Ser Asn Gly Asp Gln Gly Pro Lys Gly Asp Arg Gly Val Pro
            2885                2890                2895

Gly Ile Lys Gly Asp Arg Gly Glu Pro Gly Pro Arg Gly Gln Asp Gly
            2900                2905                2910

Asn Pro Gly Leu Pro Gly Glu Arg Gly Met Ala Gly Pro Glu Gly Lys
        2915                2920                2925

Pro Gly Leu Gln Gly Pro Arg Gly Pro Pro Gly Pro Val Gly Gly His
        2930                2935                2940

Gly Asp Pro Gly Pro Pro Gly Ala Pro Gly Leu Ala Gly Pro Ala Gly
2945                2950                2955                2960

Pro Gln Gly Pro Ser Gly Leu Lys Gly Glu Pro Gly Glu Thr Gly Pro
            2965                2970                2975

Pro Gly Arg Gly Leu Thr Gly Pro Thr Gly Ala Val Gly Leu Pro Gly
            2980                2985                2990

Pro Pro Gly Pro Ser Gly Leu Val Gly Pro Gln Gly Ser Pro Gly Leu
            2995                3000                3005

Pro Gly Gln Val Gly Glu Thr Gly Lys Pro Gly Ala Pro Gly Arg Asp
        3010                3015                3020

Gly Ala Ser Gly Lys Asp Gly Asp Arg Gly Ser Pro Gly Val Pro Gly
3025                3030                3035                3040

Ser Pro Gly Leu Pro Gly Pro Val Gly Pro Lys Gly Glu Pro Gly Pro
            3045                3050                3055

Thr Gly Ala Pro Gly Gln Ala Val Val Gly Leu Pro Gly Ala Lys Gly
            3060                3065                3070

Glu Lys Gly Ala Pro Gly Gly Leu Ala Gly Asp Leu Val Gly Glu Pro
        3075                3080                3085

Gly Ala Lys Gly Asp Arg Gly Leu Pro Gly Pro Arg Gly Glu Lys Gly
        3090                3095                3100

Glu Ala Gly Arg Ala Gly Glu Pro Gly Asp Pro Gly Glu Asp Gly Gln
3105                3110                3115                3120

Lys Gly Ala Pro Gly Pro Lys Gly Phe Lys Gly Asp Pro Gly Val Gly
            3125                3130                3135

Val Pro Gly Ser Pro Gly Pro Pro Gly Pro Pro Gly Val Lys Gly Asp
            3140                3145                3150

Leu Gly Leu Pro Gly Leu Pro Gly Ala Pro Gly Val Val Gly Phe Pro
            3155                3160                3165

Gly Gln Thr Gly Pro Arg Gly Glu Met Gly Gln Pro Gly Pro Ser Gly
            3170                3175                3180
```

-continued

Glu Arg Gly Leu Ala Gly Pro Pro Gly Arg Glu Gly Ile Pro Gly Pro
3185                3190                3195                3200

Leu Gly Pro Pro Gly Pro Pro Gly Ser Val Gly Pro Pro Gly Ala Ser
            3205                3210                3215

Gly Leu Lys Gly Asp Lys Gly Asp Pro Gly Val Gly Leu Pro Gly Pro
        3220                3225                3230

Arg Gly Glu Arg Gly Glu Pro Gly Ile Arg Gly Glu Asp Gly Arg Pro
    3235                3240                3245

Gly Gln Glu Gly Pro Arg Gly Leu Thr Gly Pro Pro Gly Ser Arg Gly
    3250                3255                3260

Glu Arg Gly Glu Lys Gly Asp Val Gly Ser Ala Gly Leu Lys Gly Asp
3265                3270                3275                3280

Lys Gly Asp Ser Ala Val Ile Leu Gly Pro Pro Gly Pro Arg Gly Ala
            3285                3290                3295

Lys Gly Asp Met Gly Glu Arg Gly Pro Arg Gly Leu Asp Gly Asp Lys
            3300                3305                3310

Gly Pro Arg Gly Asp Asn Gly Asp Pro Gly Asp Lys Gly Ser Lys Gly
        3315                3320                3325

Glu Pro Gly Asp Lys Gly Ser Ala Gly Leu Pro Gly Leu Arg Gly Leu
    3330                3335                3340

Leu Gly Pro Gln Gly Gln Pro Gly Ala Ala Gly Ile Pro Gly Asp Pro
3345                3350                3355                3360

Gly Ser Pro Gly Lys Asp Gly Val Pro Gly Ile Arg Gly Glu Lys Gly
            3365                3370                3375

Asp Val Gly Phe Met Gly Pro Arg Gly Leu Lys Gly Glu Arg Gly Val
            3380                3385                3390

Lys Gly Ala Cys Gly Leu Asp Gly Glu Lys Gly Asp Lys Gly Glu Ala
            3395                3400                3405

Gly Pro Pro Gly Arg Pro Gly Leu Ala Gly His Lys Gly Glu Met Gly
            3410                3415                3420

Glu Pro Gly Val Pro Gly Gln Ser Gly Ala Pro Gly Lys Glu Gly Leu
3425                3430                3435                3440

Ile Gly Pro Lys Gly Asp Arg Gly Phe Asp Gly Gln Pro Gly Pro Lys
            3445                3450                3455

Gly Asp Gln Gly Glu Lys Gly Glu Arg Gly Thr Pro Gly Ile Gly Gly
            3460                3465                3470

Phe Pro Gly Pro Ser Gly Asn Asp Gly Ser Ala Gly Pro Pro Gly Pro
        3475                3480                3485

Pro Gly Ser Val Gly Pro Arg Gly Pro Glu Gly Leu Gln Gly Gln Lys
    3490                3495                3500

Gly Glu Arg Gly Pro Pro Gly Glu Arg Val Val Gly Ala Pro Gly Val
3505                3510                3515                3520

Pro Gly Ala Pro Gly Glu Arg Gly Glu Gln Gly Arg Pro Gly Pro Ala
            3525                3530                3535

Gly Pro Arg Gly Glu Lys Gly Glu Ala Ala Leu Thr Glu Asp Asp Ile
        3540                3545                3550

Arg Gly Phe Val Arg Gln Glu Met Ser Gln His Cys Ala Cys Gln Gly
        3555                3560                3565

Gln Phe Ile Ala Ser Gly Ser Arg Pro Leu Pro Ser Tyr Ala Ala Asp
        3570                3575                3580

Thr Ala Gly Ser Gln Leu His Ala Val Pro Val Leu Arg Val Ser His
3585                3590                3595                3600

Ala Glu Glu Glu Glu Arg Val Pro Pro Glu Asp Asp Glu Tyr Ser Glu

```
                    3605                3610                3615
Tyr Ser Glu Tyr Ser Val Glu Glu Tyr Gln Asp Pro Glu Ala Pro Trp
            3620                3625                3630

Asp Ser Asp Asp Pro Cys Ser Leu Pro Leu Asp Glu Gly Ser Cys Thr
        3635                3640                3645

Ala Tyr Thr Leu Arg Trp Tyr His Arg Ala Val Thr Gly Ser Thr Glu
    3650                3655                3660

Ala Cys His Pro Phe Val Tyr Gly Gly Cys Gly Gly Asn Ala Asn Arg
3665                3670                3675                3680

Phe Gly Thr Arg Glu Ala Cys Glu Arg Arg Cys Pro Pro Arg Val Val
                3685                3690                3695

Gln Ser Gln Gly Thr Gly Thr Ala Gln Asp
            3700                3705

<210> SEQ ID NO 17
<211> LENGTH: 11112
<212> TYPE: DNA
<213> ORGANISM: Artificial Sequence
<220> FEATURE:
<223> OTHER INFORMATION: Synthetic Construct

<400> SEQUENCE: 17
atgacgctgc ggcttctggt ggccgcgctc tgcgccggga tcctggcaga ggcgccccga      60
gtgcgagccc agcacaggga gagagtgacc tgcacgcgcc tttacgccgc tgacattgtg     120
ttcttactgg atggctcctc atccattggc cgcagcaatt ccgcgaggt ccgcagcttt      180 ctcgaagggc tggtgctgcc tttctctgga gcagccagtg cacagggtgt gcgctttgcc     240
acagtgcagt acagcgatga cccacggaca gagttcggcc tggatgcact ggctctgggg     300
ggtgatgtga tccgcgccat ccgtgagctt agctacaagg ggggcaacac tcgcacaggg     360
gctgcaattc tccatgtggc tgaccatgtc ttcctgcccc agctggcccg acctggtgtc     420
cccaaggtct gcatcctgat cacagacggg aagtcccagg acctggtgga cacagctgcc     480
caaaggctga aggggcaggg ggtcaagcta tttgctgtgg ggatcaagaa tgctgaccct     540
gaggagctga agcgagttgc ctcacagccc accagtgact tcttcttctt cgtcaatgac     600
ttcagcatct tgaggacact actgccctc gtttccggga gagtgtgcac gactgctggt      660
ggcgtgcctg tgacccgacc tccggatgac tcgacctctg ctccacgaga cctggtgctg     720
tctgagccaa gcagccaatc cttgagagta cagtggacag cggccagtgg ccctgtgact     780
ggctacaagg tccagtacac tcctctgacg gggctgggac agccactgcc gagtgagcgg     840
caggaggtga acgtcccagc tggtgagacc agtgtgcggc tgcggggtct ccggccactg     900
accgagtacc aagtgactgt gattgccctc tacgccaaca gcatcgggga ggctgtgagc     960
gggacagctc ggaccactgc cctagaaggg ccggaactga ccatccagaa taccacagcc    1020
cacagcctcc tggtggcctg gcggagtgtg ccaggtgcca ctggctaccg tgtgacatgg    1080
cgggtcctca gtggtgggcc cacacagcag caggagctgg gccctgggca gggttcagtg    1140
ttgctgcgtg acttggagcc tggcacggac tatgaggtga ccgtgagcac cctatttggc    1200
cgcagtgtgg ggccgccac ttccctgatg gctcgcactg acgcttctgt tgagcagacc     1260
ctgcgcccgg tcatcctggg ccccacatcc atcctccttt cctggaactt ggtgcctgag    1320
gcccgtggct accggttgga atggcggcgt gagactggct tggagccacc gcagaaggtg    1380 gtactgccc tgatgtgac ccgctaccag ttggatgggc tgcagccggg cactgagtac     1440
cgcctcacac tctacactct gctggagggc cacgaggtgg ccacccctgc aaccgtggtt    1500
```

```
cccactggac cagagctgcc tgtgagccct gtaacagacc tgcaagccac cgagctgccc    1560
gggcagcggg tgcgagtgtc ctggagccca gtccctggtg ccacccagta ccgcatcatt    1620
gtgcgcagca cccagggggt tgagcggacc ctggtgcttc ctgggagtca gacagcattc    1680
gacttggatg acgttcaggc tgggcttagc tacactgtgc gggtgtctgc tcgagtgggt    1740
ccccgtgagg gcagtgccag tgtcctcact gtccgccggg agccggaaac tccacttgct    1800
gttccagggc tgcgggttgt ggtgtcagat gcaacgcgag tgaggtggc ctggggaccc     1860 gtccctggag ccagtggatt tcggattagc tggagcacag gcagtggtcc ggagtccagc    1920
cagacactgc ccccagactc tactgccaca gacatcacag gctgcagcc tggaaccacc     1980 taccaggtgg ctgtgtcggt actgcgaggc agagaggagg gccctgctgc agtcatcgtg    2040
gctcgaacgg acccactggg cccagtgagg acggtccatg tgactcaggc cagcagctca    2100
tctgtcacca ttacctggac cagggttcct ggcgccacag gatacagggt tcctggcac     2160 tcagcccacg gccagagaa atcccagttg gtttctgggg aggccacggt ggctgagctg      2220
gatggactgg agccagatac tgagtatacg gtgcatgtga gggcccatgt ggctggcgtg    2280
gatgggcccc ctgcctctgt ggttgtgagg actgccctg agcctgtggg tcgtgtgtcg      2340
aggctgcaga tcctcaatgc ttccagcgac gttctacgga tcacctgggt aggggtcact    2400
ggagccacag cttacagact ggcctggggc cggagtgaag gcggccccat gaggcaccag    2460
atactcccag gaaacacaga ctctgcagag atccggggtc tcgaaggtgg agtcagctac    2520
tcagtgcgag tgactgcact tgtcggggac cgcgagggca cctgtctc cattgttgtc       2580 actacgccgc ctgaggctcc gccagccctg ggacgcttc acgtggtgca gcgcggggag    2640
cactcgctga ggctgcgctg ggagccggtg cccagagcgc agggcttcct tctgcactgg    2700
caacctgagg gtggccagga acagtcccgg gtcctggggc ccgagctcag cagctatcac    2760
ctggacgggc tggagccagc gacacagtac cgcgtgaggc tgagtgtcct agggccagct    2820
ggagaagggc cctctgcaga ggtgactgcg cgcactgagt cacctcgtgt tccaagcatt    2880
gaactacgtg tggtggacac ctcgatcgac tcggtgactt tggcctggac tccagtgtcc    2940
agggcatcca gctacatcct atcctggcgg ccactcagag gccctggcca ggaagtgcct    3000
gggtccccgc agacacttcc agggatctca agctcccagc gggtgacagg gctagagcct    3060
ggcgtctctt acatcttctc cctgacgcct gtcctggatg gtgtgcgggg tcctgaggca    3120
tctgtcacac agacgccagt gtgcccccgt ggcctggcgg atgtggtgtt cctaccacat    3180
gccactcaag acaatgctca ccgtgcggag gctacgagga gggtcctgga gcgtctggtg    3240
ttggcacttg ggcctcttgg gccacaggca gttcaggttg gcctgctgtc ttacagtcat    3300
cggccctccc cactgttccc actgaatggc tcccatgacc ttggcattat cttgcaaagg    3360
atccgtgaca tgccctacat ggacccaagt gggaacaacc tgggcacagc cgtggtcaca    3420
gctcacagat acatgttggc accagatgct cctgggcgcc gccagcacgt accagggtg     3480 atggttctgc tagtggatga acccttgaga ggtgacatat tcagcccat ccgtgaggcc     3540 caggcttctg ggcttaatgt ggtgatgttg gaatggctg agcggaccc agagcagctg      3600 cgtcgcttgg cgccgggtat ggactctgtc cagaccttct tcgccgtgga tgatgggcca    3660
agcctggacc aggcagtcag tggtctggcc acagccctgt gtcaggcatc cttcactact    3720
cagccccggc cagagccctg cccagtgtat tgtccaaagg ccagaagggg gaacctgga    3780 gagatgggcc tgagaggaca agttgggcct cctggcgacc ctggcctccc gggcaggacc    3840
```

```
ggtgctcccg gcccccaggg gcccctgga agtgccactg ccaagggcga gaggggcttc    3900
cctggagcag atgggcgtcc aggcagccct ggccgcgccg ggaatcctgg acccctgga    3960 gcccctggcc taaagggctc tccagggttg cctggccctc gtggggaccc gggagagcga    4020
ggacctcgag gcccaaaggg ggagccgggg gctcccggac aagtcatcgg aggtgaagga    4080
cctgggcttc ctgggcggaa aggggaccct ggaccatcgg gccccctgg acctcgtgga     4140 ccactggggg acccaggacc ccgtggcccc cagggcttc ctggaacagc catgaagggt     4200
gacaaaggcg atcgtgggga gcgggtccc cctggaccag gtgaaggtgg cattgctcct     4260
ggggagcctg ggctgccggg tcttcccgga agccctggac ccaaggccc cgttggcccc     4320 cctgaaaga aaggagaaaa aggtgactct gaggatggag ctccaggcct cccaggacaa     4380
cctgggtctc cgggtgagca gggcccacgg ggacctcctg gagctattgg ccccaaaggt    4440
gaccggggct ttccagggcc cctgggtgag gctggagaga agggcgaacg tggacccca    4500 ggcccagcgg gatcccgggg gctgccaggg gttgctggac gtcctggagc caagggtcct    4560
gaagggccac caggacccac tggccgccaa ggagagaagg gggagcctgg tcgccctggg    4620
gaccctgcag tggtgggacc tgctgttgct ggacccaaag gagaaaaggg agatgtgggg    4680
cccgctgggc ccagaggagc taccggagtc aaggggaac ggggcccacc cggcttggtt      4740
cttcctggag accctggccc caagggagac cctggagacc gggtcccat tggccttact      4800 ggcagagcag gacccccagg tgactcaggg cctcctggaa agaagggaga ccctgggcgg    4860
cctggccccc caggacctgt tggcccccga ggacgagatg gtgaagttgg agagaaaggt     4920
gacgagggtc ctccgggtga cccgggtttg cctggaaaag caggcgagcg tggccttcgg     4980
ggggcacctg gagttcgggg gcctgtgggt gaaaagggag accagggaga tcctggagag    5040 gatgacgaa atggcagccc tggatcatct ggacccaagg gtgaccgtgg ggagccgggt     5100
cccccaggac ccccgggacg gctggtagac acaggacctg gagccagaga aagggagag     5160 cctggggacc gcgacaaga gggtcctcga gggcccaagg gtgatcctgg cctccctgga    5220
gcccctgggg aaagggcat tgaagggttt cggggacccc caggcccaca ggggacccca    5280
ggtgtccgag gccagcagg agaaaagggt gaccggggtc ccctgggct ggatggccgg      5340 agcggactgg atgggaaacc aggagccgct gggccctctg gccgaatgg tgctgcaggc    5400 aaagctgggg acccagggag agacgggctt ccaggcctcc gtggagaaca gggcctccct   5460
ggcccctctg gtcccctgg attaccggga aagccaggcg aggatggcaa acctggcctg    5520
aatggaaaaa acgagaaacc tggggaccct ggagaagacg ggaggaaggg agagaaagga    5580
gattcaggcg cctctgggag agaaggtcgt gatggcccca agggtgagcg tggagctcct    5640
ggtatccttg gaccccaggg gcctccaggc ctcccagggc cagtgggccc tcctggccag    5700 ggtttcctg gtgtcccagg aggcacgggc cccaagggtg accgtgggga gactggatcc    5760 aaagggagc agggcctccc tggagagcgt ggcctgcgag gagagcctgg aagtgtgccg    5820
aatgtggatc ggttgctgga aactgctggc atcaaggcat ctgccctgcg ggagatcgtg    5880
gagacctggg atgagagctc tggtagcttc ctgcctgtgc ccgaacggcg tcgaggcccc    5940
aagggggact caggcgaaca gggccccca ggcaaggagg gccccatcgg ctttcctgga    6000
gaacgcgggc tgaagggcga ccgtggagac cctggccctc aggggccacc tggtctggcc    6060
cttgggagaa ggggccccc cgggccttcc ggccttgccg gggagcctgg aaagcctggt    6120 attcccggc tccaggcag ggctgggggt gtggagagg caggaaggcc aggagagagg      6180
ggagaacggg gagagaaagg agaacgtgga gaacagggca gagatggccc tcctggactc    6240
```

```
cctggaaccc ctgggccccc cggaccccct ggccccaagg tgtctgtgga tgagccaggt    6300
cctggactct ctggagaaca gggaccccct ggactcaagg gtgctaaggg ggagccgggc    6360
agcaatggtg accaaggtcc caaaggagac aggggtgtgc caggcatcaa aggagaccgg    6420
ggagagcctg gaccgagggg tcaggacggc aacccgggtc taccaggaga gcgtggtatg    6480
gctgggcctg aagggaagcc gggtctgcag ggtccaagag gccccctgg cccagtgggt    6540 ggtcatggag accctggacc acctggtgcc ccgggtcttg ctggccctgc aggaccccaa    6600
ggaccttctg gcctgaaggg ggagcctgga gagacaggac ctccaggacg gggcctgact    6660
ggacctactg gagctgtggg acttcctgga ccccccggcc cttcaggcct tgtgggtcca    6720
caggggtctc caggtttgcc tggacaagtg ggggagacag ggaagccggg agccccaggt    6780
cgagatggtg ccagtggaaa agatggagac agagggagcc ctggtgtgcc agggtcacca    6840
ggtctgcctg gcctgtcgg acctaaagga gaacctggcc cacgggggc ccctggacag    6900 gctgtggtcg ggctccctgg agcaaaggga gagaagggag cccctggagg ccttgctgga    6960
gacctggtgg gtgagccggg agccaaaggt gaccgaggac tgccagggcc gcgaggcgag    7020
aagggtgaag ctgccgtgc aggggagccc ggagaccctg gggaagatgg tcagaaaggg    7080
gctccaggac ccaaaggttt caagggtgac ccaggagtcg gggtcccggg ctcccctggg    7140
cctcctggcc ctccaggtgt gaagggagat ctgggcctcc ctggcctgcc cggtgctcct    7200
ggtgttgttg ggttcccggg tcagacaggc cctcgaggag agatgggtca gccaggccct    7260
agtggagagc ggggtctggc aggcccccca gggagagaag gaatcccagg acccctgggg    7320
ccacctggac caccggggtc agtgggacca cctggggcct ctggactcaa aggagacaag    7380
ggagaccctg gagtagggct gcctgggccc cgaggcgagc gtgggagcc aggcatccgg    7440 ggtgaagatg gccgccccgg ccaggaggga ccccgaggac tcacggggcc ccctggcagc    7500
aggggagagc gtgggagaa gggtgatgtt ggagtgcag gactaaaggg tgacaaggga    7560
gactcagctg tgatcctggg gcctccaggc ccacggggtg ccaaggggga catgggtgaa    7620
cgagggcctc ggggcttgga tggtgacaaa ggacctcggg gagacaatgg ggaccctggt    7680
gacaagggca gcaagggaga gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aagggagcct gtggccttga tggagagaag    7920
ggagacaagg agaagctgg tcccccaggc cgccccgggc tggcaggaca caaaggagag    7980
atgggggagc ctggtgtgcc gggccagtcg ggggcccctg gcaaggaggg cctgatcggt    8040
cccaagggtg accgaggctt tgacgggcag ccaggcccca gggtgaccca gggcgagaaa    8100
ggggagcggg gaaccccagg aattgggggc ttccaggcc ccagtggaaa tgatggctct    8160
gctggtcccc cagggccacc tggcagtgtt ggtccagag gccccgaagg acttcagggc    8220
cagaagggtg agcgaggtcc ccccggagag agagtggtgg gggctcctgg ggtccctgga    8280
gctcctggcg agagaggga gcaggggcgg ccagggcctg ccggtcctcg aggcgagaag    8340
ggagaagctg cactgacgga ggatgacatc cggggctttg tgcgccaaga gatgagtcag    8400
cactgtgcct gccagggcca gttcatcgca tctggatcac gaccctcc tagttatgct    8460 gcagacactg ccggctccca gctccatgct gtgcctgtgc tccgcgtctc tcatgcgagg    8520
gaggaagagc gggtaccccc tgaggatgat gagtactctg aatactccga gtattctgtg    8580
```

```
gaggagtacc aggaccctga agctccttgg gatagtgatg acccctgttc cctgccactg   8640
gatgagggct cctgcactgc ctacaccctg cgctggtacc atcgggctgt gacaggcagc   8700
acagaggcct gtcacccttt tgtctatggt ggctgtggag ggaatgccaa ccgttttggg   8760
acccgtgagg cctgcgagcg ccgctgccca ccccgggtgg tccagagcca ggggacaggt   8820
actgcccagg acggaagcgg agctactaac ttcagcctgc tgaagcaggc tggagacgtg   8880
gaggagaacc ctggacctac ctcctcgggg cctggacccc ggttcctgct gctgctgccg   8940
ctgctgctgc ccctgcggc ctcagcctcc gaccggcccc ggggccgaga cccggtcaac   9000
ccagagaagc tgctggtgat cactgtggcc acagctgaaa ccgagggggta cctgcgtttc   9060
ctgcgctctg cggagttctt caactacact gtgcggaccc tgggcctggg agaggagtgg   9120
cgaggggggtg atgtggctcg aacagttggt ggaggacaga aggtccggtg gttaaagaag   9180
gaaatggaga aatacgctga ccgggaggat atgatcatca tgtttgtgga tagctacgac   9240
gtgattctgg ccggcagccc cacagagctg ctgaagaagt tcgtccagag tggcagccgc   9300
ctgctcttct ctgcagagag cttctgctgg cccgagtggg ggctggcgga gcagtaccct   9360
gaggtgggca cggggaagcg cttcctcaat tctggtggat tcatcggttt tgccaccacc   9420
atccaccaaa tcgtgcgcca gtggaagtac aaggatgatg acgacgacca gctgttctac   9480
acacggctct acctggaccc aggactgagg gagaaactca gccttaatct ggatcataag   9540
tctcggatct ttcagaacct caacgggggct ttagatgaag tggttttaaa gtttgatcgg   9600
aaccgtgtgc gtatccggaa cgtggcctac gacacgctcc ccattgtggt ccatggaaac   9660
ggtcccacta agctgcagct caactacctg gaaaactacg tccccaatgg ctggactcct   9720
gagggaggct gtggcttctg caaccaggac cggaggacac tcccgggggg gcagcctccc   9780
ccccgggtgt ttctggccgt gtttgtggaa cagcctactc cgtttctgcc ccgcttcctg   9840
cagcggctgc tactcctgga ctatccccc gacagggtca cccttttcct gcacaacaac   9900
gaggtcttcc atgaacccca catcgctgac tcctggccgc agctccagga ccacttctca   9960
gctgtgaagc tcgtggggcc ggaggaggct ctgagcccag gcgaggccag ggacatggcc  10020
atggacctgt gtcggcagga ccccgagtgt gagttctact tcagcctgga cgccgacgct  10080
gtcctcacca acctgcagac cctgcgtatc ctcattgagg agaacaggaa ggtgatcgcc  10140
cccatgctgt cccgccacgg caagctgtgg tccaacttct ggggcgccct gagccccgat  10200
gagtactacg cccgctccga ggactacgtg gagctggtgc agcggaagcg agtgggtgtg  10260
tggaatgtac catacatctc ccaggcctat gtgatccggg gtgataccct gcggatggag  10320
ctgccccaga gggatgtgtt ctcgggcagt gacacagacc cggacatggc cttctgtaag  10380
agctttcgag acaagggcat cttcctccat ctgagcaatc agcatgaatt tggccggctc  10440
ctggccactt ccagatacga cacggagcac ctgcaccccg acctctggca gatcttcgac  10500
aaccccgtcg actggaagga gcagtacatc cacgagaact acagccgggc cctgaagggg  10560
gaaggaatcg tggagcagcc atgcccggac gtgtactggt ccccactgct gtcagaacaa  10620
atgtgtgatg agctggtggc agagatggag cactacggcc agtggtcagg cggccggcat  10680
gaggattcaa ggctggctgg aggctacgag aatgtgccca ccgtggacat ccacatgaag  10740
caggtggggt acgaggacca gtggctgcag ctgctgcgga cgtatgtggg cccatgacc  10800
gagagcctgt ttcccggtta ccacaccaag gcgcgggcgg tgatgaactt tgtggttcgc  10860
taccggccag acgagcagcc gtctctgcgg ccacaccacg actcatccac cttcacccg  10920
aacgttgccc tcaaccacaa gggcctggac tatgaggagg tggctgccgg cttcctgcgc  10980
```

-continued

```
tacgactgtg tgatctcctc cccgaggaag ggctgggcac tcctgcaccc cggccgcctc    11040
acccactacc acgagggggct gccaacgacc tggggcacac gctacatcat ggtgtccttt    11100
gtcgacccct ga                                                         11112
```

<210> SEQ ID NO 18
<211> LENGTH: 3703
<212> TYPE: PRT
<213> ORGANISM: Artificial Sequence
<220> FEATURE:
<223> OTHER INFORMATION: Synthetic Construct

<400> SEQUENCE: 18

```
Met Thr Leu Arg Leu Leu Val Ala Ala Leu Cys Ala Gly Ile Leu Ala
 1               5                  10                  15

Glu Ala Pro Arg Val Arg Ala Gln His Arg Glu Arg Val Thr Cys Thr
             20                  25                  30

Arg Leu Tyr Ala Ala Asp Ile Val Phe Leu Leu Asp Gly Ser Ser Ser
         35                  40                  45

Ile Gly Arg Ser Asn Phe Arg Glu Val Arg Ser Phe Leu Glu Gly Leu
     50                  55                  60

Val Leu Pro Phe Ser Gly Ala Ala Ser Ala Gln Gly Val Arg Phe Ala
 65                  70                  75                  80

Thr Val Gln Tyr Ser Asp Asp Pro Arg Thr Glu Phe Gly Leu Asp Ala
                 85                  90                  95

Leu Gly Ser Gly Gly Asp Val Ile Arg Ala Ile Arg Glu Leu Ser Tyr
            100                 105                 110

Lys Gly Gly Asn Thr Arg Thr Gly Ala Ala Ile Leu His Val Ala Asp
        115                 120                 125

His Val Phe Leu Pro Gln Leu Ala Arg Pro Gly Val Pro Lys Val Cys
    130                 135                 140

Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
    290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335
```

```
Asn Thr Thr Ala His Ser Leu Leu Val Ala Trp Arg Ser Val Pro Gly
                340                 345                 350

Ala Thr Gly Tyr Arg Val Thr Trp Arg Val Leu Ser Gly Gly Pro Thr
            355                 360                 365

Gln Gln Gln Glu Leu Gly Pro Gly Gln Gly Ser Val Leu Leu Arg Asp
370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
            435                 440                 445

Arg Arg Glu Thr Gly Leu Glu Pro Pro Gln Lys Val Val Leu Pro Ser
        450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
            515                 520                 525

Ser Pro Val Pro Gly Ala Thr Gln Tyr Arg Ile Ile Val Arg Ser Thr
        530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
            595                 600                 605

Ser Asp Ala Thr Arg Val Arg Val Ala Trp Gly Pro Val Pro Gly Ala
        610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
            675                 680                 685

Val Arg Thr Val His Val Thr Gln Ala Ser Ser Ser Ser Val Thr Ile
        690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750
```

```
Val Arg Ala His Val Ala Gly Val Asp Gly Pro Ala Ser Val Val
        755                 760                 765

Val Arg Thr Ala Pro Glu Pro Val Gly Arg Val Ser Arg Leu Gln Ile
770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Pro
                805                 810                 815

Met Arg His Gln Ile Leu Pro Gly Asn Thr Asp Ser Ala Glu Ile Arg
                820                 825                 830

Gly Leu Glu Gly Gly Val Ser Tyr Ser Val Arg Val Thr Ala Leu Val
                835                 840                 845

Gly Asp Arg Glu Gly Thr Pro Val Ser Ile Val Val Thr Thr Pro Pro
850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
                900                 905                 910

Gly Pro Glu Leu Ser Ser Tyr His Leu Asp Gly Leu Glu Pro Ala Thr
                915                 920                 925

Gln Tyr Arg Val Arg Leu Ser Val Leu Gly Pro Ala Gly Glu Gly Pro
                930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
                980                 985                 990

Arg Gly Pro Gly Gln Glu Val Pro Gly Ser Pro Gln Thr Leu Pro Gly
                995                 1000                1005

Ile Ser Ser Ser Gln Arg Val Thr Gly Leu Glu Pro Gly Val Ser Tyr
                1010                1015                1020

Ile Phe Ser Leu Thr Pro Val Leu Asp Gly Val Arg Gly Pro Glu Ala
1025                1030                1035                1040

Ser Val Thr Gln Thr Pro Val Cys Pro Arg Gly Leu Ala Asp Val Val
                1045                1050                1055

Phe Leu Pro His Ala Thr Gln Asp Asn Ala His Arg Ala Glu Ala Thr
                1060                1065                1070

Arg Arg Val Leu Glu Arg Leu Val Leu Ala Leu Gly Pro Leu Gly Pro
                1075                1080                1085

Gln Ala Val Gln Val Gly Leu Leu Ser Tyr Ser His Arg Pro Ser Pro
                1090                1095                1100

Leu Phe Pro Leu Asn Gly Ser His Asp Leu Gly Ile Ile Leu Gln Arg
1105                1110                1115                1120

Ile Arg Asp Met Pro Tyr Met Asp Pro Ser Gly Asn Asn Leu Gly Thr
                1125                1130                1135

Ala Val Val Thr Ala His Arg Tyr Met Leu Ala Pro Asp Ala Pro Gly
                1140                1145                1150

Arg Arg Gln His Val Pro Gly Val Met Val Leu Leu Val Asp Glu Pro
                1155                1160                1165

Leu Arg Gly Asp Ile Phe Ser Pro Ile Arg Glu Ala Gln Ala Ser Gly
```

-continued

```
            1170                1175                1180
Leu Asn Val Val Met Leu Gly Met Ala Gly Ala Asp Pro Glu Gln Leu
1185                1190                1195                1200

Arg Arg Leu Ala Pro Gly Met Asp Ser Val Gln Thr Phe Phe Ala Val
                1205                1210                1215

Asp Asp Gly Pro Ser Leu Asp Gln Ala Val Ser Gly Leu Ala Thr Ala
                1220                1225                1230

Leu Cys Gln Ala Ser Phe Thr Thr Gln Pro Arg Pro Glu Pro Cys Pro
                1235                1240                1245

Val Tyr Cys Pro Lys Gly Gln Lys Gly Glu Pro Gly Glu Met Gly Leu
                1250                1255                1260

Arg Gly Gln Val Gly Pro Pro Gly Asp Pro Gly Leu Pro Gly Arg Thr
1265                1270                1275                1280

Gly Ala Pro Gly Pro Gln Gly Pro Pro Gly Ser Ala Thr Ala Lys Gly
                1285                1290                1295

Glu Arg Gly Phe Pro Gly Ala Asp Gly Arg Pro Gly Ser Pro Gly Arg
                1300                1305                1310

Ala Gly Asn Pro Gly Thr Pro Gly Ala Pro Gly Leu Lys Gly Ser Pro
                1315                1320                1325

Gly Leu Pro Gly Pro Arg Gly Asp Pro Gly Glu Arg Gly Pro Arg Gly
                1330                1335                1340

Pro Lys Gly Glu Pro Gly Ala Pro Gly Gln Val Ile Gly Gly Glu Gly
1345                1350                1355                1360

Pro Gly Leu Pro Gly Arg Lys Gly Asp Pro Gly Pro Ser Gly Pro Pro
                1365                1370                1375

Gly Pro Arg Gly Pro Leu Gly Asp Pro Gly Pro Arg Gly Pro Pro Gly
                1380                1385                1390

Leu Pro Gly Thr Ala Met Lys Gly Asp Lys Gly Asp Arg Gly Glu Arg
                1395                1400                1405

Gly Pro Pro Gly Pro Gly Glu Gly Gly Ile Ala Pro Gly Glu Pro Gly
                1410                1415                1420

Leu Pro Gly Leu Pro Gly Ser Pro Gly Pro Gln Gly Pro Val Gly Pro
1425                1430                1435                1440

Pro Gly Lys Lys Gly Glu Lys Gly Asp Ser Glu Asp Gly Ala Pro Gly
                1445                1450                1455

Leu Pro Gly Gln Pro Gly Ser Pro Gly Glu Gln Gly Pro Arg Gly Pro
                1460                1465                1470

Pro Gly Ala Ile Gly Pro Lys Gly Asp Arg Gly Phe Pro Gly Pro Leu
                1475                1480                1485

Gly Glu Ala Gly Glu Lys Gly Glu Arg Gly Pro Pro Gly Pro Ala Gly
                1490                1495                1500

Ser Arg Gly Leu Pro Gly Val Ala Gly Arg Pro Gly Ala Lys Gly Pro
1505                1510                1515                1520

Glu Gly Pro Pro Gly Pro Thr Gly Arg Gln Gly Glu Lys Gly Glu Pro
                1525                1530                1535

Gly Arg Pro Gly Asp Pro Ala Val Val Gly Pro Ala Val Ala Gly Pro
                1540                1545                1550

Lys Gly Glu Lys Gly Asp Val Gly Pro Ala Gly Pro Arg Gly Ala Thr
                1555                1560                1565

Gly Val Gln Gly Glu Arg Gly Pro Pro Gly Leu Val Leu Pro Gly Asp
                1570                1575                1580

Pro Gly Pro Lys Gly Asp Pro Gly Asp Arg Gly Pro Ile Gly Leu Thr
1585                1590                1595                1600
```

```
Gly Arg Ala Gly Pro Pro Gly Asp Ser Gly Pro Gly Glu Lys Gly
            1605                1610                1615

Asp Pro Gly Arg Pro Gly Pro Pro Gly Pro Val Gly Pro Arg Gly Arg
            1620                1625                1630

Asp Gly Glu Val Gly Glu Lys Gly Asp Glu Gly Pro Pro Gly Asp Pro
            1635                1640                1645

Gly Leu Pro Gly Lys Ala Gly Glu Arg Gly Leu Arg Gly Ala Pro Gly
            1650                1655                1660

Val Arg Gly Pro Val Gly Glu Lys Gly Asp Gln Gly Asp Pro Gly Glu
1665                1670                1675                1680

Asp Gly Arg Asn Gly Ser Pro Gly Ser Ser Gly Pro Lys Gly Asp Arg
            1685                1690                1695

Gly Glu Pro Gly Pro Pro Gly Pro Gly Arg Leu Val Asp Thr Gly
            1700                1705                1710

Pro Gly Ala Arg Glu Lys Gly Glu Pro Gly Asp Arg Gly Gln Glu Gly
            1715                1720                1725

Pro Arg Gly Pro Lys Gly Asp Pro Gly Leu Pro Gly Ala Pro Gly Glu
            1730                1735                1740

Arg Gly Ile Glu Gly Phe Arg Gly Pro Pro Gly Pro Gln Gly Asp Pro
1745                1750                1755                1760

Gly Val Arg Gly Pro Ala Gly Glu Lys Gly Asp Arg Gly Pro Pro Gly
            1765                1770                1775

Leu Asp Gly Arg Ser Gly Leu Asp Gly Lys Pro Gly Ala Ala Gly Pro
            1780                1785                1790

Ser Gly Pro Asn Gly Ala Ala Gly Lys Ala Gly Asp Pro Gly Arg Asp
            1795                1800                1805

Gly Leu Pro Gly Leu Arg Gly Glu Gln Gly Leu Pro Gly Pro Ser Gly
            1810                1815                1820

Pro Pro Gly Leu Pro Gly Lys Pro Gly Glu Asp Gly Lys Pro Gly Leu
1825                1830                1835                1840

Asn Gly Lys Asn Gly Glu Pro Gly Asp Pro Gly Glu Asp Gly Arg Lys
            1845                1850                1855

Gly Glu Lys Gly Asp Ser Gly Ala Ser Gly Arg Glu Gly Arg Asp Gly
            1860                1865                1870

Pro Lys Gly Glu Arg Gly Ala Pro Gly Ile Leu Gly Pro Gln Gly Pro
            1875                1880                1885

Pro Gly Leu Pro Gly Pro Val Gly Pro Pro Gly Gln Gly Phe Pro Gly
            1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
            1925                1930                1935

Gly Ser Val Pro Asn Val Asp Arg Leu Leu Glu Thr Ala Gly Ile Lys
            1940                1945                1950

Ala Ser Ala Leu Arg Glu Ile Val Glu Thr Trp Asp Glu Ser Ser Gly
            1955                1960                1965

Ser Phe Leu Pro Val Pro Glu Arg Arg Arg Gly Pro Lys Gly Asp Ser
            1970                1975                1980

Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
            2005                2010                2015
```

-continued

Pro Gly Leu Ala Leu Gly Glu Arg Gly Pro Gly Pro Ser Gly Leu
            2020                2025                2030

Ala Gly Glu Pro Gly Lys Pro Gly Ile Pro Gly Leu Pro Gly Arg Ala
        2035                2040                2045

Gly Gly Val Gly Glu Ala Gly Arg Pro Gly Glu Arg Gly Glu Arg Gly
        2050                2055                2060

Glu Lys Gly Glu Arg Gly Glu Gln Arg Asp Gly Pro Pro Gly Leu
2065            2070            2075                2080

Pro Gly Thr Pro Gly Pro Pro Gly Pro Pro Gly Lys Val Ser Val
            2085                2090                2095

Asp Glu Pro Gly Pro Gly Leu Ser Gly Glu Gln Gly Pro Pro Gly Leu
            2100                2105                2110

Lys Gly Ala Lys Gly Glu Pro Gly Ser Asn Gly Asp Gln Gly Pro Lys
            2115                2120                2125

Gly Asp Arg Gly Val Pro Gly Ile Lys Gly Asp Arg Gly Glu Pro Gly
            2130                2135                2140

Pro Arg Gly Gln Asp Gly Asn Pro Gly Leu Pro Gly Glu Arg Gly Met
2145            2150            2155                2160

Ala Gly Pro Glu Gly Lys Pro Gly Leu Gln Gly Pro Arg Gly Pro Pro
            2165                2170                2175

Gly Pro Val Gly Gly His Gly Asp Pro Gly Pro Pro Gly Ala Pro Gly
            2180                2185                2190

Leu Ala Gly Pro Ala Gly Pro Gln Gly Pro Ser Gly Leu Lys Gly Glu
            2195                2200                2205

Pro Gly Glu Thr Gly Pro Pro Gly Arg Gly Leu Thr Gly Pro Thr Gly
            2210                2215                2220

Ala Val Gly Leu Pro Gly Pro Pro Gly Pro Ser Gly Leu Val Gly Pro
2225            2230            2235                2240

Gln Gly Ser Pro Gly Leu Pro Gly Gln Val Gly Glu Thr Gly Lys Pro
            2245                2250                2255

Gly Ala Pro Gly Arg Asp Gly Ala Ser Gly Lys Asp Gly Asp Arg Gly
            2260                2265                2270

Ser Pro Gly Val Pro Gly Ser Pro Gly Leu Pro Gly Pro Val Gly Pro
            2275                2280                2285

Lys Gly Glu Pro Gly Pro Thr Gly Ala Pro Gly Gln Ala Val Val Gly
            2290                2295                2300

Leu Pro Gly Ala Lys Gly Glu Lys Gly Ala Pro Gly Gly Leu Ala Gly
2305            2310            2315                2320

Asp Leu Val Gly Glu Pro Gly Ala Lys Gly Asp Arg Gly Leu Pro Gly
            2325                2330                2335

Pro Arg Gly Glu Lys Gly Glu Ala Gly Arg Ala Gly Glu Pro Gly Asp
            2340                2345                2350

Pro Gly Glu Asp Gly Gln Lys Gly Ala Pro Gly Pro Lys Gly Phe Lys
            2355                2360                2365

Gly Asp Pro Gly Val Gly Val Pro Gly Ser Gly Pro Pro Gly Pro
            2370                2375                2380

Pro Gly Val Lys Gly Asp Leu Gly Leu Pro Gly Leu Pro Gly Ala Pro
2385            2390            2395                2400

Gly Val Val Gly Phe Pro Gly Gln Thr Gly Pro Arg Gly Glu Met Gly
            2405                2410                2415

Gln Pro Gly Pro Ser Gly Glu Arg Gly Leu Ala Gly Pro Pro Gly Arg
            2420                2425                2430

Glu Gly Ile Pro Gly Pro Leu Gly Pro Pro Gly Pro Pro Gly Ser Val

```
                  2435                2440                2445

Gly Pro Pro Gly Ala Ser Gly Leu Lys Gly Asp Lys Gly Asp Pro Gly
            2450                2455                2460

Val Gly Leu Pro Gly Pro Arg Gly Glu Arg Gly Glu Pro Gly Ile Arg
2465                2470                2475                2480

Gly Glu Asp Gly Arg Pro Gly Gln Glu Gly Pro Arg Gly Leu Thr Gly
                2485                2490                2495

Pro Pro Gly Ser Arg Gly Glu Arg Gly Glu Lys Gly Asp Val Gly Ser
            2500                2505                2510

Ala Gly Leu Lys Gly Asp Lys Gly Asp Ser Ala Val Ile Leu Gly Pro
        2515                2520                2525

Pro Gly Pro Arg Gly Ala Lys Gly Asp Met Gly Glu Arg Gly Pro Arg
    2530                2535                2540

Gly Leu Asp Gly Asp Lys Gly Pro Arg Gly Asp Asn Gly Asp Pro Gly
2545                2550                2555                2560

Asp Lys Gly Ser Lys Gly Glu Pro Gly Asp Lys Gly Ser Ala Gly Leu
                2565                2570                2575

Pro Gly Leu Arg Gly Leu Leu Gly Pro Gln Gly Gln Pro Gly Ala Ala
            2580                2585                2590

Gly Ile Pro Gly Asp Pro Gly Ser Pro Gly Lys Asp Gly Val Pro Gly
        2595                2600                2605

Ile Arg Gly Glu Lys Gly Asp Val Gly Phe Met Gly Pro Arg Gly Leu
    2610                2615                2620

Lys Gly Glu Arg Gly Val Lys Gly Ala Cys Gly Leu Asp Gly Glu Lys
2625                2630                2635                2640

Gly Asp Lys Gly Glu Ala Gly Pro Pro Gly Arg Pro Gly Leu Ala Gly
                2645                2650                2655

His Lys Gly Glu Met Gly Glu Pro Gly Val Pro Gly Gln Ser Gly Ala
            2660                2665                2670

Pro Gly Lys Glu Gly Leu Ile Gly Pro Lys Gly Asp Arg Gly Phe Asp
        2675                2680                2685

Gly Gln Pro Gly Pro Lys Gly Asp Gln Gly Glu Lys Gly Glu Arg Gly
    2690                2695                2700

Thr Pro Gly Ile Gly Gly Phe Pro Gly Pro Ser Gly Asn Asp Gly Ser
2705                2710                2715                2720

Ala Gly Pro Pro Gly Pro Pro Gly Ser Val Gly Pro Arg Gly Pro Glu
            2725                2730                2735

Gly Leu Gln Gly Gln Lys Gly Glu Arg Gly Pro Pro Gly Glu Arg Val
        2740                2745                2750

Val Gly Ala Pro Gly Val Pro Gly Ala Pro Gly Glu Arg Gly Glu Gln
    2755                2760                2765

Gly Arg Pro Gly Pro Ala Gly Pro Arg Gly Glu Lys Gly Glu Ala Ala
        2770                2775                2780

Leu Thr Glu Asp Asp Ile Arg Gly Phe Val Arg Gln Glu Met Ser Gln
2785                2790                2795                2800

His Cys Ala Cys Gln Gly Gln Phe Ile Ala Ser Gly Ser Arg Pro Leu
            2805                2810                2815

Pro Ser Tyr Ala Ala Asp Thr Ala Gly Ser Gln Leu His Ala Val Pro
        2820                2825                2830

Val Leu Arg Val Ser His Ala Glu Glu Glu Arg Val Pro Pro Glu
    2835                2840                2845

Asp Asp Glu Tyr Ser Glu Tyr Ser Glu Tyr Ser Val Glu Glu Tyr Gln
        2850                2855                2860
```

-continued

```
Asp Pro Glu Ala Pro Trp Asp Ser Asp Pro Cys Ser Leu Pro Leu
2865                2870                2875                2880

Asp Glu Gly Ser Cys Thr Ala Tyr Thr Leu Arg Trp Tyr His Arg Ala
            2885                2890                2895

Val Thr Gly Ser Thr Glu Ala Cys His Pro Phe Val Tyr Gly Gly Cys
        2900                2905                2910

Gly Gly Asn Ala Asn Arg Phe Gly Thr Arg Glu Ala Cys Glu Arg Arg
    2915                2920                2925

Cys Pro Pro Arg Val Val Gln Ser Gln Gly Thr Gly Thr Ala Gln Asp
2930                2935                2940

Gly Ser Gly Ala Thr Asn Phe Ser Leu Leu Lys Gln Ala Gly Asp Val
2945                2950                2955                2960

Glu Glu Asn Pro Gly Pro Thr Ser Ser Gly Pro Gly Pro Arg Phe Leu
            2965                2970                2975

Leu Leu Leu Pro Leu Leu Leu Pro Pro Ala Ala Ser Ala Ser Asp Arg
        2980                2985                2990

Pro Arg Gly Arg Asp Pro Val Asn Pro Glu Lys Leu Leu Val Ile Thr
    2995                3000                3005

Val Ala Thr Ala Glu Thr Glu Gly Tyr Leu Arg Phe Leu Arg Ser Ala
3010                3015                3020

Glu Phe Phe Asn Tyr Thr Val Arg Thr Leu Gly Leu Gly Glu Glu Trp
3025                3030                3035                3040

Arg Gly Gly Asp Val Ala Arg Thr Val Gly Gly Gly Gln Lys Val Arg
            3045                3050                3055

Trp Leu Lys Lys Glu Met Glu Lys Tyr Ala Asp Arg Glu Asp Met Ile
        3060                3065                3070

Ile Met Phe Val Asp Ser Tyr Asp Val Ile Leu Ala Gly Ser Pro Thr
    3075                3080                3085

Glu Leu Leu Lys Lys Phe Val Gln Ser Gly Ser Arg Leu Leu Phe Ser
3090                3095                3100

Ala Glu Ser Phe Cys Trp Pro Glu Trp Gly Leu Ala Glu Gln Tyr Pro
3105                3110                3115                3120

Glu Val Gly Thr Gly Lys Arg Phe Leu Asn Ser Gly Gly Phe Ile Gly
            3125                3130                3135

Phe Ala Thr Thr Ile His Gln Ile Val Arg Gln Trp Lys Tyr Lys Asp
        3140                3145                3150

Asp Asp Asp Asp Gln Leu Phe Tyr Thr Arg Leu Tyr Leu Asp Pro Gly
    3155                3160                3165

Leu Arg Glu Lys Leu Ser Leu Asn Leu Asp His Lys Ser Arg Ile Phe
3170                3175                3180

Gln Asn Leu Asn Gly Ala Leu Asp Glu Val Val Leu Lys Phe Asp Arg
3185                3190                3195                3200

Asn Arg Val Arg Ile Arg Asn Val Ala Tyr Asp Thr Leu Pro Ile Val
            3205                3210                3215

Val His Gly Asn Gly Pro Thr Lys Leu Gln Leu Asn Tyr Leu Gly Asn
        3220                3225                3230

Tyr Val Pro Asn Gly Trp Thr Pro Glu Gly Gly Cys Gly Phe Cys Asn
    3235                3240                3245

Gln Asp Arg Arg Thr Leu Pro Gly Gly Gln Pro Pro Arg Val Phe
3250                3255                3260

Leu Ala Val Phe Val Glu Gln Pro Thr Pro Phe Leu Pro Arg Phe Leu
3265                3270                3275                3280
```

```
Gln Arg Leu Leu Leu Leu Asp Tyr Pro Pro Asp Arg Val Thr Leu Phe
            3285                3290                3295

Leu His Asn Asn Glu Val Phe His Glu Pro His Ile Ala Asp Ser Trp
        3300                3305                3310

Pro Gln Leu Gln Asp His Phe Ser Ala Val Lys Leu Val Gly Pro Glu
        3315                3320                3325

Glu Ala Leu Ser Pro Gly Glu Ala Arg Asp Met Ala Met Asp Leu Cys
        3330                3335                3340

Arg Gln Asp Pro Glu Cys Glu Phe Tyr Phe Ser Leu Asp Ala Asp Ala
3345                3350                3355                3360

Val Leu Thr Asn Leu Gln Thr Leu Arg Ile Leu Ile Glu Glu Asn Arg
            3365                3370                3375

Lys Val Ile Ala Pro Met Leu Ser Arg His Gly Lys Leu Trp Ser Asn
            3380                3385                3390

Phe Trp Gly Ala Leu Ser Pro Asp Glu Tyr Tyr Ala Arg Ser Glu Asp
            3395                3400                3405

Tyr Val Glu Leu Val Gln Arg Lys Arg Val Gly Val Trp Asn Val Pro
            3410                3415                3420

Tyr Ile Ser Gln Ala Tyr Val Ile Arg Gly Asp Thr Leu Arg Met Glu
3425                3430                3435                3440

Leu Pro Gln Arg Asp Val Phe Ser Gly Ser Asp Thr Asp Pro Asp Met
            3445                3450                3455

Ala Phe Cys Lys Ser Phe Arg Asp Lys Gly Ile Phe Leu His Leu Ser
            3460                3465                3470

Asn Gln His Glu Phe Gly Arg Leu Leu Ala Thr Ser Arg Tyr Asp Thr
            3475                3480                3485

Glu His Leu His Pro Asp Leu Trp Gln Ile Phe Asp Asn Pro Val Asp
            3490                3495                3500

Trp Lys Glu Gln Tyr Ile His Glu Asn Tyr Ser Arg Ala Leu Glu Gly
3505                3510                3515                3520

Glu Gly Ile Val Glu Gln Pro Cys Pro Asp Val Tyr Trp Phe Pro Leu
            3525                3530                3535

Leu Ser Glu Gln Met Cys Asp Glu Leu Val Ala Glu Met Glu His Tyr
            3540                3545                3550

Gly Gln Trp Ser Gly Gly Arg His Glu Asp Ser Arg Leu Ala Gly Gly
            3555                3560                3565

Tyr Glu Asn Val Pro Thr Val Asp Ile His Met Lys Gln Val Gly Tyr
            3570                3575                3580

Glu Asp Gln Trp Leu Gln Leu Leu Arg Thr Tyr Val Gly Pro Met Thr
3585                3590                3595                3600

Glu Ser Leu Phe Pro Gly Tyr His Thr Lys Ala Arg Ala Val Met Asn
            3605                3610                3615

Phe Val Val Arg Tyr Arg Pro Asp Glu Gln Pro Ser Leu Arg Pro His
            3620                3625                3630

His Asp Ser Ser Thr Phe Thr Leu Asn Val Ala Leu Asn His Lys Gly
            3635                3640                3645

Leu Asp Tyr Glu Gly Gly Gly Cys Arg Phe Leu Arg Tyr Asp Cys Val
            3650                3655                3660

Ile Ser Ser Pro Arg Lys Gly Trp Ala Leu Leu His Pro Gly Arg Leu
3665                3670                3675                3680

Thr His Tyr His Glu Gly Leu Pro Thr Thr Trp Gly Thr Arg Tyr Ile
            3685                3690                3695

Met Val Ser Phe Val Asp Pro
```

<210> SEQ ID NO 19
<211> LENGTH: 11112
<212> TYPE: DNA
<213> ORGANISM: Artificial Sequence
<220> FEATURE:
<223> OTHER INFORMATION: Synthetic Construct

<400> SEQUENCE: 19

```
atgacctcct cggggcctgg accccggttc ctgctgctgc tgccgctgct gctgccccct      60
gcggcctcag cctccgaccg gccccggggc cgagacccgg tcaacccaga aagctgctg     120
gtgatcactg tggccacagc tgaaaccgag gggtacctgc gtttcctgcg ctctgcggag    180
ttcttcaact acactgtgcg gaccctgggc ctgggagagg agtggcgagg gggtgatgtg    240
gctcgaacag ttggtggagg acagaaggtc cggtggttaa agaaggaaat ggagaaatac    300
gctgaccggg aggatatgat catcatgttt gtggatagct acgacgtgat tctggccggc    360
agccccacag agctgctgaa gaagttcgtc cagagtggca gccgcctgct cttctctgca    420
gagagcttct gctggcccga gtggggggctg gcggagcagt accctgaggt gggcacgggg    480
aagcgcttcc tcaattctgg tggattcatc ggttttgcca ccaccatcca ccaaatcgtg    540
cgccagtgga agtacaagga tgatgacgac gaccagctgt tctacacacg gctctacctg    600
gacccaggac tgagggagaa actcagcctt aatctggatc ataagtctcg gatctttcag    660
aacctcaacg gggctttaga tgaagtggtt ttaaagtttg atcggaaccg tgtgcgtatc    720
cggaacgtgg cctacgacac gctccccatt gtggtccatg aaacggtcc cactaagctg    780
cagctcaact acctgggaaa ctacgtcccc aatggctgga ctcctgaggg aggctgtggc    840
ttctgcaacc aggaccggag gacactcccg gggggcagc ctcccccccg ggtgttctg     900
gccgtgtttg tggaacagcc tactccgttt ctgcccgct tcctgcagcg gctgctactc     960
ctggactatc ccccgacag ggtcacccctt ttcctgcaca caacgaggt cttccatgaa   1020
ccccacatcg ctgactcctg gccgcagctc caggaccact tctcagctgt gaagctcgtg   1080
gggccggagg aggctctgag cccaggcgag gccaggggaca tggccatgga cctgtgtcgg   1140
caggaccccg agtgtgagtt ctacttcagc ctggacgccg acgctgtcct caccaacctg   1200
cagaccctgc gtatcctcat tgaggagaac aggaaggtga tcgcccccat gctgtcccgc   1260
cacggcaagc tgtggtccaa cttctgggc gccctgagcc ccgatgagta ctacgcccgc   1320
tccgaggact acgtggagct ggtgcagcgg aagcgagtgg gtgtgtggaa tgtaccatac   1380
atctcccagg cctatgtgat ccggggtgat accctgcgga tggagctgcc ccagagggat   1440
gtgttctcgg gcagtgacac agacccggac atggccttct gtaagagctt cgagacaag   1500
ggcatcttcc tccatctgag caatcagcat gaatttggcc ggctcctggc cacttccaga   1560
tacgacacgg agcacctgca ccccgacctc tggcagatct cgacaacccc cgtcgactgg   1620
aaggagcagt acatccacga gaactacagc cgggccctgg aagggaagg aatcgtggag   1680
cagccatgcc cggacgtgta ctggttccca ctgctgtcag aacaaatgtg tgatgagctg   1740
gtggcagaga tggagcacta cggccagtgg tcaggcggcc ggcatgagga ttcaaggctg   1800
gctggaggct acgagaatgt gcccaccgtg gacatccaca tgaagcaggt ggggtacgag   1860
gaccagtggc tgcagctgct gcggacgtat gtgggcccca tgaccgagag cctgtttccc   1920
ggttaccaca ccaaggcgcg ggcggtgatg aactttgtgg ttcgctaccg gccagacgag   1980
cagccgtctc tgcggccaca ccacgactca tccaccttca ccctcaacgt tgccctcaac   2040
```

-continued

```
cacaagggcc tggactatga gggaggtggc tgccgcttcc tgcgctacga ctgtgtgatc    2100
tcctccccga ggaagggctg ggcactcctg caccccggcc gcctcaccca ctaccacgag    2160
gggctgccaa cgacctgggg cacacgctac atcatggtgt cctttgtcga ccccggaagc    2220
ggagctacta acttcagcct gctgaagcag gctggagacg tggaggagaa ccctggacct    2280
acgctgcggc ttctggtggc cgcgctctgc gccgggatcc tggcagaggc gccccgagtg    2340
cgagcccagc acagggagag agtgacctgc acgcgccttt acgccgctga cattgtgttc    2400
ttactggatg gctcctcatc cattggccgc agcaatttcc gcgaggtccg cagctttctc    2460
gaagggctgg tgctgccttt ctctggagca gccagtgcac agggtgtgcg ctttgccaca    2520
gtgcagtaca gcgatgaccc acggacagag ttcggcctgg atgcacttgg ctctggggt    2580
gatgtgatcc gcgccatccg tgagcttagc tacaagggg gcaacactcg cacaggggct    2640
gcaattctcc atgtggctga ccatgtcttc ctgccccagc tggcccgacc tggtgtcccc    2700
aaggtctgca tcctgatcac agacgggaag tcccaggacc tggtggacac agctgcccaa    2760
aggctgaagg ggcaggggt caagctattt gctgtgggga tcaagaatgc tgaccctgag    2820
gagctgaagc gagttgcctc acagcccacc agtgacttct tcttcttcgt caatgacttc    2880
agcatcttga ggacactact gcccctcgtt tcccggagag tgtgcacgac tgctggtggc    2940
gtgcctgtga cccgacctcc ggatgactcg acctctgctc cacgagacct ggtgctgtct    3000
gagccaagca gccaatcctt gagagtacag tggacagcgg ccagtggccc tgtgactggc    3060
tacaaggtcc agtacactcc tctgacgggg ctgggacagc cactgccgag tgagcggcag    3120
gaggtgaacg tcccagctgg tgagaccagt gtgcggctgc ggggtctccg gccactgacc    3180
gagtaccaag tgactgtgat tgccctctac gccaacagca tcggggaggc tgtgagcggg    3240
acagctcgga ccactgccct agaagggccg gaactgacca tccagaatac cacagcccac    3300
agcctcctgg tggcctggcg gagtgtgcca ggtgccactg gctaccgtgt gacatggcgg    3360
gtcctcagtg gtgggcccac acagcagcag gagctgggcc ctgggcaggg ttcagtgttg    3420
ctgcgtgact ggagcctgg cacggactat gaggtgaccg tgagcaccct atttggccgc    3480
agtgtggggc ccgccacttc cctgatggct cgcactgacg cttctgttga gcagaccctg    3540
cgcccggtca tcctgggccc cacatccatc ctccttttcct ggaacttggt gcctgaggcc    3600
cgtggctacc ggttggaatg gcggcgtgag actggcttgg agccaccgca gaaggtggta    3660
ctgcctctg atgtgaccccg ctaccagttg gatggctgc agccgggcac tgagtaccgc    3720
ctcacactct acactctgct ggagggccac gaggtggcca cccctgcaac cgtggttccc    3780
actggaccag agctgcctgt gagccctgta acagacctgc aagccaccga gctgcccggg    3840
cagcgggtgc gagtgtcctg gagcccagtc cctggtgcca cccagtaccg catcattgtg    3900
cgcagcaccc agggggttga gcggaccctg gtgcttcctg ggagtcagac agcattcgac    3960
ttggatgacg ttcaggctgg gcttagctac actgtgcggg tgtctgctcg agtgggtccc    4020
cgtgagggca gtgccagtgt cctcactgtc cgccgggagc cggaaactcc acttgctgtt    4080
ccagggctgc gggttgtggt gtcagatgca acgcgagtga gggtggcctg ggaccccgtc    4140
cctggagcca gtggatttcg gattagctgg agcacaggca gtggtccgga gtccagccag    4200
acactgcccc cagactctac tgccacagac atcacagggc tgcagcctgg aaccacctac    4260
caggtggctg tgtcggtact gcgaggcaga gaggagggcc ctgctgcagt catcgtggct    4320
cgaacggacc cactgggccc agtgaggacg gtccatgtga ctcaggccag cagctcatct    4380
```

```
gtcaccatta cctggaccag ggttcctggc gccacaggat acagggtttc ctggcactca    4440
gcccacggcc cagagaaatc ccagttggtt tctggggagg ccacggtggc tgagctggat    4500
ggactggagc cagatactga gtatacggtg catgtgaggg cccatgtggc tggcgtggat    4560 gggcccctg cctctgtggt tgtgaggact gcccctgagc ctgtgggtcg tgtgtcgagg     4620
ctgcagatcc tcaatgcttc cagcgacgtt ctacggatca cctgggtagg ggtcactgga    4680
gccacagctt acagactggc ctggggccgg agtgaaggcg gccccatgag gcaccagata    4740
ctcccaggaa acacagactc tgcagagatc cggggtctcg aaggtggagt cagctactca    4800
gtgcgagtga ctgcacttgt cggggaccgc gagggcacac ctgtctccat tgttgtcact    4860
acgccgcctg aggctccgcc agccctgggg acgcttcacg tggtgcagcg cggggagcac    4920
tcgctgaggc tgcgctggga gccggtgccc agagcgcagg gcttccttct gcactggcaa    4980
cctgagggtg gccaggaaca gtcccgggtc ctggggcccg agctcagcag ctatcacctg    5040
gacgggctgg agccagcgac acagtaccgc gtgaggctga gtgtcctagg gccagctgga    5100
gaagggccct ctgcagaggt gactgcgcgc actgagtcac ctcgtgttcc aagcattgaa    5160
ctacgtgtgg tggacacctc gatcgactcg gtgactttgg cctggactcc agtgtccagg    5220
gcatccagct acatcctatc ctggcggcca ctcagaggcc ctggcagga agtgcctggg     5280 tccccgcaga cacttccagg gatctcaagc tcccagcggg tgacagggct agagcctggc    5340
gtctcttaca tcttctccct gacgcctgtc ctggatggtg tgcggggtcc tgaggcatct    5400
gtcacacaga cgccagtgtg ccccgtggc ctggcggatg tggtgttcct accacatgcc     5460
actcaagaca atgctcaccg tgcggaggct acgaggaggg tcctggagcg tctggtgttg    5520
gcacttgggc ctcttgggcc acaggcagtt caggttggcc tgctgtctta cagtcatcgg    5580
ccctccccac tgttcccact gaatggctcc catgaccttg gcattatctt gcaaaggatc    5640
cgtgacatgc cctacatgga cccaagtggg aacaacctgg gcacagccgt ggtcacagct    5700
cacagataca tgttggcacc agatgctcct gggcgccgcc agcacgtacc aggggtgatg    5760
gttctgctag tggatgaacc cttgagaggt gacatattca gccccatccg tgaggcccag    5820
gcttctgggc ttaatgtggt gatgttggga atggctggag cggacccaga gcagctgcgt    5880
cgcttggcgc cgggtatgga ctctgtccag accttcttcg ccgtggatga tgggccaagc    5940
ctggaccagg cagtcagtgg tctgccaca gccctgtgtc aggcatcctt cactactcag     6000
ccccggccag agccctgccc agtgtattgt ccaaagggcc agaaggggga acctggagag    6060
atgggcctga ggacaaagt tgggcctcct ggcgacctg cctcccggg caggaccggt       6120 gctcccggcc ccaggggcc ccctggaagt gccactgcca agggcgagag ggcttccct     6180 ggagcagatg ggcgtccagg cagccctggc cgcgccggga tcctgggac ccctggagcc    6240 cctggcctaa agggctctcc agggttgcct ggccctcgtg ggacccggg agagcgagga    6300 cctcgaggcc caaagggga gccggggct cccggacaag tcatcggagg tgaaggacct     6360
gggcttcctg ggcggaaagg ggaccctgga ccatcgggcc ccctggacc tcgtggacca    6420 ctggggacc caggaccccg tggccccca gggcttcctg gaacagccat gaagggtgac     6480
aaaggcgatc gtggggagcg gggtcccct ggaccaggtg aaggtggcat tgctcctggg    6540
gagcctgggc tgccgggtct tcccggaagc cctggacccc aagggccgt tggccccct     6600 ggaaagaaag gagaaaaagg tgactctgag gatggagctc caggcctccc aggacaacct    6660
gggtctccgg gtgagcaggg cccacgggga cctcctggag ctattggccc caaaggtgac    6720
cggggctttc cagggcccct gggtgaggct ggagagaagg gcgaacgtgg accccaggc     6780
```

```
ccagcgggat cccggggggct gccaggggtt gctggacgtc ctggagccaa gggtcctgaa      6840
gggccaccag gacccactgg ccgccaagga gagaagggggg agcctggtcg ccctggggac      6900
cctgcagtgg tgggacctgc tgttgctgga cccaaaggag aaaagggaga tgtggggccc      6960
gctgggccca gaggagctac cggagtccaa ggggaacggg gcccacccgg cttggttctt      7020
cctggagacc ctggccccaa gggagaccct ggagaccggg gtcccattgg ccttactggc      7080
agagcaggac ccccaggtga ctcagggcct cctggagaga aggagaccc tgggcggcct       7140
ggcccccag gacctgttgg ccccgagga cgagatggtg aagttggaga gaaaggtgac        7200
gagggtcctc cgggtgaccc gggtttgcct ggaaaagcag gcgagcgtgg ccttcggggg      7260
gcacctggag ttcgggggcc tgtgggtgaa aagggagacc agggagatcc tggagaggat      7320
ggacgaaatg gcagccctgg atcatctgga cccaagggtg accgtgggga gccgggtccc      7380
ccaggacccc cgggacggct ggtagacaca ggacctggag ccagagagaa gggagagcct      7440
ggggaccgcg gacaagaggg tcctcgaggg cccaaggggt atcctggcct ccctggagcc      7500
cctggggaaa gggggcattga agggtttcgg ggaccccag gcccacaggg ggacccaggt      7560
gtccgaggcc cagcaggaga aaagggtgac cggggtcccc ctgggctgga tggccggagc      7620
ggactggatg ggaaaccagg agccgctggg ccctctgggc cgaatggtgc tgcaggcaaa      7680
gctgggggacc cagggagaga cgggcttcca ggcctccgtg gagaacaggg cctccctggc      7740
ccctctggtc ccctggatt accgggaaag ccaggcgagg atggcaaacc tggcctgaat       7800
ggaaaaaacg gagaacctgg ggaccctgga aagacgggga ggaagggaga gaaaggagat     7860
tcaggcgcct ctgggagaga aggtcgtgat ggccccaagg gtgagcgtgg agctcctggt     7920
atccttggac cccagggggcc tccaggcctc ccagggccag tgggccctcc tggccagggt     7980
tttcctggtg tcccaggagg cacgggcccc aagggtgacc gtggggagac tggatccaaa    8040
ggggagcagg gcctccctgg agagcgtggc ctgcgaggag agcctggaag tgtgccgaat    8100
gtggatcggt tgctggaaac tgctggcatc aaggcatctg ccctgcggga gatcgtggag    8160
acctgggatg agagctctgg tagcttcctg cctgtgcccg aacggcgtcg aggccccaag    8220
ggggactcag gcgaacaggg cccccccaggc aaggaggggcc ccatcggctt tcctggagaa   8280
cgcgggctga agggcgaccg tggagaccct ggccctcagg ggccacctgg tctggccctt   8340
ggggagaggg gccccccgg gccttccggc cttgccgggg agcctggaaa gcctggtatt    8400
cccgggctcc caggcagggc tggggggtgtg ggagaggcag gaaggccagg agagagggga    8460
gaacggggag agaaaggaga acgtggagaa cagggcagag atggccctcc tggactccct    8520
ggaacccctg gccccccgg acccctggc cccaaggtgt ctgtggatga gccaggtcct      8580
ggactctctg gagaacaggg acccctggga ctcaaggtg ctaaggggga gccggcagc       8640
aatggtgacc aaggtcccaa aggagacagg ggtgtgccag gcatcaaagg agaccgggga    8700
gagcctggac cgaggggtca ggacggcaac ccggtctac caggagagcg tggtatggct     8760
gggcctgaag ggaagccggg tctgcagggt ccaagaggcc ccctggccc agtgggtggt    8820
catggagacc ctggaccacc tggtgcccca ggtcttgctg ccctgcagg acccaaggga    8880
ccttctggcc tgaaggggga gcctggagag acaggacctc caggacgggg cctgactgga    8940
cctactggag ctgtgggact tcctggaccc cccggcccctt caggccttgt gggtccacag   9000
gggtctccag gtttgcctgg acaagtgggg gagacaggga agccgggagc cccaggtcga   9060
gatggtgcca gtgggaaaga tggagacaga gggagccctg gtgtgccagg gtcaccaggt    9120
```

```
ctgcctggcc ctgtcggacc taaaggagaa cctggcccca cggggcccc tggacaggct    9180 gtggtcgggc tccctggagc aaagggagag aagggagccc tggaggcct tgctggagac    9240 ctggtgggtg agccgggagc caaaggtgac cgaggactgc cagggccgcg aggcgagaag    9300
ggtgaagctg gccgtgcagg ggagcccgga ccctgggg aagatggtca gaaagggct     9360 ccaggaccca aaggtttcaa gggtgaccca ggagtcgggg tcccgggctc cctgggcct    9420 cctggccctc caggtgtgaa gggagatctg ggcctccctg gcctgccgg tgctcctggt    9480 gttgttgggt cccgggtca gacaggccct cgaggagaga tgggtcagcc aggccctagt    9540
ggagagcggg gtctggcagg ccccccaggg agagaaggaa tcccaggacc cctgggccca    9600
cctggaccac cggggtcagt gggaccacct ggggcctctg gactcaaagg agacaaggga    9660
gaccctggag tagggctgcc tgggcccga ggcgagcgtg gggagccagg catccggggt    9720
gaagatggcc gccccggcca ggagggaccc cgaggactca cggggcccc tggcagcagg    9780 ggagagcgtg gggagaaggg tgatgttggg agtgcaggac taaagggtga caagggagac    9840
tcagctgtga tcctggggcc tccaggccca cggggtgcca aggggacat gggtgaacga    9900 gggcctcggg gcttggatgg tgacaaagga cctcggggag acaatgggga ccctggtgac    9960
aagggcagca agggagagcc tggtgacaag ggctcagccg ggttgccagg actgcgtgga   10020
ctcctgggac cccagggtca acctggtgca gcagggatcc ctggtgaccc gggatcccca   10080
ggaaaggatg gagtgcctgg tatccgagga gaaaaaggag atgttggctt catgggtccc   10140
cggggcctca agggtgaacg gggagtgaag ggagcctgtg gccttgatgg agagaaggga   10200
gacaagggag aagctggtcc cccaggccgc cccgggctgg caggacacaa aggagagatg   10260
ggggagcctg gtgtgccggg ccagtcgggg gcccctggca aggagggcct gatcggtccc   10320
aagggtgacc gaggctttga cgggcagcca ggccccaagg gtgaccaggg cgagaagggg   10380
gagcggggaa ccccaggaat tgggggcttc ccaggcccca gtggaaatga tggctctgct   10440 ggtccccag ggccacctgg cagtgttggt cccagaggcc ccgaaggact tcagggccag   10500
aagggtgagc gaggtccccc cggagagaga gtggtggggg ctcctggggt ccctggagct   10560
cctggcgaga gagggagca ggggcggcca gggcctgccg gtcctcgagg cgagaaggga   10620
gaagctgcac tgacggagga tgacatccgg ggctttgtgc gccaagagat gagtcagcac   10680
tgtgcctgcc agggccagtt catcgcatct ggatcacgac ccctccctag ttatgctgca   10740
gacactgccg gctcccagct ccatgctgtg cctgtgctcc gcgtctctca tgcagaggag   10800
gaagagcggg tacccctga ggatgatgag tactctgaat actccgagta ttctgtggag   10860
gagtaccagg accctgaagc tccttgggat agtgatgacc cctgttccct gccactggat   10920
gagggctcct gcactgccta caccctgcgc tggtaccatc gggctgtgac aggcagcaca   10980
gaggcctgtc accctttgt ctatggtggc tgtggaggga atgccaaccg ttttgggacc   11040
cgtgaggcct gcgagcgccg ctgcccaccc cgggtggtcc agagccaggg gacaggtact   11100
gcccaggact ga                                                      11112
```

<210> SEQ ID NO 20  
<211> LENGTH: 3703  
<212> TYPE: PRT  
<213> ORGANISM: Artificial Sequence  
<220> FEATURE:  
<223> OTHER INFORMATION: Synthetic Construct

<400> SEQUENCE: 20

Met Thr Ser Ser Gly Pro Gly Pro Arg Phe Leu Leu Leu Leu Pro Leu

```
  1               5                    10                   15
Leu Leu Pro Pro Ala Ala Ser Ala Ser Asp Arg Pro Arg Gly Arg Asp
                20                  25                  30

Pro Val Asn Pro Glu Lys Leu Leu Val Ile Thr Val Ala Thr Ala Glu
                35                  40                  45

Thr Glu Gly Tyr Leu Arg Phe Leu Arg Ser Ala Glu Phe Phe Asn Tyr
                50                  55                  60

Thr Val Arg Thr Leu Gly Leu Gly Glu Glu Trp Arg Gly Gly Asp Val
 65                  70                  75                  80

Ala Arg Thr Val Gly Gly Gln Lys Val Arg Trp Leu Lys Lys Glu
                    85                  90                  95

Met Glu Lys Tyr Ala Asp Arg Glu Asp Met Ile Ile Met Phe Val Asp
                100                 105                 110

Ser Tyr Asp Val Ile Leu Ala Gly Ser Pro Thr Glu Leu Leu Lys Lys
                115                 120                 125

Phe Val Gln Ser Gly Ser Arg Leu Leu Phe Ser Ala Glu Ser Phe Cys
                130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
                180                 185                 190

Leu Phe Tyr Thr Arg Leu Tyr Leu Asp Pro Gly Leu Arg Glu Lys Leu
                195                 200                 205

Ser Leu Asn Leu Asp His Lys Ser Arg Ile Phe Gln Asn Leu Asn Gly
210                 215                 220

Ala Leu Asp Glu Val Val Leu Lys Phe Asp Arg Asn Arg Val Arg Ile
225                 230                 235                 240

Arg Asn Val Ala Tyr Asp Thr Leu Pro Ile Val Val His Gly Asn Gly
                245                 250                 255

Pro Thr Lys Leu Gln Leu Asn Tyr Leu Gly Asn Tyr Val Pro Asn Gly
                260                 265                 270

Trp Thr Pro Glu Gly Gly Cys Gly Phe Cys Asn Gln Asp Arg Arg Thr
                275                 280                 285

Leu Pro Gly Gly Gln Pro Pro Arg Val Phe Leu Ala Val Phe Val
290                 295                 300

Glu Gln Pro Thr Pro Phe Leu Pro Arg Phe Leu Gln Arg Leu Leu Leu
305                 310                 315                 320

Leu Asp Tyr Pro Pro Asp Arg Val Thr Leu Phe Leu His Asn Asn Glu
                325                 330                 335

Val Phe His Glu Pro His Ile Ala Asp Ser Trp Pro Gln Leu Gln Asp
                340                 345                 350

His Phe Ser Ala Val Lys Leu Val Gly Pro Glu Glu Ala Leu Ser Pro
                355                 360                 365

Gly Glu Ala Arg Asp Met Ala Met Asp Leu Cys Arg Gln Asp Pro Glu
                370                 375                 380

Cys Glu Phe Tyr Phe Ser Leu Asp Ala Asp Ala Val Leu Thr Asn Leu
385                 390                 395                 400

Gln Thr Leu Arg Ile Leu Ile Glu Glu Asn Arg Lys Val Ile Ala Pro
                405                 410                 415

Met Leu Ser Arg His Gly Lys Leu Trp Ser Asn Phe Trp Gly Ala Leu
                420                 425                 430
```

```
Ser Pro Asp Glu Tyr Tyr Ala Arg Ser Glu Asp Tyr Val Glu Leu Val
        435                 440                 445

Gln Arg Lys Arg Val Gly Val Trp Asn Val Pro Tyr Ile Ser Gln Ala
    450                 455                 460

Tyr Val Ile Arg Gly Asp Thr Leu Arg Met Glu Leu Pro Gln Arg Asp
465                 470                 475                 480

Val Phe Ser Gly Ser Asp Thr Asp Pro Asp Met Ala Phe Cys Lys Ser
                485                 490                 495

Phe Arg Asp Lys Gly Ile Phe Leu His Leu Ser Asn Gln His Glu Phe
                500                 505                 510

Gly Arg Leu Leu Ala Thr Ser Arg Tyr Asp Thr Glu His Leu His Pro
        515                 520                 525

Asp Leu Trp Gln Ile Phe Asp Asn Pro Val Asp Trp Lys Glu Gln Tyr
        530                 535                 540

Ile His Glu Asn Tyr Ser Arg Ala Leu Glu Gly Gly Ile Val Glu
545                 550                 555                 560

Gln Pro Cys Pro Asp Val Tyr Trp Phe Pro Leu Leu Ser Glu Gln Met
                565                 570                 575

Cys Asp Glu Leu Val Ala Glu Met Glu His Tyr Gly Gln Trp Ser Gly
                580                 585                 590

Gly Arg His Glu Asp Ser Arg Leu Ala Gly Gly Tyr Glu Asn Val Pro
        595                 600                 605

Thr Val Asp Ile His Met Lys Gln Val Gly Tyr Glu Asp Gln Trp Leu
        610                 615                 620

Gln Leu Leu Arg Thr Tyr Val Gly Pro Met Thr Glu Ser Leu Phe Pro
625                 630                 635                 640

Gly Tyr His Thr Lys Ala Arg Ala Val Met Asn Phe Val Val Arg Tyr
                645                 650                 655

Arg Pro Asp Glu Gln Pro Ser Leu Arg Pro His His Asp Ser Ser Thr
                660                 665                 670

Phe Thr Leu Asn Val Ala Leu Asn His Lys Gly Leu Asp Tyr Glu Gly
        675                 680                 685

Gly Gly Cys Arg Phe Leu Arg Tyr Asp Cys Val Ile Ser Ser Pro Arg
        690                 695                 700

Lys Gly Trp Ala Leu Leu His Pro Gly Arg Leu Thr His Tyr His Glu
705                 710                 715                 720

Gly Leu Pro Thr Thr Trp Gly Thr Arg Tyr Ile Met Val Ser Phe Val
                725                 730                 735

Asp Pro Gly Ser Gly Ala Thr Asn Phe Ser Leu Leu Lys Gln Ala Gly
                740                 745                 750

Asp Val Glu Glu Asn Pro Gly Pro Thr Leu Arg Leu Leu Val Ala Ala
        755                 760                 765

Leu Cys Ala Gly Ile Leu Ala Glu Ala Pro Arg Val Arg Ala Gln His
        770                 775                 780

Arg Glu Arg Val Thr Cys Thr Arg Leu Tyr Ala Ala Asp Ile Val Phe
785                 790                 795                 800

Leu Leu Asp Gly Ser Ser Ser Ile Gly Arg Ser Asn Phe Arg Glu Val
                805                 810                 815

Arg Ser Phe Leu Glu Gly Leu Val Leu Pro Phe Ser Gly Ala Ala Ser
                820                 825                 830

Ala Gln Gly Val Arg Phe Ala Thr Val Gln Tyr Ser Asp Asp Pro Arg
        835                 840                 845
```

-continued

```
Thr Glu Phe Gly Leu Asp Ala Leu Gly Ser Gly Asp Val Ile Arg
            850                 855                 860
Ala Ile Arg Glu Leu Ser Tyr Lys Gly Asn Thr Arg Thr Gly Ala
865                 870                 875                 880
Ala Ile Leu His Val Ala Asp His Val Phe Leu Pro Gln Leu Ala Arg
                885                 890                 895
Pro Gly Val Pro Lys Val Cys Ile Leu Ile Thr Asp Gly Lys Ser Gln
            900                 905                 910
Asp Leu Val Asp Thr Ala Ala Gln Arg Leu Lys Gly Gln Gly Val Lys
            915                 920                 925
Leu Phe Ala Val Gly Ile Lys Asn Ala Asp Pro Glu Glu Leu Lys Arg
            930                 935                 940
Val Ala Ser Gln Pro Thr Ser Asp Phe Phe Phe Val Asn Asp Phe
945                 950                 955                 960
Ser Ile Leu Arg Thr Leu Leu Pro Leu Val Ser Arg Arg Val Cys Thr
                965                 970                 975
Thr Ala Gly Gly Val Pro Val Thr Arg Pro Pro Asp Asp Ser Thr Ser
            980                 985                 990
Ala Pro Arg Asp Leu Val Leu Ser Glu Pro Ser Ser Gln Ser Leu Arg
            995                 1000                1005
Val Gln Trp Thr Ala Ala Ser Gly Pro Val Thr Gly Tyr Lys Val Gln
    1010                1015                1020
Tyr Thr Pro Leu Thr Gly Leu Gly Gln Pro Leu Pro Ser Glu Arg Gln
1025                1030                1035                1040
Glu Val Asn Val Pro Ala Gly Glu Thr Ser Val Arg Leu Arg Gly Leu
                1045                1050                1055
Arg Pro Leu Thr Glu Tyr Gln Val Thr Val Ile Ala Leu Tyr Ala Asn
            1060                1065                1070
Ser Ile Gly Glu Ala Val Ser Gly Thr Ala Arg Thr Thr Ala Leu Glu
            1075                1080                1085
Gly Pro Glu Leu Thr Ile Gln Asn Thr Thr Ala His Ser Leu Leu Val
            1090                1095                1100
Ala Trp Arg Ser Val Pro Gly Ala Thr Gly Tyr Arg Val Thr Trp Arg
1105                1110                1115                1120
Val Leu Ser Gly Gly Pro Thr Gln Gln Gln Glu Leu Gly Pro Gly Gln
                1125                1130                1135
Gly Ser Val Leu Leu Arg Asp Leu Glu Pro Gly Thr Asp Tyr Glu Val
            1140                1145                1150
Thr Val Ser Thr Leu Phe Gly Arg Ser Val Gly Pro Ala Thr Ser Leu
            1155                1160                1165
Met Ala Arg Thr Asp Ala Ser Val Glu Gln Thr Leu Arg Pro Val Ile
            1170                1175                1180
Leu Gly Pro Thr Ser Ile Leu Leu Ser Trp Asn Leu Val Pro Glu Ala
1185                1190                1195                1200
Arg Gly Tyr Arg Leu Glu Trp Arg Arg Glu Thr Gly Leu Glu Pro Pro
            1205                1210                1215
Gln Lys Val Val Leu Pro Ser Asp Val Thr Arg Tyr Gln Leu Asp Gly
            1220                1225                1230
Leu Gln Pro Gly Thr Glu Tyr Arg Leu Thr Leu Tyr Thr Leu Leu Glu
            1235                1240                1245
Gly His Glu Val Ala Thr Pro Ala Thr Val Val Pro Thr Gly Pro Glu
    1250                1255                1260
Leu Pro Val Ser Pro Val Thr Asp Leu Gln Ala Thr Glu Leu Pro Gly
```

```
                1265                1270                1275                1280
Gln Arg Val Arg Val Ser Trp Ser Pro Val Pro Gly Ala Thr Gln Tyr
            1285                1290                1295
Arg Ile Ile Val Arg Ser Thr Gln Gly Val Glu Arg Thr Leu Val Leu
            1300                1305                1310
Pro Gly Ser Gln Thr Ala Phe Asp Leu Asp Asp Val Gln Ala Gly Leu
            1315                1320                1325
Ser Tyr Thr Val Arg Val Ser Ala Arg Val Gly Pro Arg Glu Gly Ser
            1330                1335                1340
Ala Ser Val Leu Thr Val Arg Arg Glu Pro Glu Thr Pro Leu Ala Val
1345                1350                1355                1360
Pro Gly Leu Arg Val Val Val Ser Asp Ala Thr Arg Val Arg Val Ala
            1365                1370                1375
Trp Gly Pro Val Pro Gly Ala Ser Gly Phe Arg Ile Ser Trp Ser Thr
            1380                1385                1390
Gly Ser Gly Pro Glu Ser Ser Gln Thr Leu Pro Pro Asp Ser Thr Ala
            1395                1400                1405
Thr Asp Ile Thr Gly Leu Gln Pro Gly Thr Thr Tyr Gln Val Ala Val
            1410                1415                1420
Ser Val Leu Arg Gly Arg Glu Glu Gly Pro Ala Ala Val Ile Val Ala
1425                1430                1435                1440
Arg Thr Asp Pro Leu Gly Pro Val Arg Thr Val His Val Thr Gln Ala
            1445                1450                1455
Ser Ser Ser Ser Val Thr Ile Thr Trp Thr Arg Val Pro Gly Ala Thr
            1460                1465                1470
Gly Tyr Arg Val Ser Trp His Ser Ala His Gly Pro Glu Lys Ser Gln
            1475                1480                1485
Leu Val Ser Gly Glu Ala Thr Val Ala Glu Leu Asp Gly Leu Glu Pro
            1490                1495                1500
Asp Thr Glu Tyr Thr Val His Val Arg Ala His Val Ala Gly Val Asp
1505                1510                1515                1520
Gly Pro Pro Ala Ser Val Val Val Arg Thr Ala Pro Glu Pro Val Gly
            1525                1530                1535
Arg Val Ser Arg Leu Gln Ile Leu Asn Ala Ser Ser Asp Val Leu Arg
            1540                1545                1550
Ile Thr Trp Val Gly Val Thr Gly Ala Thr Ala Tyr Arg Leu Ala Trp
            1555                1560                1565
Gly Arg Ser Glu Gly Gly Pro Met Arg His Gln Ile Leu Pro Gly Asn
            1570                1575                1580
Thr Asp Ser Ala Glu Ile Arg Gly Leu Glu Gly Gly Val Ser Tyr Ser
1585                1590                1595                1600
Val Arg Val Thr Ala Leu Val Gly Asp Arg Glu Gly Thr Pro Val Ser
            1605                1610                1615
Ile Val Val Thr Thr Pro Pro Glu Ala Pro Ala Leu Gly Thr Leu
            1620                1625                1630
His Val Val Gln Arg Gly Glu His Ser Leu Arg Leu Arg Trp Glu Pro
            1635                1640                1645
Val Pro Arg Ala Gln Gly Phe Leu Leu His Trp Gln Pro Glu Gly Gly
            1650                1655                1660
Gln Glu Gln Ser Arg Val Leu Gly Pro Glu Leu Ser Ser Tyr His Leu
1665                1670                1675                1680
Asp Gly Leu Glu Pro Ala Thr Gln Tyr Arg Val Arg Leu Ser Val Leu
            1685                1690                1695
```

```
Gly Pro Ala Gly Glu Gly Pro Ser Ala Glu Val Thr Ala Arg Thr Glu
            1700                1705                1710

Ser Pro Arg Val Pro Ser Ile Glu Leu Arg Val Val Asp Thr Ser Ile
            1715                1720                1725

Asp Ser Val Thr Leu Ala Trp Thr Pro Val Ser Arg Ala Ser Ser Tyr
            1730                1735                1740

Ile Leu Ser Trp Arg Pro Leu Arg Gly Pro Gly Gln Glu Val Pro Gly
1745                1750                1755                1760

Ser Pro Gln Thr Leu Pro Gly Ile Ser Ser Ser Gln Arg Val Thr Gly
            1765                1770                1775

Leu Glu Pro Gly Val Ser Tyr Ile Phe Ser Leu Thr Pro Val Leu Asp
            1780                1785                1790

Gly Val Arg Gly Pro Glu Ala Ser Val Thr Gln Thr Pro Val Cys Pro
            1795                1800                1805

Arg Gly Leu Ala Asp Val Val Phe Leu Pro His Ala Thr Gln Asp Asn
            1810                1815                1820

Ala His Arg Ala Glu Ala Thr Arg Arg Val Leu Glu Arg Leu Val Leu
1825                1830                1835                1840

Ala Leu Gly Pro Leu Gly Pro Gln Ala Val Gln Val Gly Leu Leu Ser
            1845                1850                1855

Tyr Ser His Arg Pro Ser Pro Leu Phe Pro Leu Asn Gly Ser His Asp
            1860                1865                1870

Leu Gly Ile Ile Leu Gln Arg Ile Arg Asp Met Pro Tyr Met Asp Pro
            1875                1880                1885

Ser Gly Asn Asn Leu Gly Thr Ala Val Val Thr Ala His Arg Tyr Met
            1890                1895                1900

Leu Ala Pro Asp Ala Pro Gly Arg Arg Gln His Val Pro Gly Val Met
1905                1910                1915                1920

Val Leu Leu Val Asp Glu Pro Leu Arg Gly Asp Ile Phe Ser Pro Ile
            1925                1930                1935

Arg Glu Ala Gln Ala Ser Gly Leu Asn Val Val Met Leu Gly Met Ala
            1940                1945                1950

Gly Ala Asp Pro Glu Gln Leu Arg Arg Leu Ala Pro Gly Met Asp Ser
            1955                1960                1965

Val Gln Thr Phe Phe Ala Val Asp Asp Gly Pro Ser Leu Asp Gln Ala
            1970                1975                1980

Val Ser Gly Leu Ala Thr Ala Leu Cys Gln Ala Ser Phe Thr Thr Gln
1985                1990                1995                2000

Pro Arg Pro Glu Pro Cys Pro Val Tyr Cys Pro Lys Gly Gln Lys Gly
            2005                2010                2015

Glu Pro Gly Glu Met Gly Leu Arg Gly Gln Val Gly Pro Pro Gly Asp
            2020                2025                2030

Pro Gly Leu Pro Gly Arg Thr Gly Ala Pro Gly Pro Gln Gly Pro Pro
            2035                2040                2045

Gly Ser Ala Thr Ala Lys Gly Glu Arg Gly Phe Pro Gly Ala Asp Gly
            2050                2055                2060

Arg Pro Gly Ser Pro Gly Arg Ala Gly Asn Pro Gly Thr Pro Gly Ala
2065                2070                2075                2080

Pro Gly Leu Lys Gly Ser Pro Gly Leu Pro Gly Pro Arg Gly Asp Pro
            2085                2090                2095

Gly Glu Arg Gly Pro Arg Gly Pro Lys Gly Glu Pro Gly Ala Pro Gly
            2100                2105                2110
```

-continued

Gln Val Ile Gly Gly Glu Gly Pro Gly Leu Pro Gly Arg Lys Gly Asp
              2115                2120                2125

Pro Gly Pro Ser Gly Pro Pro Gly Pro Arg Gly Leu Gly Asp Pro
        2130                2135                2140

Gly Pro Arg Gly Pro Pro Gly Leu Pro Gly Thr Ala Met Lys Gly Asp
2145                2150                2155                2160

Lys Gly Asp Arg Gly Glu Arg Gly Pro Pro Gly Glu Gly Gly
              2165                2170                2175

Ile Ala Pro Gly Glu Pro Gly Leu Pro Gly Leu Pro Gly Ser Pro Gly
              2180                2185                2190

Pro Gln Gly Pro Val Gly Pro Gly Lys Lys Gly Glu Lys Gly Asp
        2195                2200                2205

Ser Glu Asp Gly Ala Pro Gly Leu Pro Gly Gln Pro Gly Ser Pro Gly
        2210                2215                2220

Glu Gln Gly Pro Arg Gly Pro Pro Gly Ala Ile Gly Pro Lys Gly Asp
2225                2230                2235                2240

Arg Gly Phe Pro Gly Pro Leu Gly Glu Ala Gly Glu Lys Gly Glu Arg
              2245                2250                2255

Gly Pro Pro Gly Pro Ala Gly Ser Arg Gly Leu Pro Gly Val Ala Gly
              2260                2265                2270

Arg Pro Gly Ala Lys Gly Pro Glu Gly Pro Pro Gly Pro Thr Gly Arg
              2275                2280                2285

Gln Gly Glu Lys Gly Glu Pro Gly Arg Pro Gly Asp Pro Ala Val Val
              2290                2295                2300

Gly Pro Ala Val Ala Gly Pro Lys Gly Glu Lys Gly Asp Val Gly Pro
2305                2310                2315                2320

Ala Gly Pro Arg Gly Ala Thr Gly Val Gln Gly Glu Arg Gly Pro Pro
              2325                2330                2335

Gly Leu Val Leu Pro Gly Asp Pro Gly Pro Lys Gly Asp Pro Gly Asp
              2340                2345                2350

Arg Gly Pro Ile Gly Leu Thr Gly Arg Ala Gly Pro Pro Gly Asp Ser
              2355                2360                2365

Gly Pro Pro Gly Glu Lys Gly Asp Pro Gly Arg Pro Gly Pro Pro Gly
        2370                2375                2380

Pro Val Gly Pro Arg Gly Arg Asp Gly Glu Val Gly Glu Lys Gly Asp
2385                2390                2395                2400

Glu Gly Pro Pro Gly Asp Pro Gly Leu Pro Gly Lys Ala Gly Glu Arg
              2405                2410                2415

Gly Leu Arg Gly Ala Pro Gly Val Arg Gly Pro Val Gly Glu Lys Gly
              2420                2425                2430

Asp Gln Gly Asp Pro Gly Glu Asp Gly Arg Asn Gly Ser Pro Gly Ser
              2435                2440                2445

Ser Gly Pro Lys Gly Asp Arg Gly Glu Pro Gly Pro Pro Gly Pro Pro
        2450                2455                2460

Gly Arg Leu Val Asp Thr Gly Pro Gly Ala Arg Glu Lys Gly Glu Pro
2465                2470                2475                2480

Gly Asp Arg Gly Gln Glu Gly Pro Arg Gly Pro Lys Gly Asp Pro Gly
              2485                2490                2495

Leu Pro Gly Ala Pro Gly Glu Arg Gly Ile Glu Gly Phe Arg Gly Pro
              2500                2505                2510

Pro Gly Pro Gln Gly Asp Pro Gly Val Arg Gly Pro Ala Gly Glu Lys
              2515                2520                2525

Gly Asp Arg Gly Pro Pro Gly Leu Asp Gly Arg Ser Gly Leu Asp Gly

```
                2530                2535                2540

Lys Pro Gly Ala Ala Gly Pro Ser Gly Pro Asn Gly Ala Ala Gly Lys
2545                2550                2555                2560

Ala Gly Asp Pro Gly Arg Asp Gly Leu Pro Gly Leu Arg Gly Glu Gln
                2565                2570                2575

Gly Leu Pro Gly Pro Ser Gly Pro Pro Gly Leu Pro Gly Lys Pro Gly
                2580                2585                2590

Glu Asp Gly Lys Pro Gly Leu Asn Gly Lys Asn Gly Glu Pro Gly Asp
                2595                2600                2605

Pro Gly Glu Asp Gly Arg Lys Gly Glu Lys Gly Asp Ser Gly Ala Ser
                2610                2615                2620

Gly Arg Glu Gly Arg Asp Gly Pro Lys Gly Glu Arg Gly Ala Pro Gly
2625                2630                2635                2640

Ile Leu Gly Pro Gln Gly Pro Pro Gly Leu Pro Gly Pro Val Gly Pro
                2645                2650                2655

Pro Gly Gln Gly Phe Pro Gly Val Pro Gly Gly Thr Gly Pro Lys Gly
                2660                2665                2670

Asp Arg Gly Glu Thr Gly Ser Lys Gly Glu Gln Gly Leu Pro Gly Glu
                2675                2680                2685

Arg Gly Leu Arg Gly Glu Pro Gly Ser Val Pro Asn Val Asp Arg Leu
                2690                2695                2700

Leu Glu Thr Ala Gly Ile Lys Ala Ser Ala Leu Arg Glu Ile Val Glu
2705                2710                2715                2720

Thr Trp Asp Glu Ser Ser Gly Ser Phe Leu Pro Val Pro Glu Arg Arg
                2725                2730                2735

Arg Gly Pro Lys Gly Asp Ser Gly Glu Gln Gly Pro Pro Gly Lys Glu
                2740                2745                2750

Gly Pro Ile Gly Phe Pro Gly Glu Arg Gly Leu Lys Gly Asp Arg Gly
                2755                2760                2765

Asp Pro Gly Pro Gln Gly Pro Pro Gly Leu Ala Leu Gly Glu Arg Gly
                2770                2775                2780

Pro Pro Gly Pro Ser Gly Leu Ala Gly Glu Pro Gly Lys Pro Gly Ile
2785                2790                2795                2800

Pro Gly Leu Pro Gly Arg Ala Gly Gly Val Gly Glu Ala Gly Arg Pro
                2805                2810                2815

Gly Glu Arg Gly Glu Arg Gly Glu Lys Gly Glu Arg Gly Glu Gln Gly
                2820                2825                2830

Arg Asp Gly Pro Pro Gly Leu Pro Gly Thr Pro Gly Pro Pro Gly Pro
                2835                2840                2845

Pro Gly Pro Lys Val Ser Val Asp Glu Pro Gly Pro Gly Leu Ser Gly
2850                2855                2860

Glu Gln Gly Pro Pro Gly Leu Lys Gly Ala Lys Gly Glu Pro Gly Ser
2865                2870                2875                2880

Asn Gly Asp Gln Gly Pro Lys Gly Asp Arg Gly Val Pro Gly Ile Lys
                2885                2890                2895

Gly Asp Arg Gly Glu Pro Gly Pro Arg Gly Gln Asp Gly Asn Pro Gly
                2900                2905                2910

Leu Pro Gly Glu Arg Gly Met Ala Gly Pro Glu Gly Lys Pro Gly Leu
                2915                2920                2925

Gln Gly Pro Arg Gly Pro Pro Gly Pro Val Gly Gly His Gly Asp Pro
                2930                2935                2940

Gly Pro Pro Gly Ala Pro Gly Leu Ala Gly Pro Ala Gly Pro Gln Gly
2945                2950                2955                2960
```

```
Pro Ser Gly Leu Lys Gly Glu Pro Gly Glu Thr Pro Pro Gly Arg
            2965                2970                2975

Gly Leu Thr Gly Pro Thr Gly Ala Val Gly Leu Pro Gly Pro Gly
            2980                2985                2990

Pro Ser Gly Leu Val Gly Pro Gln Gly Ser Pro Gly Leu Pro Gly Gln
            2995                3000                3005

Val Gly Glu Thr Gly Lys Pro Gly Ala Pro Gly Arg Asp Gly Ala Ser
3010                3015                3020

Gly Lys Asp Gly Asp Arg Gly Ser Pro Gly Val Pro Gly Ser Pro Gly
3025                3030                3035                3040

Leu Pro Gly Pro Val Gly Pro Lys Gly Glu Pro Gly Pro Thr Gly Ala
            3045                3050                3055

Pro Gly Gln Ala Val Val Gly Leu Pro Gly Ala Lys Gly Glu Lys Gly
            3060                3065                3070

Ala Pro Gly Gly Leu Ala Gly Asp Leu Val Gly Glu Pro Gly Ala Lys
            3075                3080                3085

Gly Asp Arg Gly Leu Pro Gly Pro Arg Gly Glu Lys Gly Glu Ala Gly
            3090                3095                3100

Arg Ala Gly Glu Pro Gly Asp Pro Gly Glu Asp Gly Gln Lys Gly Ala
3105                3110                3115                3120

Pro Gly Pro Lys Gly Phe Lys Gly Asp Pro Gly Val Gly Val Pro Gly
            3125                3130                3135

Ser Pro Gly Pro Pro Gly Pro Gly Val Lys Gly Asp Leu Gly Leu
            3140                3145                3150

Pro Gly Leu Pro Gly Ala Pro Gly Val Val Gly Phe Pro Gly Gln Thr
            3155                3160                3165

Gly Pro Arg Gly Glu Met Gly Gln Pro Gly Pro Ser Gly Glu Arg Gly
            3170                3175                3180

Leu Ala Gly Pro Pro Gly Arg Glu Gly Ile Pro Gly Pro Leu Gly Pro
3185                3190                3195                3200

Pro Gly Pro Pro Gly Ser Val Gly Pro Pro Gly Ala Ser Gly Leu Lys
            3205                3210                3215

Gly Asp Lys Gly Asp Pro Gly Val Gly Leu Pro Gly Pro Arg Gly Glu
            3220                3225                3230

Arg Gly Glu Pro Gly Ile Arg Gly Glu Asp Gly Arg Pro Gly Gln Glu
            3235                3240                3245

Gly Pro Arg Gly Leu Thr Gly Pro Pro Gly Ser Arg Gly Glu Arg Gly
            3250                3255                3260

Glu Lys Gly Asp Val Gly Ser Ala Gly Leu Lys Gly Asp Lys Gly Asp
3265                3270                3275                3280

Ser Ala Val Ile Leu Gly Pro Pro Gly Pro Arg Gly Ala Lys Gly Asp
            3285                3290                3295

Met Gly Glu Arg Gly Pro Arg Gly Leu Asp Gly Asp Lys Gly Pro Arg
            3300                3305                3310

Gly Asp Asn Gly Asp Pro Gly Asp Lys Gly Ser Lys Gly Glu Pro Gly
            3315                3320                3325

Asp Lys Gly Ser Ala Gly Leu Pro Gly Leu Arg Gly Leu Leu Gly Pro
            3330                3335                3340

Gln Gly Gln Pro Gly Ala Ala Gly Ile Pro Gly Asp Pro Gly Ser Pro
3345                3350                3355                3360

Gly Lys Asp Gly Val Pro Gly Ile Arg Gly Glu Lys Gly Asp Val Gly
            3365                3370                3375
```

Phe Met Gly Pro Arg Gly Leu Lys Gly Glu Arg Val Lys Gly Ala
            3380                3385                3390

Cys Gly Leu Asp Gly Glu Lys Gly Asp Lys Gly Glu Ala Gly Pro Pro
        3395                3400                3405

Gly Arg Pro Gly Leu Ala Gly His Lys Gly Glu Met Gly Glu Pro Gly
    3410                3415                3420

Val Pro Gly Gln Ser Gly Ala Pro Gly Lys Glu Gly Leu Ile Gly Pro
3425                3430                3435                3440

Lys Gly Asp Arg Gly Phe Asp Gly Gln Pro Gly Lys Gly Asp Gln
            3445                3450                3455

Gly Glu Lys Gly Glu Arg Gly Thr Pro Gly Ile Gly Gly Phe Pro Gly
        3460                3465                3470

Pro Ser Gly Asn Asp Gly Ser Ala Gly Pro Pro Gly Pro Pro Gly Ser
            3475                3480                3485

Val Gly Pro Arg Gly Pro Glu Gly Leu Gln Gly Gln Lys Gly Glu Arg
        3490                3495                3500

Gly Pro Pro Gly Glu Arg Val Val Gly Ala Pro Gly Val Pro Gly Ala
3505                3510                3515                3520

Pro Gly Glu Arg Gly Glu Gln Gly Arg Pro Gly Pro Ala Gly Pro Arg
            3525                3530                3535

Gly Glu Lys Gly Glu Ala Ala Leu Thr Glu Asp Asp Ile Arg Gly Phe
        3540                3545                3550

Val Arg Gln Glu Met Ser Gln His Cys Ala Cys Gln Gly Gln Phe Ile
            3555                3560                3565

Ala Ser Gly Ser Arg Pro Leu Pro Ser Tyr Ala Ala Asp Thr Ala Gly
        3570                3575                3580

Ser Gln Leu His Ala Val Pro Val Leu Arg Val Ser His Ala Glu Glu
3585                3590                3595                3600

Glu Glu Arg Val Pro Pro Glu Asp Asp Glu Tyr Ser Glu Tyr Ser Glu
            3605                3610                3615

Tyr Ser Val Glu Glu Tyr Gln Asp Pro Glu Ala Pro Trp Asp Ser Asp
        3620                3625                3630

Asp Pro Cys Ser Leu Pro Leu Asp Glu Gly Ser Cys Thr Ala Tyr Thr
            3635                3640                3645

Leu Arg Trp Tyr His Arg Ala Val Thr Gly Ser Thr Glu Ala Cys His
        3650                3655                3660

Pro Phe Val Tyr Gly Gly Cys Gly Gly Asn Ala Asn Arg Phe Gly Thr
3665                3670                3675                3680

Arg Glu Ala Cys Glu Arg Arg Cys Pro Pro Arg Val Gln Ser Gln
            3685                3690                3695

Gly Thr Gly Thr Ala Gln Asp
            3700

<210> SEQ ID NO 21
<211> LENGTH: 11115
<212> TYPE: DNA
<213> ORGANISM: Artificial Sequence
<220> FEATURE:
<223> OTHER INFORMATION: Synthetic Construct

<400> SEQUENCE: 21
atgacgctgc ggcttctggt ggccgcgctc tgcgccggga tcctggcaga ggcgccccga      60
gtgcgagccc agcacaggga gagagtgacc tgcacgcgcc tttacgccgc tgacattgtg     120
ttcttactgg atggctcctc atccattggc cgcagcaatt tccgcgaggt ccgcagcttt     180

```
ctcgaagggc tggtgctgcc tttctctgga gcagccagtg cacagggtgt gcgctttgcc      240
acagtgcagt acagcgatga cccacggaca gagttcggcc tggatgcact tggctctggg      300
ggtgatgtga tccgcgccat ccgtgagctt agctacaagg ggggcaacac tcgcacaggg      360
gctgcaattc tccatgtggc tgaccatgtc ttcctgcccc agctggcccg acctggtgtc      420
cccaaggtct gcatcctgat cacagacggg aagtcccagg acctggtgga cacagctgcc      480
caaaggctga aggggcaggg ggtcaagcta tttgctgtgg ggatcaagaa tgctgaccct      540
gaggagctga agcgagttgc ctcacagccc accagtgact tcttcttctt cgtcaatgac      600
ttcagcatct tgaggacact actgcccctc gtttcccgga gagtgtgcac gactgctggt      660
ggcgtgcctg tgacccgacc tccggatgac tcgacctctg ctccacgaga cctggtgctg      720
tctgagccaa gcagccaatc cttgagagta cagtggacag cggccagtgg ccctgtgact      780
ggctacaagg tccagtacac tcctctgacg gggctgggac agccactgcc gagtgagcgg      840
caggaggtga acgtcccagc tggtgagacc agtgtgcggc tgcggggtct ccggccactg      900
accgagtacc aagtgactgt gattgccctc tacgccaaca gcatcgggga ggctgtgagc      960
gggacagctc ggaccactgc cctagaaggg ccggaactga ccatccagaa taccacagcc     1020
cacagcctcc tggtggcctg gcggagtgtg ccaggtgcca ctggctaccg tgtgacatgg     1080
cgggtcctca gtggtgggcc cacacagcag caggagctgg gccctgggca gggttcagtg     1140
ttgctgcgtg acttggagcc tggcacggac tatgaggtga ccgtgagcac cctatttggc     1200
cgcagtgtgg ggcccgccac ttccctgatg gctcgcactg acgcttctgt tgagcagacc     1260
ctgcgcccgg tcatcctggg ccccacatcc atcctccttt cctggaactt ggtgcctgag     1320
gcccgtggct accggttgga atggcggcgt gagactggct ggagccaccg cagaaggtg      1380 gtactgccct ctgatgtgac ccgctaccag ttggatgggc tgcagccggg cactgagtac     1440
cgcctcacac tctacactct gctggagggc cacgaggtgg ccacccctgc aaccgtggtt     1500
cccactggac cagagctgcc tgtgagccct gtaacagacc tgcaagccac cgagctgccc     1560
ggcagcgggg tgcgagtgtc ctggagccca gtccctggtg ccacccagta ccgcatcatt     1620
gtgcgcagca cccagggggt tgagcggacc ctggtgcttc ctgggagtca gacagcattc     1680
gacttggatg acgttcaggc tgggcttagc tacactgtgc gggtgtctgc tcgagtgggt     1740
ccccgtgagg gcagtgccag tgtcctcact gtccgccggg agccggaaac tccacttgct     1800
gttccagggc tgcgggttgt ggtgtcagat gcaacgcgag tgagggtggc ctggggaccc     1860
gtccctggag ccagtggatt tcggattagc tggagcacag gcagtggtcc ggagtccagc     1920
cagacactgc ccccagactc tactgccaca gacatcacag ggctgcagcc tggaaccacc     1980
taccaggtgg ctgtgtcggt actgcgaggc agagaggagg gccctgctgc agtcatcgtg     2040
gctcgaacgg acccactggg cccagtgagg acggtccatg tgactcaggc cagcagctca     2100
tctgtcacca ttacctggac cagggttcct ggcgccacag gatacagggt ttcctggcac     2160
tcagcccacg gccagagaaa atcccagttg gtttctgggg aggccacggt ggctgagctg     2220
gatggactgg agccagatac tgagtatacg gtgcatgtga gggcccatgt ggctggcgtg     2280
gatgggcccc ctgcctctgt ggttgtgagg actgcccctg agcctgtggg tcgtgtgtcg     2340
aggctgcaga tcctcaatgc ttccagcgac gttctacgga tcacctgggt aggggtcact     2400
ggagccacag cttacagact ggcctggggc cggagtgaag gcggccccat gaggcaccag     2460
atactcccag gaaacacaga ctctgcagag atccgggggtc tcgaaggtgg agtcagctac     2520
tcagtgcgag tgactgcact tgtcgggac cgcgagggca cacctgtctc cattgttgtc     2580
```

```
actacgccgc ctgaggctcc gccagccctg gggacgcttc acgtggtgca gcgcggggag    2640
cactcgctga ggctgcgctg ggagccggtg cccagagcgc agggcttcct tctgcactgg    2700
caacctgagg gtggccagga acagtcccgg gtcctggggc ccgagctcag cagctatcac    2760
ctggacgggc tggagccagc gacacagtac cgcgtgaggc tgagtgtcct agggccagct    2820
ggagaagggc cctctgcaga ggtgactgcg cgcactgagt cacctcgtgt tccaagcatt    2880
gaactacgtg tggtggacac ctcgatcgac tcggtgactt tggcctggac tccagtgtcc    2940
agggcatcca gctacatcct atcctggcgg ccactcagag ccctggcca  ggaagtgcct    3000
gggtccccgc agacacttcc agggatctca agctcccagc gggtgacagg gctagagcct    3060
ggcgtctctt acatcttctc cctgacgcct gtcctggatg gtgtgcgggg tcctgaggca    3120
tctgtcacac agacgccagt gtgccccgt  ggcctggcgg atgtggtgtt cctaccacat    3180
gccactcaag acaatgctca ccgtgcggag gctacgagga gggtcctgga gcgtctggtg    3240
ttggcacttg ggcctcttgg gccacaggca gttcaggttg gctgctgtc  ttacagtcat    3300
cggccctccc cactgttccc actgaatggc tcccatgacc ttggcattat cttgcaaagg    3360
atccgtgaca tgccctacat ggacccaagt gggaacaacc tgggcacagc cgtggtcaca    3420
gctcacagat acatgttggc accagatgct cctgggcgcc gccagcacgt accaggggtg    3480
atggttctgc tagtggatga cccttgaga  ggtgacatat tcagccccat ccgtgaggcc    3540
caggcttctg ggcttaatgt ggtgatgttg gaatggctg  agcggaccc  agagcagctg    3600
cgtcgcttgg cgccgggtat ggactctgtc cagaccttct tcgccgtgga tgatgggcca    3660
agcctggacc aggcagtcag tggtctggcc acagccctgt gtcaggcatc cttcactact    3720
cagcccccggc cagagccctg cccagtgtat tgtccaaagg gccagaaggg ggaacctgga    3780
gagatgggcc tgagaggaca agttgggcct cctggcgacc ctggcctccc gggcaggacc    3840
ggtgctcccg gccccaggg  gcccctgga  agtgccactg ccaagggcga gaggggcttc    3900
cctggagcag atgggcgtcc aggcagccct ggccgcgccg ggaatcctgg gaccctgga   3960
gcccctggcc taaagggctc tccagggttg cctggccctc gtggggaccc gggagagcga    4020
ggacctcgag gcccaaaggg ggagccgggg gctcccggac aagtcatcgg aggtgaagga    4080
cctgggcttc ctgggcggaa aggggaccct ggaccatcgg gccccctgg  acctcgtgga    4140
ccactggggg acccaggacc ccgtggcccc cagggcttc  ctggaacagc catgaagggt    4200
gacaaaggcg atcgtgggga gcgggtccc  cctggaccag gtgaaggtgg cattgctcct    4260
ggggagcctg ggctgccggg tcttcccgga agccctggac ccaaggccc  cgttggcccc    4320
cctggaaaga aggagaaaa  aggtgactct gaggatggag ctccaggcct cccaggacaa    4380
cctgggtctc cggtgagca  gggcccacgg ggacctcctg gagctattgg ccccaaaggt    4440
gaccggggct ttccagggcc cctgggtgag gctggagaga agggcgaacg tggaccccca    4500
ggcccagcgg gatcccgggg gctgccaggg gttgctggac gtcctggagc caagggtcct    4560
gaagggccac caggacccac tggccgccaa ggagagaagg gggagcctgg tcgccctggg    4620
gaccctgcag tggtgggacc tgctgttgct ggacccaaag gagaaaaggg agatgtgggg    4680
cccgctgggc cagaggagc  taccggagtc aagggggaac ggggcccacc cggcttggtt    4740
cttcctggag accctggccc caagggagac cctggagacc gggtcccat  tggccttact    4800
ggcagagcag gaccccagg  tgactcaggg cctcctggag agagggaga  ccctgggcgg    4860
cctggccccc caggacctgt tggccccga  ggacgagatg gtgaagttgg agagaaaggt    4920
```

-continued

```
gacgagggtc ctccgggtga cccgggtttg cctggaaaag caggcgagcg tggccttcgg    4980
ggggcacctg gagttcgggg gcctgtgggt gaaaagggag accagggaga tcctggagag    5040
gatggacgaa atggcagccc tggatcatct ggacccaagg gtgaccgtgg ggagccgggt    5100
cccccaggac ccccgggacg gctggtagac acaggacctg gagccagaga aagggagag    5160 cctggggacc gcggacaaga gggtcctcga gggcccaagg gtgatcctgg cctccctgga    5220
gcccctgggg aaagggcat tgaagggttt cggggacccc caggcccaca ggggaccca    5280 ggtgtccgag gcccagcagg agaaaaggt gaccgggtc cccctgggct ggatggccgg    5340
agcggactgg atgggaaacc aggagccgct gggccctctg gccgaatgg tgctgcaggc    5400 aaagctgggg acccagggag agacgggctt ccaggcctcc gtggagaaca gggcctccct    5460
ggcccctctg gtcccctgg attacccggga aagccaggcg aggatggcaa acctggcctg    5520
aatggaaaaa acgagaacc tggggaccct ggagaagacg gaggaaggg agagaaagga    5580 gattcaggcg cctctgggag agaaggtcgt gatggcccca agggtgagcg tggagctcct    5640
ggtatccttg gaccccaggg gcctccaggc ctcccagggc cagtgggccc tcctggccag    5700
ggttttcctg gtgtcccagg aggcacgggc cccaagggtg accgtgggga gactggatcc    5760
aaaggggagc agggcctccc tggagagcgt ggcctgcgag gagagcctgg aagtgtgccg    5820 aatgtgatc ggttgctgga aactgctggc atcaaggcat ctgccctgcg ggagatcgtg    5880
gagacctggg atgagagctc tggtagcttc ctgcctgtgc ccgaacgcg tcgaggcccc    5940 aaggggact caggcgaaca gggccccca ggcaaggagg ccccatcgg ctttcctgga    6000 gaacgcgggc tgaagggcga ccgtggagac cctggccctc aggggccacc tggtctggcc    6060
cttggggaga ggggccccc cgggccttcc ggccttgccg gggagcctgg aaagcctggt    6120
attcccgggc tccaggcag ggctggggt gtgggagagg caggaaggcc aggagagagg    6180
ggagaacggg gagagaaagg agaacgtgga gaacagggca gagatggccc tcctggactc    6240
cctgaacccc ctgggccccc cggacccct ggccccaagg tgtctgtgga tgagccaggt    6300
cctggactct ctggagaaca gggaccccct ggactcaagg gtgctaaggg ggagccgggc    6360
agcaatggtg accaaggtcc caaaggagac agggtgtgc caggcatcaa aggagaccgg    6420
ggagagcctg gaccgagggg tcaggacggc aacccgggtc taccaggaga gcgtggtatg    6480
gctgggcctg aagggaagcc gggtctgcag ggtccaagag gcccccctgg cccagtgggt    6540
ggtcatggag accctggacc acctggtgcc ccgggtcttg ctggccctgc aggacccaa    6600 ggaccttctg gcctgaaggg ggagcctgga gagacaggac ctccaggacg gggcctgact    6660
ggacctactg gagctgtggg acttcctgga ccccccggcc cttcaggcct tgtgggtcca    6720 cagggtctc caggtttgcc tggacaagtg ggggagacag gaagccggg agccccaggt    6780 cgagatggtg ccagtggaaa agatggagac agagggagcc ctggtgtgcc agggtcacca    6840
ggtctgcctg gccctgtcgg acctaaagga gaacctggcc cacgggggc ccctggacag    6900 gctgtggtcg ggctccctgg agcaaaggga gagaaggag cccctggagg ccttgctgga    6960
gacctggtgg gtgagccggg agccaaaggt gaccgaggac tgccagggcc gcgaggcgag    7020
aagggtgaag ctgccgtgc aggggagccc ggagaccctg ggaagatgg tcagaaaggg    7080 gctccaggac ccaaaggttt caagggtgac ccaggagtcg ggtcccggg ctcccctggg    7140 cctcctggcc ctcaggtgt gaagggagat ctgggcctcc ctggcctgcc cggtgctcct    7200
ggtgttgttg ggttcccggg tcagacaggc cctcgaggag agatgggtca gccaggccct    7260
agtggagagc ggggtctggc aggcccccca gggagagaag gaatcccagg accctggggg    7320
```

```
ccacctggac caccggggtc agtgggacca cctggggcct ctggactcaa aggagacaag    7380
ggagaccctg gagtagggct gcctgggccc cgaggcgagc gtggggagcc aggcatccgg    7440
ggtgaagatg gccgccccgg ccaggaggga ccccgaggac tcacggggcc ccctggcagc    7500
aggggagagc gtgggagaa gggtgatgtt gggagtgcag gactaaaggg tgacaaggga    7560
gactcagctg tgatcctggg gcctccaggc ccacggggtg ccaaggggga catgggtgaa    7620
cgagggcctc ggggcttgga tggtgacaaa ggacctcggg gagacaatgg ggaccctggt    7680
gacaagggca gcagggagaa gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aaggagcct gtggccttga tggagagaag     7920
ggagacaagg gagaagctgg tcccccaggc cgccccgggc tggcaggaca caaaggagag    7980 atggggagc ctggtgtgcc gggccagtcg ggggcccctg gcaaggaggg cctgatcggt     8040
cccaagggtg accgaggctt tgacgggcag ccaggcccca gggtgaccca gggcgagaaa    8100
ggggagcggg gaaccccagg aattgggggc ttcccaggcc ccagtggaaa tgatggctct    8160
gctggtcccc cagggccacc tggcagtgtt ggtcccagag gccccgaagg acttcagggc    8220
cagaagggtg agcgaggtcc ccccggagag agagtggtgg gggctcctgg ggtccctgga    8280
gctcctggcg agagaggga gcaggggcgg ccagggcctg ccggtcctcg aggcgagaag    8340
ggagaagctg cactgacgga ggatgacatc cggggctttg tgcgccaaga gatgagtcag    8400
cactgtgcct gccagggcca gttcatcgca tctggatcac gacccctccc tagttatgct    8460
gcagacactg ccggctccca gctccatgct gtgcctgtgc tccgcgtctc tcatgcagag    8520
gaggaagagc gggtaccccc tgaggatgat gagtactctg aatactccga gtattctgtg    8580
gaggagtacc aggaccctga agctccttgg gatagtgatg accctgttc cctgccactg     8640 gatgagggct cctgcactgc ctacaccctg cgctggtacc atcgggctgt gacaggcagc    8700
acagaggcct gtcacccttt tgtctatggt ggctgtggag ggaatgccaa ccgtttgg     8760 acccgtgagg cctgcgagcg ccgctgccca ccccgggtgg tccagagcca ggggacaggt    8820
actgcccagg acggaagcgg acagtgtact aattatgctc tcttgaaatt ggctggagat    8880
gttgagagca accctggacc tacctcctcg gggcctggac cccggttcct gctgctgctg    8940
ccgctgctgc tgcccctgc ggcctcagcc tccgaccggc cccggggccg agaccggtc     9000 aacccagaga agctgctggt gatcactgtg gccacagctg aaaccgaggg gtacctgcgt    9060
ttcctgcgct ctgcggagtt cttcaactac actgtgcgga ccctgggcct gggagaggag    9120
tggcgagggg gtgatgtggc tcgaacagtt ggtggaggac agaaggtccg gtggttaaag    9180
aaggaaatgg agaaatacgc tgaccgggag gatatgatca tcatgtttgt ggatagctac    9240
gacgtgattc tggccggcag ccccacagag ctgctgaaga gttcgtcca gagtggcagc    9300 cgcctgctct tctctgcaga gagcttctgc tggcccgagt gggggctggc ggagcagtac    9360
cctgaggtgg gcacggggaa gcgcttcctc aattctggtg gattcatcgg ttttgccacc    9420
accatccacc aaatcgtgcg ccagtggaag tacaaggatg atgacgacga ccagctgttc    9480
tacacacggc tctacctgga cccaggactg agggagaaac tcagccttaa tctggatcat    9540
aagtctcgga tctttcagaa cctcaacggg gctttagatg aagtggtttt aaagtttgat    9600
cggaaccgtg tgcgtatccg gaacgtggcc tacgacacgc tccccattgt ggtccatgga    9660
```

```
aacggtccca ctaagctgca gctcaactac ctgggaaact acgtcccaa tggctggact    9720 cctgagggag gctgtggctt ctgcaaccag gaccggagga cactcccggg ggggcagcct    9780
cccccccggg tgtttctggc cgtgtttgtg aacagcctaa ctccgtttct gccccgcttc    9840
ctgcagcggc tgctactcct ggactatccc cccgacaggg tcacccttt cctgcacaac      9900 aacgaggtct tccatgaacc ccacatcgct gactcctggc cgcagctcca ggaccacttc    9960
tcagctgtga agctcgtggg gccggaggag gctctgagcc caggcgaggc cagggacatg    10020
gccatggacc tgtgtcggca ggaccccgag tgtgagttct acttcagcct ggacgccgac    10080
gctgtcctca ccaacctgca gaccctgcgt atcctcattg aggagaacag gaaggtgatc    10140
gcccccatgc tgtcccgcca cggcaagctg tggtccaact tctggggcgc cctgagcccc    10200
gatgagtact acgcccgctc cgaggactac gtggagctgg tgcagcggaa gcgagtgggt    10260
gtgtggaatg taccatacat ctcccaggcc tatgtgatcc ggggtgatac cctgcggatg    10320
gagctgcccc agagggatgt gttctcgggc agtgacacag accggacat ggccttctgt       10380 aagagctttc gagacaaggg catcttcctc catctgagca atcagcatga atttggccgg    10440
ctcctggcca cttccagata cgacacggag cacctgcacc ccgacctctg cagatcttc      10500 gacaaccccg tcgactggaa ggagcagtac atccacgaga actacagccg ggccctggaa    10560
ggggaaggaa tcgtggagca gccatgcccg gacgtgtact ggttcccact gctgtcagaa    10620
caaatgtgtg atgagctggt ggcagagatg gagcactacg ccagtggtc aggcggccgg       10680 catgaggatt caaggctggc tggaggctac gagaatgtgc ccaccgtgga catccacatg    10740
aagcaggtgg ggtacgagga ccagtggctg cagctgctgc ggacgtatgt gggccccatg    10800
accgagagcc tgtttcccgg ttaccacacc aaggcgcggg cggtgatgaa ctttgtggtt    10860
cgctaccggc cagacgagca gccgtctctg cggccacacc acgactcatc caccttcacc    10920
ctcaacgttg ccctcaacca aagggcctg gactatgagg aggtggctg ccgcttcctg        10980 cgctacgact gtgtgatctc ctccccgagg aagggctggg cactcctgca ccccggccgc    11040
ctcacccact accacgaggg gctgccaacg acctggggca cacgctacat catggtgtcc    11100
tttgtcgacc cctga                                                    11115

<210> SEQ ID NO 22
<211> LENGTH: 3704
<212> TYPE: PRT
<213> ORGANISM: Artificial Sequence
<220> FEATURE:
<223> OTHER INFORMATION: Synthetic Construct

<400> SEQUENCE: 22

Met Thr Leu Arg Leu Leu Val Ala Ala Leu Cys Ala Gly Ile Leu Ala
 1               5                  10                  15

Glu Ala Pro Arg Val Arg Ala Gln His Arg Glu Arg Val Thr Cys Thr
                20                  25                  30

Arg Leu Tyr Ala Ala Asp Ile Val Phe Leu Leu Asp Gly Ser Ser Ser
            35                  40                  45

Ile Gly Arg Ser Asn Phe Arg Glu Val Arg Ser Phe Leu Glu Gly Leu
        50                  55                  60

Val Leu Pro Phe Ser Gly Ala Ala Ser Ala Gln Gly Val Arg Phe Ala
65                  70                  75                  80

Thr Val Gln Tyr Ser Asp Asp Pro Arg Thr Glu Phe Gly Leu Asp Ala
                85                  90                  95

Leu Gly Ser Gly Gly Asp Val Ile Arg Ala Ile Arg Glu Leu Ser Tyr
```

```
                100              105                 110
Lys Gly Gly Asn Thr Arg Thr Gly Ala Ala Ile Leu His Val Ala Asp
            115                 120                 125

His Val Phe Leu Pro Gln Leu Ala Arg Pro Gly Val Pro Lys Val Cys
130             135                 140

Ile Leu Ile Thr Asp Gly Lys Ser Gln Asp Leu Val Asp Thr Ala Ala
145             150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
        210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
                260                 265                 270

Gly Gln Pro Leu Pro Ser Glu Arg Gln Glu Val Asn Val Pro Ala Gly
            275                 280                 285

Glu Thr Ser Val Arg Leu Arg Gly Leu Arg Pro Leu Thr Glu Tyr Gln
            290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
                340                 345                 350

Ala Thr Gly Tyr Arg Val Thr Trp Arg Val Leu Ser Gly Gly Pro Thr
            355                 360                 365

Gln Gln Gln Glu Leu Gly Pro Gly Gln Gly Ser Val Leu Leu Arg Asp
            370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
            435                 440                 445

Arg Arg Glu Thr Gly Leu Glu Pro Pro Gln Lys Val Val Leu Pro Ser
450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
            515                 520                 525
```

```
Ser Pro Val Pro Gly Ala Thr Gln Tyr Arg Ile Ile Val Arg Ser Thr
    530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
        595                 600                 605

Ser Asp Ala Thr Arg Val Arg Val Ala Trp Pro Val Pro Gly Ala
    610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
        675                 680                 685

Val Arg Thr Val His Val Thr Gln Ala Ser Ser Ser Val Thr Ile
    690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750

Val Arg Ala His Val Ala Gly Val Asp Gly Pro Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940
```

-continued

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
            965                 970                 975

Thr Pro Val Ser Arg Ala Ser Ser Tyr Ile Leu Ser Trp Arg Pro Leu
                980                 985                 990

Arg Gly Pro Gly Gln Glu Val Pro Gly Ser Pro Gln Thr Leu Pro Gly
            995                 1000                1005

Ile Ser Ser Gln Arg Val Thr Gly Leu Glu Pro Gly Val Ser Tyr
1010                1015                1020

Ile Phe Ser Leu Thr Pro Val Leu Asp Gly Val Arg Gly Pro Glu Ala
1025                1030                1035                1040

Ser Val Thr Gln Thr Pro Val Cys Pro Arg Gly Leu Ala Asp Val Val
                1045                1050                1055

Phe Leu Pro His Ala Thr Gln Asp Asn Ala His Arg Ala Glu Ala Thr
            1060                1065                1070

Arg Arg Val Leu Glu Arg Val Leu Ala Leu Gly Pro Leu Gly Pro
            1075                1080                1085

Gln Ala Val Gln Val Gly Leu Leu Ser Tyr Ser His Arg Pro Ser Pro
1090                1095                1100

Leu Phe Pro Leu Asn Gly Ser His Asp Leu Gly Ile Ile Leu Gln Arg
1105                1110                1115                1120

Ile Arg Asp Met Pro Tyr Met Pro Ser Gly Asn Asn Leu Gly Thr
                1125                1130                1135

Ala Val Val Thr Ala His Arg Tyr Met Leu Ala Pro Asp Ala Pro Gly
                1140                1145                1150

Arg Arg Gln His Val Pro Gly Val Met Val Leu Leu Val Asp Glu Pro
            1155                1160                1165

Leu Arg Gly Asp Ile Phe Ser Pro Ile Arg Glu Ala Gln Ala Ser Gly
1170                1175                1180

Leu Asn Val Val Met Leu Gly Met Ala Gly Ala Asp Pro Glu Gln Leu
1185                1190                1195                1200

Arg Arg Leu Ala Pro Gly Met Asp Ser Val Gln Thr Phe Phe Ala Val
                1205                1210                1215

Asp Asp Gly Pro Ser Leu Asp Gln Ala Val Ser Gly Leu Ala Thr Ala
                1220                1225                1230

Leu Cys Gln Ala Ser Phe Thr Thr Gln Pro Arg Pro Glu Pro Cys Pro
            1235                1240                1245

Val Tyr Cys Pro Lys Gly Gln Lys Gly Glu Pro Gly Glu Met Gly Leu
1250                1255                1260

Arg Gly Gln Val Gly Pro Pro Gly Asp Pro Gly Leu Pro Gly Arg Thr
1265                1270                1275                1280

Gly Ala Pro Gly Pro Gln Gly Pro Pro Gly Ser Ala Thr Ala Lys Gly
            1285                1290                1295

Glu Arg Gly Phe Pro Gly Ala Asp Gly Arg Pro Gly Ser Pro Gly Arg
            1300                1305                1310

Ala Gly Asn Pro Gly Thr Pro Gly Ala Pro Gly Leu Lys Gly Ser Pro
            1315                1320                1325

Gly Leu Pro Gly Pro Arg Gly Asp Pro Gly Glu Arg Gly Pro Arg Gly
            1330                1335                1340

Pro Lys Gly Glu Pro Gly Ala Pro Gly Gln Val Ile Gly Gly Glu Gly
1345                1350                1355                1360

Pro Gly Leu Pro Gly Arg Lys Gly Asp Pro Gly Pro Ser Gly Pro Pro

-continued

```
                1365                1370                1375
Gly Pro Arg Gly Pro Leu Gly Asp Pro Gly Pro Arg Gly Pro Pro Gly
            1380                1385                1390
Leu Pro Gly Thr Ala Met Lys Gly Asp Lys Gly Asp Arg Gly Glu Arg
        1395                1400                1405
Gly Pro Pro Gly Pro Gly Glu Gly Ile Ala Pro Gly Glu Pro Gly
    1410                1415                1420
Leu Pro Gly Leu Pro Gly Ser Pro Gly Pro Gln Gly Pro Val Gly Pro
1425                1430                1435                1440
Pro Gly Lys Lys Gly Glu Lys Gly Asp Ser Glu Asp Gly Ala Pro Gly
                1445                1450                1455
Leu Pro Gly Gln Pro Gly Ser Pro Gly Glu Gln Gly Pro Arg Gly Pro
            1460                1465                1470
Pro Gly Ala Ile Gly Pro Lys Gly Asp Arg Gly Phe Pro Gly Pro Leu
        1475                1480                1485
Gly Glu Ala Gly Glu Lys Gly Glu Arg Gly Pro Pro Gly Pro Ala Gly
    1490                1495                1500
Ser Arg Gly Leu Pro Gly Val Ala Gly Arg Pro Gly Ala Lys Gly Pro
1505                1510                1515                1520
Glu Gly Pro Pro Gly Pro Thr Gly Arg Gln Gly Glu Lys Gly Glu Pro
                1525                1530                1535
Gly Arg Pro Gly Asp Pro Ala Val Val Gly Pro Ala Val Ala Gly Pro
            1540                1545                1550
Lys Gly Glu Lys Gly Asp Val Gly Pro Ala Gly Pro Arg Gly Ala Thr
        1555                1560                1565
Gly Val Gln Gly Glu Arg Gly Pro Pro Gly Leu Val Leu Pro Gly Asp
    1570                1575                1580
Pro Gly Pro Lys Gly Asp Pro Gly Asp Arg Gly Pro Ile Gly Leu Thr
1585                1590                1595                1600
Gly Arg Ala Gly Pro Pro Gly Asp Ser Gly Pro Pro Gly Glu Lys Gly
                1605                1610                1615
Asp Pro Gly Arg Pro Gly Pro Pro Gly Pro Val Gly Pro Arg Gly Arg
            1620                1625                1630
Asp Gly Glu Val Gly Glu Lys Gly Asp Glu Gly Pro Pro Gly Asp Pro
        1635                1640                1645
Gly Leu Pro Gly Lys Ala Gly Glu Arg Gly Leu Arg Gly Ala Pro Gly
    1650                1655                1660
Val Arg Gly Pro Val Gly Glu Lys Gly Asp Gln Gly Asp Pro Gly Glu
1665                1670                1675                1680
Asp Gly Arg Asn Gly Ser Pro Gly Ser Ser Gly Pro Lys Gly Asp Arg
                1685                1690                1695
Gly Glu Pro Gly Pro Pro Gly Pro Gly Arg Leu Val Asp Thr Gly
            1700                1705                1710
Pro Gly Ala Arg Glu Lys Gly Glu Pro Gly Asp Arg Gly Gln Glu Gly
        1715                1720                1725
Pro Arg Gly Pro Lys Gly Asp Pro Gly Leu Pro Gly Ala Pro Gly Glu
    1730                1735                1740
Arg Gly Ile Glu Gly Phe Arg Gly Pro Pro Gly Pro Gln Gly Asp Pro
1745                1750                1755                1760
Gly Val Arg Gly Pro Ala Gly Glu Lys Gly Asp Arg Gly Pro Pro Gly
                1765                1770                1775
Leu Asp Gly Arg Ser Gly Leu Asp Gly Lys Pro Gly Ala Ala Gly Pro
            1780                1785                1790
```

```
Ser Gly Pro Asn Gly Ala Ala Gly Lys Ala Gly Asp Pro Gly Arg Asp
        1795                1800                1805

Gly Leu Pro Gly Leu Arg Gly Glu Gln Gly Leu Pro Gly Pro Ser Gly
        1810                1815                1820

Pro Pro Gly Leu Pro Gly Lys Pro Gly Glu Asp Gly Lys Pro Gly Leu
1825                1830                1835                1840

Asn Gly Lys Asn Gly Glu Pro Gly Asp Pro Gly Glu Asp Gly Arg Lys
        1845                1850                1855

Gly Glu Lys Gly Asp Ser Gly Ala Ser Gly Arg Glu Gly Arg Asp Gly
        1860                1865                1870

Pro Lys Gly Glu Arg Gly Ala Pro Gly Ile Leu Gly Pro Gln Gly Pro
        1875                1880                1885

Pro Gly Leu Pro Gly Pro Val Gly Pro Pro Gly Gln Gly Phe Pro Gly
        1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
        1925                1930                1935

Gly Ser Val Pro Asn Val Asp Arg Leu Leu Glu Thr Ala Gly Ile Lys
        1940                1945                1950

Ala Ser Ala Leu Arg Glu Ile Val Glu Thr Trp Asp Glu Ser Ser Gly
        1955                1960                1965

Ser Phe Leu Pro Val Pro Glu Arg Arg Arg Gly Pro Lys Gly Asp Ser
        1970                1975                1980

Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
        2005                2010                2015

Pro Gly Leu Ala Leu Gly Glu Arg Gly Pro Pro Gly Pro Ser Gly Leu
        2020                2025                2030

Ala Gly Glu Pro Gly Lys Pro Gly Ile Pro Gly Leu Pro Gly Arg Ala
        2035                2040                2045

Gly Gly Val Gly Glu Ala Gly Arg Pro Gly Glu Arg Gly Glu Arg Gly
        2050                2055                2060

Glu Lys Gly Glu Arg Gly Glu Gln Gly Arg Asp Gly Pro Pro Gly Leu
2065                2070                2075                2080

Pro Gly Thr Pro Gly Pro Pro Gly Pro Pro Gly Pro Lys Val Ser Val
                2085                2090                2095

Asp Glu Pro Gly Pro Gly Leu Ser Gly Glu Gln Gly Pro Pro Gly Leu
        2100                2105                2110

Lys Gly Ala Lys Gly Glu Pro Gly Ser Asn Gly Asp Gln Gly Pro Lys
        2115                2120                2125

Gly Asp Arg Gly Val Pro Gly Ile Lys Gly Asp Arg Gly Glu Pro Gly
        2130                2135                2140

Pro Arg Gly Gln Asp Gly Asn Pro Gly Leu Pro Gly Glu Arg Gly Met
2145                2150                2155                2160

Ala Gly Pro Glu Gly Lys Pro Gly Leu Gln Gly Pro Arg Gly Pro Pro
        2165                2170                2175

Gly Pro Val Gly Gly His Gly Asp Pro Gly Pro Pro Gly Ala Pro Gly
        2180                2185                2190

Leu Ala Gly Pro Ala Gly Pro Gln Gly Pro Ser Gly Leu Lys Gly Glu
        2195                2200                2205
```

```
Pro Gly Glu Thr Gly Pro Pro Gly Arg Gly Leu Thr Gly Pro Thr Gly
        2210                2215                2220

Ala Val Gly Leu Pro Gly Pro Gly Pro Ser Gly Leu Val Gly Pro
2225                2230                2235                2240

Gln Gly Ser Pro Gly Leu Pro Gly Gln Val Gly Glu Thr Gly Lys Pro
            2245                2250                2255

Gly Ala Pro Gly Arg Asp Gly Ala Ser Gly Lys Asp Gly Asp Arg Gly
                2260                2265                2270

Ser Pro Gly Val Pro Gly Ser Pro Gly Leu Pro Gly Pro Val Gly Pro
            2275                2280                2285

Lys Gly Glu Pro Gly Pro Thr Gly Ala Pro Gly Gln Ala Val Val Gly
            2290                2295                2300

Leu Pro Gly Ala Lys Gly Glu Lys Gly Ala Pro Gly Gly Leu Ala Gly
2305                2310                2315                2320

Asp Leu Val Gly Glu Pro Gly Ala Lys Gly Asp Arg Gly Leu Pro Gly
                2325                2330                2335

Pro Arg Gly Glu Lys Gly Glu Ala Gly Arg Ala Gly Glu Pro Gly Asp
            2340                2345                2350

Pro Gly Glu Asp Gly Gln Lys Gly Ala Pro Gly Pro Lys Gly Phe Lys
            2355                2360                2365

Gly Asp Pro Gly Val Gly Val Pro Gly Ser Pro Gly Pro Pro Gly Pro
            2370                2375                2380

Pro Gly Val Lys Gly Asp Leu Gly Leu Pro Gly Leu Pro Gly Ala Pro
2385                2390                2395                2400

Gly Val Val Gly Phe Pro Gly Gln Thr Gly Pro Arg Gly Glu Met Gly
                2405                2410                2415

Gln Pro Gly Pro Ser Gly Glu Arg Gly Leu Ala Gly Pro Pro Gly Arg
            2420                2425                2430

Glu Gly Ile Pro Gly Pro Leu Gly Pro Pro Gly Pro Pro Gly Ser Val
            2435                2440                2445

Gly Pro Pro Gly Ala Ser Gly Leu Lys Gly Asp Lys Gly Asp Pro Gly
            2450                2455                2460

Val Gly Leu Pro Gly Pro Arg Gly Glu Arg Gly Glu Pro Gly Ile Arg
2465                2470                2475                2480

Gly Glu Asp Gly Arg Pro Gly Gln Glu Gly Pro Arg Gly Leu Thr Gly
                2485                2490                2495

Pro Pro Gly Ser Arg Gly Glu Arg Gly Glu Lys Gly Asp Val Gly Ser
            2500                2505                2510

Ala Gly Leu Lys Gly Asp Lys Gly Asp Ser Ala Val Ile Leu Gly Pro
            2515                2520                2525

Pro Gly Pro Arg Gly Ala Lys Gly Asp Met Gly Glu Arg Gly Pro Arg
            2530                2535                2540

Gly Leu Asp Gly Asp Lys Gly Pro Arg Gly Asp Asn Gly Asp Pro Gly
2545                2550                2555                2560

Asp Lys Gly Ser Lys Gly Glu Pro Gly Asp Lys Gly Ser Ala Gly Leu
            2565                2570                2575

Pro Gly Leu Arg Gly Leu Leu Gly Gln Gly Gln Pro Gly Ala Ala
            2580                2585                2590

Gly Ile Pro Gly Asp Pro Gly Ser Pro Gly Lys Asp Gly Val Pro Gly
            2595                2600                2605

Ile Arg Gly Glu Lys Gly Asp Val Gly Phe Met Gly Pro Arg Gly Leu
            2610                2615                2620

Lys Gly Glu Arg Gly Val Lys Gly Ala Cys Gly Leu Asp Gly Glu Lys
```

```
                2625                2630                2635                2640
Gly Asp Lys Gly Glu Ala Gly Pro Gly Arg Pro Gly Leu Ala Gly
            2645                2650                2655
His Lys Gly Glu Met Gly Glu Pro Gly Val Pro Gly Gln Ser Gly Ala
            2660                2665                2670
Pro Gly Lys Glu Gly Leu Ile Gly Pro Lys Gly Asp Arg Gly Phe Asp
            2675                2680                2685
Gly Gln Pro Gly Pro Lys Gly Asp Gln Gly Glu Lys Gly Glu Arg Gly
            2690                2695                2700
Thr Pro Gly Ile Gly Gly Phe Pro Gly Pro Ser Gly Asn Asp Gly Ser
2705                2710                2715                2720
Ala Gly Pro Pro Gly Pro Pro Gly Ser Val Gly Pro Arg Gly Pro Glu
            2725                2730                2735
Gly Leu Gln Gly Gln Lys Gly Glu Arg Gly Pro Pro Gly Glu Arg Val
            2740                2745                2750
Val Gly Ala Pro Gly Val Pro Gly Ala Pro Gly Glu Arg Gly Glu Gln
            2755                2760                2765
Gly Arg Pro Gly Pro Ala Gly Pro Arg Gly Glu Lys Gly Glu Ala Ala
            2770                2775                2780
Leu Thr Glu Asp Asp Ile Arg Gly Phe Val Arg Gln Glu Met Ser Gln
2785                2790                2795                2800
His Cys Ala Cys Gln Gly Gln Phe Ile Ala Ser Gly Ser Arg Pro Leu
            2805                2810                2815
Pro Ser Tyr Ala Ala Asp Thr Ala Gly Ser Gln Leu His Ala Val Pro
            2820                2825                2830
Val Leu Arg Val Ser His Ala Glu Glu Glu Arg Val Pro Pro Glu
            2835                2840                2845
Asp Asp Glu Tyr Ser Glu Tyr Ser Glu Tyr Ser Val Glu Glu Tyr Gln
            2850                2855                2860
Asp Pro Glu Ala Pro Trp Asp Ser Asp Asp Pro Cys Ser Leu Pro Leu
2865                2870                2875                2880
Asp Glu Gly Ser Cys Thr Ala Tyr Thr Leu Arg Trp Tyr His Arg Ala
            2885                2890                2895
Val Thr Gly Ser Thr Glu Ala Cys His Pro Phe Val Tyr Gly Gly Cys
            2900                2905                2910
Gly Gly Asn Ala Asn Arg Phe Gly Thr Arg Glu Ala Cys Glu Arg Arg
            2915                2920                2925
Cys Pro Pro Arg Val Gln Ser Gln Gly Thr Gly Thr Ala Gln Asp
            2930                2935                2940
Gly Ser Gly Gln Cys Thr Asn Tyr Ala Leu Leu Lys Leu Ala Gly Asp
2945                2950                2955                2960
Val Glu Ser Asn Pro Gly Pro Thr Ser Ser Gly Pro Gly Pro Arg Phe
            2965                2970                2975
Leu Leu Leu Leu Pro Leu Leu Leu Pro Pro Ala Ala Ser Ala Ser Asp
            2980                2985                2990
Arg Pro Arg Gly Arg Asp Pro Val Asn Pro Glu Lys Leu Leu Val Ile
            2995                3000                3005
Thr Val Ala Thr Ala Glu Thr Glu Gly Tyr Leu Arg Phe Leu Arg Ser
            3010                3015                3020
Ala Glu Phe Phe Asn Tyr Thr Val Arg Thr Leu Gly Leu Gly Glu Glu
3025                3030                3035                3040
Trp Arg Gly Gly Asp Val Ala Arg Thr Val Gly Gly Gly Gln Lys Val
            3045                3050                3055
```

```
Arg Trp Leu Lys Lys Glu Met Glu Lys Tyr Ala Asp Arg Glu Asp Met
            3060                3065                3070

Ile Ile Met Phe Val Asp Ser Tyr Asp Val Ile Leu Ala Gly Ser Pro
            3075                3080            3085

Thr Glu Leu Leu Lys Lys Phe Val Gln Ser Gly Ser Arg Leu Leu Phe
            3090                3095            3100

Ser Ala Glu Ser Phe Cys Trp Pro Glu Trp Gly Leu Ala Glu Gln Tyr
3105                3110                3115                3120

Pro Glu Val Gly Thr Gly Lys Arg Phe Leu Asn Ser Gly Phe Ile
                3125                3130            3135

Gly Phe Ala Thr Thr Ile His Gln Ile Val Arg Gln Trp Lys Tyr Lys
                3140                3145            3150

Asp Asp Asp Asp Asp Gln Leu Phe Tyr Thr Arg Leu Tyr Leu Asp Pro
            3155                3160            3165

Gly Leu Arg Glu Lys Leu Ser Leu Asn Leu Asp His Lys Ser Arg Ile
            3170                3175            3180

Phe Gln Asn Leu Asn Gly Ala Leu Asp Glu Val Val Leu Lys Phe Asp
3185                3190                3195                3200

Arg Asn Arg Val Arg Ile Arg Asn Val Ala Tyr Asp Thr Leu Pro Ile
            3205                3210            3215

Val Val His Gly Asn Gly Pro Thr Lys Leu Gln Leu Asn Tyr Leu Gly
            3220                3225            3230

Asn Tyr Val Pro Asn Gly Trp Thr Pro Glu Gly Gly Cys Gly Phe Cys
            3235                3240            3245

Asn Gln Asp Arg Arg Thr Leu Pro Gly Gly Gln Pro Pro Arg Val
            3250                3255            3260

Phe Leu Ala Val Phe Val Glu Gln Pro Thr Pro Phe Leu Pro Arg Phe
3265                3270                3275                3280

Leu Gln Arg Leu Leu Leu Leu Asp Tyr Pro Pro Asp Arg Val Thr Leu
            3285                3290            3295

Phe Leu His Asn Asn Glu Val Phe His Glu Pro His Ile Ala Asp Ser
            3300                3305            3310

Trp Pro Gln Leu Gln Asp His Phe Ser Ala Val Lys Leu Val Gly Pro
            3315                3320            3325

Glu Glu Ala Leu Ser Pro Gly Glu Ala Arg Asp Met Ala Met Asp Leu
            3330                3335            3340

Cys Arg Gln Asp Pro Glu Cys Glu Phe Tyr Phe Ser Leu Asp Ala Asp
3345                3350                3355                3360

Ala Val Leu Thr Asn Leu Gln Thr Leu Arg Ile Leu Ile Glu Glu Asn
            3365                3370            3375

Arg Lys Val Ile Ala Pro Met Leu Ser Arg His Gly Lys Leu Trp Ser
            3380                3385            3390

Asn Phe Trp Gly Ala Leu Ser Pro Asp Glu Tyr Tyr Ala Arg Ser Glu
            3395                3400            3405

Asp Tyr Val Glu Leu Val Gln Arg Lys Arg Val Gly Val Trp Asn Val
            3410                3415            3420

Pro Tyr Ile Ser Gln Ala Tyr Val Ile Arg Gly Asp Thr Leu Arg Met
3425                3430                3435                3440

Glu Leu Pro Gln Arg Asp Val Phe Ser Gly Ser Asp Thr Asp Pro Asp
                3445                3450            3455

Met Ala Phe Cys Lys Ser Phe Arg Asp Lys Gly Ile Phe Leu His Leu
            3460                3465            3470
```

```
Ser Asn Gln His Glu Phe Gly Arg Leu Leu Ala Thr Ser Arg Tyr Asp
    3475                3480                3485

Thr Glu His Leu His Pro Asp Leu Trp Gln Ile Phe Asp Asn Pro Val
    3490                3495                3500

Asp Trp Lys Glu Gln Tyr Ile His Glu Asn Tyr Ser Arg Ala Leu Glu
3505                3510                3515                3520

Gly Glu Gly Ile Val Glu Gln Pro Cys Pro Asp Val Tyr Trp Phe Pro
                3525                3530                3535

Leu Leu Ser Glu Gln Met Cys Asp Glu Leu Val Ala Glu Met Glu His
            3540                3545                3550

Tyr Gly Gln Trp Ser Gly Gly Arg His Glu Asp Ser Arg Leu Ala Gly
    3555                3560                3565

Gly Tyr Glu Asn Val Pro Thr Val Asp Ile His Met Lys Gln Val Gly
    3570                3575                3580

Tyr Glu Asp Gln Trp Leu Gln Leu Leu Arg Thr Val Gly Pro Met
3585                3590                3595                3600

Thr Glu Ser Leu Phe Pro Gly Tyr His Thr Lys Ala Arg Ala Val Met
            3605                3610                3615

Asn Phe Val Val Arg Tyr Arg Pro Asp Glu Gln Pro Ser Leu Arg Pro
    3620                3625                3630

His His Asp Ser Ser Thr Phe Thr Leu Asn Val Ala Leu Asn His Lys
    3635                3640                3645

Gly Leu Asp Tyr Glu Gly Gly Gly Cys Arg Phe Leu Arg Tyr Asp Cys
    3650                3655                3660

Val Ile Ser Ser Pro Arg Lys Gly Trp Ala Leu Leu His Pro Gly Arg
3665                3670                3675                3680

Leu Thr His Tyr His Glu Gly Leu Pro Thr Thr Trp Gly Thr Arg Tyr
    3685                3690                3695

Ile Met Val Ser Phe Val Asp Pro
            3700

<210> SEQ ID NO 23
<211> LENGTH: 11115
<212> TYPE: DNA
<213> ORGANISM: Artificial Sequence
<220> FEATURE:
<223> OTHER INFORMATION: Synthetic Construct

<400> SEQUENCE: 23
atgacctcct cggggcctgg accccggttc ctgctgctgc tgccgctgct gctgccccct      60
gcggcctcag cctccgaccg gccccggggc cgagacccgg tcaacccaga gaagctgctg     120
gtgatcactg tggccacagc tgaaaccgag ggtacctgc gtttcctgcg ctctgcggag      180
ttcttcaact acactgtgcg gaccctgggc ctggagagg agtggcgagg gggtgatgtg      240
gctcgaacag ttggtggagg acagaaggtc cggtggttaa agaaggaaat ggagaaatac     300
gctgaccggg aggatatgat catcatgttt gtggatagct acgacgtgat tctggccggc     360
agccccacag agctgctgaa gaagttcgtc cagagtggca gccgcctgct cttctctgca     420
gagagcttct gctggcccga gtgggggctg gcggagcagt accctgaggt gggcacgggg     480
aagcgcttcc tcaattctgg tggattcatc ggttttgcca ccaccatcca ccaaatcgtg     540
cgccagtgga agtacaagga tgatgacgac gaccagctgt tctacacacg gctctacctg     600
gacccaggac tgagggagaa actcagcctt aatctggatc ataagtctcg gatcttcag      660 aacctcaacg gggctttaga tgaagtggt ttaaagtttg atcggaaccg tgtgcgtatc      720
```

-continued

```
cggaacgtgg cctacgacac gctccccatt gtggtccatg gaaacggtcc cactaagctg    780
cagctcaact acctgggaaa ctacgtcccc aatggctgga ctcctgaggg aggctgtggc    840
ttctgcaacc aggaccggag gacactcccg gggggcagc ctccccccg ggtgtttctg      900
gccgtgtttg tggaacagcc tactccgttt ctgccccgct tcctgcagcg gctgctactc    960
ctggactatc cccccgacag ggtcacccctt ttcctgcaca caacgaggt cttccatgaa   1020
ccccacatcg ctgactcctg gccgcagctc caggaccact tctcagctgt gaagctcgtg   1080
gggccggagg aggctctgag cccaggcgag gccagggaca tggccatgga cctgtgtcgg   1140
caggaccccg agtgtgagtt ctacttcagc ctggacgccg acgctgtcct caccaacctg   1200
cagaccctgc gtatcctcat tgaggagaac aggaaggtga tcgcccccat gctgtcccgc   1260
cacggcaagc tgtggtccaa cttctggggc gccctgagcc ccgatgagta ctacgcccgc   1320
tccgaggact acgtggagct ggtgcagcgg aagcgagtgg gtgtgtggaa tgtaccatac   1380
atctcccagg cctatgtgat ccggggtgat accctgcgga tggagctgcc ccagagggat   1440
gtgttctcgg gcagtgacac agacccggac atggccttct gtaagagctt cgagacaag    1500
ggcatcttcc tccatctgag caatcagcat gaatttggcc ggctcctggc cacttccaga   1560
tacgacacgg agcacctgca ccccgacctc tggcagatct cgacaaccc cgtcgactgg   1620
aaggagcagt acatccacga gaactacagc cgggccctgg aagggaagg aatcgtggag   1680
cagccatgcc cggacgtgta ctggttccca ctgctgtcag aacaaatgtg tgatgagctg   1740
gtggcagaga tggagcacta cggccagtgg tcaggcggcc ggcatgagga ttcaaggctg   1800
gctggaggct acgagaatgt gcccaccgtg gacatccaca tgaagcaggt ggggtacgag   1860
gaccagtggc tgcagctgct gcggacgtat gtgggcccca tgaccgagag cctgtttccc   1920
ggttaccaca ccaaggcgcg ggcggtgatg aactttgtgg ttcgctaccg gccagacgag   1980
cagccgtctc tgcggccaca ccacgactca tccaccttca ccctcaacgt tgccctcaac   2040
cacaagggcc tggactatga gggaggtggc tgccgcttcc tgcgctacga ctgtgtgatc   2100
tcctccccga ggaagggctg ggcactcctg caccccggcc gcctcaccca ctaccacgag   2160
gggctgccaa cgacctgggg cacacgctac atcatggtgt cctttgtcga ccccggaagc   2220
ggacagtgta ctaattatgc tctcttgaaa ttggctggag atgttgagag caaccctgga   2280
cctacgctgc ggcttctggt ggccgcgctc tgccgcggga tcctggcaga ggcgccccga   2340
gtgcgagccc agcacaggga gagtgacc tgcacgcgcc tttacgccgc tgacattgtg   2400
ttcttactgg atggctcctc atccattggc cgcagcaatt ccgcgaggt ccgcagcttt   2460
ctcgaagggc tggtgctgcc tttctctgga gcagccagtg cacagggtgt gcgctttgcc   2520
acagtgcagt acagcgatga cccacggaca gagttcggcc tggatgcact ggctctgggg   2580
ggtgatgtga tccgcgccat ccgtgagctt agctacaagg ggggcaacac tcgcacaggg   2640
gctgcaattc tccatgtggc tgaccatgtc ttcctgcccc agctggcccg acctggtgtc   2700
cccaaggtct gcatcctgat cacagacggg aagtcccagg acctggtgga cacagctgcc   2760
caaaggctga agggggcaggg ggtcaagcta tttgctgtgg ggatcaagaa tgctgaccct   2820
gaggagctga gcgagttgc ctcacagccc accagtgact tcttcttctt cgtcaatgac   2880
ttcagcatct tgaggacact actgccccctc gtttcccgga gagtgtgcac gactgctggt   2940
ggcgtgcctg tgacccgacc tccggatgac tcgacctctg ctccacgaga cctggtgctg   3000
tctgagccaa gcagccaatc cttgagagta cagtggacag cggccagtgg ccctgtgact   3060
ggctacaagg tccagtacac tcctctgacg gggctgggac agccactgcc gagtgagcgg   3120
```

```
caggaggtga acgtcccagc tggtgagacc agtgtgcggc tgcggggtct ccggccactg   3180
accgagtacc aagtgactgt gattgccctc tacgccaaca gcatcgggga ggctgtgagc   3240
gggacagctc ggaccactgc cctagaaggg ccggaactga ccatccagaa taccacagcc   3300
cacagcctcc tggtggcctg gcggagtgtg ccaggtgcca ctggctaccg tgtgacatgg   3360
cgggtcctca gtggtgggcc cacacagcag caggagctgg gccctgggca gggttcagtg   3420
ttgctgcgtg acttggagcc tggcacggac tatgaggtga ccgtgagcac cctatttggc   3480
cgcagtgtgg ggcccgccac ttccctgatg gctcgcactg acgcttctgt tgagcagacc   3540
ctgcgcccgg tcatcctggg ccccacatcc atcctccttt cctggaactt ggtgcctgag   3600
gcccgtggct accggttgga atggcggcgt gagactggct tggagccacc gcagaaggtg   3660
gtactgccct ctgatgtgac ccgctaccag ttggatgggc tgcagccggg cactgagtac   3720
cgcctcacac tctacactct gctggagggc cacgaggtgg ccaccccctgc aaccgtggtt   3780
cccactggac cagagctgcc tgtgagccct gtaacagacc tgcaagccac cgagctgccc   3840
gggcagcggg tgcgagtgtc ctggagccca gtccctggtg ccacccagta ccgcatcatt   3900
gtgcgcagca cccaggggt tgagcggacc ctggtgcttc ctgggagtca gacagcattc   3960
gacttggatg acgttcaggc tgggcttagc tacactgtgc gggtgtctgc tcgagtgggt   4020
ccccgtgagg gcagtgccag tgtcctcact gtccgccggg agccggaaac tccacttgct   4080
gttccagggc tgcgggttgt ggtgtcagat gcaacgcgag tgagggtggc ctggggaccc   4140
gtccctggag ccagtggatt tcggattagc tggagcacag gcagtggtcc ggagtccagc   4200
cagacactgc ccccagactc tactgccaca gacatcacag ggctgcagcc tggaaccacc   4260
taccaggtgg ctgtgtcggt actgcgaggc agagaggagg gccctgctgc agtcatcgtg   4320
gctcgaacgg acccactggg cccagtgagg acggtccatg tgactcaggc cagcagctca   4380
tctgtcacca ttacctggac cagggttcct ggcgccacag gatacagggt ttcctggcac   4440
tcagcccacg gcccagagaa atcccagttg gttctgggg aggccacggt ggctgagctg   4500
gatggactgg agccagatac tgagtatacg gtgcatgtga gggcccatgt ggctggcgtg   4560
gatgggcccc ctgcctctgt ggttgtgagg actgcccctg agcctgtggg tcgtgtgtcg   4620
aggctgcaga tcctcaatgc ttccagcgac gttctacgga tcacctgggt aggggtcact   4680
ggagccacag cttacagact ggcctggggc cggagtgaag cggcccat gaggcaccag   4740
atactcccag gaaacacaga ctctgcagag atccggggtc tcgaaggtgg agtcagctac   4800
tcagtgcgag tgactgcact tgtcggggac cgcgagggca cctgtctctc cattgttgtc   4860
actacgccgc ctgaggctcc gccagccctg gggacgcttc acgtggtgca gcgcggggag   4920
cactcgctga ggctgcgctg ggagccggtg cccagagcgc agggcttcct tctgcactgg   4980
caacctgagg gtggccagga acagtcccgg gtcctggggc ccgagctcag cagctatcac   5040
ctggacgggc tggagccagc gacacagtac cgcgtgagc tgagtgtcct agggccagct   5100
ggagaagggc cctctgcaga ggtgactgcg cgcactgagt cacctcgtgt tccaagcatt   5160
gaactacgtg tggtggacac ctcgatcgac tcggtgactt tggcctggac tccagtgtcc   5220
agggcatcca gctacatcct atcctggcgg ccactcagag gccctggcca ggaagtgcct   5280
gggtccccgc agacacttcc agggatctca agctcccagc gggtgacagg ctagagcct   5340
ggcgtctctt acatcttctc cctgacgcct gtcctggatg gtgtgcgggg tcctgaggca   5400
tctgtcacac agacgccagt gtgccccccgt ggcctggcgg atgtggtgtt cctaccacat   5460
```

```
gccactcaag acaatgctca ccgtgcggag gctacgagga gggtcctgga gcgtctggtg    5520
ttggcacttg ggcctcttgg gccacaggca gttcaggttg gcctgctgtc ttacagtcat    5580
cggccctccc cactgttccc actgaatggc tcccatgacc ttggcattat cttgcaaagg    5640
atccgtgaca tgccctacat ggacccaagt gggaacaacc tgggcacagc cgtggtcaca    5700
gctcacagat acatgttggc accagatgct cctgggcgcc gccagcacgt accagggGtg    5760
atggttctgc tagtggatga acccttgaga ggtgacatat tcagcccat ccgtgaggcc     5820
caggcttctg ggcttaatgt ggtgatgttg ggaatggctg gagcggaccc agagcagctg    5880
cgtcgcttgg cgccgggtat ggactctgtc cagaccttct tcgccgtgga tgatgggcca    5940
agcctggacc aggcagtcag tggtctggcc acagccctgt gtcaggcatc cttcactact    6000
cagccccggc cagagccctg cccagtgtat tgtccaaagg ccagaagggg gaacctggaa    6060
gagatgggcc tgagaggaca agttgggcct cctggcgacc ctggcctccc gggcaggacc    6120
ggtgctcccg gcccccaggg gcccctggaa gtgccactg ccaagggcga gaggggcttc      6180
cctggagcag atgggcgtcc aggcagccct ggccgcgccg gaatcctgg gacccctgga     6240
gcccctggcc taaagggctc tccagggttg cctggccctc gtggggaccc gggagagcga    6300
ggacctcgag gcccaaaggg ggagccgggg gctcccggac aagtcatcgg aggtgaagga    6360
cctgggcttc ctgggcggaa aggggaccct ggaccatcgg gccccctgg acctcgtgga     6420
ccactggggg acccaggacc ccgtggcccc cagggcttc ctggaacagc catgaagggt      6480
gacaaaggcg atcgtgggga gcggggtccc cctggaccag gtgaaggtgg cattgctcct    6540
ggggagcctg ggctgccggg tcttcccgga agccctggac cccaaggccc cgttggcccc    6600
cctggaaaga aggagaaaa aggtgactct gaggatggag ctccaggcct cccaggacaa     6660
cctgggtctc cgggtgagca gggcccacgg ggacctcctg gagctattgg ccccaaaggt    6720
gaccggggct ttccagggcc cctgggtgag gctggagaga agggcgaacg tggacccca    6780
ggcccagcgg gatcccgggg gctgccaggg gttgctggac gtcctggagc caagggtcct    6840
gaagggccac caggacccac tggccgccaa ggagagaagg gggagcctgg tcgccctggg    6900
gaccctgcag tggtgggacc tgctgttgct ggacccaaag gagaaaaggg agatgtgggg    6960
cccgctgggc ccagaggagc taccggagtc caaggggaac ggggcccacc cggcttggtt    7020
cttcctggag accctggccc caaggggac cctggagacc ggggtcccat tggccttact     7080
ggcagagcag gaccccagg tgactcaggg cctcctggag agaagggaga ccctgggcgg     7140
cctggccccc caggacctgt tggccccga ggacgagatg gtgaagttgg agagaaaggt      7200
gacgagggtc ctccgggtga cccgggtttg cctggaaaag caggcgagcg tggccttcgg    7260
ggggcacctg gagttcgggg gcctgtgggt gaaaagggag accagggaga tcctggagag    7320
gatggacgaa atggcagccc tggatcatct ggacccaagg gtgaccgtgg ggagccgggt    7380
cccccaggac ccccgggacg gctggtagac acaggaccctg gagccagaga gaagggagag    7440
cctggggacc gcgacaaga gggtcctcga gggcccaagg gtgatcctgg cctccctgga     7500
gcccctgggg aaaggggcat tgaagggttt cggggacccc caggcccaca ggggacccca    7560
ggtgtccgag gccagcagg agaaaagggt gaccgggtc cccctgggct ggatggccgg      7620
agcggactgg atgggaaacc aggagccgct gggccctctg gccgaatgg tgctgcaggc     7680
aaagctgggg acccagggag agacgggctt ccaggcctcc gtggagaaca gggcctccct    7740
ggcccctctg gtccccctgg attaccggga aagccaggcg aggatggcaa acctggcctg    7800
aatgaaaaaa acggagaacc tggggaccct ggagaagacg ggaggaaggg agagaaagga    7860
```

```
gattcaggcg cctctgggag agaaggtcgt gatggcccca agggtgagcg tggagctcct   7920
ggtatccttg accccaggg gcctccaggc ctcccagggc cagtgggccc tcctggccag    7980
ggttttcctg gtgtcccagg aggcacgggc cccaagggtg accgtgggga gactggatcc   8040
aaaggggagc agggcctccc tggagagcgt ggcctgcgag gagagcctgg aagtgtgccg   8100
aatgtggatc ggttgctgga aactgctggc atcaaggcat ctgccctgcg ggagatcgtg   8160
gagacctggg atgagagctc tggtagcttc ctgcctgtgc ccaacggcg tcgaggcccc    8220
aaggggact caggcgaaca gggccccca ggcaaggagg ccccatcgg ctttcctgga      8280
gaacgcgggc tgaagggcga ccgtggagac cctggccctc aggggccacc tggtctggcc   8340
cttggggaga ggggcccccc cgggccttcc ggccttgccg gggagcctgg aaagcctggt   8400
attcccggc tcccaggcag ggctgggggt gtgggagagg caggaaggcc aggagagagg    8460
ggagaacggg gagagaaagg agaacgtgga gaacagggca gagatggccc tcctggactc   8520
cctggaaccc ctgggccccc cggacccct ggccccaagg tgtctgtgga tgagccaggt    8580
cctggactct ctggagaaca gggacccct ggactcaagg gtgctaaggg ggagccgggc    8640
agcaatggtg accaaggtcc caaaggagac aggggtgtgc caggcatcaa aggagaccgg   8700
ggagagcctg gaccgagggg tcaggacggc aacccgggtc taccaggaga gcgtggtatg   8760
gctgggcctg aagggaagcc gggtctgcag ggtccaagag gccccctgg cccagtgggt    8820
ggtcatggag accctggacc acctggtgcc ccgggtcttg ctggccctgc aggacccaa    8880
ggaccttctg gcctgaaggg ggagcctgga gagacaggac ctccaggacg gggcctgact   8940
ggacctactg gagctgtggg acttcctgga cccccggcc cttcaggcct tgtgggtcca    9000
caggggtctc caggttttgcc tggacaagtg ggggagacag ggaagccggg agccccaggt  9060
cgagatggtg ccagtggaaa agatggagac agagggagcc ctggtgtgcc agggtcacca   9120
ggtctgcctg gccctgtcgg acctaaagga gaacctggcc ccacggggc ccctggacag    9180
gctgtggtcg ggctccctgg agcaaaggga gagaaggag cccctggagg ccttgctgga    9240
gacctggtgg gtgagccggg agccaaaggt gaccgaggac tgccaggcc gcgaggcgag    9300
aagggtgaag ctggccgtgc aggggagccc ggagaccctg gggaagatgg tcagaaaggg   9360
gctccaggac ccaaaggttt caagggtgac ccaggagtcg gggtcccggg ctcccctggg   9420
cctcctggcc ctcaggtgt gaaggagat ctgggcctcc ctggcctgcc cggtgctcct    9480
ggtgttgttg ggttcccggg tcagacaggc cctcgaggag agatgggtca gccaggccct   9540
agtggagagc ggggtctggc aggcccccca gggagagaag gaatcccagg accccctggg   9600
ccacctggac caccggggtc agtgggacca cctggggcct ctggactcaa aggagacaag   9660
ggagaccctg gagtagggct gcctgggccc gaggcgagc gtgggagcc aggcatccgg     9720
ggtgaagatg gccgcccgg ccaggaggga ccccgaggac tcacggggcc cctggcagc    9780
aggggagagc gtgggagaa gggtgatgtt gggagtgcag gactaaaggg tgacaaggga    9840
gactcagctg tgatcctggg gcctccaggc ccacggggtg ccaaggggga catgggtgaa   9900
cgagggcctc ggggcttgga tgtgacaaa ggaccttcgg gagacaatgg ggaccctggt    9960
gacaagggca gcaagggaga gcctggtgac aagggctcag ccgggttgcc aggactgcgt   10020
ggactcctgg gaccccaggg tcaacctggt gcagcaggga tccctggtga cccgggatcc   10080
ccaggaaagg atggagtgcc tggtatccga ggagaaaaag gagatgttgg cttcatgggt   10140
ccccggggcc tcaagggtga acggggagtg aagggagcct gtggccttga tggagagaag   10200
```

```
ggagacaagg gagaagctgg tcccccaggc cgccccgggc tggcaggaca caaaggagag    10260 atggggggagc tggtgtgcc gggccagtcg ggggcccctg gcaaggaggg cctgatcggt    10320
cccaagggtg accgaggctt tgacgggcag ccaggcccca agggtgacca gggcgagaaa    10380
ggggagcggg gaaccccagg aattgggggc ttcccaggcc ccagtggaaa tgatggctct    10440
gctggtcccc cagggccacc tggcagtgtt ggtcccagag gccccgaagg acttcagggc    10500
cagaagggtg agcgaggtcc ccccggagag agagtggtgg gggctcctgg ggtccctgga    10560
gctcctggcg agagagggga gcaggggcgg ccagggcctg ccggtcctcg aggcgagaag    10620
ggagaagctg cactgacgga ggatgacatc cggggctttg tgcgccaaga gatgagtcag    10680
cactgtgcct gccagggcca gttcatcgca tctggatcac gacccctccc tagttatgct    10740
gcagacactg ccggctccca gctccatgct gtgcctgtgc tccgcgtctc tcatgcagag    10800
gaggaagagc gggtaccccc tgaggatgat gagtactctg aatactccga gtattctgtg    10860
gaggagtacc aggaccctga agctccttgg gatagtgatg acccctgttc cctgccactg    10920
gatgagggct cctgcactgc ctacaccctg cgctggtacc atcgggctgt gacaggcagc    10980
acagaggcct gtcaccettt tgtctatggt ggctgtggag ggaatgccaa ccgttttggg    11040 accegtgagg cctgcgagcg ccgctgccca cccegggtgg tccagagcca ggggacaggt    11100
actgcccagg actga                                                    11115
```

<210> SEQ ID NO 24
<211> LENGTH: 3704
<212> TYPE: PRT
<213> ORGANISM: Artificial Sequence
<220> FEATURE:
<223> OTHER INFORMATION: Synthetic Construct

<400> SEQUENCE: 24

```
Met Thr Ser Ser Gly Pro Gly Pro Arg Phe Leu Leu Leu Pro Leu
 1               5                  10                  15

Leu Leu Pro Pro Ala Ala Ser Ala Ser Asp Arg Pro Arg Gly Arg Asp
             20                  25                  30

Pro Val Asn Pro Glu Lys Leu Leu Val Ile Thr Val Ala Thr Ala Glu
         35                  40                  45

Thr Glu Gly Tyr Leu Arg Phe Leu Arg Ser Ala Glu Phe Phe Asn Tyr
     50                  55                  60

Thr Val Arg Thr Leu Gly Leu Gly Glu Glu Trp Arg Gly Gly Asp Val
 65                  70                  75                  80

Ala Arg Thr Val Gly Gly Gly Gln Lys Val Arg Trp Leu Lys Lys Glu
                 85                  90                  95

Met Glu Lys Tyr Ala Asp Arg Glu Asp Met Ile Ile Met Phe Val Asp
            100                 105                 110

Ser Tyr Asp Val Ile Leu Ala Gly Ser Pro Thr Glu Leu Leu Lys Lys
        115                 120                 125

Phe Val Gln Ser Gly Ser Arg Leu Leu Phe Ser Ala Glu Ser Phe Cys
    130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
            180                 185                 190

Leu Phe Tyr Thr Arg Leu Tyr Leu Asp Pro Gly Leu Arg Glu Lys Leu
```

```
            195                 200                 205
Ser Leu Asn Leu Asp His Lys Ser Arg Ile Phe Gln Asn Leu Asn Gly
    210                 215                 220

Ala Leu Asp Glu Val Val Leu Lys Phe Asp Arg Asn Arg Val Arg Ile
225                 230                 235                 240

Arg Asn Val Ala Tyr Asp Thr Leu Pro Ile Val Val His Gly Asn Gly
                245                 250                 255

Pro Thr Lys Leu Gln Leu Asn Tyr Leu Gly Asn Tyr Val Pro Asn Gly
            260                 265                 270

Trp Thr Pro Glu Gly Gly Cys Gly Phe Cys Asn Gln Asp Arg Arg Thr
        275                 280                 285

Leu Pro Gly Gly Gln Pro Pro Arg Val Phe Leu Ala Val Phe Val
    290                 295                 300

Glu Gln Pro Thr Pro Phe Leu Pro Arg Phe Leu Gln Arg Leu Leu Leu
305                 310                 315                 320

Leu Asp Tyr Pro Pro Asp Arg Val Thr Leu Phe Leu His Asn Asn Glu
                325                 330                 335

Val Phe His Glu Pro His Ile Ala Asp Ser Trp Pro Gln Leu Gln Asp
            340                 345                 350

His Phe Ser Ala Val Lys Leu Val Gly Pro Glu Ala Leu Ser Pro
        355                 360                 365

Gly Glu Ala Arg Asp Met Ala Met Asp Leu Cys Arg Gln Asp Pro Glu
370                 375                 380

Cys Glu Phe Tyr Phe Ser Leu Asp Ala Asp Ala Val Leu Thr Asn Leu
385                 390                 395                 400

Gln Thr Leu Arg Ile Leu Ile Glu Glu Asn Arg Lys Val Ile Ala Pro
                405                 410                 415

Met Leu Ser Arg His Gly Lys Leu Trp Ser Asn Phe Trp Gly Ala Leu
            420                 425                 430

Ser Pro Asp Glu Tyr Tyr Ala Arg Ser Glu Asp Tyr Val Glu Leu Val
        435                 440                 445

Gln Arg Lys Arg Val Gly Val Trp Asn Val Pro Tyr Ile Ser Gln Ala
450                 455                 460

Tyr Val Ile Arg Gly Asp Thr Leu Arg Met Glu Leu Pro Gln Arg Asp
465                 470                 475                 480

Val Phe Ser Gly Ser Asp Thr Asp Pro Asp Met Ala Phe Cys Lys Ser
                485                 490                 495

Phe Arg Asp Lys Gly Ile Phe Leu His Leu Ser Asn Gln His Glu Phe
            500                 505                 510

Gly Arg Leu Leu Ala Thr Ser Arg Tyr Asp Thr Glu His Leu His Pro
        515                 520                 525

Asp Leu Trp Gln Ile Phe Asp Asn Pro Val Asp Trp Lys Glu Gln Tyr
    530                 535                 540

Ile His Glu Asn Tyr Ser Arg Ala Leu Glu Gly Glu Gly Ile Val Glu
545                 550                 555                 560

Gln Pro Cys Pro Asp Val Tyr Trp Phe Pro Leu Leu Ser Glu Gln Met
                565                 570                 575

Cys Asp Glu Leu Val Ala Glu Met Glu His Tyr Gly Gln Trp Ser Gly
            580                 585                 590

Gly Arg His Glu Asp Ser Arg Leu Ala Gly Gly Tyr Glu Asn Val Pro
        595                 600                 605

Thr Val Asp Ile His Met Lys Gln Val Gly Tyr Glu Asp Gln Trp Leu
    610                 615                 620
```

```
Gln Leu Leu Arg Thr Tyr Val Gly Pro Met Thr Glu Ser Leu Phe Pro
625                 630                 635                 640

Gly Tyr His Thr Lys Ala Arg Ala Val Met Asn Phe Val Val Arg Tyr
            645                 650                 655

Arg Pro Asp Glu Gln Pro Ser Leu Arg Pro His His Asp Ser Ser Thr
            660                 665                 670

Phe Thr Leu Asn Val Ala Leu Asn His Lys Gly Leu Asp Tyr Glu Gly
            675                 680                 685

Gly Gly Cys Arg Phe Leu Arg Tyr Asp Cys Val Ile Ser Ser Pro Arg
            690                 695                 700

Lys Gly Trp Ala Leu Leu His Pro Gly Arg Leu Thr His Tyr His Glu
705                 710                 715                 720

Gly Leu Pro Thr Thr Trp Gly Thr Arg Tyr Ile Met Val Ser Phe Val
            725                 730                 735

Asp Pro Gly Ser Gly Gln Cys Thr Asn Tyr Ala Leu Leu Lys Leu Ala
            740                 745                 750

Gly Asp Val Glu Ser Asn Pro Gly Pro Thr Leu Arg Leu Leu Val Ala
            755                 760                 765

Ala Leu Cys Ala Gly Ile Leu Ala Glu Ala Pro Arg Val Arg Ala Gln
770                 775                 780

His Arg Glu Arg Val Thr Cys Thr Arg Leu Tyr Ala Ala Asp Ile Val
785                 790                 795                 800

Phe Leu Leu Asp Gly Ser Ser Ser Ile Gly Arg Ser Asn Phe Arg Glu
            805                 810                 815

Val Arg Ser Phe Leu Glu Gly Leu Val Leu Pro Phe Ser Gly Ala Ala
            820                 825                 830

Ser Ala Gln Gly Val Arg Phe Ala Thr Val Gln Tyr Ser Asp Asp Pro
            835                 840                 845

Arg Thr Glu Phe Gly Leu Asp Ala Leu Gly Ser Gly Gly Asp Val Ile
850                 855                 860

Arg Ala Ile Arg Glu Leu Ser Tyr Lys Gly Gly Asn Thr Arg Thr Gly
865                 870                 875                 880

Ala Ala Ile Leu His Val Ala Asp His Val Phe Leu Pro Gln Leu Ala
            885                 890                 895

Arg Pro Gly Val Pro Lys Val Cys Ile Leu Ile Thr Asp Gly Lys Ser
            900                 905                 910

Gln Asp Leu Val Asp Thr Ala Ala Gln Arg Leu Lys Gly Gln Gly Val
            915                 920                 925

Lys Leu Phe Ala Val Gly Ile Lys Asn Ala Asp Pro Glu Glu Leu Lys
            930                 935                 940

Arg Val Ala Ser Gln Pro Thr Ser Asp Phe Phe Phe Val Asn Asp
945                 950                 955                 960

Phe Ser Ile Leu Arg Thr Leu Leu Pro Leu Val Ser Arg Arg Val Cys
            965                 970                 975

Thr Thr Ala Gly Gly Val Pro Val Thr Arg Pro Pro Asp Asp Ser Thr
            980                 985                 990

Ser Ala Pro Arg Asp Leu Val Leu Ser Glu Pro Ser Ser Gln Ser Leu
            995                 1000                1005

Arg Val Gln Trp Thr Ala Ala Ser Gly Pro Val Thr Gly Tyr Lys Val
            1010                1015                1020

Gln Tyr Thr Pro Leu Thr Gly Leu Gly Gln Pro Leu Pro Ser Glu Arg
1025                1030                1035                1040
```

-continued

Gln Glu Val Asn Val Pro Ala Gly Glu Thr Ser Val Arg Leu Arg Gly
            1045                1050                1055

Leu Arg Pro Leu Thr Glu Tyr Gln Val Thr Val Ile Ala Leu Tyr Ala
            1060                1065                1070

Asn Ser Ile Gly Glu Ala Val Ser Gly Thr Ala Arg Thr Thr Ala Leu
            1075                1080                1085

Glu Gly Pro Glu Leu Thr Ile Gln Asn Thr Thr Ala His Ser Leu Leu
            1090                1095                1100

Val Ala Trp Arg Ser Val Pro Gly Ala Thr Gly Tyr Arg Val Thr Trp
1105                1110                1115                1120

Arg Val Leu Ser Gly Gly Pro Thr Gln Gln Gln Glu Leu Gly Pro Gly
            1125                1130                1135

Gln Gly Ser Val Leu Leu Arg Asp Leu Glu Pro Gly Thr Asp Tyr Glu
            1140                1145                1150

Val Thr Val Ser Thr Leu Phe Gly Arg Ser Val Gly Pro Ala Thr Ser
            1155                1160                1165

Leu Met Ala Arg Thr Asp Ala Ser Val Glu Gln Thr Leu Arg Pro Val
            1170                1175                1180

Ile Leu Gly Pro Thr Ser Ile Leu Leu Ser Trp Asn Leu Val Pro Glu
1185                1190                1195                1200

Ala Arg Gly Tyr Arg Leu Glu Trp Arg Arg Glu Thr Gly Leu Glu Pro
            1205                1210                1215

Pro Gln Lys Val Val Leu Pro Ser Asp Val Thr Arg Tyr Gln Leu Asp
            1220                1225                1230

Gly Leu Gln Pro Gly Thr Glu Tyr Arg Leu Thr Leu Tyr Thr Leu Leu
            1235                1240                1245

Glu Gly His Glu Val Ala Thr Pro Ala Thr Val Val Pro Thr Gly Pro
            1250                1255                1260

Glu Leu Pro Val Ser Pro Val Thr Asp Leu Gln Ala Thr Glu Leu Pro
1265                1270                1275                1280

Gly Gln Arg Val Arg Val Ser Trp Ser Pro Val Pro Gly Ala Thr Gln
            1285                1290                1295

Tyr Arg Ile Ile Val Arg Ser Thr Gln Gly Val Glu Arg Thr Leu Val
            1300                1305                1310

Leu Pro Gly Ser Gln Thr Ala Phe Asp Leu Asp Asp Val Gln Ala Gly
            1315                1320                1325

Leu Ser Tyr Thr Val Arg Val Ser Ala Arg Val Gly Pro Arg Glu Gly
            1330                1335                1340

Ser Ala Ser Val Leu Thr Val Arg Arg Glu Pro Glu Thr Pro Leu Ala
1345                1350                1355                1360

Val Pro Gly Leu Arg Val Val Val Ser Asp Ala Thr Arg Val Arg Val
            1365                1370                1375

Ala Trp Gly Pro Val Pro Gly Ala Ser Gly Phe Arg Ile Ser Trp Ser
            1380                1385                1390

Thr Gly Ser Gly Pro Glu Ser Ser Gln Thr Leu Pro Pro Asp Ser Thr
            1395                1400                1405

Ala Thr Asp Ile Thr Gly Leu Gln Pro Gly Thr Thr Tyr Gln Val Ala
            1410                1415                1420

Val Ser Val Leu Arg Gly Arg Glu Glu Gly Pro Ala Ala Val Ile Val
1425                1430                1435                1440

Ala Arg Thr Asp Pro Leu Gly Pro Val Arg Thr Val His Val Thr Gln
            1445                1450                1455

Ala Ser Ser Ser Ser Val Thr Ile Thr Trp Thr Arg Val Pro Gly Ala

```
            1460              1465                1470
Thr Gly Tyr Arg Val Ser Trp His Ser Ala His Gly Pro Glu Lys Ser
        1475              1480                1485

Gln Leu Val Ser Gly Glu Ala Thr Val Ala Glu Leu Asp Gly Leu Glu
    1490              1495              1500

Pro Asp Thr Glu Tyr Thr Val His Val Arg Ala His Val Ala Gly Val
1505              1510              1515              1520

Asp Gly Pro Pro Ala Ser Val Val Arg Thr Ala Pro Glu Pro Val
            1525              1530              1535

Gly Arg Val Ser Arg Leu Gln Ile Leu Asn Ala Ser Ser Asp Val Leu
        1540              1545              1550

Arg Ile Thr Trp Val Gly Val Thr Gly Ala Thr Ala Tyr Arg Leu Ala
        1555              1560              1565

Trp Gly Arg Ser Glu Gly Gly Pro Met Arg His Gln Ile Leu Pro Gly
        1570              1575              1580

Asn Thr Asp Ser Ala Glu Ile Arg Gly Leu Glu Gly Gly Val Ser Tyr
1585              1590              1595              1600

Ser Val Arg Val Thr Ala Leu Val Gly Asp Arg Glu Gly Thr Pro Val
                1605              1610              1615

Ser Ile Val Val Thr Thr Pro Pro Glu Ala Pro Ala Leu Gly Thr
            1620              1625              1630

Leu His Val Val Gln Arg Gly Glu His Ser Leu Arg Leu Arg Trp Glu
        1635              1640              1645

Pro Val Pro Arg Ala Gln Gly Phe Leu Leu His Trp Gln Pro Glu Gly
    1650              1655              1660

Gly Gln Glu Gln Ser Arg Val Leu Gly Pro Glu Leu Ser Ser Tyr His
1665              1670              1675              1680

Leu Asp Gly Leu Glu Pro Ala Thr Gln Tyr Arg Val Arg Leu Ser Val
            1685              1690              1695

Leu Gly Pro Ala Gly Glu Gly Pro Ser Ala Glu Val Thr Ala Arg Thr
            1700              1705              1710

Glu Ser Pro Arg Val Pro Ser Ile Glu Leu Arg Val Val Asp Thr Ser
        1715              1720              1725

Ile Asp Ser Val Thr Leu Ala Trp Thr Pro Val Ser Arg Ala Ser Ser
        1730              1735              1740

Tyr Ile Leu Ser Trp Arg Pro Leu Arg Gly Pro Gly Gln Glu Val Pro
1745              1750              1755              1760

Gly Ser Pro Gln Thr Leu Pro Gly Ile Ser Ser Ser Gln Arg Val Thr
            1765              1770              1775

Gly Leu Glu Pro Gly Val Ser Tyr Ile Phe Ser Leu Thr Pro Val Leu
            1780              1785              1790

Asp Gly Val Arg Gly Pro Glu Ala Ser Val Thr Gln Thr Pro Val Cys
        1795              1800              1805

Pro Arg Gly Leu Ala Asp Val Val Phe Leu Pro His Ala Thr Gln Asp
        1810              1815              1820

Asn Ala His Arg Ala Glu Ala Thr Arg Arg Val Leu Glu Arg Leu Val
1825              1830              1835              1840

Leu Ala Leu Gly Pro Leu Gly Pro Gln Ala Val Gln Val Gly Leu Leu
            1845              1850              1855

Ser Tyr Ser His Arg Pro Ser Pro Leu Phe Pro Leu Asn Gly Ser His
            1860              1865              1870

Asp Leu Gly Ile Ile Leu Gln Arg Ile Arg Asp Met Pro Tyr Met Asp
        1875              1880              1885
```

```
Pro Ser Gly Asn Asn Leu Gly Thr Ala Val Val Thr Ala His Arg Tyr
    1890                1895                1900

Met Leu Ala Pro Asp Ala Pro Gly Arg Arg Gln His Val Pro Gly Val
1905                1910                1915                1920

Met Val Leu Leu Val Asp Glu Pro Leu Arg Gly Asp Ile Phe Ser Pro
            1925                1930                1935

Ile Arg Glu Ala Gln Ala Ser Gly Leu Asn Val Val Met Leu Gly Met
        1940                1945                1950

Ala Gly Ala Asp Pro Glu Gln Leu Arg Arg Leu Ala Pro Gly Met Asp
    1955                1960                1965

Ser Val Gln Thr Phe Phe Ala Val Asp Asp Gly Pro Ser Leu Asp Gln
    1970                1975                1980

Ala Val Ser Gly Leu Ala Thr Ala Leu Cys Gln Ala Ser Phe Thr Thr
1985                1990                1995                2000

Gln Pro Arg Pro Glu Pro Cys Pro Val Tyr Cys Pro Lys Gly Gln Lys
            2005                2010                2015

Gly Glu Pro Gly Glu Met Gly Leu Arg Gly Gln Val Gly Pro Pro Gly
        2020                2025                2030

Asp Pro Gly Leu Pro Gly Arg Thr Gly Ala Pro Gly Pro Gln Gly Pro
    2035                2040                2045

Pro Gly Ser Ala Thr Ala Lys Gly Glu Arg Gly Phe Pro Gly Ala Asp
    2050                2055                2060

Gly Arg Pro Gly Ser Pro Gly Arg Ala Gly Asn Pro Gly Thr Pro Gly
2065                2070                2075                2080

Ala Pro Gly Leu Lys Gly Ser Pro Gly Leu Pro Gly Pro Arg Gly Asp
            2085                2090                2095

Pro Gly Glu Arg Gly Pro Arg Gly Pro Lys Gly Glu Pro Gly Ala Pro
        2100                2105                2110

Gly Gln Val Ile Gly Gly Glu Gly Pro Gly Leu Pro Gly Arg Lys Gly
    2115                2120                2125

Asp Pro Gly Pro Ser Gly Pro Pro Gly Pro Arg Gly Pro Leu Gly Asp
    2130                2135                2140

Pro Gly Pro Arg Gly Pro Pro Gly Leu Pro Gly Thr Ala Met Lys Gly
2145                2150                2155                2160

Asp Lys Gly Asp Arg Gly Glu Arg Gly Pro Pro Gly Pro Gly Glu Gly
            2165                2170                2175

Gly Ile Ala Pro Gly Glu Pro Gly Leu Pro Gly Leu Pro Gly Ser Pro
        2180                2185                2190

Gly Pro Gln Gly Pro Val Gly Pro Pro Gly Lys Lys Gly Glu Lys Gly
    2195                2200                2205

Asp Ser Glu Asp Gly Ala Pro Gly Leu Pro Gly Gln Pro Gly Ser Pro
    2210                2215                2220

Gly Glu Gln Gly Pro Arg Gly Pro Pro Gly Ala Ile Gly Pro Lys Gly
2225                2230                2235                2240

Asp Arg Gly Phe Pro Gly Pro Leu Gly Glu Ala Gly Glu Lys Gly Glu
            2245                2250                2255

Arg Gly Pro Pro Gly Pro Ala Gly Ser Arg Gly Leu Pro Gly Val Ala
        2260                2265                2270

Gly Arg Pro Gly Ala Lys Gly Pro Glu Gly Pro Pro Gly Pro Thr Gly
    2275                2280                2285

Arg Gln Gly Glu Lys Gly Glu Pro Gly Arg Pro Gly Asp Pro Ala Val
    2290                2295                2300
```

```
Val Gly Pro Ala Val Ala Gly Pro Lys Gly Glu Lys Gly Asp Val Gly
2305                2310                2315                2320

Pro Ala Gly Pro Arg Gly Ala Thr Gly Val Gln Gly Glu Arg Gly Pro
            2325                2330                2335

Pro Gly Leu Val Leu Pro Gly Asp Pro Gly Pro Lys Gly Asp Pro Gly
            2340                2345                2350

Asp Arg Gly Pro Ile Gly Leu Thr Gly Arg Ala Gly Pro Pro Gly Asp
            2355                2360                2365

Ser Gly Pro Pro Gly Glu Lys Gly Asp Pro Gly Arg Pro Gly Pro Pro
            2370                2375                2380

Gly Pro Val Gly Pro Arg Gly Arg Asp Gly Glu Val Gly Glu Lys Gly
2385                2390                2395                2400

Asp Glu Gly Pro Pro Gly Asp Pro Gly Leu Pro Gly Lys Ala Gly Glu
            2405                2410                2415

Arg Gly Leu Arg Gly Ala Pro Gly Val Arg Gly Pro Val Gly Glu Lys
            2420                2425                2430

Gly Asp Gln Gly Asp Pro Gly Glu Asp Gly Arg Asn Gly Ser Pro Gly
            2435                2440                2445

Ser Ser Gly Pro Lys Gly Asp Arg Gly Glu Pro Gly Pro Pro Gly Pro
            2450                2455                2460

Pro Gly Arg Leu Val Asp Thr Gly Pro Gly Ala Arg Glu Lys Gly Glu
2465                2470                2475                2480

Pro Gly Asp Arg Gly Gln Glu Gly Pro Arg Gly Pro Lys Gly Asp Pro
            2485                2490                2495

Gly Leu Pro Gly Ala Pro Gly Glu Arg Gly Ile Glu Gly Phe Arg Gly
            2500                2505                2510

Pro Pro Gly Pro Gln Gly Asp Pro Gly Val Arg Gly Pro Ala Gly Glu
            2515                2520                2525

Lys Gly Asp Arg Gly Pro Pro Gly Leu Asp Gly Arg Ser Gly Leu Asp
            2530                2535                2540

Gly Lys Pro Gly Ala Ala Gly Pro Ser Gly Pro Asn Gly Ala Ala Gly
2545                2550                2555                2560

Lys Ala Gly Asp Pro Gly Arg Asp Gly Leu Pro Gly Leu Arg Gly Glu
            2565                2570                2575

Gln Gly Leu Pro Gly Pro Ser Gly Pro Pro Gly Leu Pro Gly Lys Pro
            2580                2585                2590

Gly Glu Asp Gly Lys Pro Gly Leu Asn Gly Lys Asn Gly Glu Pro Gly
            2595                2600                2605

Asp Pro Gly Glu Asp Gly Arg Lys Gly Glu Lys Gly Asp Ser Gly Ala
            2610                2615                2620

Ser Gly Arg Glu Gly Arg Asp Gly Pro Lys Gly Glu Arg Gly Ala Pro
2625                2630                2635                2640

Gly Ile Leu Gly Pro Gln Gly Pro Pro Gly Leu Pro Gly Pro Val Gly
            2645                2650                2655

Pro Pro Gly Gln Gly Phe Pro Gly Val Pro Gly Gly Thr Gly Pro Lys
            2660                2665                2670

Gly Asp Arg Gly Glu Thr Gly Ser Lys Gly Glu Gln Gly Leu Pro Gly
            2675                2680                2685

Glu Arg Gly Leu Arg Gly Glu Pro Gly Ser Val Pro Asn Val Asp Arg
            2690                2695                2700

Leu Leu Glu Thr Ala Gly Ile Lys Ala Ser Ala Leu Arg Glu Ile Val
2705                2710                2715                2720

Glu Thr Trp Asp Glu Ser Ser Gly Ser Phe Leu Pro Val Pro Glu Arg
```

```
                  2725                2730                2735
Arg Arg Gly Pro Lys Gly Asp Ser Gly Glu Gln Gly Pro Gly Lys
            2740                2745                2750
Glu Gly Pro Ile Gly Phe Pro Gly Glu Arg Gly Leu Lys Gly Asp Arg
        2755                2760                2765
Gly Asp Pro Gly Pro Gln Gly Pro Pro Gly Leu Ala Leu Gly Glu Arg
    2770                2775                2780
Gly Pro Pro Gly Pro Ser Gly Leu Ala Gly Glu Pro Gly Lys Pro Gly
2785                2790                2795                2800
Ile Pro Gly Leu Pro Gly Arg Ala Gly Val Gly Glu Ala Gly Arg
            2805                2810                2815
Pro Gly Glu Arg Gly Glu Arg Gly Glu Lys Gly Glu Arg Gly Glu Gln
        2820                2825                2830
Gly Arg Asp Gly Pro Pro Gly Leu Pro Gly Thr Pro Gly Pro Pro Gly
    2835                2840                2845
Pro Pro Gly Pro Lys Val Ser Val Asp Glu Pro Gly Pro Gly Leu Ser
    2850                2855                2860
Gly Glu Gln Gly Pro Pro Gly Leu Lys Gly Ala Lys Gly Glu Pro Gly
2865                2870                2875                2880
Ser Asn Gly Asp Gln Gly Pro Lys Gly Asp Arg Gly Val Pro Gly Ile
            2885                2890                2895
Lys Gly Asp Arg Gly Glu Pro Gly Pro Arg Gly Gln Asp Gly Asn Pro
        2900                2905                2910
Gly Leu Pro Gly Glu Arg Gly Met Ala Gly Pro Glu Gly Lys Pro Gly
    2915                2920                2925
Leu Gln Gly Pro Arg Gly Pro Pro Gly Pro Val Gly His Gly Asp
    2930                2935                2940
Pro Gly Pro Pro Gly Ala Pro Gly Leu Ala Gly Pro Ala Gly Pro Gln
2945                2950                2955                2960
Gly Pro Ser Gly Leu Lys Gly Glu Pro Gly Glu Thr Gly Pro Pro Gly
            2965                2970                2975
Arg Gly Leu Thr Gly Pro Thr Gly Ala Val Gly Leu Pro Gly Pro Pro
        2980                2985                2990
Gly Pro Ser Gly Leu Val Gly Pro Gln Gly Ser Pro Gly Leu Pro Gly
    2995                3000                3005
Gln Val Gly Glu Thr Gly Lys Pro Gly Ala Pro Gly Arg Asp Gly Ala
    3010                3015                3020
Ser Gly Lys Asp Gly Asp Arg Gly Ser Pro Gly Val Pro Gly Ser Pro
3025                3030                3035                3040
Gly Leu Pro Gly Pro Val Gly Pro Lys Gly Glu Pro Gly Pro Thr Gly
            3045                3050                3055
Ala Pro Gly Gln Ala Val Val Gly Leu Pro Gly Ala Lys Gly Glu Lys
        3060                3065                3070
Gly Ala Pro Gly Gly Leu Ala Gly Asp Leu Val Gly Glu Pro Gly Ala
    3075                3080                3085
Lys Gly Asp Arg Gly Leu Pro Gly Pro Arg Gly Glu Lys Gly Glu Ala
    3090                3095                3100
Gly Arg Ala Gly Glu Pro Gly Asp Pro Gly Glu Asp Gly Gln Lys Gly
3105                3110                3115                3120
Ala Pro Gly Pro Lys Gly Phe Lys Gly Asp Pro Gly Val Gly Val Pro
            3125                3130                3135
Gly Ser Pro Gly Pro Pro Gly Pro Pro Gly Val Lys Gly Asp Leu Gly
            3140                3145                3150
```

Leu Pro Gly Leu Pro Gly Ala Pro Gly Val Gly Phe Pro Gly Gln
            3155                3160                3165

Thr Gly Pro Arg Gly Glu Met Gly Gln Pro Gly Pro Ser Gly Glu Arg
    3170                3175                3180

Gly Leu Ala Gly Pro Pro Gly Arg Glu Gly Ile Pro Gly Pro Leu Gly
3185                3190                3195                3200

Pro Pro Gly Pro Pro Gly Ser Val Gly Pro Pro Gly Ala Ser Gly Leu
            3205                3210                3215

Lys Gly Asp Lys Gly Asp Pro Gly Val Gly Leu Pro Gly Pro Arg Gly
            3220                3225                3230

Glu Arg Gly Glu Pro Gly Ile Arg Gly Glu Asp Gly Arg Pro Gly Gln
            3235                3240                3245

Glu Gly Pro Arg Gly Leu Thr Gly Pro Pro Gly Ser Arg Gly Glu Arg
            3250                3255                3260

Gly Glu Lys Gly Asp Val Gly Ser Ala Gly Leu Lys Gly Asp Lys Gly
3265                3270                3275                3280

Asp Ser Ala Val Ile Leu Gly Pro Pro Gly Pro Arg Gly Ala Lys Gly
            3285                3290                3295

Asp Met Gly Glu Arg Gly Pro Arg Gly Leu Asp Gly Asp Lys Gly Pro
            3300                3305                3310

Arg Gly Asp Asn Gly Asp Pro Gly Asp Lys Gly Ser Lys Gly Glu Pro
            3315                3320                3325

Gly Asp Lys Gly Ser Ala Gly Leu Pro Gly Leu Arg Gly Leu Leu Gly
            3330                3335                3340

Pro Gln Gly Gln Pro Gly Ala Ala Gly Ile Pro Gly Asp Pro Gly Ser
3345                3350                3355                3360

Pro Gly Lys Asp Gly Val Pro Gly Ile Arg Gly Glu Lys Gly Asp Val
            3365                3370                3375

Gly Phe Met Gly Pro Arg Gly Leu Lys Gly Glu Arg Gly Val Lys Gly
            3380                3385                3390

Ala Cys Gly Leu Asp Gly Glu Lys Gly Asp Lys Gly Glu Ala Gly Pro
            3395                3400                3405

Pro Gly Arg Pro Gly Leu Ala Gly His Lys Gly Glu Met Gly Glu Pro
            3410                3415                3420

Gly Val Pro Gly Gln Ser Gly Ala Pro Gly Lys Glu Gly Leu Ile Gly
3425                3430                3435                3440

Pro Lys Gly Asp Arg Gly Phe Asp Gly Gln Pro Gly Pro Lys Gly Asp
            3445                3450                3455

Gln Gly Glu Lys Gly Glu Arg Gly Thr Pro Gly Ile Gly Gly Phe Pro
            3460                3465                3470

Gly Pro Ser Gly Asn Asp Gly Ser Ala Gly Pro Pro Gly Pro Pro Gly
            3475                3480                3485

Ser Val Gly Pro Arg Gly Pro Glu Gly Leu Gln Gly Gln Lys Gly Glu
            3490                3495                3500

Arg Gly Pro Pro Gly Glu Arg Val Val Gly Ala Pro Gly Val Pro Gly
3505                3510                3515                3520

Ala Pro Gly Glu Arg Gly Glu Gln Gly Arg Pro Gly Pro Ala Gly Pro
            3525                3530                3535

Arg Gly Glu Lys Gly Glu Ala Ala Leu Thr Glu Asp Asp Ile Arg Gly
            3540                3545                3550

Phe Val Arg Gln Glu Met Ser Gln His Cys Ala Cys Gln Gly Gln Phe
            3555                3560                3565

```
Ile Ala Ser Gly Ser Arg Pro Leu Pro Ser Tyr Ala Ala Asp Thr Ala
        3570                3575                3580

Gly Ser Gln Leu His Ala Val Pro Val Leu Arg Val Ser His Ala Glu
3585                3590                3595                3600

Glu Glu Glu Arg Val Pro Pro Glu Asp Asp Glu Tyr Ser Glu Tyr Ser
                3605                3610                3615

Glu Tyr Ser Val Glu Glu Tyr Gln Asp Pro Glu Ala Pro Trp Asp Ser
        3620                3625                3630

Asp Asp Pro Cys Ser Leu Pro Leu Asp Glu Gly Ser Cys Thr Ala Tyr
            3635                3640                3645

Thr Leu Arg Trp Tyr His Arg Ala Val Thr Gly Ser Thr Glu Ala Cys
        3650                3655                3660

His Pro Phe Val Tyr Gly Gly Cys Gly Gly Asn Ala Asn Arg Phe Gly
3665                3670                3675                3680

Thr Arg Glu Ala Cys Glu Arg Arg Cys Pro Pro Arg Val Val Gln Ser
                3685                3690                3695

Gln Gly Thr Gly Thr Ala Gln Asp
        3700
```

<210> SEQ ID NO 25
<211> LENGTH: 11121
<212> TYPE: DNA
<213> ORGANISM: Artificial Sequence
<220> FEATURE:
<223> OTHER INFORMATION: Synthetic Construct

<400> SEQUENCE: 25

| | | |
|---|---|---|
| atgacgctgc ggcttctggt ggccgcgctc tgcgccggga tcctggcaga ggcgccccga | 60 |
| gtgcagcccc agcacaggga gagagtgacc tgcacgcgcc tttacgccgc tgacattgtg | 120 |
| ttcttactgg atggctcctc atccattggc cgcagcaatt tccgcgaggt ccgcagcttt | 180 |
| ctcgaagggc tggtgctgcc tttctctgga gcagccagtg cacagggtgt gcgctttgcc | 240 |
| acagtgcagt acagcgatga cccacggaca gagttcggcc tggatgcact ggctctgggg | 300 |
| ggtgatgtga tccgcgccat ccgtgagctt agctacaagg ggggcaacac tcgcacaggg | 360 |
| gctgcaattc tccatgtggc tgaccatgtc ttcctgcccc agctgccccg acctggtgtc | 420 |
| cccaaggtct gcatcctgat cacagacggg aagtcccagg acctggtgga cacagctgcc | 480 |
| caaaggctga aggggcaggg ggtcaagcta tttgctgtgg ggatcaagaa tgctgaccct | 540 |
| gaggagctga gcgagttgc ctcacagccc accagtgact tcttcttctt cgtcaatgac | 600 |
| ttcagcatct tgaggacact actgccctc gtttcccgga gagtgtgcac gactgctggt | 660 |
| ggcgtgcctg tgacccgacc tccggatgac tcgacctctg ctccacgaga cctggtgctg | 720 |
| tctgagccaa gcagccaatc cttgagagta cagtggacag cggccagtgg ccctgtgact | 780 |
| ggctacaagg tccagtacac tcctctgacg gggctgggac agccactgcc gagtgagcgg | 840 |
| caggaggtga acgtcccagc tggtgagacc agtgtgcggc tgcggggtct ccggccactg | 900 |
| accgagtacc aagtgactgt gattgccctc tacgccaaca gcatcgggga ggctgtgagc | 960 |
| gggacagctc ggaccactgc cctagaaggg ccggaactga ccatccagaa taccacagcc | 1020 |
| cacagcctcc tggtggcctg gcggagtgtg ccaggtgcca ctggctaccg tgtgacatgg | 1080 |
| cgggtcctca gtggtgggcc cacacagcag caggagctgg ccctgggca gggttcagtg | 1140 |
| ttgctgcgtg acttggagcc tggcacggac tatgaggtga ccgtgagcac cctatttggc | 1200 |
| cgcagtgtgg ggcccgccac ttccctgatg gctcgcactg acgcttctgt tgagcagacc | 1260 |

```
ctgcgcccgg tcatcctggg ccccacatcc atcctccttt cctggaactt ggtgcctgag    1320
gcccgtggct accggttgga atggcggcgt gagactggct tggagccacc gcagaaggtg    1380
gtactgccct ctgatgtgac ccgctaccag ttggatgggc tgcagccggg cactgagtac    1440
cgcctcacac tctacactct gctggagggc cacgaggtgg ccaccccctgc aaccgtggtt    1500
cccactggac cagagctgcc tgtgagccct gtaacagacc tgcaagccac cgagctgccc    1560
gggcagcggg tgcgagtgtc ctggagccca gtccctggtg ccacccagta ccgcatcatt    1620
gtgcgcagca cccaggggt tgagcggacc ctggtgcttc ctgggagtca gacagcattc    1680
gacttggatg acgttcaggc tgggcttagc tacactgtgc gggtgtctgc tcgagtgggt    1740
ccccgtgagg gcagtgccag tgtcctcact gtccgccggg agccggaaac tccacttgct    1800
gttccagggc tgcgggttgt ggtgtcagat gcaacgcgag tgagggtggc ctggggaccc    1860
gtccctggag ccagtggatt tcggattagc tggagcacag gcagtggtcc ggagtccagc    1920
cagacactgc ccccagactc tactgccaca gacatcacag gctgcagcc tggaaccacc    1980
taccaggtgg ctgtgtcggt actgcgaggc agagaggagg ccctgctgc agtcatcgtg    2040
gctcgaacgg acccactggg cccagtgagg acggtccatg tgactcaggc cagcagctca    2100
tctgtcacca ttacctggac cagggttcct ggcgccacag gatacagggt ttcctggcac    2160
tcagcccacg gcccagagaa atcccagttg gtttctgggg aggccacggt ggctgagctg    2220
gatggactgg agccagatac tgagtatacg gtgcatgtga gggcccatgt ggctggcgtg    2280
gatgggcccc ctgcctctgt ggttgtgagg actgcccctg agcctgtggg tcgtgtgtcg    2340
aggctgcaga tcctcaatgc ttccagcgac gttctacgga tcacctgggt aggggtcact    2400
ggagccacag cttacagact ggcctggggc cggagtgaag gcggcccat gaggcaccag    2460
atactcccag gaaacacaga ctctgcagag atccgggggtc tcgaaggtgg agtcagctac    2520
tcagtgcgag tgactgcact tgtcggggac gcgagggca cctgtctc cattgttgtc    2580
actacgccgc ctgaggctcc gccagccctg ggacgcttc acgtggtgca gcgcggggag    2640
cactcgctga ggctgcgctg ggagccggtg cccagagcgc agggcttcct tctgcactgg    2700
caacctgagg gtggccagga acagtcccgg gtcctggggc ccgagctcag cagctatcac    2760
ctggacgggc tggagccagc gacacagtac cgcgtgaggc tgagtgtcct agggccagct    2820
ggagaagggc cctctgcaga ggtgactgcg cgcactgagt cacctcgtgt tccaagcatt    2880
gaactacgtg tggtggacac ctcgatcgac tcggtgactt tggcctggac tccagtgtcc    2940
agggcatcca gctacatcct atcctggcgg ccactcagag gccctggcca ggaagtgcct    3000
gggtccccgc agacacttcc agggatctca agctcccagc gggtgacagg gctagagcct    3060
ggcgtctctt acatcttctc cctgacgcct gtcctggatg gtgtgcgggg tcctgaggca    3120
tctgtcacac agacgccagt gtgcccccgt ggcctggcgg atgtggtgtt cctaccacat    3180
gccactcaag acaatgctca ccgtgcggag gctacgagga gggtcctgga gcgtctggtg    3240
ttggcacttg ggcctcttgg gccacaggca gttcaggttg gcctgctgtc ttacagtcat    3300
cggcccctcc cactgttccc actgaatggc tcccatgacc ttggcattat cttgcaaagg    3360
atccgtgaca tgcccctacat ggacccaagt gggaacaacc tggcacagc cgtggtcaca    3420
gctcacagat acatgttggc accagatgct cctgggcgcc gccagcacgt accaggggtg    3480
atggttctgc tagtgatga cccttgaga ggtgacatat tcagcccat ccgtgaggcc    3540
caggcttctg ggcttaatgt ggtgatgttg ggaatggctg gagcggaccc agagcagctg    3600
cgtcgcttgg cgccgggtat ggactctgtc cagaccttct tcgccgtgga tgatgggcca    3660
```

```
agcctggacc aggcagtcag tggtctggcc acagccctgt gtcaggcatc cttcactact    3720
cagccccggc cagagccctg cccagtgtat tgtccaaagg gccagaaggg ggaacctgga    3780
gagatgggcc tgagaggaca agttgggcct cctggcgacc ctggcctccc gggcaggacc    3840
ggtgctcccg gccccagggg gccccctgga agtgccactg ccaagggcga gagggggcttc   3900 cctggagcag atgggcgtcc aggcagccct ggccgcgccg ggaatcctgg accctggga    3960 gcccctggcc taaagggctc tccagggttg cctggccctc gtggggaccc gggagagcga    4020
ggacctcgag gcccaaaggg ggagccgggg gctcccggac aagtcatcgg aggtgaagga    4080
cctgggcttc ctgggcggaa aggggaccct ggaccatcgg gccccctgg acctcgtgga     4140 ccactggggg acccaggacc ccgtggcccc cagggcttc ctggaacagc catgaagggt     4200
gacaaaggcg atcgtgggga gcggggtccc cctggaccag gtgaaggtgg cattgctcct    4260
ggggagcctg ggctgccggg tcttcccgga agccctggac cccaaggccc cgttggcccc   4320
cctggaaaga aggagaaaaa aggtgactct gaggatggag ctccaggcct cccaggacaa    4380
cctgggtctc cgggtgagca gggcccacgg ggacctcctg gagctattgg ccccaaaggt   4440
gaccggggct ttccagggcc cctgggtgag gctggagaga agggcgaacg tggaccccca    4500
ggcccagcgg gatcccgggg gctgccaggg gttgctggac gtcctggagc caagggtcct    4560
gaagggccac caggacccac tggccgccaa ggagagaagg gggagcctgg tcgccctggg    4620
gaccctgcag tggtgggacc tgctgttgct ggacccaaag gagaaagggg agatgtgggg    4680
cccgctgggc ccagaggagc taccggagtc caagggaac ggggcccacc cggcttggtt     4740
cttcctggag accctggccc caaggggagac cctggagacc ggggtcccat tggccttact   4800
ggcagagcag gaccccagg tgactcaggg cctcctggag agaagggaga ccctgggcgg    4860
cctggccccc caggacctgt tggcccccga ggacgagatg gtgaagttgg agagaaaggt    4920
gacgagggtc ctccgggtga cccgggtttg cctggaaaag caggcgagcg tggccttcgg    4980
ggggcacctg gagttcgggg gcctgtgggt gaaaagggag accagggaga tcctggagag    5040
gatggacgaa atggcagccc tggatcatct ggacccaagg gtgaccgtgg ggagccgggt    5100
cccccaggac ccccgggacg gctggtagac acaggacctg gagccagaga gaaggagag    5160 cctggggacc gcggacaaga gggtcctcga gggcccaagg gtgatcctgg cctccctgga   5220
gcccctgggg aaagggcat tgaagggttt cggggacccc caggcccaca ggggaccca     5280 ggtgtccgag gccagcagg agaaaagggt gaccggggtc ccctgggct ggatggccgg     5340 agcggactgg atgggaaacc aggagccgct gggccctctg gccgaatgg tgctgcaggc   5400 aaagctgggg acccagggag agacgggctt ccaggcctcc gtggagaaca gggcctccct    5460
ggcccctctg gtcccctgg attaccggga aagccaggcg aggatggcaa acctggcctg   5520
aatggaaaaa acggagaacc tggggaccct ggagaagacg ggaggaaggg agagaaagga   5580
gattcaggcg cctctgggag agaaggtcgt gatggcccca agggtgagcg tggagctcct    5640
ggtatccttg gaccccaggg gcctccaggc ctccagggc cagtgggccc tcctggccag    5700
ggttttcctg gtgtcccagg aggcacgggc cccaagggtg accgtgggga gactggatcc    5760 aaagggagc agggcctccc tggagagcgt ggcctgcgag gagagcctgg aagtgtgccg    5820
aatgtggatc ggttgctgga aactgctggc atcaaggcat ctgccctgcg ggagatcgtg    5880
gagacctggg atgagagctc tggtagcttc ctgcctgtgc ccgaacggcg tcgaggcccc    5940
aagggggact caggcgaaca gggccccca ggcaaggagg gccccatcgg ctttcctgga    6000
```

```
gaacgcgggc tgaagggcga ccgtggagac cctggccctc aggggccacc tggtctggcc    6060
cttggggaga ggggcccccc cgggccttcc ggccttgccg gggagcctgg aaagcctggt    6120
attcccgggc tcccaggcag ggctgggggt gtgggagagg caggaaggcc aggagagagg    6180
ggagaacggg gagagaaagg agaacgtgga gaacagggca gagatggccc tcctggactc    6240
cctggaaccc ctgggccccc cggacccect ggccccaagg tgtctgtgga tgagccaggt    6300
cctggactct ctggagaaca gggacccect ggactcaagg gtgctaaggg ggagccgggc    6360
agcaatggtg accaaggtcc caaggagac aggggtgtgc caggcatcaa aggagaccgg    6420
ggagagcctg gaccgagggg tcaggacggc aacccgggtc taccaggaga gcgtggtatg    6480
gctgggcctg aagggaagcc gggtctgcag ggtccaagag gccccctgg cccagtgggt    6540 ggtcatggag accctggacc acctggtgcc ccgggtcttg ctggccctgc aggaccccaa    6600
ggaccttctg gcctgaaggg ggagcctgga gagacaggac ctccaggacg gggcctgact    6660
ggacctactg gagctgtggg acttcctgga ccccccggcc cttcaggcct tgtgggtcca    6720
caggggtctc caggtttgcc tggacaagtg ggggagacag ggaagccggg agccccaggt    6780
cgagatggtg ccagtggaaa agatggagac agagggagcc ctggtgtgcc agggtcacca    6840
ggtctgcctg gccctgtcgg acctaaagga gaacctggcc ccacggggc ccctggacag    6900 gctgtggtcg ggctccctgg agcaaaggga gagaagggag cccctggagg ccttgctgga    6960
gacctggtgg gtgagccggg agccaaaggt gaccgaggac tgccagggcc gcgaggcgag    7020
aagggtgaag ctggccgtgc aggggagccc ggagaccctg ggaagatgg tcagaaaggg    7080 gctccaggac ccaaaggttt caagggtgac ccaggagtcg gggtcccggg ctcccctggg    7140
cctcctggcc ctccaggtgt gaagggagat ctgggcctcc ctggcctgcc cggtgctcct    7200
ggtgttgttg ggttcccggg tcagacaggc cctcgaggag agatgggtca gccaggccct    7260
agtggagagc ggggtctggc aggcccccca gggagagaag gaatcccagg accctggg    7320 ccacctggac caccggggtc agtgggacca cctgggcct ctggactcaa aggagacaag    7380
ggagaccctg gagtagggct gcctggccc cgaggcgagc gtggggagcc aggcatccgg    7440
ggtgaagatg gccgccccgg ccaggaggga ccccgaggac tcacggggcc cctggcagc    7500 aggggagagc gtgggagaa gggtgatgtt gggagtgcag gactaaaggg tgacaaggga    7560
gactcagctg tgatcctggg gcctccaggc cacggggtg ccaaggggga catgggtgaa    7620
cgagggcctc ggggcttgga tggtgacaaa ggacctcggg gagacaatgg ggaccctggt    7680
gacaagggca gcaagggaga gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aagggagcct gtggccttga tggagagaag    7920
ggagacaagg gagaagctgg tccccaggc cgccccgggc tggcaggaca caaaggagag    7980 atggggagc ctggtgtgcc gggccagtcg ggggcccctg gcaaggaggg cctgatcggt    8040
cccaagggtg accgaggctt tgacgggcag ccaggcccca gggtgaccca gggcgagaaa    8100
ggggagcggg gaaccccagg aattgggggc ttcccaggcc ccagtggaaa tgatggctct    8160
gctggtcccc cagggccacc tggcagtgtt ggtcccagag gccccgaagg acttcagggc    8220
cagaagggtg agcgaggtcc ccccggagag agagtggtgg gggctcctgg ggtccctgga    8280
gctcctggcg agagagggga gcaggggcgg ccagggcctg ccggtcctcg aggcgagaag    8340
ggagaagctg cactgacgga ggatgacatc cggggctttg tgcgccaaga gatgagtcag    8400
```

```
cactgtgcct gccagggcca gttcatcgca tctggatcac gaccoctccc tagttatgct    8460
gcagacactg ccggctccca gctccatgct gtgcctgtgc tccgcgtctc tcatgcagag    8520
gaggaagagc gggtaccccc tgaggatgat gagtactctg aatactccga gtattctgtg    8580
gaggagtacc aggaccctga agctccttgg gatagtgatg acccctgttc cctgccactg    8640
gatgagggct cctgcactgc ctacaccctg cgctggtacc atcgggctgt gacaggcagc    8700
acagaggcct gtcacccttt tgtctatggt ggctgtggag ggaatgccaa ccgttttggg    8760
acccgtgagg cctgcgagcg ccgctgccca ccccgggtgg tccagagcca ggggacaggt    8820
actgcccagg acgaagcgg agtgaaacag actttgaatt ttgaccttct caagttggcg    8880
ggagacgtgg agtccaaccc tggacctacc tcctcggggc ctggaccccg gttcctgctg    8940
ctgctgccgc tgctgctgcc ccctgcggcc tcagcctccg accggccccg gggccgagac    9000
ccggtcaacc cagagaagct gctggtgatc actgtggcca cagctgaaac cgaggggtac    9060
ctgcgttttcc tgcgctctgc ggagttcttc aactacactg tgcggaccct gggcctggga    9120
gaggagtggc gagggggtga tgtggctcga acagttggtg gaggacagaa ggtccggtgg    9180
ttaaagaagg aaatggagaa atacgctgac cggaggata tgatcatcat gtttgtggat    9240
agctacgacg tgattctggc cggcagcccc acagagctgc tgaagaagtt cgtccagagt    9300
ggcagccgcc tgctcttctc tgcagagagc ttctgctggc ccgagtgggg gctggcggag    9360
cagtaccctg aggtgggcac ggggaagcgc ttcctcaatt ctggtggatt catcggtttt    9420
gccaccacca tccaccaaat cgtgcgccag tggaagtaca aggatgatga cgacgaccag    9480
ctgttctaca cacggctcta cctggaccca ggactgaggg agaaactcag ccttaatctg    9540
gatcataagt ctcggatctt tcagaacctc aacggggctt tagatgaagt ggttttaaag    9600
tttgatcgga accgtgtgcg tatccggaac gtggcctacg acacgctccc cattgtggtc    9660
catgaaacg gtcccactaa gctgcagctc aactacctgg gaaactacgt ccccaatggc    9720
tggactcctg agggaggctg tggcttctgc aaccaggacc ggaggacact cccggggggg    9780
cagcctcccc cccgggtgtt tctggccgtg tttgtggaac agcctactcc gtttctgccc    9840
cgcttcctgc agcggctgct actcctggac tatccccccg acagggtcac ccttttcctg    9900
cacaacaacg aggtcttcca tgaaccccac atcgctgact cctggccgca gctccaggac    9960
cacttctcag ctgtgaagct cgtggggccg gaggaggctc tgagcccagg cgaggccagg   10020
gacatggcca tggacctgtg tcggcaggac cccgagtgtg agttctactt cagcctggac   10080
gccgacgctg tcctcaccaa cctgcagacc ctgcgtatcc tcattgagga aacaggaag   10140
gtgatcgccc ccatgctgtc ccgccacggc aagctgtggt ccaacttctg gggcgccctg   10200
agccccgatg agtactacgc ccgctccgag gactacgtgg agctggtgca gcggaagcga   10260
gtgggtgtgt ggaatgtacc atacatctcc caggcctatg tgatccgggg tgataccctg   10320
cggatggagc tgcccagag ggatgtgttc tcggcagtg acacagaccc ggacatggcc   10380
ttctgtaaga gctttcgaga caagggcatc ttcctccatc tgagcaatca gcatgaattt   10440
ggccggctcc tggccacttc cagatacgac acggagcacc tgcacccga cctctggcag   10500
atcttcgaca accccgtcga ctggaaggag cagtacatcc acgagaacta cagccggcc   10560
ctggaagggg aaggaatcgt ggagcagcca tgcccggacg tgtactggtt cccactgctg   10620
tcagaacaaa tgtgtgatga gctggtggca gagatggagc actacggcca gtggtcaggc   10680
ggccggcatg aggattcaag gctggctgga ggctacgaga atgtgcccac cgtggacatc   10740
```

```
cacatgaagc aggtggggta cgaggaccag tggctgcagc tgctgcggac gtatgtgggc   10800
cccatgaccg agagcctgtt tcccggttac cacaccaagg cgcgggcggt gatgaacttt   10860
gtggttcgct accggccaga cgagcagccg tctctgcggc acaccacga ctcatccacc    10920 ttcaccctca acgttgccct caaccacaag ggcctggact atgagggagg tggctgccgc   10980
ttcctgcgct acgactgtgt gatctcctcc ccgaggaagg gctgggcact cctgcacccc   11040
ggccgcctca cccactacca cgaggggctg ccaacgacct ggggcacacg ctacatcatg   11100
gtgtcctttg tcgacccctg a                                             11121
```

<210> SEQ ID NO 26
<211> LENGTH: 3706
<212> TYPE: PRT
<213> ORGANISM: Artificial Sequence
<220> FEATURE:
<223> OTHER INFORMATION: Synthetic Construct

<400> SEQUENCE: 26

```
Met Thr Leu Arg Leu Leu Val Ala Ala Leu Cys Ala Gly Ile Leu Ala
 1               5                  10                  15

Glu Ala Pro Arg Val Arg Ala Gln His Arg Glu Arg Val Thr Cys Thr
            20                  25                  30

Arg Leu Tyr Ala Ala Asp Ile Val Phe Leu Leu Asp Gly Ser Ser Ser
        35                  40                  45

Ile Gly Arg Ser Asn Phe Arg Glu Val Arg Ser Phe Leu Glu Gly Leu
    50                  55                  60

Val Leu Pro Phe Ser Gly Ala Ala Ser Ala Gln Gly Val Arg Phe Ala
65                  70                  75                  80

Thr Val Gln Tyr Ser Asp Asp Pro Arg Thr Glu Phe Gly Leu Asp Ala
                85                  90                  95

Leu Gly Ser Gly Gly Asp Val Ile Arg Ala Ile Arg Glu Leu Ser Tyr
           100                 105                 110

Lys Gly Gly Asn Thr Arg Thr Gly Ala Ala Ile Leu His Val Ala Asp
       115                 120                 125

His Val Phe Leu Pro Gln Leu Ala Arg Pro Gly Val Pro Lys Val Cys
   130                 135                 140

Ile Leu Ile Thr Asp Gly Lys Ser Gln Asp Leu Val Asp Thr Ala Ala
145                 150                 155                 160

Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
```

-continued

```
              290                 295                 300
Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
                340                 345                 350

Ala Thr Gly Tyr Arg Val Thr Trp Arg Val Leu Ser Gly Gly Pro Thr
                355                 360                 365

Gln Gln Gln Glu Leu Gly Pro Gly Gln Gly Ser Val Leu Leu Arg Asp
                370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
                420                 425                 430

Leu Ser Trp Asn Leu Val Pro Glu Ala Arg Gly Tyr Arg Leu Glu Trp
                435                 440                 445

Arg Arg Glu Thr Gly Leu Glu Pro Pro Gln Lys Val Val Leu Pro Ser
                450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
                500                 505                 510

Asp Leu Gln Ala Thr Glu Leu Pro Gly Gln Arg Val Arg Val Ser Trp
                515                 520                 525

Ser Pro Val Pro Gly Ala Thr Gln Tyr Arg Ile Ile Val Arg Ser Thr
530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
                580                 585                 590

Arg Glu Pro Glu Thr Pro Leu Ala Val Pro Gly Leu Arg Val Val Val
                595                 600                 605

Ser Asp Ala Thr Arg Val Arg Val Ala Trp Gly Pro Val Pro Gly Ala
610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
                660                 665                 670

Glu Gly Pro Ala Ala Val Ile Val Ala Arg Thr Asp Pro Leu Gly Pro
                675                 680                 685

Val Arg Thr Val His Val Thr Gln Ala Ser Ser Ser Ser Val Thr Ile
                690                 695                 700

Thr Trp Thr Arg Val Pro Gly Ala Thr Gly Tyr Arg Val Ser Trp His
705                 710                 715                 720
```

```
Ser Ala His Gly Pro Glu Lys Ser Gln Leu Val Ser Gly Glu Ala Thr
            725                 730                 735

Val Ala Glu Leu Asp Gly Leu Glu Pro Asp Thr Glu Tyr Thr Val His
        740                 745                 750

Val Arg Ala His Val Ala Gly Val Asp Gly Pro Pro Ala Ser Val Val
            755                 760                 765

Val Arg Thr Ala Pro Glu Pro Val Gly Arg Val Ser Arg Leu Gln Ile
        770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
            980                 985                 990

Arg Gly Pro Gly Gln Glu Val Pro Gly Ser Pro Gln Thr Leu Pro Gly
        995                 1000                1005

Ile Ser Ser Ser Gln Arg Val Thr Gly Leu Glu Pro Gly Val Ser Tyr
    1010                1015                1020

Ile Phe Ser Leu Thr Pro Val Leu Asp Gly Val Arg Gly Pro Glu Ala
1025                1030                1035                1040

Ser Val Thr Gln Thr Pro Val Cys Pro Arg Gly Leu Ala Asp Val Val
                1045                1050                1055

Phe Leu Pro His Ala Thr Gln Asp Asn Ala His Arg Ala Glu Ala Thr
            1060                1065                1070

Arg Arg Val Leu Glu Arg Leu Val Leu Ala Leu Gly Pro Leu Gly Pro
        1075                1080                1085

Gln Ala Val Gln Val Gly Leu Leu Ser Tyr Ser His Arg Pro Ser Pro
    1090                1095                1100

Leu Phe Pro Leu Asn Gly Ser His Asp Leu Gly Ile Ile Leu Gln Arg
1105                1110                1115                1120

Ile Arg Asp Met Pro Tyr Met Asp Pro Ser Gly Asn Asn Leu Gly Thr
                1125                1130                1135
```

```
Ala Val Val Thr Ala His Arg Tyr Met Leu Ala Pro Asp Ala Pro Gly
            1140                1145                1150

Arg Arg Gln His Val Pro Gly Val Met Val Leu Leu Val Asp Glu Pro
        1155                1160                1165

Leu Arg Gly Asp Ile Phe Ser Pro Ile Arg Glu Ala Gln Ala Ser Gly
    1170                1175                1180

Leu Asn Val Val Met Leu Gly Met Ala Gly Ala Asp Pro Glu Gln Leu
1185                1190                1195                1200

Arg Arg Leu Ala Pro Gly Met Asp Ser Val Gln Thr Phe Phe Ala Val
            1205                1210                1215

Asp Asp Gly Pro Ser Leu Asp Gln Ala Val Ser Gly Leu Ala Thr Ala
            1220                1225                1230

Leu Cys Gln Ala Ser Phe Thr Thr Gln Pro Arg Pro Glu Pro Cys Pro
            1235                1240                1245

Val Tyr Cys Pro Lys Gly Gln Lys Gly Glu Pro Gly Glu Met Gly Leu
            1250                1255                1260

Arg Gly Gln Val Gly Pro Pro Gly Asp Pro Gly Leu Pro Gly Arg Thr
1265                1270                1275                1280

Gly Ala Pro Gly Pro Gln Gly Pro Pro Gly Ser Ala Thr Ala Lys Gly
            1285                1290                1295

Glu Arg Gly Phe Pro Gly Ala Asp Gly Arg Pro Gly Ser Pro Gly Arg
            1300                1305                1310

Ala Gly Asn Pro Gly Thr Pro Gly Ala Pro Gly Leu Lys Gly Ser Pro
            1315                1320                1325

Gly Leu Pro Gly Pro Arg Gly Asp Pro Gly Glu Arg Gly Pro Arg Gly
            1330                1335                1340

Pro Lys Gly Glu Pro Gly Ala Pro Gly Gln Val Ile Gly Gly Glu Gly
1345                1350                1355                1360

Pro Gly Leu Pro Gly Arg Lys Gly Asp Pro Gly Ser Gly Pro Pro
            1365                1370                1375

Gly Pro Arg Gly Pro Leu Gly Asp Pro Gly Pro Arg Gly Pro Pro Gly
            1380                1385                1390

Leu Pro Gly Thr Ala Met Lys Gly Asp Lys Gly Asp Arg Gly Glu Arg
            1395                1400                1405

Gly Pro Pro Gly Pro Gly Glu Gly Gly Ile Ala Pro Gly Glu Pro Gly
            1410                1415                1420

Leu Pro Gly Leu Pro Gly Ser Pro Gly Pro Gln Gly Pro Val Gly Pro
1425                1430                1435                1440

Pro Gly Lys Lys Gly Glu Lys Gly Asp Ser Glu Asp Gly Ala Pro Gly
            1445                1450                1455

Leu Pro Gly Gln Pro Gly Ser Pro Gly Glu Gln Gly Pro Arg Gly Pro
            1460                1465                1470

Pro Gly Ala Ile Gly Pro Lys Gly Asp Arg Gly Phe Pro Gly Pro Leu
            1475                1480                1485

Gly Glu Ala Gly Glu Lys Gly Glu Arg Gly Pro Pro Gly Pro Ala Gly
            1490                1495                1500

Ser Arg Gly Leu Pro Gly Val Ala Gly Arg Pro Gly Ala Lys Gly Pro
1505                1510                1515                1520

Glu Gly Pro Pro Gly Pro Thr Gly Arg Gln Gly Glu Lys Gly Glu Pro
            1525                1530                1535

Gly Arg Pro Gly Asp Pro Ala Val Val Gly Pro Ala Val Ala Gly Pro
            1540                1545                1550

Lys Gly Glu Lys Gly Asp Val Gly Pro Ala Gly Pro Arg Gly Ala Thr
```

|           |           | 1555      |           |           |           | 1560      |           |           |           | 1565      |           |

Gly Val Gln Gly Glu Arg Gly Pro Pro Gly Leu Val Leu Pro Gly Asp
            1570                1575                1580

Pro Gly Pro Lys Gly Asp Pro Gly Asp Arg Gly Pro Ile Gly Leu Thr
1585                1590                1595                1600

Gly Arg Ala Gly Pro Pro Gly Asp Ser Gly Pro Pro Gly Glu Lys Gly
            1605                1610                1615

Asp Pro Gly Arg Pro Gly Pro Pro Gly Pro Val Gly Pro Arg Gly Arg
            1620                1625                1630

Asp Gly Glu Val Gly Glu Lys Gly Asp Glu Gly Pro Pro Gly Asp Pro
            1635                1640                1645

Gly Leu Pro Gly Lys Ala Gly Glu Arg Gly Leu Arg Gly Ala Pro Gly
            1650                1655                1660

Val Arg Gly Pro Val Gly Glu Lys Gly Asp Gln Gly Asp Pro Gly Glu
1665                1670                1675                1680

Asp Gly Arg Asn Gly Ser Pro Gly Ser Ser Gly Pro Lys Gly Asp Arg
            1685                1690                1695

Gly Glu Pro Gly Pro Pro Gly Pro Pro Gly Arg Leu Val Asp Thr Gly
            1700                1705                1710

Pro Gly Ala Arg Glu Lys Gly Glu Pro Gly Asp Arg Gly Gln Glu Gly
            1715                1720                1725

Pro Arg Gly Pro Lys Gly Asp Pro Gly Leu Pro Gly Ala Pro Gly Glu
            1730                1735                1740

Arg Gly Ile Glu Gly Phe Arg Gly Pro Pro Gly Pro Gln Gly Asp Pro
1745                1750                1755                1760

Gly Val Arg Gly Pro Ala Gly Glu Lys Gly Asp Arg Gly Pro Pro Gly
            1765                1770                1775

Leu Asp Gly Arg Ser Gly Leu Asp Gly Lys Pro Gly Ala Ala Gly Pro
            1780                1785                1790

Ser Gly Pro Asn Gly Ala Ala Gly Lys Ala Gly Asp Pro Gly Arg Asp
            1795                1800                1805

Gly Leu Pro Gly Leu Arg Gly Glu Gln Gly Leu Pro Gly Pro Ser Gly
            1810                1815                1820

Pro Pro Gly Leu Pro Gly Lys Pro Gly Glu Asp Gly Lys Pro Gly Leu
1825                1830                1835                1840

Asn Gly Lys Asn Gly Glu Pro Gly Asp Pro Gly Glu Asp Gly Arg Lys
            1845                1850                1855

Gly Glu Lys Gly Asp Ser Gly Ala Ser Gly Arg Glu Gly Arg Asp Gly
            1860                1865                1870

Pro Lys Gly Glu Arg Gly Ala Pro Gly Ile Leu Gly Pro Gln Gly Pro
            1875                1880                1885

Pro Gly Leu Pro Gly Pro Val Gly Pro Pro Gly Gln Gly Phe Pro Gly
            1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
            1925                1930                1935

Gly Ser Val Pro Asn Val Asp Arg Leu Leu Glu Thr Ala Gly Ile Lys
            1940                1945                1950

Ala Ser Ala Leu Arg Glu Ile Val Glu Thr Trp Asp Glu Ser Ser Gly
            1955                1960                1965

Ser Phe Leu Pro Val Pro Glu Arg Arg Gly Pro Lys Gly Asp Ser
            1970                1975                1980

```
Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
                2005                2010                2015

Pro Gly Leu Ala Leu Gly Glu Arg Gly Pro Pro Gly Pro Ser Gly Leu
            2020                2025                2030

Ala Gly Glu Pro Gly Lys Pro Gly Ile Pro Gly Leu Pro Gly Arg Ala
        2035                2040                2045

Gly Gly Val Gly Glu Ala Gly Arg Pro Gly Glu Arg Gly Glu Arg Gly
    2050                2055                2060

Glu Lys Gly Glu Arg Gly Glu Gln Gly Arg Asp Gly Pro Pro Gly Leu
2065                2070                2075                2080

Pro Gly Thr Pro Gly Pro Pro Gly Pro Pro Gly Pro Lys Val Ser Val
            2085                2090                2095

Asp Glu Pro Gly Pro Gly Leu Ser Gly Glu Gln Gly Pro Pro Gly Leu
            2100                2105                2110

Lys Gly Ala Lys Gly Glu Pro Gly Ser Asn Gly Asp Gln Gly Pro Lys
        2115                2120                2125

Gly Asp Arg Gly Val Pro Gly Ile Lys Gly Asp Arg Gly Glu Pro Gly
    2130                2135                2140

Pro Arg Gly Gln Asp Gly Asn Pro Gly Leu Pro Gly Glu Arg Gly Met
2145                2150                2155                2160

Ala Gly Pro Glu Gly Lys Pro Gly Leu Gln Gly Pro Arg Gly Pro Pro
            2165                2170                2175

Gly Pro Val Gly Gly His Gly Asp Pro Gly Pro Pro Gly Ala Pro Gly
            2180                2185                2190

Leu Ala Gly Pro Ala Gly Pro Gln Gly Pro Ser Gly Leu Lys Gly Glu
            2195                2200                2205

Pro Gly Glu Thr Gly Pro Pro Gly Arg Gly Leu Thr Gly Pro Thr Gly
            2210                2215                2220

Ala Val Gly Leu Pro Gly Pro Pro Gly Pro Ser Gly Leu Val Gly Pro
2225                2230                2235                2240

Gln Gly Ser Pro Gly Leu Pro Gly Gln Val Gly Glu Thr Gly Lys Pro
            2245                2250                2255

Gly Ala Pro Gly Arg Asp Gly Ala Ser Gly Lys Asp Gly Asp Arg Gly
            2260                2265                2270

Ser Pro Gly Val Pro Gly Ser Pro Gly Leu Pro Gly Pro Val Gly Pro
            2275                2280                2285

Lys Gly Glu Pro Gly Pro Thr Gly Ala Pro Gly Gln Ala Val Val Gly
        2290                2295                2300

Leu Pro Gly Ala Lys Gly Glu Lys Gly Ala Pro Gly Gly Leu Ala Gly
2305                2310                2315                2320

Asp Leu Val Gly Glu Pro Gly Ala Lys Gly Asp Arg Gly Leu Pro Gly
            2325                2330                2335

Pro Arg Gly Glu Lys Gly Glu Ala Gly Arg Ala Gly Glu Pro Gly Asp
            2340                2345                2350

Pro Gly Glu Asp Gly Gln Lys Gly Ala Pro Gly Pro Lys Gly Phe Lys
            2355                2360                2365

Gly Asp Pro Gly Val Gly Val Pro Gly Ser Pro Gly Pro Pro Gly Pro
            2370                2375                2380

Pro Gly Val Lys Gly Asp Leu Gly Leu Pro Gly Leu Pro Gly Ala Pro
2385                2390                2395                2400
```

Gly Val Val Gly Phe Pro Gly Gln Thr Gly Pro Arg Gly Glu Met Gly
                2405                2410                2415

Gln Pro Gly Pro Ser Gly Glu Arg Gly Leu Ala Gly Pro Pro Gly Arg
            2420                2425                2430

Glu Gly Ile Pro Gly Pro Leu Gly Pro Pro Gly Pro Pro Gly Ser Val
        2435                2440                2445

Gly Pro Pro Gly Ala Ser Gly Leu Lys Gly Asp Lys Gly Asp Pro Gly
    2450                2455                2460

Val Gly Leu Pro Gly Pro Arg Gly Glu Arg Gly Glu Pro Gly Ile Arg
2465                2470                2475                2480

Gly Glu Asp Gly Arg Pro Gly Gln Glu Gly Pro Arg Gly Leu Thr Gly
                2485                2490                2495

Pro Pro Gly Ser Arg Gly Glu Arg Gly Glu Lys Gly Asp Val Gly Ser
            2500                2505                2510

Ala Gly Leu Lys Gly Asp Lys Gly Asp Ser Ala Val Ile Leu Gly Pro
        2515                2520                2525

Pro Gly Pro Arg Gly Ala Lys Gly Asp Met Gly Glu Arg Gly Pro Arg
    2530                2535                2540

Gly Leu Asp Gly Asp Lys Gly Pro Arg Gly Asp Asn Gly Asp Pro Gly
2545                2550                2555                2560

Asp Lys Gly Ser Lys Gly Glu Pro Gly Asp Lys Gly Ser Ala Gly Leu
                2565                2570                2575

Pro Gly Leu Arg Gly Leu Leu Gly Pro Gln Gly Gln Pro Gly Ala Ala
            2580                2585                2590

Gly Ile Pro Gly Asp Pro Gly Ser Pro Gly Lys Asp Gly Val Pro Gly
        2595                2600                2605

Ile Arg Gly Glu Lys Gly Asp Val Gly Phe Met Gly Pro Arg Gly Leu
    2610                2615                2620

Lys Gly Glu Arg Gly Val Lys Gly Ala Cys Gly Leu Asp Gly Glu Lys
2625                2630                2635                2640

Gly Asp Lys Gly Glu Ala Gly Pro Pro Gly Arg Pro Gly Leu Ala Gly
                2645                2650                2655

His Lys Gly Glu Met Gly Glu Pro Gly Val Pro Gly Gln Ser Gly Ala
            2660                2665                2670

Pro Gly Lys Glu Gly Leu Ile Gly Pro Lys Gly Asp Arg Gly Phe Asp
        2675                2680                2685

Gly Gln Pro Gly Pro Lys Gly Asp Gln Gly Glu Lys Gly Glu Arg Gly
    2690                2695                2700

Thr Pro Gly Ile Gly Gly Phe Pro Gly Pro Ser Gly Asn Asp Gly Ser
2705                2710                2715                2720

Ala Gly Pro Pro Gly Pro Pro Gly Ser Val Gly Pro Arg Gly Pro Glu
                2725                2730                2735

Gly Leu Gln Gly Gln Lys Gly Glu Arg Gly Pro Pro Gly Glu Arg Val
            2740                2745                2750

Val Gly Ala Pro Gly Val Pro Gly Ala Pro Gly Glu Arg Gly Glu Gln
        2755                2760                2765

Gly Arg Pro Gly Pro Ala Gly Pro Arg Gly Glu Lys Gly Glu Ala Ala
    2770                2775                2780

Leu Thr Glu Asp Asp Ile Arg Gly Phe Val Arg Gln Glu Met Ser Gln
2785                2790                2795                2800

His Cys Ala Cys Gln Gly Gln Phe Ile Ala Ser Gly Ser Arg Pro Leu
                2805                2810                2815

Pro Ser Tyr Ala Ala Asp Thr Ala Gly Ser Gln Leu His Ala Val Pro

```
                    2820               2825               2830
        Val Leu Arg Val Ser His Ala Glu Glu Glu Arg Val Pro Pro Glu
                    2835               2840               2845

Asp Asp Glu Tyr Ser Glu Tyr Ser Glu Tyr Ser Val Glu Glu Tyr Gln
                    2850               2855               2860

Asp Pro Glu Ala Pro Trp Asp Ser Asp Pro Cys Ser Leu Pro Leu
        2865               2870               2875               2880

Asp Glu Gly Ser Cys Thr Ala Tyr Thr Leu Arg Trp Tyr His Arg Ala
                    2885               2890               2895

Val Thr Gly Ser Thr Glu Ala Cys His Pro Phe Val Tyr Gly Gly Cys
                    2900               2905               2910

Gly Gly Asn Ala Asn Arg Phe Gly Thr Arg Glu Ala Cys Glu Arg Arg
                    2915               2920               2925

Cys Pro Pro Arg Val Val Gln Ser Gln Gly Thr Gly Thr Ala Gln Asp
                    2930               2935               2940

Gly Ser Gly Val Lys Gln Thr Leu Asn Phe Asp Leu Leu Lys Leu Ala
        2945               2950               2955               2960

Gly Asp Val Glu Ser Asn Pro Gly Pro Thr Ser Ser Gly Pro Gly Pro
                    2965               2970               2975

Arg Phe Leu Leu Leu Leu Pro Leu Leu Pro Ala Ala Ser Ala
                    2980               2985               2990

Ser Asp Arg Pro Arg Gly Arg Asp Pro Val Asn Pro Glu Lys Leu Leu
                    2995               3000               3005

Val Ile Thr Val Ala Thr Ala Glu Thr Glu Gly Tyr Leu Arg Phe Leu
                    3010               3015               3020

Arg Ser Ala Glu Phe Phe Asn Tyr Thr Val Arg Thr Leu Gly Leu Gly
        3025               3030               3035               3040

Glu Glu Trp Arg Gly Gly Asp Val Ala Arg Thr Val Gly Gly Gly Gln
                    3045               3050               3055

Lys Val Arg Trp Leu Lys Lys Glu Met Glu Lys Tyr Ala Asp Arg Glu
                    3060               3065               3070

Asp Met Ile Ile Met Phe Val Asp Ser Tyr Asp Val Ile Leu Ala Gly
                    3075               3080               3085

Ser Pro Thr Glu Leu Leu Lys Lys Phe Val Gln Ser Gly Ser Arg Leu
                    3090               3095               3100

Leu Phe Ser Ala Glu Ser Phe Cys Trp Pro Glu Trp Gly Leu Ala Glu
        3105               3110               3115               3120

Gln Tyr Pro Glu Val Gly Thr Gly Lys Arg Phe Leu Asn Ser Gly Gly
                    3125               3130               3135

Phe Ile Gly Phe Ala Thr Thr Ile His Gln Ile Val Arg Gln Trp Lys
                    3140               3145               3150

Tyr Lys Asp Asp Asp Asp Gln Leu Phe Tyr Thr Arg Leu Tyr Leu
                    3155               3160               3165

Asp Pro Gly Leu Arg Glu Lys Leu Ser Leu Asn Leu Asp His Lys Ser
                    3170               3175               3180

Arg Ile Phe Gln Asn Leu Asn Gly Ala Leu Asp Glu Val Val Leu Lys
        3185               3190               3195               3200

Phe Asp Arg Asn Arg Val Arg Ile Arg Asn Val Ala Tyr Asp Thr Leu
                    3205               3210               3215

Pro Ile Val Val His Gly Asn Gly Pro Thr Lys Leu Gln Leu Asn Tyr
                    3220               3225               3230

Leu Gly Asn Tyr Val Pro Asn Gly Trp Thr Pro Glu Gly Gly Cys Gly
                    3235               3240               3245
```

```
Phe Cys Asn Gln Asp Arg Arg Thr Leu Pro Gly Gly Gln Pro Pro Pro
        3250                3255                3260

Arg Val Phe Leu Ala Val Phe Val Glu Gln Pro Thr Pro Phe Leu Pro
3265                3270                3275                3280

Arg Phe Leu Gln Arg Leu Leu Leu Leu Asp Tyr Pro Pro Asp Arg Val
            3285                3290                3295

Thr Leu Phe Leu His Asn Asn Glu Val Phe His Glu Pro His Ile Ala
        3300                3305                3310

Asp Ser Trp Pro Gln Leu Gln Asp His Phe Ser Ala Val Lys Leu Val
        3315                3320                3325

Gly Pro Glu Glu Ala Leu Ser Pro Gly Glu Ala Arg Asp Met Ala Met
        3330                3335                3340

Asp Leu Cys Arg Gln Asp Pro Glu Cys Glu Phe Tyr Phe Ser Leu Asp
3345                3350                3355                3360

Ala Asp Ala Val Leu Thr Asn Leu Gln Thr Leu Arg Ile Leu Ile Glu
            3365                3370                3375

Glu Asn Arg Lys Val Ile Ala Pro Met Leu Ser Arg His Gly Lys Leu
        3380                3385                3390

Trp Ser Asn Phe Trp Gly Ala Leu Ser Pro Asp Glu Tyr Tyr Ala Arg
        3395                3400                3405

Ser Glu Asp Tyr Val Glu Leu Val Gln Arg Lys Arg Val Gly Val Trp
        3410                3415                3420

Asn Val Pro Tyr Ile Ser Gln Ala Tyr Val Ile Arg Gly Asp Thr Leu
3425                3430                3435                3440

Arg Met Glu Leu Pro Gln Arg Asp Val Phe Ser Gly Ser Asp Thr Asp
            3445                3450                3455

Pro Asp Met Ala Phe Cys Lys Ser Phe Arg Asp Lys Gly Ile Phe Leu
        3460                3465                3470

His Leu Ser Asn Gln His Glu Phe Gly Arg Leu Leu Ala Thr Ser Arg
        3475                3480                3485

Tyr Asp Thr Glu His Leu His Pro Asp Leu Trp Gln Ile Phe Asp Asn
        3490                3495                3500

Pro Val Asp Trp Lys Glu Gln Tyr Ile His Glu Asn Tyr Ser Arg Ala
3505                3510                3515                3520

Leu Glu Gly Glu Gly Ile Val Glu Gln Pro Cys Pro Asp Val Tyr Trp
            3525                3530                3535

Phe Pro Leu Leu Ser Glu Gln Met Cys Asp Glu Leu Val Ala Glu Met
        3540                3545                3550

Glu His Tyr Gly Gln Trp Ser Gly Gly Arg His Glu Asp Ser Arg Leu
        3555                3560                3565

Ala Gly Gly Tyr Glu Asn Val Pro Thr Val Asp Ile His Met Lys Gln
        3570                3575                3580

Val Gly Tyr Glu Asp Gln Trp Leu Gln Leu Leu Arg Thr Tyr Val Gly
3585                3590                3595                3600

Pro Met Thr Glu Ser Leu Phe Pro Gly Tyr His Thr Lys Ala Arg Ala
            3605                3610                3615

Val Met Asn Phe Val Val Arg Tyr Arg Pro Asp Glu Gln Pro Ser Leu
        3620                3625                3630

Arg Pro His His Asp Ser Ser Thr Phe Thr Leu Asn Val Ala Leu Asn
        3635                3640                3645

His Lys Gly Leu Asp Tyr Glu Gly Gly Gly Cys Arg Phe Leu Arg Tyr
        3650                3655                3660
```

-continued

Asp Cys Val Ile Ser Ser Pro Arg Lys Gly Trp Ala Leu Leu His Pro
3665                3670                3675                3680

Gly Arg Leu Thr His Tyr His Glu Gly Leu Pro Thr Thr Trp Gly Thr
            3685                3690                3695

Arg Tyr Ile Met Val Ser Phe Val Asp Pro
            3700                3705

<210> SEQ ID NO 27
<211> LENGTH: 11121
<212> TYPE: DNA
<213> ORGANISM: Artificial Sequence
<220> FEATURE:
<223> OTHER INFORMATION: Synthetic Construct

<400> SEQUENCE: 27

```
atgacctcct cggggcctgg accccggttc ctgctgctgc tgccgctgct gctgccccct      60
gcggcctcag cctccgaccg gccccggggc cgagacccgg tcaacccaga gaagctgctg     120
gtgatcactg tggccacagc tgaaaccgag gggtacctgc gtttcctgcg ctctgcggag     180
ttcttcaact acactgtgcg gaccctgggc ctgggagagg agtggcgagg gggtgatgtg     240
gctcgaacag ttggtggagg acagaaggtc cggtggttaa agaaggaaat ggagaaatac     300
gctgaccggg aggatatgat catcatgttt gtggatagct acgacgtgat tctggccggc     360
agccccacag agctgctgaa gaagttcgtc cagagtggca gccgcctgct cttctctgca     420
gagagcttct gctggcccga gtggggggctg gcggagcagt accctgaggt gggcacgggg     480
aagcgcttcc tcaattctgg tggattcatc ggttttgcca ccaccatcca ccaaatcgtg     540
cgccagtgga agtacaagga tgatgacgac gaccagctgt tctacacacg gctctacctg     600
gacccaggac tgagggagaa actcagcctt aatctggatc ataagtctcg gatcttcagg     660
aacctcaacg gggctttaga tgaagtggtt ttaaagtttg atcggaaccg tgtgcgtatc     720
cggaacgtgg cctacgacac gctccccatt gtggtccatg aaacggtcc cactaagctg     780
cagctcaact acctgggaaa ctacgtcccc aatggctgga ctcctgaggg aggctgtggc     840
ttctgcaacc aggaccggag gacactcccg gggggggcagc ctccccccg ggtgtttctg     900
gccgtgtttg tggaacagcc tactccgttt ctgccccgct cctgcagcg gctgctactc     960
ctggactatc cccccgacag ggtcacccctt ttcctgcaca caacgaggt cttccatgaa    1020
ccccacatcg ctgactcctg gccgcagctc caggaccact tctcagctgt gaagctcgtg    1080
gggccggagg aggctctgag cccaggcgag gccagggaca tggccatgga cctgtgtcgg    1140
caggaccccg agtgtgagtt ctacttcagc ctggacgccg acgctgtcct caccaacctg    1200
cagaccctgc gtatcctcat tgaggagaac aggaaggtga tcgcccccat gctgtcccgc    1260
cacggcaagc tgtggtccaa cttctggggc gccctgagcc ccgatgagta ctacgcccgc    1320
tccgaggact acgtggagct ggtgcagcgg aagcgagtgg gtgtgtggaa tgtaccatac    1380
atctcccagg cctatgtgat ccggggtgat acctgcgga tggagctgcc ccagagggat    1440
gtgttctcgg gcagtgacac agacccggac atggccttct gtaagagctt cgagacaag    1500
ggcatcttcc tccatctgag caatcagcat gaatttggcc ggctcctggc cacttccaga    1560
tacgacacgg agcacctgca ccccgacctc tggcagatct cgacaaccc cgtcgactgg    1620
aaggagcagt acatccacga gaactacagc cgggccctgg aagggaagg aatcgtggag    1680
cagccatgcc cggacgtgta ctggttccca ctgctgtcag aacaaatgtg tgatgagctg    1740
gtggcagaga tggagcacta cggccagtgg tcaggcggcc ggcatgagga ttcaaggctg    1800
```

```
gctggaggct acgagaatgt gcccaccgtg gacatccaca tgaagcaggt ggggtacgag    1860
gaccagtggc tgcagctgct gcggacgtat gtgggcccca tgaccgagag cctgtttccc    1920
ggttaccaca ccaaggcgcg ggcggtgatg aactttgtgg ttcgctaccg gccagacgag    1980
cagccgtctc tgcggccaca ccacgactca tccaccttca ccctcaacgt tgccctcaac    2040
cacaagggcc tggactatga gggaggtggc tgccgcttcc tgcgctacga ctgtgtgatc    2100
tcctccccga ggaagggctg ggcactcctg caccccggcc gcctcaccca ctaccacgag    2160
gggctgccaa cgacctgggg cacacgctac atcatggtgt cctttgtcga ccccggaagc    2220
ggagtgaaac agactttgaa ttttgacctt ctcaagttgg cgggagacgt ggagtccaac    2280
cctggaccta cgctgcggct tctggtggcc gcgctctgcg ccgggatcct ggcagaggcg    2340
ccccgagtgc gagcccagca cagggagaga gtgacctgca cgcgccttta cgccgctgac    2400
attgtgttct tactggatgg ctcctcatcc attggccgca gcaatttccg cgaggtccgc    2460
agctttctcg aagggctggt gctgcctttc tctggagcag ccagtgcaca gggtgtgcgc    2520
tttgccacag tgcagtacag cgatgaccca cggacagagt tcggcctgga tgcacttggc    2580
tctgggggtg atgtgatccg cgccatccgt gagcttagct acaagggggg caacactcgc    2640
acaggggctg caattctcca tgtggctgac catgtcttcc tgccccagct ggcccgacct    2700
ggtgtcccca aggtctgcat cctgatcaca gacgggaagt cccaggacct ggtggacaca    2760
gctgcccaaa ggctgaaggg gcaggggtc aagctatttg ctgtggggat caagaatgct    2820
gaccctgagg agctgaagcg agttgcctca cagcccacca gtgacttctt cttcttcgtc    2880
aatgacttca gcatcttgag gacactactg cccctcgttt cccggagagt gtgcacgact    2940
gctggtggcg tgcctgtgac ccgacctccg gatgactcga cctctgctcc acgagacctg    3000
gtgctgtctg agccaagcag ccaatccttg agagtacagt ggacagcggc cagtggccct    3060
gtgactggct acaaggtcca gtacactcct ctgacggggc tgggacagcc actgccgagt    3120
gagcggcagg aggtgaacgt cccagctggt gagaccagtg tgcggctgcg gggtctccgg    3180
ccactgaccg agtaccaagt gactgtgatt gccctctacg ccaacagcat cggggaggct    3240
gtgagcggga cagctcggac cactgcccta gaagggccgg aactgaccat ccagaatacc    3300
acagcccaca gcctcctggt ggcctggcgg agtgtgccag gtgccactgg ctaccgtgtg    3360
acatggcggg tcctcagtgg tgggcccaca cagcagcagg agctgggccc tgggcagggt    3420
tcagtgttgc tgcgtgactt ggagcctggc acggactatg aggtgaccgt gagcaccacta    3480
tttggccgca gtgtggggcc cgccacttcc ctgatggctc gcactgacgc ttctgttgag    3540
cagaccctgc gcccggtcat cctgggcccc acatccatcc tcctttcctg gaacttggtg    3600
cctgaggccc gtggctaccg gttggaatgg cggcgtgaga ctggcttgga gccaccgcag    3660
aaggtggtac tgccctctga tgtgacccgc taccagttgg atgggctgca gccgggcact    3720
gagtaccgcc tcacactcta cactctgctg gagggcacg aggtggccac ccctgcaacc    3780
gtggttccca ctggaccaga gctgcctgtg agccctgtaa cagacctgca agccaccgag    3840
ctgcccgggc agcgggtgcg agtgtcctgg agcccagtcc ctggtgccac ccagtaccgc    3900
atcattgtgc gcagcacccca ggggttgag cggaccctgg tgcttcctgg gagtcagaca    3960
gcattcgact tggatgacgt tcaggctggg cttagctaca ctgtgcgggt gtctgctcga    4020
gtgggtcccg tgagggcag tgccagtgtc ctcactgtcc gccgggagcc ggaaactcca    4080
cttgctgttc cagggctgcg ggttgtggtg tcagatgcaa cgcgagtgag ggtggcctgg    4140
ggacccgtcc ctggagccag tggatttcgg attagctgga gcacaggcag tggtccggag    4200
```

-continued

```
tccagccaga cactgccccc agactctact gccacagaca tcacagggct gcagcctgga  4260
accacctacc aggtggctgt gtcggtactg cgaggcagag aggagggccc tgctgcagtc  4320
atcgtggctc gaacggaccc actgggccca gtgaggacgg tccatgtgac tcaggccagc  4380
agctcatctg tcaccattac ctggaccagg gttcctggcg ccacaggata cagggtttcc  4440
tggcactcag cccacggccc agagaaatcc cagttggttt ctggggaggc cacggtggct  4500
gagctggatg gactggagcc agatactgag tatacggtgc atgtgagggc ccatgtggct  4560
ggcgtggatg ggcccctgc ctctgtggtt gtgaggactg ccctgagcc tgtgggtcgt  4620
gtgtcgaggc tgcagatcct caatgcttcc agcgacgttc tacggatcac ctgggtaggg  4680
gtcactggag ccacagctta cagactggcc tggggccgga gtgaaggcgg ccccatgagg  4740
caccagatac tccaggaaa cacagactct gcagagatcc ggggtctcga aggtggagtc  4800
agctactcag tgcgagtgac tgcacttgtc ggggaccgcg agggcacacc tgtctccatt  4860
gttgtcacta cgccgcctga ggctccgcca gccctgggga cgcttcacgt ggtgcagcgc  4920
ggggagcact cgctgaggct gcgctgggag ccggtgccca gagcgcaggg cttccttctg  4980
cactggcaac ctgagggtgg ccaggaacag tcccgggtcc tggggcccga gctcagcagc  5040
tatcacctgg acgggctgga gccagcgaca cagtaccgcg tgaggctgag tgtcctaggg  5100
ccagctggag aagggccctc tgcagaggtg actgcgcgca ctgagtcacc tcgtgttcca  5160
agcattgaac tacgtgtggt ggacacctcg atcgactcgg tgactttggc ctggactcca  5220
gtgtccaggg catccagcta catcctatcc tggcggccac tcagaggccc tggccaggaa  5280
gtgcctgggt ccccgcagac acttccaggg atctcaagct cccagcgggt gacagggcta  5340
gagcctggcg tctcttacat cttctcccctg acgcctgtcc tggatggtgt gcggggtcct  5400
gaggcatctg tcacacagac gccagtgtgc cccgtggcc tggcggatgt ggtgttccta  5460
ccacatgcca ctcaagacaa tgctcaccgt gcggaggcta cgaggagggt cctggagcgt  5520
ctggtgttgg cacttgggcc tcttgggcca caggcagttc aggttggcct gctgtcttac  5580
agtcatcggc cctccccact gttcccactg aatggctccc atgaccttgg cattatcttg  5640
caaaggatcc gtgacatgcc ctacatggac ccaagtggga caacctggg cacagccgtg  5700
gtcacagctc acagatacat gttggcacca gatgctcctg ggcgccgcca gcacgtacca  5760
ggggtgatgg ttctgctagt ggatgaaccc ttgagaggtg acatattcag ccccatccgt  5820
gaggcccagg cttctgggct taatgtggtg atgttgggaa tggctggagc ggacccagag  5880
cagctgcgtc gcttggcgcc gggtatggac tctgtccaga ccttcttcgc cgtggatgat  5940
gggccaagcc tggaccaggc agtcagtggt ctggccacag ccctgtgtca ggcatccttc  6000
actactcagc cccggccaga gccctgccca gtgtattgtc caaagggcca gaagggggaa  6060
cctggagaga tgggcctgag aggacaagtt gggcctcctg gcgaccctgg cctcccgggc  6120
aggaccggtg ctcccggccc caggggccc cctggaagtg ccactgccaa gggcgagagg  6180
ggcttccctg gagcagatgg gcgtccaggc agccctggcc gcgccgggaa tcctgggacc  6240
cctggagccc ctggcctaaa gggctctcca gggttgcctg ccctcgtgg gacccgggga  6300
gagcgaggac ctcgaggccc aaagggggag ccggggctc ccggacaagt catcggaggt  6360
gaaggacctg ggcttcctgg gcggaaaggg gaccctggac catcgggccc cctggaccct  6420
cgtgaccac tggggaccc aggaccccgt ggccccccag ggcttcctgg aacagccatg  6480
aagggtgaca aggcgatcg tggggagcgg ggtccccctg gaccaggtga aggtggcatt  6540
```

-continued

```
gctcctgggg agcctgggct gccgggtctt cccggaagcc ctggacccca aggccccgtt    6600 ggccccctg gaaagaaagg agaaaaaggt gactctgagg atggagctcc aggcctccca    6660
ggacaacctg ggtctccggg tgagcagggc ccacggggac ctcctggagc tattggcccc    6720
aaaggtgacc ggggctttcc agggcccctg ggtgaggctg gagagaaggg cgaacgtgga    6780
cccccaggcc cagcgggatc ccgggggctg ccaggggttg ctggacgtcc tggagccaag    6840
ggtcctgaag ggccaccagg acccactggc cgccaaggag agaaggggga gcctggtcgc    6900
cctggggacc ctgcagtggt gggacctgct gttgctggac ccaaaggaga aagggagat    6960 gtggggcccg ctgggcccag aggagctacc ggagtccaag gggaacgggg cccacccggc    7020
ttggttcttc ctggagaccc tggccccaag ggagaccctg agaccggggt tcccattggc    7080
cttactggca gagcaggacc cccaggtgac tcagggcctc ctggagagaa gggagaccct    7140
gggcggcctg gcccccagg acctgttggc ccccgaggac gagatggtga agttggagag    7200
aaaggtgacg agggtcctcc gggtgacccg ggtttgcctg gaaagcaggc gagcgtggc    7260 cttcggggg cacctggagt tcgggggcct gtgggtgaaa agggagacca gggagatcct    7320
ggagaggatg gacgaaatgg cagccctgga tcatctggac caagggtga ccgtggggag    7380 ccgggtcccc caggaccccc gggacggctg gtagacacag acctggagc cagagagaag    7440 ggagagcctg ggaccgcgg acaagagggt cctcgagggc caagggtga tcctggcctc    7500 cctggagccc ctggggaaag gggcattgaa gggtttcggg accccccagg cccacagggg    7560
gacccaggtg tccgaggccc agcaggagaa aagggtgacc ggggtccccc tgggctggat    7620
ggccggagcg gactggatgg gaaaccagga gccgctgggc cctctgggcc gaatggtgct    7680
gcaggcaaag ctggggaccc agggagagac gggcttccag gcctccgtgg agaacagggc    7740
ctccctggcc cctctggtcc ccctggatta ccgggaaagc caggcgagga tgcaaacct    7800 ggcctgaatg gaaaaaacgg agaacctggg gaccctggag aagacgggag gaagggagag    7860
aaaggagatt caggcgcctc tgggagagaa ggtcgtgatg ccccaagggg tgagcgtgga    7920
gctcctggta ccttggaccc caggggcct ccaggcctcc cagggccagt gggccctcct    7980
ggccagggtt ttcctggtgt cccaggagcc acgggcccca aggtgaccg tggggagact    8040 ggatccaaag gggagcaggg cctccctgga gagcgtggcc tgcgaggaga gcctggaagt    8100
gtgccgaatg tggatcggtt gctggaaact gctggcatca aggcatctgc cctgcgggag    8160
atcgtggaga cctgggatga gagctctggt agcttcctgc ctgtgcccga acggcgtcga    8220
ggccccaagg gggactcagg cgaacagggc ccccaggca aggagggccc catcggcttt    8280
cctggagaac gcgggctgaa gggcgaccgt ggagaccctg gccctcaggg gccacctggt    8340
ctggcccttg gggagagggg cccccccggg ccttccggcc ttgccgggga gcctggaaag    8400
cctggtattc ccgggctccc aggcagggct ggggtgtgg gagaggcagg aaggccagga    8460 gagagggag aacggggaga gaaaggagaa cgtggagaac agggcagaga tggccctcct    8520
ggactccctg gaacccctgg gccccccgga ccccctggcc ccaaggtgtc tgtggatgag    8580
ccaggtcctg gactctctgg agaacaggga ccccctggac tcaagggtgc taaggggggag    8640 ccgggcagca atggtgacca aggtcccaaa ggagacaggg gtgtgccagg catcaaagga    8700 gaccgggag agcctggacc gagggtcag gacggcaacc cgggtctacc aggagagcgt    8760
ggtatggctg gcctgaagg gaagccgggt ctgcagggtc caagaggccc cctggccca    8820 gtgggtggtc atgagacccc tggaccacct ggtgccccgg tcttgctgg ccctgcagga    8880 ccccaaggac cttctggcct gaaggggag cctggagaga caggacctcc aggacgggc    8940
```

-continued

| | |
|---|---|
| ctgactggac ctactggagc tgtgggactt cctggacccc ccggcccttc aggccttgtg | 9000 |
| ggtccacagg ggtctccagg tttgcctgga caagtggggg agacagggaa gccgggagcc | 9060 |
| ccaggtcgag atggtgccag tggaaaagat ggagacagag ggagccctgg tgtgccaggg | 9120 |
| tcaccaggtc tgcctggccc tgtcggacct aaaggagaac ctggcccac gggggcccct | 9180 |
| ggacaggctg tggtcgggct ccctggagca agggagaga agggagcccc tggaggcctt | 9240 |
| gctggagacc tggtgggtga gccgggagcc aaaggtgacc gaggactgcc agggccgcga | 9300 |
| ggcgagaagg gtgaagctgg ccgtgcaggg gagcccggag accctgggga agatggtcag | 9360 |
| aaagggctc caggacccaa aggtttcaag ggtgacccag gagtcggggt cccgggctcc | 9420 |
| cctgggcctc ctggccctcc agtgtgaag ggagatctgg gcctccctgg cctgcccggt | 9480 |
| gctcctggtg ttgttgggtt cccgggtcag acaggccctc gaggagagat gggtcagcca | 9540 |
| ggccctagtg gagagcgggg tctggcaggc cccccaggga gagaaggaat cccaggaccc | 9600 |
| ctggggccac ctggaccacc ggggtcagtg ggaccacctg gggcctctgg actcaaagga | 9660 |
| gacaagggag accctggagt agggctgcct gggccccgag gcgagcgtgg ggagccaggc | 9720 |
| atccggggtg aagatggccg ccccggccag gagggacccc gaggactcac ggggcccct | 9780 |
| ggcagcaggg gagagcgtgg ggagaagggt gatgttggga gtgcaggact aaagggtgac | 9840 |
| aagggagact cagctgtgat cctggggcct ccaggcccac gggtgccaa ggggacatg | 9900 |
| ggtgaacgag ggcctcgggg cttggatggt gacaaaggac ctcggggaga caatgggac | 9960 |
| cctggtgaca agggcagcaa gggagagcct ggtgacaagg gctcagccgg gttgccagga | 10020 |
| ctgcgtggac tcctgggacc ccagggtcaa cctggtgcag cagggatccc tggtgacccg | 10080 |
| ggatccccag gaaaggatgg agtgcctggt atccgaggaa aaaaaggaga tgttggcttc | 10140 |
| atgggtcccc ggggcctcaa gggtgaacgg ggagtgaagg gagcctgtgg ccttgatgga | 10200 |
| gagaagggag acaagggaga agctggtccc ccaggccgcc ccgggctggc aggacacaaa | 10260 |
| ggagagatgg gggagcctgg tgtgccgggc cagtcggggg cccctggcaa ggagggcctg | 10320 |
| atcggtccca gggtgaccg aggctttgac gggcagccag gccccaaggg tgaccagggc | 10380 |
| gagaaggggg agcgggaac cccaggaatt gggggcttcc caggccccag tggaaatgat | 10440 |
| ggctctgctg gtccccagg gccacctggc agtgttggtc ccagaggccc cgaaggactt | 10500 |
| cagggccaga agggtgagcg aggtccccc ggagagagag tggtgggggc tcctggggtc | 10560 |
| cctggagctc ctggcgagag aggggagcag gggcggccag ggcctgccgg tcctcgaggc | 10620 |
| gagaagggag aagctgcact gacgaggat gacatccggg gctttgtgcg ccaagagatg | 10680 |
| agtcagcact gtgcctgcca gggccagttc atcgcatctg gatcacgacc cctccctagt | 10740 |
| tatgctgcag acactgccgg ctcccagctc catgctgtgc ctgtgctccg cgtctctcat | 10800 |
| gcagaggagg aagagcgggt acccccctgag gatgatgagt actctgaata ctccgagtat | 10860 |
| tctgtggagg agtaccagga ccctgaagct ccttgggata tgatgaccc ctgttccctg | 10920 |
| ccactggatg agggctcctg cactgcctac accctgcgct ggtaccatcg ggctgtgaca | 10980 |
| ggcagcacag aggcctgtca ccctttttgtc tatggtggct gtggagggaa tgccaaccgt | 11040 |
| tttgggaccc gtgaggcctg cgagcgccgc tgcccacccc gggtggtcca gagccagggg | 11100 |
| acaggtactg cccaggactg a | 11121 |

<210> SEQ ID NO 28
<211> LENGTH: 3706
<212> TYPE: PRT

<213> ORGANISM: Artificial Sequence
<220> FEATURE:
<223> OTHER INFORMATION: Synthetic Construct

<400> SEQUENCE: 28

```
Met Thr Ser Ser Gly Pro Gly Pro Arg Phe Leu Leu Leu Pro Leu
  1               5                  10                  15

Leu Leu Pro Pro Ala Ala Ser Ala Ser Asp Arg Pro Arg Gly Arg Asp
             20                  25                  30

Pro Val Asn Pro Glu Lys Leu Leu Val Ile Thr Val Ala Thr Ala Glu
             35                  40                  45

Thr Glu Gly Tyr Leu Arg Phe Leu Arg Ser Ala Glu Phe Phe Asn Tyr
         50                  55                  60

Thr Val Arg Thr Leu Gly Leu Gly Glu Glu Trp Arg Gly Gly Asp Val
 65                  70                  75                  80

Ala Arg Thr Val Gly Gly Gly Gln Lys Val Arg Trp Leu Lys Lys Glu
                 85                  90                  95

Met Glu Lys Tyr Ala Asp Arg Glu Asp Met Ile Ile Met Phe Val Asp
             100                 105                 110

Ser Tyr Asp Val Ile Leu Ala Gly Ser Pro Thr Glu Leu Leu Lys Lys
         115                 120                 125

Phe Val Gln Ser Gly Ser Arg Leu Leu Phe Ser Ala Glu Ser Phe Cys
         130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                 165                 170                 175

His Gln Ile Val Arg Gln Trp Lys Tyr Lys Asp Asp Asp Asp Gln
             180                 185                 190

Leu Phe Tyr Thr Arg Leu Tyr Leu Asp Pro Gly Leu Arg Glu Lys Leu
         195                 200                 205

Ser Leu Asn Leu Asp His Lys Ser Arg Ile Phe Gln Asn Leu Asn Gly
         210                 215                 220

Ala Leu Asp Glu Val Val Leu Lys Phe Asp Arg Asn Arg Val Arg Ile
225                 230                 235                 240

Arg Asn Val Ala Tyr Asp Thr Leu Pro Ile Val Val His Gly Asn Gly
                 245                 250                 255

Pro Thr Lys Leu Gln Leu Asn Tyr Leu Gly Asn Tyr Val Pro Asn Gly
             260                 265                 270

Trp Thr Pro Glu Gly Gly Cys Gly Phe Cys Asn Gln Asp Arg Arg Thr
             275                 280                 285

Leu Pro Gly Gly Gln Pro Pro Arg Val Phe Leu Ala Val Phe Val
         290                 295                 300

Glu Gln Pro Thr Pro Phe Leu Pro Arg Phe Leu Gln Arg Leu Leu Leu
305                 310                 315                 320

Leu Asp Tyr Pro Pro Asp Arg Val Thr Leu Phe Leu His Asn Asn Glu
             325                 330                 335

Val Phe His Glu Pro His Ile Ala Asp Ser Trp Pro Gln Leu Gln Asp
             340                 345                 350

His Phe Ser Ala Val Lys Leu Val Gly Pro Glu Glu Ala Leu Ser Pro
         355                 360                 365

Gly Glu Ala Arg Asp Met Ala Met Asp Leu Cys Arg Gln Asp Pro Glu
370                 375                 380

Cys Glu Phe Tyr Phe Ser Leu Asp Ala Asp Ala Val Leu Thr Asn Leu
```

```
            385                 390                 395                 400
Gln Thr Leu Arg Ile Leu Ile Glu Glu Asn Arg Lys Val Ile Ala Pro
                    405                 410                 415
Met Leu Ser Arg His Gly Lys Leu Trp Ser Asn Phe Trp Gly Ala Leu
                420                 425                 430
Ser Pro Asp Glu Tyr Tyr Ala Arg Ser Glu Asp Tyr Val Glu Leu Val
            435                 440                 445
Gln Arg Lys Arg Val Gly Val Trp Asn Val Pro Tyr Ile Ser Gln Ala
        450                 455                 460
Tyr Val Ile Arg Gly Asp Thr Leu Arg Met Glu Leu Pro Gln Arg Asp
465                 470                 475                 480
Val Phe Ser Gly Ser Asp Thr Asp Pro Asp Met Ala Phe Cys Lys Ser
                485                 490                 495
Phe Arg Asp Lys Gly Ile Phe Leu His Leu Ser Asn Gln His Glu Phe
                500                 505                 510
Gly Arg Leu Leu Ala Thr Ser Arg Tyr Asp Thr Glu His Leu His Pro
            515                 520                 525
Asp Leu Trp Gln Ile Phe Asp Asn Pro Val Asp Trp Lys Glu Gln Tyr
        530                 535                 540
Ile His Glu Asn Tyr Ser Arg Ala Leu Glu Gly Gly Ile Val Glu
545                 550                 555                 560
Gln Pro Cys Pro Asp Val Tyr Trp Phe Pro Leu Leu Ser Glu Gln Met
                565                 570                 575
Cys Asp Glu Leu Val Ala Glu Met Glu His Tyr Gly Gln Trp Ser Gly
                580                 585                 590
Gly Arg His Glu Asp Ser Arg Leu Ala Gly Gly Tyr Glu Asn Val Pro
            595                 600                 605
Thr Val Asp Ile His Met Lys Gln Val Gly Tyr Glu Asp Gln Trp Leu
        610                 615                 620
Gln Leu Leu Arg Thr Tyr Val Gly Pro Met Thr Glu Ser Leu Phe Pro
625                 630                 635                 640
Gly Tyr His Thr Lys Ala Arg Ala Val Met Asn Phe Val Val Arg Tyr
                645                 650                 655
Arg Pro Asp Glu Gln Pro Ser Leu Arg Pro His His Asp Ser Ser Thr
                660                 665                 670
Phe Thr Leu Asn Val Ala Leu Asn His Lys Gly Leu Asp Tyr Glu Gly
            675                 680                 685
Gly Gly Cys Arg Phe Leu Arg Tyr Asp Cys Val Ile Ser Ser Pro Arg
        690                 695                 700
Lys Gly Trp Ala Leu Leu His Pro Gly Arg Leu Thr His Tyr His Glu
705                 710                 715                 720
Gly Leu Pro Thr Thr Trp Gly Thr Arg Tyr Ile Met Val Ser Phe Val
                725                 730                 735
Asp Pro Gly Ser Gly Val Lys Gln Thr Leu Asn Phe Asp Leu Leu Lys
            740                 745                 750
Leu Ala Gly Asp Val Glu Ser Asn Pro Gly Pro Thr Leu Arg Leu Leu
        755                 760                 765
Val Ala Ala Leu Cys Ala Gly Ile Leu Ala Glu Ala Pro Arg Val Arg
770                 775                 780
Ala Gln His Arg Glu Arg Val Thr Cys Thr Arg Leu Tyr Ala Ala Asp
785                 790                 795                 800
Ile Val Phe Leu Leu Asp Gly Ser Ser Ser Ile Gly Arg Ser Asn Phe
                805                 810                 815
```

```
Arg Glu Val Arg Ser Phe Leu Glu Gly Leu Val Leu Pro Phe Ser Gly
            820                 825                 830

Ala Ala Ser Ala Gln Gly Val Arg Phe Ala Thr Val Gln Tyr Ser Asp
        835                 840                 845

Asp Pro Arg Thr Glu Phe Gly Leu Asp Ala Leu Gly Ser Gly Gly Asp
850                 855                 860

Val Ile Arg Ala Ile Arg Glu Leu Ser Tyr Lys Gly Gly Asn Thr Arg
865                 870                 875                 880

Thr Gly Ala Ala Ile Leu His Val Ala Asp His Val Phe Leu Pro Gln
                885                 890                 895

Leu Ala Arg Pro Gly Val Pro Lys Val Cys Ile Leu Ile Thr Asp Gly
            900                 905                 910

Lys Ser Gln Asp Leu Val Asp Thr Ala Ala Gln Arg Leu Lys Gly Gln
        915                 920                 925

Gly Val Lys Leu Phe Ala Val Gly Ile Lys Asn Ala Asp Pro Glu Glu
    930                 935                 940

Leu Lys Arg Val Ala Ser Gln Pro Thr Ser Asp Phe Phe Phe Phe Val
945                 950                 955                 960

Asn Asp Phe Ser Ile Leu Arg Thr Leu Leu Pro Leu Val Ser Arg Arg
                965                 970                 975

Val Cys Thr Thr Ala Gly Gly Val Pro Val Thr Arg Pro Pro Asp Asp
            980                 985                 990

Ser Thr Ser Ala Pro Arg Asp Leu Val Leu Ser Glu Pro Ser Ser Gln
        995                 1000                1005

Ser Leu Arg Val Gln Trp Thr Ala Ala Ser Gly Pro Val Thr Gly Tyr
    1010                1015                1020

Lys Val Gln Tyr Thr Pro Leu Thr Gly Leu Gly Gln Pro Leu Pro Ser
1025                1030                1035                1040

Glu Arg Gln Glu Val Asn Val Pro Ala Gly Glu Thr Ser Val Arg Leu
                1045                1050                1055

Arg Gly Leu Arg Pro Leu Thr Glu Tyr Gln Val Thr Val Ile Ala Leu
            1060                1065                1070

Tyr Ala Asn Ser Ile Gly Glu Ala Val Ser Gly Thr Ala Arg Thr Thr
        1075                1080                1085

Ala Leu Glu Gly Pro Glu Leu Thr Ile Gln Asn Thr Thr Ala His Ser
    1090                1095                1100

Leu Leu Val Ala Trp Arg Ser Val Pro Gly Ala Thr Gly Tyr Arg Val
1105                1110                1115                1120

Thr Trp Arg Val Leu Ser Gly Gly Pro Thr Gln Gln Gln Glu Leu Gly
                1125                1130                1135

Pro Gly Gln Gly Ser Val Leu Leu Arg Asp Leu Glu Pro Gly Thr Asp
            1140                1145                1150

Tyr Glu Val Thr Val Ser Thr Leu Phe Gly Arg Ser Val Gly Pro Ala
        1155                1160                1165

Thr Ser Leu Met Ala Arg Thr Asp Ala Ser Val Glu Gln Thr Leu Arg
    1170                1175                1180

Pro Val Ile Leu Gly Pro Thr Ser Ile Leu Leu Ser Trp Asn Leu Val
1185                1190                1195                1200

Pro Glu Ala Arg Gly Tyr Arg Leu Glu Trp Arg Arg Glu Thr Gly Leu
                1205                1210                1215

Glu Pro Pro Gln Lys Val Val Leu Pro Ser Asp Val Thr Arg Tyr Gln
            1220                1225                1230
```

-continued

Leu Asp Gly Leu Gln Pro Gly Thr Glu Tyr Arg Leu Thr Leu Tyr Thr
         1235                1240                1245

Leu Leu Glu Gly His Glu Val Ala Thr Pro Ala Thr Val Val Pro Thr
         1250                1255                1260

Gly Pro Glu Leu Pro Val Ser Pro Val Thr Asp Leu Gln Ala Thr Glu
1265                1270                1275                1280

Leu Pro Gly Gln Arg Val Arg Val Ser Trp Ser Pro Val Pro Gly Ala
            1285                1290                1295

Thr Gln Tyr Arg Ile Ile Val Arg Ser Thr Gln Gly Val Glu Arg Thr
            1300                1305                1310

Leu Val Leu Pro Gly Ser Gln Thr Ala Phe Asp Leu Asp Asp Val Gln
            1315                1320                1325

Ala Gly Leu Ser Tyr Thr Val Arg Val Ser Ala Arg Val Gly Pro Arg
            1330                1335                1340

Glu Gly Ser Ala Ser Val Leu Thr Val Arg Arg Glu Pro Glu Thr Pro
1345                1350                1355                1360

Leu Ala Val Pro Gly Leu Arg Val Val Ser Asp Ala Thr Arg Val
            1365                1370                1375

Arg Val Ala Trp Gly Pro Val Pro Gly Ala Ser Gly Phe Arg Ile Ser
            1380                1385                1390

Trp Ser Thr Gly Ser Gly Pro Glu Ser Ser Gln Thr Leu Pro Pro Asp
        1395                1400                1405

Ser Thr Ala Thr Asp Ile Thr Gly Leu Gln Pro Gly Thr Thr Tyr Gln
        1410                1415                1420

Val Ala Val Ser Val Leu Arg Gly Arg Glu Glu Gly Pro Ala Ala Val
1425                1430                1435                1440

Ile Val Ala Arg Thr Asp Pro Leu Gly Pro Val Arg Thr Val His Val
            1445                1450                1455

Thr Gln Ala Ser Ser Ser Ser Val Thr Ile Thr Trp Thr Arg Val Pro
            1460                1465                1470

Gly Ala Thr Gly Tyr Arg Val Ser Trp His Ser Ala His Gly Pro Glu
            1475                1480                1485

Lys Ser Gln Leu Val Ser Gly Glu Ala Thr Val Ala Glu Leu Asp Gly
            1490                1495                1500

Leu Glu Pro Asp Thr Glu Tyr Thr Val His Val Arg Ala His Val Ala
1505                1510                1515                1520

Gly Val Asp Gly Pro Pro Ala Ser Val Val Val Arg Thr Ala Pro Glu
            1525                1530                1535

Pro Val Gly Arg Val Ser Arg Leu Gln Ile Leu Asn Ala Ser Ser Asp
            1540                1545                1550

Val Leu Arg Ile Thr Trp Val Gly Val Thr Gly Ala Thr Ala Tyr Arg
            1555                1560                1565

Leu Ala Trp Gly Arg Ser Glu Gly Gly Pro Met Arg His Gln Ile Leu
            1570                1575                1580

Pro Gly Asn Thr Asp Ser Ala Glu Ile Arg Gly Leu Glu Gly Gly Val
1585                1590                1595                1600

Ser Tyr Ser Val Arg Val Thr Ala Leu Val Gly Asp Arg Glu Gly Thr
            1605                1610                1615

Pro Val Ser Ile Val Val Thr Thr Pro Pro Glu Ala Pro Pro Ala Leu
            1620                1625                1630

Gly Thr Leu His Val Val Gln Arg Gly Glu His Ser Leu Arg Leu Arg
            1635                1640                1645

Trp Glu Pro Val Pro Arg Ala Gln Gly Phe Leu Leu His Trp Gln Pro

-continued

```
             1650                1655                1660

Glu Gly Gly Gln Glu Gln Ser Arg Val Leu Gly Pro Glu Leu Ser Ser
1665                1670                1675                1680

Tyr His Leu Asp Gly Leu Glu Pro Ala Thr Gln Tyr Arg Val Arg Leu
                    1685                1690                1695

Ser Val Leu Gly Pro Ala Gly Glu Gly Pro Ser Ala Glu Val Thr Ala
                    1700                1705                1710

Arg Thr Glu Ser Pro Arg Val Pro Ser Ile Glu Leu Arg Val Val Asp
                    1715                1720                1725

Thr Ser Ile Asp Ser Val Thr Leu Ala Trp Thr Pro Val Ser Arg Ala
                    1730                1735                1740

Ser Ser Tyr Ile Leu Ser Trp Arg Pro Leu Arg Gly Pro Gly Gln Glu
1745                1750                1755                1760

Val Pro Gly Ser Pro Gln Thr Leu Pro Gly Ile Ser Ser Ser Gln Arg
                    1765                1770                1775

Val Thr Gly Leu Glu Pro Gly Val Ser Tyr Ile Phe Ser Leu Thr Pro
                    1780                1785                1790

Val Leu Asp Gly Val Arg Gly Pro Glu Ala Ser Val Thr Gln Thr Pro
                    1795                1800                1805

Val Cys Pro Arg Gly Leu Ala Asp Val Val Phe Leu Pro His Ala Thr
                    1810                1815                1820

Gln Asp Asn Ala His Arg Ala Glu Ala Thr Arg Arg Val Leu Glu Arg
1825                1830                1835                1840

Leu Val Leu Ala Leu Gly Pro Leu Gly Pro Gln Ala Val Gln Val Gly
                    1845                1850                1855

Leu Leu Ser Tyr Ser His Arg Pro Ser Pro Leu Phe Pro Leu Asn Gly
                    1860                1865                1870

Ser His Asp Leu Gly Ile Ile Leu Gln Arg Ile Arg Asp Met Pro Tyr
                    1875                1880                1885

Met Asp Pro Ser Gly Asn Asn Leu Gly Thr Ala Val Val Thr Ala His
                    1890                1895                1900

Arg Tyr Met Leu Ala Pro Asp Ala Pro Gly Arg Arg Gln His Val Pro
1905                1910                1915                1920

Gly Val Met Val Leu Leu Val Asp Glu Pro Leu Arg Gly Asp Ile Phe
                    1925                1930                1935

Ser Pro Ile Arg Glu Ala Gln Ala Ser Gly Leu Asn Val Val Met Leu
                    1940                1945                1950

Gly Met Ala Gly Ala Asp Pro Glu Gln Leu Arg Arg Leu Ala Pro Gly
                    1955                1960                1965

Met Asp Ser Val Gln Thr Phe Phe Ala Val Asp Asp Gly Pro Ser Leu
                    1970                1975                1980

Asp Gln Ala Val Ser Gly Leu Ala Thr Ala Leu Cys Gln Ala Ser Phe
1985                1990                1995                2000

Thr Thr Gln Pro Arg Pro Glu Pro Cys Pro Val Tyr Cys Pro Lys Gly
                    2005                2010                2015

Gln Lys Gly Glu Pro Gly Glu Met Gly Leu Arg Gly Gln Val Gly Pro
                    2020                2025                2030

Pro Gly Asp Pro Gly Leu Pro Gly Arg Thr Gly Ala Pro Gly Pro Gln
                    2035                2040                2045

Gly Pro Pro Gly Ser Ala Thr Ala Lys Gly Glu Arg Gly Phe Pro Gly
                    2050                2055                2060

Ala Asp Gly Arg Pro Gly Ser Pro Gly Arg Ala Gly Asn Pro Gly Thr
2065                2070                2075                2080
```

```
Pro Gly Ala Pro Gly Leu Lys Gly Ser Pro Gly Leu Pro Gly Pro Arg
            2085                2090                2095

Gly Asp Pro Gly Glu Arg Gly Pro Arg Gly Pro Lys Gly Glu Pro Gly
            2100                2105                2110

Ala Pro Gly Gln Val Ile Gly Gly Gly Pro Gly Leu Pro Gly Pro Arg
            2115                2120                2125

Lys Gly Asp Pro Gly Pro Ser Gly Pro Pro Gly Pro Arg Gly Pro Leu
            2130                2135                2140

Gly Asp Pro Gly Pro Arg Gly Pro Gly Leu Pro Gly Thr Ala Met
2145                2150                2155                2160

Lys Gly Asp Lys Gly Asp Arg Gly Glu Arg Gly Pro Pro Gly Pro Gly
            2165                2170                2175

Glu Gly Gly Ile Ala Pro Gly Glu Pro Gly Leu Pro Gly Leu Pro Gly
            2180                2185                2190

Ser Pro Gly Pro Gln Gly Pro Val Gly Pro Pro Gly Lys Lys Gly Glu
            2195                2200                2205

Lys Gly Asp Ser Glu Asp Gly Ala Pro Gly Leu Pro Gly Gln Pro Gly
            2210                2215                2220

Ser Pro Gly Glu Gln Gly Pro Arg Gly Pro Pro Gly Ala Ile Gly Pro
2225                2230                2235                2240

Lys Gly Asp Arg Gly Phe Pro Gly Pro Leu Gly Glu Ala Gly Glu Lys
            2245                2250                2255

Gly Glu Arg Gly Pro Pro Gly Pro Ala Gly Ser Arg Gly Leu Pro Gly
            2260                2265                2270

Val Ala Gly Arg Pro Gly Ala Lys Gly Pro Glu Gly Pro Pro Gly Pro
            2275                2280                2285

Thr Gly Arg Gln Gly Glu Lys Gly Glu Pro Gly Arg Pro Gly Asp Pro
            2290                2295                2300

Ala Val Val Gly Pro Ala Val Ala Gly Pro Lys Gly Glu Lys Gly Asp
2305                2310                2315                2320

Val Gly Pro Ala Gly Pro Arg Gly Ala Thr Gly Val Gln Gly Glu Arg
            2325                2330                2335

Gly Pro Pro Gly Leu Val Leu Pro Gly Asp Pro Gly Pro Lys Gly Asp
            2340                2345                2350

Pro Gly Asp Arg Gly Pro Ile Gly Leu Thr Gly Arg Ala Gly Pro Pro
            2355                2360                2365

Gly Asp Ser Gly Pro Pro Gly Glu Lys Gly Asp Pro Gly Arg Pro Gly
            2370                2375                2380

Pro Pro Gly Pro Val Gly Pro Arg Gly Arg Asp Gly Glu Val Gly Glu
2385                2390                2395                2400

Lys Gly Asp Glu Gly Pro Pro Gly Asp Pro Gly Leu Pro Gly Lys Ala
            2405                2410                2415

Gly Glu Arg Gly Leu Arg Gly Ala Pro Gly Val Arg Gly Pro Val Gly
            2420                2425                2430

Glu Lys Gly Asp Gln Gly Asp Pro Gly Glu Asp Gly Arg Asn Gly Ser
            2435                2440                2445

Pro Gly Ser Ser Gly Pro Lys Gly Asp Arg Gly Glu Pro Gly Pro Pro
            2450                2455                2460

Gly Pro Pro Gly Arg Leu Val Asp Thr Gly Pro Gly Ala Arg Glu Lys
2465                2470                2475                2480

Gly Glu Pro Gly Asp Arg Gly Gln Glu Gly Pro Arg Gly Pro Lys Gly
            2485                2490                2495
```

-continued

Asp Pro Gly Leu Pro Gly Ala Pro Gly Glu Arg Gly Ile Glu Gly Phe
                2500                2505                2510

Arg Gly Pro Pro Gly Pro Gln Gly Asp Pro Gly Val Arg Gly Pro Ala
            2515                2520                2525

Gly Glu Lys Gly Asp Arg Gly Pro Pro Gly Leu Asp Gly Arg Ser Gly
        2530                2535                2540

Leu Asp Gly Lys Pro Gly Ala Ala Gly Pro Ser Gly Pro Asn Gly Ala
2545                2550                2555                2560

Ala Gly Lys Ala Gly Asp Pro Gly Arg Asp Gly Leu Pro Gly Leu Arg
            2565                2570                2575

Gly Glu Gln Gly Leu Pro Gly Pro Ser Gly Pro Pro Gly Leu Pro Gly
        2580                2585                2590

Lys Pro Gly Glu Asp Gly Lys Pro Gly Leu Asn Gly Lys Asn Gly Glu
            2595                2600                2605

Pro Gly Asp Pro Gly Glu Asp Gly Arg Lys Gly Glu Lys Gly Asp Ser
        2610                2615                2620

Gly Ala Ser Gly Arg Glu Gly Arg Asp Gly Pro Lys Gly Glu Arg Gly
2625                2630                2635                2640

Ala Pro Gly Ile Leu Gly Pro Gln Gly Pro Pro Gly Leu Pro Gly Pro
            2645                2650                2655

Val Gly Pro Pro Gly Gln Gly Phe Pro Gly Val Pro Gly Gly Thr Gly
        2660                2665                2670

Pro Lys Gly Asp Arg Gly Glu Thr Gly Ser Lys Gly Glu Gln Gly Leu
            2675                2680                2685

Pro Gly Glu Arg Gly Leu Arg Gly Glu Pro Gly Ser Val Pro Asn Val
        2690                2695                2700

Asp Arg Leu Leu Glu Thr Ala Gly Ile Lys Ala Ser Ala Leu Arg Glu
2705                2710                2715                2720

Ile Val Glu Thr Trp Asp Glu Ser Ser Gly Ser Phe Leu Pro Val Pro
            2725                2730                2735

Glu Arg Arg Arg Gly Pro Lys Gly Asp Ser Gly Glu Gln Gly Pro Pro
        2740                2745                2750

Gly Lys Glu Gly Pro Ile Gly Phe Pro Gly Glu Arg Gly Leu Lys Gly
            2755                2760                2765

Asp Arg Gly Asp Pro Gly Pro Gln Gly Pro Pro Gly Leu Ala Leu Gly
        2770                2775                2780

Glu Arg Gly Pro Pro Gly Pro Ser Gly Leu Ala Gly Glu Pro Gly Lys
2785                2790                2795                2800

Pro Gly Ile Pro Gly Leu Pro Gly Arg Ala Gly Gly Val Gly Glu Ala
            2805                2810                2815

Gly Arg Pro Gly Glu Arg Gly Glu Arg Gly Lys Gly Glu Arg Gly
        2820                2825                2830

Glu Gln Gly Arg Asp Gly Pro Pro Gly Leu Pro Gly Thr Pro Gly Pro
        2835                2840                2845

Pro Gly Pro Pro Gly Pro Lys Val Ser Val Asp Glu Pro Gly Pro Gly
            2850                2855                2860

Leu Ser Gly Glu Gln Gly Pro Pro Gly Leu Lys Gly Ala Lys Gly Glu
2865                2870                2875                2880

Pro Gly Ser Asn Gly Asp Gln Gly Pro Lys Gly Asp Arg Gly Val Pro
            2885                2890                2895

Gly Ile Lys Gly Asp Arg Gly Glu Pro Gly Pro Arg Gly Gln Asp Gly
            2900                2905                2910

Asn Pro Gly Leu Pro Gly Glu Arg Gly Met Ala Gly Pro Glu Gly Lys

-continued

```
            2915                2920                2925
Pro Gly Leu Gln Gly Pro Arg Gly Pro Pro Gly Pro Val Gly Gly His
            2930                2935                2940
Gly Asp Pro Gly Pro Pro Gly Ala Pro Gly Leu Ala Gly Pro Ala Gly
2945                2950                2955                2960
Pro Gln Gly Pro Ser Gly Leu Lys Gly Glu Pro Gly Glu Thr Gly Pro
            2965                2970                2975
Pro Gly Arg Gly Leu Thr Gly Pro Thr Gly Ala Val Gly Leu Pro Gly
            2980                2985                2990
Pro Pro Gly Pro Ser Gly Leu Val Gly Pro Gln Gly Ser Pro Gly Leu
            2995                3000                3005
Pro Gly Gln Val Gly Glu Thr Gly Lys Pro Gly Ala Pro Gly Arg Asp
            3010                3015                3020
Gly Ala Ser Gly Lys Asp Gly Asp Arg Gly Ser Pro Gly Val Pro Gly
            3025                3030                3035                3040
Ser Pro Gly Leu Pro Gly Pro Val Gly Pro Lys Gly Glu Pro Gly Pro
            3045                3050                3055
Thr Gly Ala Pro Gly Gln Ala Val Val Gly Leu Pro Gly Ala Lys Gly
            3060                3065                3070
Glu Lys Gly Ala Pro Gly Gly Leu Ala Gly Asp Leu Val Gly Glu Pro
            3075                3080                3085
Gly Ala Lys Gly Asp Arg Gly Leu Pro Gly Pro Arg Gly Glu Lys Gly
            3090                3095                3100
Glu Ala Gly Arg Ala Gly Glu Pro Gly Asp Pro Gly Glu Asp Gly Gln
3105                3110                3115                3120
Lys Gly Ala Pro Gly Pro Lys Gly Phe Lys Gly Asp Pro Gly Val Gly
            3125                3130                3135
Val Pro Gly Ser Pro Gly Pro Pro Gly Pro Pro Gly Val Lys Gly Asp
            3140                3145                3150
Leu Gly Leu Pro Gly Leu Pro Gly Ala Pro Gly Val Val Gly Phe Pro
            3155                3160                3165
Gly Gln Thr Gly Pro Arg Gly Glu Met Gly Gln Pro Gly Pro Ser Gly
            3170                3175                3180
Glu Arg Gly Leu Ala Gly Pro Pro Gly Arg Glu Gly Ile Pro Gly Pro
3185                3190                3195                3200
Leu Gly Pro Pro Gly Pro Pro Gly Ser Val Gly Pro Pro Gly Ala Ser
            3205                3210                3215
Gly Leu Lys Gly Asp Lys Gly Asp Pro Gly Val Gly Leu Pro Gly Pro
            3220                3225                3230
Arg Gly Glu Arg Gly Glu Pro Gly Ile Arg Gly Glu Asp Gly Arg Pro
            3235                3240                3245
Gly Gln Glu Gly Pro Arg Gly Leu Thr Gly Pro Pro Gly Ser Arg Gly
            3250                3255                3260
Glu Arg Gly Glu Lys Gly Asp Val Gly Ser Ala Gly Leu Lys Gly Asp
3265                3270                3275                3280
Lys Gly Asp Ser Ala Val Ile Leu Gly Pro Pro Gly Pro Arg Gly Ala
            3285                3290                3295
Lys Gly Asp Met Gly Glu Arg Gly Pro Arg Gly Leu Asp Gly Asp Lys
            3300                3305                3310
Gly Pro Arg Gly Asp Asn Gly Asp Pro Gly Asp Lys Gly Ser Lys Gly
            3315                3320                3325
Glu Pro Gly Asp Lys Gly Ser Ala Gly Leu Pro Gly Leu Arg Gly Leu
            3330                3335                3340
```

Leu Gly Pro Gln Gly Gln Pro Gly Ala Ala Gly Ile Pro Gly Asp Pro
3345                3350                3355                3360

Gly Ser Pro Gly Lys Asp Gly Val Pro Gly Ile Arg Gly Glu Lys Gly
            3365                3370                3375

Asp Val Gly Phe Met Gly Pro Arg Gly Leu Lys Gly Glu Arg Gly Val
        3380                3385                3390

Lys Gly Ala Cys Gly Leu Asp Gly Glu Lys Gly Asp Lys Gly Glu Ala
    3395                3400                3405

Gly Pro Pro Gly Arg Pro Gly Leu Ala Gly His Lys Gly Glu Met Gly
        3410                3415                3420

Glu Pro Gly Val Pro Gly Gln Ser Gly Ala Pro Gly Lys Glu Gly Leu
3425                3430                3435                3440

Ile Gly Pro Lys Gly Asp Arg Gly Phe Asp Gly Gln Pro Gly Pro Lys
            3445                3450                3455

Gly Asp Gln Gly Glu Lys Gly Glu Arg Gly Thr Pro Gly Ile Gly Gly
            3460                3465                3470

Phe Pro Gly Pro Ser Gly Asn Asp Gly Ser Ala Gly Pro Pro Gly Pro
        3475                3480                3485

Pro Gly Ser Val Gly Pro Arg Gly Pro Glu Gly Leu Gln Gly Gln Lys
        3490                3495                3500

Gly Glu Arg Gly Pro Pro Gly Glu Arg Val Val Gly Ala Pro Gly Val
3505                3510                3515                3520

Pro Gly Ala Pro Gly Glu Arg Gly Glu Gln Gly Arg Pro Gly Pro Ala
            3525                3530                3535

Gly Pro Arg Gly Glu Lys Gly Glu Ala Ala Leu Thr Glu Asp Asp Ile
            3540                3545                3550

Arg Gly Phe Val Arg Gln Glu Met Ser Gln His Cys Ala Cys Gln Gly
        3555                3560                3565

Gln Phe Ile Ala Ser Gly Ser Arg Pro Leu Pro Ser Tyr Ala Ala Asp
    3570                3575                3580

Thr Ala Gly Ser Gln Leu His Ala Val Pro Val Leu Arg Val Ser His
3585                3590                3595                3600

Ala Glu Glu Glu Arg Val Pro Pro Glu Asp Glu Tyr Ser Glu
            3605                3610                3615

Tyr Ser Glu Tyr Ser Val Glu Gly Tyr Gln Asp Pro Glu Ala Pro Trp
        3620                3625                3630

Asp Ser Asp Asp Pro Cys Ser Leu Pro Leu Asp Glu Gly Ser Cys Thr
        3635                3640                3645

Ala Tyr Thr Leu Arg Trp Tyr His Arg Ala Val Thr Gly Ser Thr Glu
    3650                3655                3660

Ala Cys His Pro Phe Val Tyr Gly Gly Cys Gly Gly Asn Ala Asn Arg
3665                3670                3675                3680

Phe Gly Thr Arg Glu Ala Cys Glu Arg Arg Cys Pro Pro Arg Val Val
            3685                3690                3695

Gln Ser Gln Gly Thr Gly Thr Ala Gln Asp
            3700                3705

<210> SEQ ID NO 29
<211> LENGTH: 1299
<212> TYPE: DNA
<213> ORGANISM: Homo sapiens

<400> SEQUENCE: 29
atgaccacct ccatccgcca gttcacctcc tccagctcca tcaagggctc ctccggcctg    60

```
gggggcggct cgtcccgcac ctcctgccgg ctgtctggcg gcctgggtgc cggctcctgc    120
aggctgggat ctgctggcgg cctgggcagc accctcgggg gtagcagcta ctccagctgc    180
tacagctttg gctctggtgg tggctatggc agcagctttg ggggtgttga tgggctgctg    240
gctggaggtg agaaggccac catgcagaac ctcaatgacc gcctggcctc ctacctggac    300
aaggtgcgtg ccctggagga ggccaacact gagctggagg tgaagatccg tgactggtac    360
cagaggcagg cccgggggcc cgcccgtgac tacagccagt actacaggac aattgaggag    420
ctgcagaaca agatcctcac agccaccgtg acaatgccaa catcctgct acagattgac     480 aatgcccgtc tggctgctga tgacttccgc accaagtttg agacagagca ggccctgcgc    540
ctgagtgtgg aggccgacat caatggcctg cgcagggtgc tggatgagct gaccctggcc    600
agagccgacc tggagatgca gattgagaac ctcaaggagg agctggccta cctgaagaag    660
aaccacgagg aggagatgaa cgccctgcga ggccaggtgg gtggtgagat caatgtggag    720
atggacgctg ccccaggcgt ggacctgagc cgcatcctca cgagatgcg tgaccagtat     780 gagaagatgg cagagaagaa ccgcaaggat gccgaggatt ggttcttcag caagacagag    840
gaactgaacc gcgaggtggc caccaacagt gagctggtgc agagtggcaa gagtgagatc    900
tcggagctcc ggcgcaccat gcaggccttg agatagagc tgcagtccca gctcagcatg     960
aaagcatccc tggagggcaa cctggcggag acagagaacc gctactgcgt gcagctgtcc    1020
cagatccagg ggctgattgg cagcgtggag gagcagctgg cccagcttcg ctgcgagatg    1080
gagcagcaga accaggaata caaaatcctg ctggatgtga agacgcggct ggagcaggag    1140
attgccacct accgccgcct gctggaggga gaggatgccc acctgactca gtacaagaaa    1200
gaaccggtga ccaccgtca ggtgcgtacc attgtggaag aggtccagga tggcaaggtc     1260
atctcctccc gcgagcaggt ccaccagacc acccgctga                           1299
```

<210> SEQ ID NO 30
<211> LENGTH: 432
<212> TYPE: PRT
<213> ORGANISM: Homo sapiens

<400> SEQUENCE: 30

```
Met Thr Thr Ser Ile Arg Gln Phe Thr Ser Ser Ser Ile Lys Gly
 1               5                  10                  15

Ser Ser Gly Leu Gly Gly Gly Ser Ser Arg Thr Ser Cys Arg Leu Ser
                20                  25                  30

Gly Gly Leu Gly Ala Gly Ser Cys Arg Leu Gly Ser Ala Gly Gly Leu
            35                  40                  45

Gly Ser Thr Leu Gly Gly Ser Ser Tyr Ser Ser Cys Tyr Ser Phe Gly
        50                  55                  60

Ser Gly Gly Gly Tyr Gly Ser Ser Phe Gly Gly Val Asp Gly Leu Leu
 65                  70                  75                  80

Ala Gly Gly Glu Lys Ala Thr Met Gln Asn Leu Asn Asp Arg Leu Ala
                85                  90                  95

Ser Tyr Leu Asp Lys Val Arg Ala Leu Glu Glu Ala Asn Thr Glu Leu
            100                 105                 110

Glu Val Lys Ile Arg Asp Trp Tyr Gln Arg Gln Ala Pro Gly Pro Ala
        115                 120                 125

Arg Asp Tyr Ser Gln Tyr Tyr Arg Thr Ile Glu Glu Leu Gln Asn Lys
    130                 135                 140

Ile Leu Thr Ala Thr Val Asp Asn Ala Asn Ile Leu Leu Gln Ile Asp
```

```
145                 150                 155                 160
Asn Ala Arg Leu Ala Ala Asp Asp Phe Arg Thr Lys Phe Glu Thr Glu
                165                 170                 175
Gln Ala Leu Arg Leu Ser Val Glu Ala Asp Ile Asn Gly Leu Arg Arg
                180                 185                 190
Val Leu Asp Glu Leu Thr Leu Ala Arg Ala Asp Leu Glu Met Gln Ile
            195                 200                 205
Glu Asn Leu Lys Glu Glu Leu Ala Tyr Leu Lys Lys Asn His Glu Glu
        210                 215                 220
Glu Met Asn Ala Leu Arg Gly Gln Val Gly Gly Glu Ile Asn Val Glu
225                 230                 235                 240
Met Asp Ala Ala Pro Gly Val Asp Leu Ser Arg Ile Leu Asn Glu Met
                245                 250                 255
Arg Asp Gln Tyr Glu Lys Met Ala Glu Lys Asn Arg Lys Asp Ala Glu
                260                 265                 270
Asp Trp Phe Phe Ser Lys Thr Glu Glu Leu Asn Arg Glu Val Ala Thr
            275                 280                 285
Asn Ser Glu Leu Val Gln Ser Gly Lys Ser Glu Ile Ser Glu Leu Arg
        290                 295                 300
Arg Thr Met Gln Ala Leu Glu Ile Glu Leu Gln Ser Gln Leu Ser Met
305                 310                 315                 320
Lys Ala Ser Leu Glu Gly Asn Leu Ala Glu Thr Glu Asn Arg Tyr Cys
                325                 330                 335
Val Gln Leu Ser Gln Ile Gln Gly Leu Ile Gly Ser Val Glu Glu Gln
                340                 345                 350
Leu Ala Gln Leu Arg Cys Glu Met Glu Gln Gln Asn Gln Glu Tyr Lys
            355                 360                 365
Ile Leu Leu Asp Val Lys Thr Arg Leu Glu Gln Glu Ile Ala Thr Tyr
        370                 375                 380
Arg Arg Leu Leu Glu Gly Glu Asp Ala His Leu Thr Gln Tyr Lys Lys
385                 390                 395                 400
Glu Pro Val Thr Thr Arg Gln Val Arg Thr Ile Val Glu Glu Val Gln
                405                 410                 415
Asp Gly Lys Val Ile Ser Ser Arg Glu Gln Val His Gln Thr Thr Arg
                420                 425                 430
```